(12) United States Patent
Jouhanneaud et al.

(10) Patent No.: US 10,858,423 B2
(45) Date of Patent: *Dec. 8, 2020

(54) COMPOSITION FOR THE TREATMENT OF IGF-1R EXPRESSING CANCER

(71) Applicant: PIERRE FABRE MEDICAMENT, Boulogne-Billancourt (FR)

(72) Inventors: Alexandra Jouhanneaud, Bonneville (FR); Liliane Goetsch, Ayze (FR); Matthieu Broussas, Seyssel (FR); Charlotte Beau-Larvor, Jonzier Epagny (FR); Thierry Champion, Saint Julien en Genevois (FR); Alain Robert, Annemasse (FR); Jean-François Haeuw, Beaumont (FR); Ian Rilatt, Castres (FR); Michel Perez, Castres (FR); Marie Lamothe, Montredon Labessonnie (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 194 days.

This patent is subject to a terminal disclaimer.

(21) Appl. No.: 15/771,082

(22) PCT Filed: Oct. 26, 2016

(86) PCT No.: PCT/EP2016/075858
§ 371 (c)(1),
(2) Date: Apr. 25, 2018

(87) PCT Pub. No.: WO2017/072196
PCT Pub. Date: May 4, 2017

(65) Prior Publication Data
US 2019/0202901 A1 Jul. 4, 2019

(30) Foreign Application Priority Data
Oct. 26, 2015 (EP) .................................. 15306707

(51) Int. Cl.
*A61K 39/00* (2006.01)
*C07K 16/22* (2006.01)
*A61K 47/68* (2017.01)
*A61K 47/65* (2017.01)
*A61P 35/00* (2006.01)

(52) U.S. Cl.
CPC .............. *C07K 16/22* (2013.01); *A61K 47/65* (2017.08); *A61K 47/6811* (2017.08); *A61K 47/6849* (2017.08); *A61K 47/6851* (2017.08); *A61P 35/00* (2018.01)

(58) Field of Classification Search
CPC .................................................... C07K 16/22
See application file for complete search history.

(56) References Cited

U.S. PATENT DOCUMENTS

| | | | |
|---|---|---|---|
| 5,530,101 A | 6/1996 | Queen et al. | |
| 5,585,089 A | 12/1996 | Queen et al. | |
| 5,639,641 A | 6/1997 | Pedersen et al. | |
| 5,693,761 A | 12/1997 | Queen et al. | |
| 5,877,293 A | 3/1999 | Adair et al. | |
| 5,886,152 A | 3/1999 | Nakatani et al. | |
| 6,054,297 A | 4/2000 | Carter et al. | |
| 6,180,370 B1 | 1/2001 | Queen et al. | |
| 7,521,541 B2 | 4/2009 | Eigenbrot et al. | |
| 7,723,485 B2 | 5/2010 | Junutula et al. | |
| 10,457,734 B2 * | 10/2019 | Jouhanneaud | ..... A61K 47/6803 |
| 2010/0316639 A1 | 12/2010 | Lackner | |
| 2013/0095033 A1 | 4/2013 | Chang et al. | |

FOREIGN PATENT DOCUMENTS

| | | |
|---|---|---|
| EP | 0 682 040 B1 | 8/1999 |
| EP | 0 566 647 B1 | 10/2003 |
| EP | 0 451 216 B9 | 6/2012 |
| EP | 0 939 127 B1 | 9/2014 |
| WO | WO 2008/079849 A2 | 7/2008 |
| WO | WO 2008/079849 A3 | 7/2008 |
| WO | WO 2009/052249 A1 | 4/2009 |
| WO | WO 2010/037835 A2 | 4/2010 |
| WO | WO 2010/037835 A3 | 4/2010 |
| WO | WO 2015/162291 A1 | 10/2015 |
| WO | WO 2015/162292 A1 | 10/2015 |
| WO | WO 2015/162293 A1 | 10/2015 |
| WO | WO 2016/174051 A1 | 11/2016 |
| WO | WO 2016/174053 A1 | 11/2016 |

OTHER PUBLICATIONS

Strome et al., The Oncologist, 2007; 12:1084-95 (Year: 2007).*
Brand et al., Anticancer Res. 2006; 26:463-70 (Year: 2006).*
Brown et al J. Immunol. May 1996; 156(9):3285-3291 (Year: 1996).*
Vajdos et al (J. Mol. Biol. Jul. 5, 2002;320(2); 415-428) (Year: 2002).*
George et al. (Circulation. 1998; 97: 900-906), (Year: 1998).*
Cox, D. R., "Regression Models and Life-Tables", Journal of the Royal Statistical Society. Series B (Methodological) 34(2):187-220 (1972).
Dornan, D. et al., "Therapeutic Potential of an Anti-CD79b Antibody-Drug Conjugate, Anti-CD79n-vc-MMAE, for the Treatment of Non-Hodgkin Lymphoma," *Blood*, 114:2721-2729 (2009).
Doronina, Svetlana O. et al., "Development of potent monoclonal antibody auristatin conjugates for cancer therapy," nature biotechnology 21:778-784 (XP-002280966) (2003).
Harvey, Jennet M. et al., "Estrogen Receptor Status by Immunohistochemistry is Superior to the Ligand-Binding Assay for Predicting Response to Adjuvant Endocrine Therapy in Breast Cancer", J. Clin. Oncol. 17:1474-1481 (1999).

(Continued)

*Primary Examiner* — Sheela J. Huff
(74) *Attorney, Agent, or Firm* — Finnegan, Henderson, Farabow, Garrett & Dunner, LLP

(57) ABSTRACT

The present invention relates to a method for the treatment of IGF-IR expressing cancers as well as to a compositions and a kit for said traitment. From one aspect, the invention relates to the combined use of a first antibody for the determination of the IGF-IR status of a cancer and a second antibody used as an ADC for the treatment of said cancer.

14 Claims, 33 Drawing Sheets

Figure 1A:
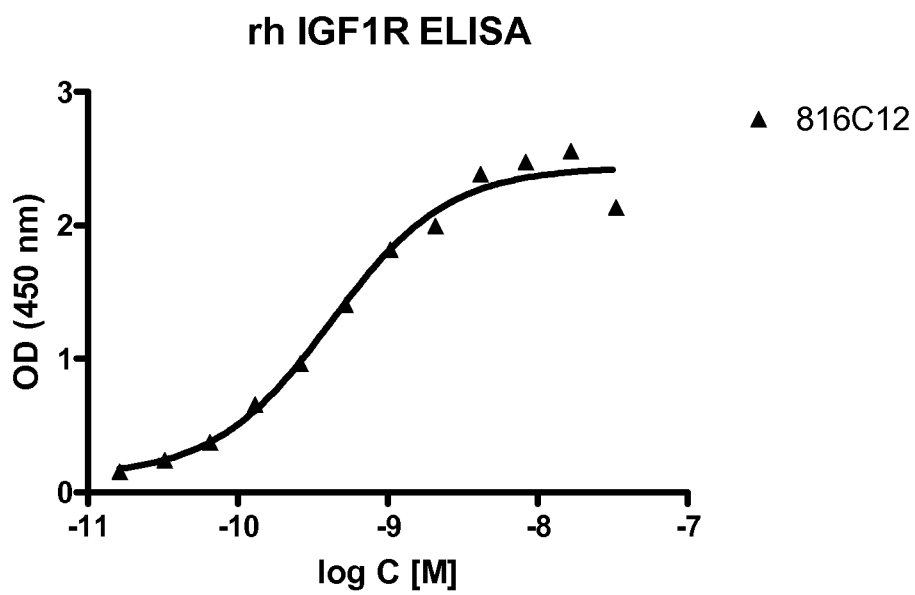

Specification includes a Sequence Listing.

(56) References Cited

OTHER PUBLICATIONS

Hosmer, David W. et al., "Applied Logistic Regression Second Edition", Wiley Series in Probability and Statistics (2000).

Junutula, J. et al., "Site-Specific Conjugation of a Cytotoxic Drug to an Antibody Improves the Therapeutic Index," *Nature Biotech.*, 26:925-932, (2008).

Kaas, Q. et al., "IMGAT/3Dstructure-DB and IMGT/StructuralQuery, a Database and a Tool for Immunoglobulin, T Cell Receptor and MHC Structural Data," *Nucleic Acids Res.*, 32:D208-D210 (2004).

Kaas, Q. et al., "IMGT Colliers de Perles: Standardized Sequence-Structure Representations of the IgSF and MhcSF Superfamily Domains," *Curr. Bioinform.*, 2:21-30 (2007).

Kohler, G. et al., "Continuous Cultures of Fused Cells Secreting Antibody of Predefined Specificity," *Nature*, 256:495-497 (1975).

LeFranc, M.P. et al., "IMGT Unique Numbering for Immunoglobulin and T Cell Receptor Variable Domains and Ig Superfamily V-Like Domains," *Devl. & Comp. Immuno.*, 27:55-77 (2003).

LeFranc, M.P. et al., "The IMGT Unique Numbering for Immunoglobulins, T-Cell Receptors, and Ig-Like Domains," *The Immuno.*, 7:132-136 (1999).

LeFranc, M.P. et al., "Unique Database Numbering System for Immunogenetic Analysis," *Immuno. Today*, 18:509 (1997).

Liu, H. et al., "Disulfide Bond Structures of IgG Molecules," mAbs, 4:17-23 (2012).

Needleman, S.B. et al., "A General Method Applicable to the search for Similarities in the Amino Acid of Two Proteins," *J. Mol. Biol.*, 48:443-453 (1970).

Payne et al., "Predictive markers in breast cancer—the present", Histopathology 52:82-90 (2008).

Pearson, W.R. et al., "Improved Tools for Biological Sequence Comparison," *Proc. Natl. Acad. Sci.*, 85:2444-2449 (1988).

Ruiz, M. et al., "IMGT Gene Identificatoin and Colliers de Perles of Human Immunoglobulins with Known 3D Structures," *Immunogen.*, 53:857-883, (2002).

Simpson et al., "Prognostic Value of Histologic Grade and Proliferative Activity in Axillary Node—Positive Breast Cancer: Results From the Eastern Cooperative Oncology Group Companion Study, EST 4189", Journal of Clinical Oncology, vol. 18, No. 10, pp. 2059-2069 (2000).

Smith, M.S. et al, "Comparison of Biosequences," *Advan. App. Math.*, 2:482-489, (1981).

Tatusova et al., "Blast 2 sequences—a new tool for comparing protein and nucleotide sequences", FEMS Microbiology Letters, 174:247-250 (1999).

Extended European Search Report from the European Patent Office for counterpart European Application No. 15306707.9 dated Apr. 26, 2016.

International Search Report from the European Patent Office for International Application No. PCT/EP2016/075858 dated Jan. 31, 2017.

\* cited by examiner

SEQUENCE LISTING

<160> NUMBER OF SEQ ID NOS: 95

<210> SEQ ID NO 1
<211> LENGTH: 8
<212> TYPE: PRT
<213> ORGANISM: artificial
<220> FEATURE:
<223> OTHER INFORMATION: 810D12 I-4893, heavy chain, CDR-H1

<400> SEQUENCE: 1

Gly His Thr Phe Thr Ser Tyr Met
1               5

<210> SEQ ID NO 2
<211> LENGTH: 8
<212> TYPE: PRT
<213> ORGANISM: artificial
<220> FEATURE:
<223> OTHER INFORMATION: 810D12 I-4893, heavy chain, CDR-H2

<400> SEQUENCE: 2

Ile Asn Pro Tyr Asn Asp Val Thr
1               5

<210> SEQ ID NO 3
<211> LENGTH: 14
<212> TYPE: PRT
<213> ORGANISM: artificial
<220> FEATURE:
<223> OTHER INFORMATION: 810D12 I-4893, heavy chain, CDR-H3

<400> SEQUENCE: 3

Val Thr Thr Ala Tyr Tyr Gly Asn Gly Arg Tyr Phe Asp Val
1               5                   10

<210> SEQ ID NO 4
<211> LENGTH: 6
<212> TYPE: PRT
<213> ORGANISM: artificial
<220> FEATURE:
<223> OTHER INFORMATION: 810D12 I-4893, light chain, CDR-L1

<400> SEQUENCE: 4

Gln Asp Ile Thr Asn Tyr
1               5

<210> SEQ ID NO 5
<211> LENGTH: 3
<212> TYPE: PRT
<213> ORGANISM: artificial
<220> FEATURE:
<223> OTHER INFORMATION: 810D12 I-4893, light chain, CDR-L2

<400> SEQUENCE: 5

Tyr Thr Ser
1

<210> SEQ ID NO 6
<211> LENGTH: 9
<212> TYPE: PRT
<213> ORGANISM: artificial
<220> FEATURE:
<223> OTHER INFORMATION: 810D12 I-4893, light chain, CDR-L3

<400> SEQUENCE: 6

Gln Gln Gly Tyr Ser Leu Pro Trp Thr
1               5

<210> SEQ ID NO 7
<211> LENGTH: 121
<212> TYPE: PRT
<213> ORGANISM: artificial
<220> FEATURE:
<223> OTHER INFORMATION: 810D12 I-4893, heavy chain, Variable domain

<400> SEQUENCE: 7

Glu Val Gln Leu Gln Gln Ser Gly Pro Glu Leu Val Lys Pro Gly Ala
1               5                   10                  15

Ser Val Lys Met Ser Cys Lys Ala Ser Gly His Thr Phe Thr Ser Tyr
            20                  25                  30

Met Leu His Trp Val Lys Gln Lys Pro Gly Gln Gly Leu Glu Trp Leu
        35                  40                  45

Gly Phe Ile Asn Pro Tyr Asn Asp Val Thr Lys Tyr Asn Glu Asn Phe
    50                  55                  60

Lys Gly Lys Ala Thr Leu Thr Ser Asp Lys Ser Ser Ser Thr Ala Tyr
65                  70                  75                  80

Met Glu Leu Asn Ser Leu Thr Ser Glu Asp Ser Ala Val Tyr Phe Cys
                85                  90                  95

Val Thr Thr Ala Tyr Tyr Gly Asn Gly Arg Tyr Phe Asp Val Trp Gly
            100                 105                 110

Ala Gly Thr Thr Val Thr Val Ser Ser
        115                 120

<210> SEQ ID NO 8
<211> LENGTH: 107
<212> TYPE: PRT
<213> ORGANISM: artificial
<220> FEATURE:
<223> OTHER INFORMATION: 810D12 I-4893, light chain, Variable domain

<400> SEQUENCE: 8

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Thr Asn Tyr
            20                  25                  30

Leu Thr Trp Tyr Gln Gln Lys Pro Asp Gly Thr Val Lys Val Leu Ile
        35                  40                  45

Tyr Tyr Thr Ser Arg Leu Tyr Ser Gly Val Pro Ser Arg Phe Ser Gly
    50                  55                  60

Ser Gly Ser Gly Ser Asp Tyr Ser Leu Thr Ile Asn Asn Leu Glu Gln
65                  70                  75                  80

Glu Asp Ile Ala Thr Tyr Phe Cys Gln Gln Gly Tyr Ser Leu Pro Trp
                85                  90                  95

Thr Phe Gly Gly Gly Thr Lys Leu Glu Ile Lys
            100                 105

<210> SEQ ID NO 9
<211> LENGTH: 363
<212> TYPE: DNA
<213> ORGANISM: artificial
<220> FEATURE:
<223> OTHER INFORMATION: 810D12 I-4893, heavy chain, Variable domain

<400> SEQUENCE: 9
gaggtccagc tgcagcagtc tggacctgaa ctggtaaagc ctggggcttc agtgaagatg      60
tcctgcaagg cttctggaca cacattcact agctatatgc tgcactgggt gaagcagaag     120

```
cctgggcagg gccttgagtg gcttggattt attaatcctt acaatgatgt tactaagtac    180
aatgagaact tcaaaggcaa ggccacactg acttcagaca atcctccag cacagcctac    240 atggagctca acagcctgac ctctgaggac tctgcggtct atttctgtgt aactaccgcc    300
tactatggta acggccggta cttcgatgtc tggggcgcag ggaccacggt caccgtctcc    360
tca                                                                 363
```

```
<210> SEQ ID NO 10
<211> LENGTH: 321
<212> TYPE: DNA
<213> ORGANISM: artificial
<220> FEATURE:
<223> OTHER INFORMATION: 810D12 I-4893, light chain, Variable domain

<400> SEQUENCE: 10
```

```
gatatccaga tgacacagac tacatcttcc ctgtctgcct ctctgggaga cagagtcacc     60
atcagttgca gggcaagtca ggacattacc aattatttaa cctggtatca gcagaaacca    120
gatggaactg ttaaagttct gatctactac acatcaagat atactcagg agtcccatca    180 aggttcagtg gcagtgggtc tggatcagat tattctctca ccattaacaa cctggagcaa    240
gaagatattg ccacttactt ttgccaacag ggttattcgc ttccgtggac gttcggtgga    300
ggcaccaagc tggaaatcaa a                                              321
```

```
<210> SEQ ID NO 11
<211> LENGTH: 8
<212> TYPE: PRT
<213> ORGANISM: artificial
<220> FEATURE:
<223> OTHER INFORMATION: 816C12 I-4894, heavy chain, CDR-H1

<400> SEQUENCE: 11

Gly His Thr Phe Thr Ser Tyr Val
1               5
```

```
<210> SEQ ID NO 12
<211> LENGTH: 8
<212> TYPE: PRT
<213> ORGANISM: artificial
<220> FEATURE:
<223> OTHER INFORMATION: 816C12 I-4894, heavy chain, CDR-H2

<400> SEQUENCE: 12

Ile Asn Pro His Asn Asp Val Thr
1               5
```

```
<210> SEQ ID NO 13
<211> LENGTH: 14
<212> TYPE: PRT
<213> ORGANISM: artificial
<220> FEATURE:
<223> OTHER INFORMATION: 816C12 I-4894, heavy chain, CDR-H3

<400> SEQUENCE: 13

Val Ser Thr Ala Tyr Tyr Gly Asn Gly Arg Tyr Phe Asp Val
1               5                   10
```

```
<210> SEQ ID NO 14
<211> LENGTH: 6
<212> TYPE: PRT
<213> ORGANISM: artificial
<220> FEATURE:
<223> OTHER INFORMATION: 816C12 I-4894, light chain, CDR-L1
```

<400> SEQUENCE: 14

Gln Asp Ile Asn Asn Tyr
1               5

<210> SEQ ID NO 15
<211> LENGTH: 3
<212> TYPE: PRT
<213> ORGANISM: artificial
<220> FEATURE:
<223> OTHER INFORMATION: 816C12 I-4894, light chain, CDR-L2

<400> SEQUENCE: 15

Tyr Thr Ser
1

<210> SEQ ID NO 16
<211> LENGTH: 9
<212> TYPE: PRT
<213> ORGANISM: artificial
<220> FEATURE:
<223> OTHER INFORMATION: 816C12 I-4894, light chain, CDR-L3

<400> SEQUENCE: 16

Gln Gln Gly Asn Thr Leu Pro Trp Thr
1               5

<210> SEQ ID NO 17
<211> LENGTH: 121
<212> TYPE: PRT
<213> ORGANISM: artificial
<220> FEATURE:
<223> OTHER INFORMATION: 816C12 I-4894, heavy chain, Variable domain

<400> SEQUENCE: 17

Glu Val Gln Leu Gln Gln Ser Gly Pro Glu Leu Val Lys Pro Gly Ala
1               5                   10                  15

Ser Val Lys Met Ser Cys Lys Ala Ser Gly His Thr Phe Thr Ser Tyr
            20                  25                  30

Val Leu His Trp Met Lys Arg Lys Pro Gly Gln Gly Leu Glu Trp Ile
        35                  40                  45

Gly Tyr Ile Asn Pro His Asn Asp Val Thr Lys Tyr Asn Glu Asn Phe
    50                  55                  60

Lys Gly Lys Ala Thr Leu Thr Ser Asp Lys Tyr Ser Ser Thr Val Tyr
65                  70                  75                  80

Met Glu Val Ser Ser Leu Thr Ser Glu Asp Ser Ala Val Tyr Tyr Cys
                85                  90                  95

Val Ser Thr Ala Tyr Tyr Gly Asn Gly Arg Tyr Phe Asp Val Trp Gly
            100                 105                 110

Ala Gly Thr Thr Val Thr Val Ser Ser
        115                 120

<210> SEQ ID NO 18
<211> LENGTH: 107
<212> TYPE: PRT
<213> ORGANISM: artificial
<220> FEATURE:
<223> OTHER INFORMATION: 816C12 I-4894, light chain, Variable domain

<400> SEQUENCE: 18

Asp Ile Gln Met Thr Gln Thr Thr Ser Ser Leu Ser Ala Ser Leu Gly
1               5                   10                  15

```
Asp Arg Val Thr Ile Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Ser Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 19
<211> LENGTH: 363
<212> TYPE: DNA
<213> ORGANISM: artificial
<220> FEATURE:
<223> OTHER INFORMATION: 816C12 I-4894, heavy chain, Variable domain

<400> SEQUENCE: 19
gaggtccagc tgcagcagtc tggacctgag ctggtaaagc tggggcttc  agtgaagatg      60 tcctgcaagg cttctggaca cacattcact agctatgttt tgcactggat gaagcggaag     120
cctgggcagg gccttgagtg gattggatat attaatcctc acaatgatgt tactaagtac     180
aatgagaatt tcaaaggcaa ggccacactg acttcagaca atactccag  cacagtctac     240 atggaggtca gcagcctgac ctctgaggac tctgcggtgt attactgtgt aagtaccgcc     300
tactatggta acggccggta cttcgatgtc tggggcgcag ggaccacggt caccgtctcc     360
tca                                                                  363

<210> SEQ ID NO 20
<211> LENGTH: 321
<212> TYPE: DNA
<213> ORGANISM: artificial
<220> FEATURE:
<223> OTHER INFORMATION: 816C12 I-4894, light chain, Variable domain

<400> SEQUENCE: 20
gatatccaga tgacacagac tacatcctcc ctgtctgcct ctctgggaga cagagtcacc      60
atcagttgca gggcaagtca ggacattaac aattatttaa actggtatca gcagaaacca     120
gatggaactg ttaaactcct gatctactac acatcaagat acactcagg  agtctcatca     180 aggttcagtg gcagtgggtc tggaacagat tattctctca ccattagcaa cctggagcaa     240
gaagatattg ccacttattt ttgccaacag ggtaatacgc ttccgtggac gttcggtgga     300
ggcaccaagc tggaaatcaa a                                              321

<210> SEQ ID NO 21
<211> LENGTH: 8
<212> TYPE: PRT
<213> ORGANISM: artificial
<220> FEATURE:
<223> OTHER INFORMATION: Consensus, heavy chain, CDR-H1
<220> FEATURE:
<221> NAME/KEY: MISC_FEATURE
<222> LOCATION: (3)..(3)
<223> OTHER INFORMATION: Thr may be replaced by Ser
<220> FEATURE:
<221> NAME/KEY: MISC_FEATURE
<222> LOCATION: (8)..(8)
<223> OTHER INFORMATION: Tyr may be replaced by Phe
```

```
<400> SEQUENCE: 21

Gly Tyr Thr Phe Thr Ser Tyr Tyr
1               5

<210> SEQ ID NO 22
<211> LENGTH: 8
<212> TYPE: PRT
<213> ORGANISM: artificial
<220> FEATURE:
<223> OTHER INFORMATION: Consensus, heavy chain, CDR-H2

<400> SEQUENCE: 22

Ile Trp Pro Gly Asp Gly Ser Thr
1               5

<210> SEQ ID NO 23
<211> LENGTH: 13
<212> TYPE: PRT
<213> ORGANISM: artificial
<220> FEATURE:
<223> OTHER INFORMATION: Consensus, heavy chain, CDR-H3

<400> SEQUENCE: 23

Ala Ser Pro Met Ile Thr Pro Asn Tyr Ala Met Asp Tyr
1               5                   10

<210> SEQ ID NO 24
<211> LENGTH: 6
<212> TYPE: PRT
<213> ORGANISM: artificial
<220> FEATURE:
<223> OTHER INFORMATION: Consensus, light chain, CDR-L1
<220> FEATURE:
<221> NAME/KEY: MISC_FEATURE
<222> LOCATION: (4)..(4)
<223> OTHER INFORMATION: Ser may be replaced by Asn

<400> SEQUENCE: 24

Gln Asp Ile Ser Lys Tyr
1               5

<210> SEQ ID NO 25
<211> LENGTH: 3
<212> TYPE: PRT
<213> ORGANISM: artificial
<220> FEATURE:
<223> OTHER INFORMATION: Consensus, light chain, CDR-L2

<400> SEQUENCE: 25

Tyr Thr Ser
1

<210> SEQ ID NO 26
<211> LENGTH: 9
<212> TYPE: PRT
<213> ORGANISM: artificial
<220> FEATURE:
<223> OTHER INFORMATION: Consensus, light chain, CDR-L3
<220> FEATURE:
<221> NAME/KEY: MISC_FEATURE
<222> LOCATION: (5)..(5)
<223> OTHER INFORMATION: Thr may be replaced by Ala

<400> SEQUENCE: 26

Gln Gln Gly Ser Thr Leu Pro Tyr Thr
1               5
```

```
<210> SEQ ID NO 27
<211> LENGTH: 8
<212> TYPE: PRT
<213> ORGANISM: artificial
<220> FEATURE:
<223> OTHER INFORMATION: heavy chain, CDR-H1

<400> SEQUENCE: 27

Gly Tyr Thr Phe Thr Ser Tyr Tyr
1               5

<210> SEQ ID NO 28
<211> LENGTH: 8
<212> TYPE: PRT
<213> ORGANISM: artificial
<220> FEATURE:
<223> OTHER INFORMATION: heavy chain, CDR-H1

<400> SEQUENCE: 28

Gly Tyr Ser Phe Thr Ser Tyr Phe
1               5

<210> SEQ ID NO 29
<211> LENGTH: 6
<212> TYPE: PRT
<213> ORGANISM: artificial
<220> FEATURE:
<223> OTHER INFORMATION: light chain, CDR-L1

<400> SEQUENCE: 29

Gln Asp Ile Ser Lys Tyr
1               5

<210> SEQ ID NO 30
<211> LENGTH: 6
<212> TYPE: PRT
<213> ORGANISM: artificial
<220> FEATURE:
<223> OTHER INFORMATION: light chain, CDR-L1

<400> SEQUENCE: 30

Gln Asp Ile Asn Lys Tyr
1               5

<210> SEQ ID NO 31
<211> LENGTH: 9
<212> TYPE: PRT
<213> ORGANISM: artificial
<220> FEATURE:
<223> OTHER INFORMATION: light chain, CDR-L3

<400> SEQUENCE: 31

Gln Gln Gly Ser Thr Leu Pro Tyr Thr
1               5

<210> SEQ ID NO 32
<211> LENGTH: 9
<212> TYPE: PRT
<213> ORGANISM: artificial
<220> FEATURE:
<223> OTHER INFORMATION: light chain, CDR-L3

<400> SEQUENCE: 32

Gln Gln Gly Ser Ala Leu Pro Tyr Thr
1               5
```

```
<210> SEQ ID NO 33
<211> LENGTH: 120
<212> TYPE: PRT
<213> ORGANISM: artificial
<220> FEATURE:
<223> OTHER INFORMATION: hz208F2 heavy chain H037, VH

<400> SEQUENCE: 33
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Lys Ser Ser Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

```
<210> SEQ ID NO 34
<211> LENGTH: 107
<212> TYPE: PRT
<213> ORGANISM: artificial
<220> FEATURE:
<223> OTHER INFORMATION: hz208F2 Light chain L018, VL

<400> SEQUENCE: 34
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
    50                  55                  60

Arg Gly Ser Gly Thr Asp Tyr Ser Leu Thr Ile Ser Ser Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys
            100                 105

```
<210> SEQ ID NO 35
<211> LENGTH: 449
<212> TYPE: PRT
<213> ORGANISM: artificial
<220> FEATURE:
<223> OTHER INFORMATION: hz208F2 heavy chain H037, full length

<400> SEQUENCE: 35
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
 50                  55                  60

Gln Gly Arg Val Thr Met Thr Arg Asp Lys Ser Ser Thr Val Tyr
 65                  70                  75                  80

Met Glu Leu Ser Ser Leu Arg Ser Glu Asp Thr Ala Val Tyr Phe Cys
                 85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

```
<210> SEQ ID NO 36
<211> LENGTH: 214
<212> TYPE: PRT
<213> ORGANISM: artificial
<220> FEATURE:
<223> OTHER INFORMATION: hz208F2 light chain L018, full length

<400> SEQUENCE: 36
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
50                  55                  60

Arg Gly Ser Gly Thr Asp Tyr Ser Leu Thr Ile Ser Ser Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 37
<211> LENGTH: 107
<212> TYPE: PRT
<213> ORGANISM: artificial
<220> FEATURE:
<223> OTHER INFORMATION: hz208F2 Light chain L021, VL

<400> SEQUENCE: 37
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Phe Ser Leu Thr Ile Ser Ser Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys
            100                 105

<210> SEQ ID NO 38
<211> LENGTH: 214
<212> TYPE: PRT
<213> ORGANISM: artificial
<220> FEATURE:
<223> OTHER INFORMATION: hz208F2 light chain L021, full length

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Phe Ser Leu Thr Ile Ser Ser Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 39
<211> LENGTH: 120
<212> TYPE: PRT
<213> ORGANISM: artificial
<220> FEATURE:
<223> OTHER INFORMATION: hz208F2 heavy chain H047, VH

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
50                  55                  60

-continued

Gln Gly Arg Val Thr Met Thr Arg Asp Thr Ser Ser Asn Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 40
<211> LENGTH: 449
<212> TYPE: PRT
<213> ORGANISM: artificial
<220> FEATURE:
<223> OTHER INFORMATION: hz208F2 heavy chain H047, full length

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Ser Asn Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 41
<211> LENGTH: 120
<212> TYPE: PRT
<213> ORGANISM: artificial
<220> FEATURE:
<223> OTHER INFORMATION: hz208F2 heavy chain H049, VH

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Lys Ser Ser Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
                100                 105                 110

Gly Thr Leu Val Thr Val Ser Ser
        115                 120

<210> SEQ ID NO 42
<211> LENGTH: 449
<212> TYPE: PRT
<213> ORGANISM: artificial
<220> FEATURE:
<223> OTHER INFORMATION: hz208F2 heavy chain H049, full length

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
 50                  55                  60

Gln Gly Arg Val Thr Met Thr Arg Asp Lys Ser Ser Thr Val Tyr
 65                  70                  75                  80

Met Glu Leu Ser Ser Leu Arg Ser Glu Asp Thr Ala Val Tyr Tyr Cys
                 85                  90                  95

Ala Ser Pro Met Ile Thr Pro Asn Tyr Ala Met Asp Tyr Trp Gly Gln
             100                 105                 110

Gly Thr Leu Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
     130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
         195                 200                 205

Pro Ser Asn Thr Lys Val Asp Lys Arg Val Glu Pro Lys Ser Cys Asp
     210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
         275                 280                 285

Asn Ala Lys Thr Lys Pro Arg Glu Glu Gln Tyr Asn Ser Thr Tyr Arg
     290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Arg Glu Glu Met Thr Lys Asn Gln Val Ser Leu
         355                 360                 365

Thr Cys Leu Val Lys Gly Phe Tyr Pro Ser Asp Ile Ala Val Glu Trp
     370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Gln Gly Asn Val Phe Ser Cys Ser Val Met His
             420                 425                 430

Glu Ala Leu His Asn His Tyr Thr Gln Lys Ser Leu Ser Leu Ser Pro
         435                 440                 445

Gly

<210> SEQ ID NO 43
<211> LENGTH: 120
<212> TYPE: PRT
<213> ORGANISM: artificial
<220> FEATURE:
<223> OTHER INFORMATION: hz208F2 heavy chain H051, VH

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Ser Asn Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 44
<211> LENGTH: 449
<212> TYPE: PRT
<213> ORGANISM: artificial
<220> FEATURE:
<223> OTHER INFORMATION: hz208F2 heavy chain H051, full length

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Ser Asn Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200             205

Pro Ser Asn Thr Lys Val Asp Lys Arg Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 45
<211> LENGTH: 120
<212> TYPE: PRT
<213> ORGANISM: artificial
<220> FEATURE:
<223> OTHER INFORMATION: hz208F2 heavy chain H052, VH

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Trp Ile Trp Pro Gly Asp Gly Ser Thr Lys Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Phe Cys

-continued

```
                        85                  90                  95

Ala Ser Pro Met Ile Thr Pro Asn Tyr Ala Met Asp Tyr Trp Gly Gln
            100                 105                 110

Gly Thr Leu Val Thr Val Ser Ser
            115                 120

<210> SEQ ID NO 46
<211> LENGTH: 449
<212> TYPE: PRT
<213> ORGANISM: artificial
<220> FEATURE:
<223> OTHER INFORMATION: hz208F2 heavy chain H052, full length

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
```

```
            325                 330                 335
Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 47
<211> LENGTH: 120
<212> TYPE: PRT
<213> ORGANISM: artificial
<220> FEATURE:
<223> OTHER INFORMATION: hz208F2 heavy chain H057, VH

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Lys Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 48
<211> LENGTH: 449
<212> TYPE: PRT
<213> ORGANISM: artificial
<220> FEATURE:
<223> OTHER INFORMATION: hz208F2 heavy chain H057, full length

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
```

```
            50                  55                  60
Gln Gly Arg Val Thr Met Thr Arg Asp Lys Ser Thr Asn Thr Val Tyr
 65                  70                  75                  80
Met Glu Leu Ser Ser Leu Arg Ser Glu Asp Thr Ala Val Tyr Tyr Cys
                     85                  90                  95
Ala Ser Pro Met Ile Thr Pro Asn Tyr Ala Met Asp Tyr Trp Gly Gln
                100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Arg Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
                355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
            435                 440                 445
Gly

<210> SEQ ID NO 49
<211> LENGTH: 120
```

```
<212> TYPE: PRT
<213> ORGANISM: artificial
<220> FEATURE:
<223> OTHER INFORMATION: hz208F2 heavy chain H068, VH

<400> SEQUENCE: 49
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
50                  55                  60

Gln Gly Arg Val Thr Met Thr Arg Asp Thr Ser Thr Asn Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
            115                 120

```
<210> SEQ ID NO 50
<211> LENGTH: 449
<212> TYPE: PRT
<213> ORGANISM: artificial
<220> FEATURE:
<223> OTHER INFORMATION: hz208F2 heavy chain H068, full length

<400> SEQUENCE: 50
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
50                  55                  60

Gln Gly Arg Val Thr Met Thr Arg Asp Thr Ser Thr Asn Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

```
Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 51
<211> LENGTH: 120
<212> TYPE: PRT
<213> ORGANISM: artificial
<220> FEATURE:
<223> OTHER INFORMATION: hz208F2 heavy chain H070, VH

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110
```

```
Gly Thr Leu Val Thr Val Ser Ser
        115                 120

<210> SEQ ID NO 52
<211> LENGTH: 449
<212> TYPE: PRT
<213> ORGANISM: artificial
<220> FEATURE:
<223> OTHER INFORMATION: hz208F2 heavy chain H070, full length

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 53
<211> LENGTH: 120
<212> TYPE: PRT
<213> ORGANISM: artificial
<220> FEATURE:
<223> OTHER INFORMATION: hz208F2 heavy chain H071, VH

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 54
<211> LENGTH: 449
<212> TYPE: PRT
<213> ORGANISM: artificial
<220> FEATURE:
<223> OTHER INFORMATION: hz208F2 heavy chain H071, full length

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Asn Thr Val Tyr
65                  70                  75                  80

```
Met Glu Leu Ser Ser Leu Arg Ser Glu Asp Thr Ala Val Tyr Tyr Cys
             85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 55
<211> LENGTH: 120
<212> TYPE: PRT
<213> ORGANISM: artificial
<220> FEATURE:
<223> OTHER INFORMATION: hz208F2 heavy chain H076, VH
```

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 56
<211> LENGTH: 449
<212> TYPE: PRT
<213> ORGANISM: artificial
<220> FEATURE:
<223> OTHER INFORMATION: hz208F2 heavy chain H076, full length

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly 225                 230                 235                 240
Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 57
<211> LENGTH: 120
<212> TYPE: PRT
<213> ORGANISM: artificial
<220> FEATURE:
<223> OTHER INFORMATION: hz208F2 heavy chain H077, VH

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser
        115                 120

<210> SEQ ID NO 58

```
<211> LENGTH: 449
<212> TYPE: PRT
<213> ORGANISM: artificial
<220> FEATURE:
<223> OTHER INFORMATION: hz208F2 heavy chain H077, full length

<400> SEQUENCE: 58
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Trp Pro Gly Asp Gly Ser Thr Lys Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 59
<211> LENGTH: 120
<212> TYPE: PRT
<213> ORGANISM: artificial
<220> FEATURE:
<223> OTHER INFORMATION: hz208F2 heavy chain H026, VH

<400> SEQUENCE: 59

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
                20                  25                  30

Tyr Ile Tyr Trp Val Lys Gln Ala Pro Gly Gln Gly Leu Glu Trp Leu
            35                  40                  45

Gly Trp Ile Trp Pro Gly Asp Gly Ser Thr Lys Tyr Asn Glu Lys Phe
    50                  55                  60

Gln Gly Arg Val Thr Leu Thr Ala Asp Lys Ser Asn Thr Ala Tyr
65                  70                  75                  80

Met Phe Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
                100                 105                 110

Gly Thr Leu Val Thr Val Ser Ser
            115                 120

<210> SEQ ID NO 60
<211> LENGTH: 107
<212> TYPE: PRT
<213> ORGANISM: artificial
<220> FEATURE:
<223> OTHER INFORMATION: hz208F2 Light chain L024, VL

<400> SEQUENCE: 60

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Lys Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Arg Gly Ser Gly Thr Asp Tyr Ser Leu Thr Ile Ser Asn Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys
                100                 105
```

<210> SEQ ID NO 61
<211> LENGTH: 449
<212> TYPE: PRT
<213> ORGANISM: artificial
<220> FEATURE:
<223> OTHER INFORMATION: hz208F2 heavy chain H026, full length

<400> SEQUENCE: 61

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Tyr Ile Tyr Trp Val Lys Gln Ala Pro Gly Gln Gly Leu Glu Trp Leu
        35                  40                  45

Gly Trp Ile Trp Pro Gly Asp Gly Ser Thr Lys Tyr Asn Glu Lys Phe
    50                  55                  60

Gln Gly Arg Val Thr Leu Thr Ala Asp Lys Ser Ser Asn Thr Ala Tyr
65                  70                  75                  80

Met Phe Leu Ser Ser Leu Arg Ser Glu Asp Thr Ala Val Tyr Phe Cys
                85                  90                  95

Ala Ser Pro Met Ile Thr Pro Asn Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly

<210> SEQ ID NO 62
<211> LENGTH: 214
<212> TYPE: PRT
<213> ORGANISM: artificial
<220> FEATURE:
<223> OTHER INFORMATION: hz208F2 light chain L024, full length

<400> SEQUENCE: 62

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Leu Gln Pro
65                  70                  75                  80

Glu Asp Phe Ala Thr Tyr Phe Cys Gln Gln Gly Ser Thr Leu Pro Tyr
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 63
<211> LENGTH: 120
<212> TYPE: PRT
<213> ORGANISM: artificial
<220> FEATURE:
<223> OTHER INFORMATION: c208F2 heavy chain, VH

<400> SEQUENCE: 63
```

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile Tyr Trp Val Lys Gln Arg Pro Gly Gln Gly Leu Glu Trp Leu
        35                  40                  45

Gly Trp Ile Trp Pro Gly Asp Gly Ser Thr Lys Tyr Asn Glu Lys Phe
    50                  55                  60

Lys Asp Lys Thr Thr Leu Thr Ala Asp Lys Ser Ser Asn Thr Ala Tyr
65              70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser
        115                 120

<210> SEQ ID NO 64
<211> LENGTH: 120
<212> TYPE: PRT
<213> ORGANISM: artificial
<220> FEATURE:
<223> OTHER INFORMATION: c212A11 heavy chain, VH

<400> SEQUENCE: 64

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Gly Trp Ile Trp Pro Gly Asp Gly Ser Thr Lys Tyr Asn Glu Lys Phe
    50                  55                  60

Lys Gly Lys Thr Thr Leu Thr Ala Asp Lys Ser Ser Ser Thr Ala Tyr
65              70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser
        115                 120

<210> SEQ ID NO 65
<211> LENGTH: 120
<212> TYPE: PRT
<213> ORGANISM: artificial
<220> FEATURE:
<223> OTHER INFORMATION: c214F8 heavy chain, VH

<400> SEQUENCE: 65

Gln Val Gln Leu Gln Gln Ser Gly Ser Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Gly Trp Ile Trp Pro Gly Asp Gly Ser Thr Lys Tyr Asn Glu Arg Phe

```
                 50                  55                  60
Lys Gly Lys Thr Thr Leu Thr Ala Asp Lys Ser Ser Thr Ala Tyr
 65                  70                  75                  80

Met Phe Leu Ser Ser Leu Thr Ser Glu Asp Ser Ala Val Tyr Phe Cys
                 85                  90                  95

Ala Ser Pro Met Ile Thr Pro Asn Tyr Ala Met Asp Tyr Trp Gly Gln
                100                 105                 110

Gly Ala Ser Val Thr Val Ser Ser
            115                 120

<210> SEQ ID NO 66
<211> LENGTH: 120
<212> TYPE: PRT
<213> ORGANISM: artificial
<220> FEATURE:
<223> OTHER INFORMATION: c219D6 heavy chain, VH

<400> SEQUENCE: 66

Gln Val Gln Leu Gln Gln Ser Gly Pro Glu Leu Val Lys Pro Gly Asp
 1               5                  10                  15

Ser Val Lys Met Ser Cys Lys Ala Ser Gly Tyr Ser Phe Thr Ser Tyr
                20                  25                  30

Phe Ile His Trp Val Lys Gln Arg Pro Gly Gln Gly Leu Glu Trp Ile
             35                  40                  45

Gly Trp Ile Trp Pro Gly Asp Gly Ser Thr Lys Tyr Asn Glu Lys Phe
         50                  55                  60

Lys Gly Lys Thr Thr Leu Thr Thr Asp Lys Ser Ser Thr Ala Tyr
 65                  70                  75                  80

Met Phe Leu Asn Ser Leu Thr Ser Glu Asp Ser Ala Val Tyr Phe Cys
                 85                  90                  95

Ala Ser Pro Met Ile Thr Pro Asn Tyr Ala Met Asp Tyr Trp Gly Gln
                100                 105                 110

Gly Ala Ser Val Thr Val Ser Ser
            115                 120

<210> SEQ ID NO 67
<211> LENGTH: 120
<212> TYPE: PRT
<213> ORGANISM: artificial
<220> FEATURE:
<223> OTHER INFORMATION: c213B10 heavy chain, VH

<400> SEQUENCE: 67

Gln Val Gln Leu Gln Gln Ser Gly Ser Glu Leu Val Lys Pro Gly Ala
 1               5                  10                  15

Ser Val Lys Met Ser Cys Lys Ala Ser Gly Tyr Thr Phe Thr Ser Tyr
                20                  25                  30

Tyr Ile His Trp Val Lys Gln Arg Pro Gly Gln Gly Leu Glu Trp Ile
             35                  40                  45

Gly Trp Ile Trp Pro Gly Asp Gly Ser Thr Lys Tyr Asn Glu Arg Phe
         50                  55                  60

Lys Gly Lys Thr Thr Leu Thr Ala Asp Lys Ser Ser Thr Ala Tyr
 65                  70                  75                  80

Met Phe Leu Ser Ser Leu Thr Ser Glu Asp Ser Ala Val Tyr Phe Cys
                 85                  90                  95

Ala Ser Pro Met Ile Thr Pro Asn Tyr Ala Met Asp Tyr Trp Gly Gln
                100                 105                 110
```

Gly Ala Ser Val Thr Val Ser Ser
        115                 120

<210> SEQ ID NO 68
<211> LENGTH: 107
<212> TYPE: PRT
<213> ORGANISM: artificial
<220> FEATURE:
<223> OTHER INFORMATION: c208F2 light chain, VL

<400> SEQUENCE: 68

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Pro Asp Gly Thr Ile Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Val Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys
            100                 105

<210> SEQ ID NO 69
<211> LENGTH: 107
<212> TYPE: PRT
<213> ORGANISM: artificial
<220> FEATURE:
<223> OTHER INFORMATION: c212A11 light chain, VL

<400> SEQUENCE: 69

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Lys Tyr
            20                  25                  30

Leu Asn Trp Tyr Gln Gln Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys
            100                 105

<210> SEQ ID NO 70
<211> LENGTH: 107
<212> TYPE: PRT
<213> ORGANISM: artificial
<220> FEATURE:
<223> OTHER INFORMATION: c214F8 light chain, VL

<400> SEQUENCE: 70

Asp Ile Gln Met Thr Gln Thr Thr Ser Ser Leu Ser Ala Ser Leu Gly
1               5                   10                  15

Asp Arg Val Thr Phe Ser Cys Arg Ala Ser Gln Asp Ile Ser Lys Tyr

```
                20                  25                  30

Leu Asn Trp Tyr Gln Gln Pro Asp Gly Thr Ile Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Thr Asn Leu Glu Gln
65                  70                  75                  80

Glu Asp Ile Ala Thr Tyr Phe Cys Gln Gln Gly Ser Ala Leu Pro Tyr
                85                  90                  95

Thr Phe Gly Gly Gly Thr Lys Leu Glu Ile Lys
            100                 105

<210> SEQ ID NO 71
<211> LENGTH: 107
<212> TYPE: PRT
<213> ORGANISM: artificial
<220> FEATURE:
<223> OTHER INFORMATION: c219D6 light chain, VL

<400> SEQUENCE: 71

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys
            100                 105

<210> SEQ ID NO 72
<211> LENGTH: 107
<212> TYPE: PRT
<213> ORGANISM: artificial
<220> FEATURE:
<223> OTHER INFORMATION: c213B10 light chain, VL

<400> SEQUENCE: 72

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Pro Asp Gly Thr Ile Lys Leu Leu Ile
        35                  40                  45

Tyr Tyr Thr Ser Arg Leu His Ser Gly Val Pro Ser Arg Phe Ser Gly
    50                  55                  60

Arg Gly Ser Gly Thr Asp Tyr Ser Leu Thr Ile Thr Asn Leu Glu Gln
65                  70                  75                  80

Glu Asp Ile Ala Thr Tyr Phe Cys Gln Gln Gly Ser Ala Leu Pro Tyr
                85                  90                  95

Thr Phe Gly Gly Gly Thr Lys Leu Glu Ile Lys
            100                 105
```

```
<210> SEQ ID NO 73
<211> LENGTH: 449
<212> TYPE: PRT
<213> ORGANISM: artificial
<220> FEATURE:
<223> OTHER INFORMATION: c208F2 heavy chain, full length

<400> SEQUENCE: 73
```

| | | | | | | | | | | | | | | | |
|---|---|---|---|---|---|---|---|---|---|---|---|---|---|---|---|
| Gln | Val | Gln | Leu | Gln | Gln | Ser | Gly | Pro | Glu | Leu | Val | Lys | Pro | Gly | Ala |
| 1 | | | | 5 | | | | | 10 | | | | | 15 | |
| Ser | Val | Lys | Met | Ser | Cys | Lys | Ala | Ser | Gly | Tyr | Thr | Phe | Thr | Ser | Tyr |
| | | | 20 | | | | | 25 | | | | | 30 | | |
| Tyr | Ile | Tyr | Trp | Val | Lys | Gln | Arg | Pro | Gly | Gln | Gly | Leu | Glu | Trp | Leu |
| | | | 35 | | | | | 40 | | | | | 45 | | |
| Gly | Trp | Ile | Trp | Pro | Gly | Asp | Gly | Ser | Thr | Lys | Tyr | Asn | Glu | Lys | Phe |
| | 50 | | | | | 55 | | | | | 60 | | | | |
| Lys | Asp | Lys | Thr | Thr | Leu | Thr | Ala | Asp | Lys | Ser | Ser | Asn | Thr | Ala | Tyr |
| 65 | | | | | 70 | | | | | 75 | | | | | 80 |
| Met | Phe | Leu | Ser | Ser | Leu | Thr | Ser | Glu | Asp | Ser | Ala | Val | Tyr | Phe | Cys |
| | | | | 85 | | | | | 90 | | | | | 95 | |
| Ala | Ser | Pro | Met | Ile | Thr | Pro | Asn | Tyr | Ala | Met | Asp | Tyr | Trp | Gly | Gln |
| | | | 100 | | | | | 105 | | | | | 110 | | |
| Gly | Ala | Ser | Val | Thr | Val | Ser | Ser | Ala | Ser | Thr | Lys | Gly | Pro | Ser | Val |
| | | | 115 | | | | | 120 | | | | | 125 | | |
| Phe | Pro | Leu | Ala | Pro | Ser | Ser | Lys | Ser | Thr | Ser | Gly | Gly | Thr | Ala | Ala |
| | 130 | | | | | 135 | | | | | 140 | | | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |
| Ser | Ser | Ser | Leu | Gly | Thr | Gln | Thr | Tyr | Ile | Cys | Asn | Val | Asn | His | Lys |
| | | | 195 | | | | | 200 | | | | | 205 | | |
| Pro | Ser | Asn | Thr | Lys | Val | Asp | Lys | Arg | Val | Glu | Pro | Lys | Ser | Cys | Asp |
| | 210 | | | | | 215 | | | | | 220 | | | | |
| Lys | Thr | His | Thr | Cys | Pro | Pro | Cys | Pro | Ala | Pro | Glu | Leu | Leu | Gly | Gly |
| 225 | | | | | 230 | | | | | 235 | | | | | 240 |
| Pro | Ser | Val | Phe | Leu | Phe | Pro | Pro | Lys | Pro | Lys | Asp | Thr | Leu | Met | Ile |
| | | | | 245 | | | | | 250 | | | | | 255 | |
| Ser | Arg | Thr | Pro | Glu | Val | Thr | Cys | Val | Val | Val | Asp | Val | Ser | His | Glu |
| | | | 260 | | | | | 265 | | | | | 270 | | |
| Asp | Pro | Glu | Val | Lys | Phe | Asn | Trp | Tyr | Val | Asp | Gly | Val | Glu | Val | His |
| | | | 275 | | | | | 280 | | | | | 285 | | |
| Asn | Ala | Lys | Thr | Lys | Pro | Arg | Glu | Glu | Gln | Tyr | Asn | Ser | Thr | Tyr | Arg |
| | 290 | | | | | 295 | | | | | 300 | | | | |
| Val | Val | Ser | Val | Leu | Thr | Val | Leu | His | Gln | Asp | Trp | Leu | Asn | Gly | Lys |
| 305 | | | | | 310 | | | | | 315 | | | | | 320 |
| Glu | Tyr | Lys | Cys | Lys | Val | Ser | Asn | Lys | Ala | Leu | Pro | Ala | Pro | Ile | Glu |
| | | | | 325 | | | | | 330 | | | | | 335 | |
| Lys | Thr | Ile | Ser | Lys | Ala | Lys | Gly | Gln | Pro | Arg | Glu | Pro | Gln | Val | Tyr |
| | | | 340 | | | | | 345 | | | | | 350 | | |
| Thr | Leu | Pro | Pro | Ser | Arg | Glu | Glu | Met | Thr | Lys | Asn | Gln | Val | Ser | Leu |
| | | | 355 | | | | | 360 | | | | | 365 | | |

```
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 74
<211> LENGTH: 449
<212> TYPE: PRT
<213> ORGANISM: artificial
<220> FEATURE:
<223> OTHER INFORMATION: c212A11 heavy chain, full length

<400> SEQUENCE: 74

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Tyr Ile His Trp Val Lys Gln Arg Pro Gly Gln Gly Leu Glu Trp Ile
                35                  40                  45

Gly Trp Ile Trp Pro Gly Asp Gly Ser Thr Lys Tyr Asn Glu Lys Phe
    50                  55                  60

Lys Gly Lys Thr Thr Leu Thr Ala Asp Lys Ser Ser Ser Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
                100                 105                 110

Gly Ala Ser Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
```

```
                275                 280                 285
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 75
<211> LENGTH: 449
<212> TYPE: PRT
<213> ORGANISM: artificial
<220> FEATURE:
<223> OTHER INFORMATION: c214F8 heavy chain, full length

<400> SEQUENCE: 75

Gln Val Gln Leu Gln Gln Ser Gly Ser Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Gly Trp Ile Trp Pro Gly Asp Gly Ser Thr Lys Tyr Asn Glu Arg Phe
    50                  55                  60

Lys Gly Lys Thr Thr Leu Thr Ala Asp Lys Ser Ser Ser Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 76
<211> LENGTH: 449
<212> TYPE: PRT
<213> ORGANISM: artificial
<220> FEATURE:
<223> OTHER INFORMATION: c219D6 heavy chain, full length

<400> SEQUENCE: 76

Gln Val Gln Leu Gln Gln Ser Gly Pro Glu Leu Val Lys Pro Gly Asp
1               5                   10                  15

Ser Val Lys Met Ser Cys Lys Ala Ser Gly Tyr Ser Phe Thr Ser Tyr
                20                  25                  30

Phe Ile His Trp Val Lys Gln Arg Pro Gly Gln Gly Leu Glu Trp Ile
            35                  40                  45

Gly Trp Ile Trp Pro Gly Asp Gly Ser Thr Lys Tyr Asn Glu Lys Phe
        50                  55                  60

Lys Gly Lys Thr Thr Leu Thr Thr Asp Lys Ser Ser Ser Thr Ala Tyr
65                  70                  75                  80

Met Phe Leu Asn Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 77
<211> LENGTH: 449
<212> TYPE: PRT
<213> ORGANISM: artificial
<220> FEATURE:
<223> OTHER INFORMATION: c213B10 heavy chain, full length

<400> SEQUENCE: 77

Gln Val Gln Leu Gln Gln Ser Gly Ser Glu Leu Val Lys Pro Gly Ala

-continued

```
1               5                   10                  15
Ser Val Lys Met Ser Cys Lys Ala Ser Gly Tyr Thr Phe Thr Ser Tyr
                20                  25                  30

Tyr Ile His Trp Val Lys Gln Arg Pro Gly Gln Gly Leu Glu Trp Ile
            35                  40                  45

Gly Trp Ile Trp Pro Gly Asp Gly Ser Thr Lys Tyr Asn Glu Arg Phe
    50                  55                  60

Lys Gly Lys Thr Thr Leu Thr Ala Asp Lys Ser Ser Ser Thr Ala Tyr
65                  70                  75                  80

Met Phe Leu Ser Ser Leu Thr Ser Glu Asp Ser Ala Val Tyr Phe Cys
                85                  90                  95

Ala Ser Pro Met Ile Thr Pro Asn Tyr Ala Met Asp Tyr Trp Gly Gln
                100                 105                 110

Gly Ala Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430
```

-continued

```
Glu Ala Leu His Asn His Tyr Thr Gln Lys Ser Leu Ser Leu Ser Pro
            435                 440                 445
Gly

<210> SEQ ID NO 78
<211> LENGTH: 214
<212> TYPE: PRT
<213> ORGANISM: artificial
<220> FEATURE:
<223> OTHER INFORMATION: c208F2 light chain, full length

<400> SEQUENCE: 78

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Gln Pro Asp Gly Thr Ile Lys Leu Leu Ile
            35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Ser Asn Val Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 79
<211> LENGTH: 214
<212> TYPE: PRT
<213> ORGANISM: artificial
<220> FEATURE:
<223> OTHER INFORMATION: c212A11 light chain, full length

<400> SEQUENCE: 79

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Lys Tyr
            20                  25                  30

Leu Asn Trp Tyr Gln Gln Gln Pro Asp Gly Thr Val Lys Leu Leu Ile
            35                  40                  45

Tyr Tyr Thr Ser Arg Leu His Ser Gly Val Pro Ser Arg Phe Ser Gly
50                  55                  60
```

Arg Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 80
<211> LENGTH: 214
<212> TYPE: PRT
<213> ORGANISM: artificial
<220> FEATURE:
<223> OTHER INFORMATION: c214F8 light chain, full length

<400> SEQUENCE: 80

Asp Ile Gln Met Thr Gln Thr Thr Ser Ser Leu Ser Ala Ser Leu Gly
1               5                   10                  15

Asp Arg Val Thr Phe Ser Cys Arg Ala Ser Gln Asp Ile Ser Lys Tyr
            20                  25                  30

Leu Asn Trp Tyr Gln Gln Pro Asp Gly Thr Ile Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Thr Asn Leu Glu Gln
65                  70                  75                  80

Glu Asp Ile Ala Thr Tyr Phe Cys Gln Gln Gly Ser Ala Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 81
<211> LENGTH: 214
<212> TYPE: PRT
<213> ORGANISM: artificial
<220> FEATURE:
<223> OTHER INFORMATION: c219D6 light chain, full length

<400> SEQUENCE: 81

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 82
<211> LENGTH: 214
<212> TYPE: PRT
<213> ORGANISM: artificial
<220> FEATURE:
<223> OTHER INFORMATION: c213B10 light chain, full length

<400> SEQUENCE: 82

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Pro Asp Gly Thr Ile Lys Leu Leu Ile
        35                  40                  45

Tyr Tyr Thr Ser Arg Leu His Ser Gly Val Pro Ser Arg Phe Ser Gly
50                  55                  60

Arg Gly Ser Gly Thr Asp Tyr Ser Leu Thr Ile Thr Asn Leu Glu Gln

```
                65                   70                   75                   80
Glu Asp Ile Ala Thr Tyr Phe Cys Gln Gln Gly Ser Ala Leu Pro Tyr
                    85                   90                   95

Thr Phe Gly Gly Gly Thr Lys Leu Glu Ile Lys Arg Thr Val Ala Ala
                100                  105                  110

Pro Ser Val Phe Ile Phe Pro Ser Asp Glu Gln Leu Lys Ser Gly
                115                  120                  125

Thr Ala Ser Val Val Cys Leu Leu Asn Asn Phe Tyr Pro Arg Glu Ala
            130                  135                  140

Lys Val Gln Trp Lys Val Asp Asn Ala Leu Gln Ser Gly Asn Ser Gln
145                  150                  155                  160

Glu Ser Val Thr Glu Gln Asp Ser Lys Asp Ser Thr Tyr Ser Leu Ser
                    165                  170                  175

Ser Thr Leu Thr Leu Ser Lys Ala Asp Tyr Glu Lys His Lys Val Tyr
                180                  185                  190

Ala Cys Glu Val Thr His Gln Gly Leu Ser Ser Pro Val Thr Lys Ser
            195                  200                  205

Phe Asn Arg Gly Glu Cys
    210

<210> SEQ ID NO 83
<211> LENGTH: 329
<212> TYPE: PRT
<213> ORGANISM: artificial
<220> FEATURE:
<223> OTHER INFORMATION: constant domain (VH) IgG1

<400> SEQUENCE: 83

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
```

```
                210                 215                 220
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 84
<211> LENGTH: 326
<212> TYPE: PRT
<213> ORGANISM: artificial
<220> FEATURE:
<223> OTHER INFORMATION: constant domain (VH) IgG4 (S228P)

<400> SEQUENCE: 84

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
```

```
                        245                 250                 255
Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 85
<211> LENGTH: 107
<212> TYPE: PRT
<213> ORGANISM: artificial
<220> FEATURE:
<223> OTHER INFORMATION: Domain kappa (VL)

<400> SEQUENCE: 85

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 86
<211> LENGTH: 98
<212> TYPE: PRT
<213> ORGANISM: artificial
<220> FEATURE:
<223> OTHER INFORMATION: human germline IGHV1-46*01

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg
```

```
<210> SEQ ID NO 87
<211> LENGTH: 95
<212> TYPE: PRT
<213> ORGANISM: artificial
<220> FEATURE:
<223> OTHER INFORMATION: human germline IGKV1-39*01

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 88
<211> LENGTH: 15
<212> TYPE: PRT
<213> ORGANISM: artificial
<220> FEATURE:
<223> OTHER INFORMATION: human germline IGHJ4*01

<400> SEQUENCE: 88

Tyr Phe Asp Tyr Trp Gly Gln Gly Thr Leu Val Thr Val Ser Ser
1               5                   10                  15

<210> SEQ ID NO 89
<211> LENGTH: 12
<212> TYPE: PRT
<213> ORGANISM: artificial
<220> FEATURE:
<223> OTHER INFORMATION: human germline IGKJ4*01

<400> SEQUENCE: 89

Leu Thr Phe Gly Gly Gly Thr Lys Val Glu Ile Lys
1               5                   10

<210> SEQ ID NO 90
<211> LENGTH: 1367
<212> TYPE: PRT
<213> ORGANISM: Homo sapiens
<220> FEATURE:
<221> NAME/KEY: MISC_FEATURE
<223> OTHER INFORMATION: IGF-1R

<400> SEQUENCE: 90

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
50                  55                  60

Ser Lys Ala Glu Asp Tyr Arg Ser Tyr Arg Phe Pro Lys Leu Thr Val
65                  70                  75                  80
```

```
Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
            115                 120                 125

Gly Leu Tyr Asn Leu Arg Asn Ile Thr Arg Gly Ala Ile Arg Ile Glu
            130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
            195                 200                 205

Asn Arg Cys Gln Lys Met Cys Pro Ser Thr Cys Gly Lys Arg Ala Cys
            210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
            275                 280                 285

Glu Ser Ser Asp Ser Glu Gly Phe Val Ile His Asp Gly Glu Cys Met
290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
            325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
            370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
            450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Ile Thr Trp His Arg Tyr
```

-continued

```
                500                 505                 510
    Arg Pro Pro Asp Tyr Arg Asp Leu Ile Ser Phe Thr Val Tyr Tyr Lys
                    515                 520                 525
    Glu Ala Pro Phe Lys Asn Val Thr Glu Tyr Asp Gly Gln Asp Ala Cys
                530                 535                 540
    Gly Ser Asn Ser Trp Asn Met Val Asp Val Asp Leu Pro Pro Asn Lys
    545                 550                 555                 560
    Asp Val Glu Pro Gly Ile Leu Leu His Gly Leu Lys Pro Trp Thr Gln
                    565                 570                 575
    Tyr Ala Val Tyr Val Lys Ala Val Thr Leu Thr Met Val Glu Asn Asp
                580                 585                 590
    His Ile Arg Gly Ala Lys Ser Glu Ile Leu Tyr Ile Arg Thr Asn Ala
                595                 600                 605
    Ser Val Pro Ser Ile Pro Leu Asp Val Leu Ser Ala Ser Asn Ser Ser
                610                 615                 620
    Ser Gln Leu Ile Val Lys Trp Asn Pro Pro Ser Leu Pro Asn Gly Asn
    625                 630                 635                 640
    Leu Ser Tyr Tyr Ile Val Arg Trp Gln Arg Gln Pro Gln Asp Gly Tyr
                    645                 650                 655
    Leu Tyr Arg His Asn Tyr Cys Ser Lys Asp Lys Ile Pro Ile Arg Lys
                660                 665                 670
    Tyr Ala Asp Gly Thr Ile Asp Ile Glu Glu Val Thr Glu Asn Pro Lys
                675                 680                 685
    Thr Glu Val Cys Gly Gly Glu Lys Gly Pro Cys Cys Ala Cys Pro Lys
                690                 695                 700
    Thr Glu Ala Glu Lys Gln Ala Glu Lys Glu Glu Ala Glu Tyr Arg Lys
    705                 710                 715                 720
    Val Phe Glu Asn Phe Leu His Asn Ser Ile Phe Val Pro Arg Pro Glu
                    725                 730                 735
    Arg Lys Arg Arg Asp Val Met Gln Val Ala Asn Thr Thr Met Ser Ser
                    740                 745                 750
    Arg Ser Arg Asn Thr Thr Ala Ala Asp Thr Tyr Asn Ile Thr Asp Pro
                755                 760                 765
    Glu Glu Leu Glu Thr Glu Tyr Pro Phe Phe Glu Ser Arg Val Asp Asn
                770                 775                 780
    Lys Glu Arg Thr Val Ile Ser Asn Leu Arg Pro Phe Thr Leu Tyr Arg
    785                 790                 795                 800
    Ile Asp Ile His Ser Cys Asn His Glu Ala Glu Lys Leu Gly Cys Ser
                    805                 810                 815
    Ala Ser Asn Phe Val Phe Ala Arg Thr Met Pro Ala Glu Gly Ala Asp
                820                 825                 830
    Asp Ile Pro Gly Pro Val Thr Trp Glu Pro Arg Pro Glu Asn Ser Ile
                835                 840                 845
    Phe Leu Lys Trp Pro Glu Pro Glu Asn Pro Asn Gly Leu Ile Leu Met
                850                 855                 860
    Tyr Glu Ile Lys Tyr Gly Ser Gln Val Glu Asp Gln Arg Glu Cys Val
    865                 870                 875                 880
    Ser Arg Gln Glu Tyr Arg Lys Tyr Gly Gly Ala Lys Leu Asn Arg Leu
                    885                 890                 895
    Asn Pro Gly Asn Tyr Thr Ala Arg Ile Gln Ala Thr Ser Leu Ser Gly
                900                 905                 910
    Asn Gly Ser Trp Thr Asp Pro Val Phe Phe Tyr Val Gln Ala Lys Thr
                915                 920                 925
```

```
Gly Tyr Glu Asn Phe Ile His Leu Ile Ile Ala Leu Pro Val Ala Val
        930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
            980                 985                 990

Glu Val Ala Arg Glu Lys Ile Thr Met Ser Arg Glu Leu Gly Gln Gly
        995                 1000                1005

Ser Phe Gly Met Val Tyr Glu Gly Val Ala Lys Gly Val Val Lys
    1010                1015                1020

Asp Glu Pro Glu Thr Arg Val Ala Ile Lys Thr Val Asn Glu Ala
    1025                1030                1035

Ala Ser Met Arg Glu Arg Ile Glu Phe Leu Asn Glu Ala Ser Val
    1040                1045                1050

Met Lys Glu Phe Asn Cys His His Val Val Arg Leu Leu Gly Val
    1055                1060                1065

Val Ser Gln Gly Gln Pro Thr Leu Val Ile Met Glu Leu Met Thr
    1070                1075                1080

Arg Gly Asp Leu Lys Ser Tyr Leu Arg Ser Leu Arg Pro Glu Met
    1085                1090                1095

Glu Asn Asn Pro Val Leu Ala Pro Pro Ser Leu Ser Lys Met Ile
    1100                1105                1110

Gln Met Ala Gly Glu Ile Ala Asp Gly Met Ala Tyr Leu Asn Ala
    1115                1120                1125

Asn Lys Phe Val His Arg Asp Leu Ala Ala Arg Asn Cys Met Val
    1130                1135                1140

Ala Glu Asp Phe Thr Val Lys Ile Gly Asp Phe Gly Met Thr Arg
    1145                1150                1155

Asp Ile Tyr Glu Thr Asp Tyr Tyr Arg Lys Gly Gly Lys Gly Leu
    1160                1165                1170

Leu Pro Val Arg Trp Met Ser Pro Glu Ser Leu Lys Asp Gly Val
    1175                1180                1185

Phe Thr Thr Tyr Ser Asp Val Trp Ser Phe Gly Val Val Leu Trp
    1190                1195                1200

Glu Ile Ala Thr Leu Ala Glu Gln Pro Tyr Gln Gly Leu Ser Asn
    1205                1210                1215

Glu Gln Val Leu Arg Phe Val Met Glu Gly Gly Leu Leu Asp Lys
    1220                1225                1230

Pro Asp Asn Cys Pro Asp Met Leu Phe Glu Leu Met Arg Met Cys
    1235                1240                1245

Trp Gln Tyr Asn Pro Lys Met Arg Pro Ser Phe Leu Glu Ile Ile
    1250                1255                1260

Ser Ser Ile Lys Glu Glu Met Glu Pro Gly Phe Arg Glu Val Ser
    1265                1270                1275

Phe Tyr Tyr Ser Glu Glu Asn Lys Leu Pro Glu Pro Glu Glu Leu
    1280                1285                1290

Asp Leu Glu Pro Glu Asn Met Glu Ser Val Pro Leu Asp Pro Ser
    1295                1300                1305

Ala Ser Ser Ser Ser Leu Pro Leu Pro Asp Arg His Ser Gly His
    1310                1315                1320
```

```
Lys Ala Glu Asn Gly Pro Gly Pro Gly Val Leu Val Leu Arg Ala
    1325            1330                1335

Ser Phe Asp Glu Arg Gln Pro Tyr Ala His Met Asn Gly Gly Arg
    1340            1345                1350

Lys Asn Glu Arg Ala Leu Pro Leu Pro Gln Ser Ser Thr Cys
    1355            1360                1365

<210> SEQ ID NO 91
<211> LENGTH: 932
<212> TYPE: PRT
<213> ORGANISM: artificial
<220> FEATURE:
<223> OTHER INFORMATION: IGF-1R ECD

<400> SEQUENCE: 91

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
                35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
                100                 105                 110

Tyr Asn Tyr Ala Leu Val Ile Phe Glu Met Thr Asn Leu Lys Asp Ile
                115                 120                 125

Gly Leu Tyr Asn Leu Arg Asn Ile Thr Arg Gly Ala Ile Arg Ile Glu
                130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
                180                 185                 190

Glu Lys Thr Thr Ile Asn Asn Glu Tyr Asn Tyr Arg Cys Trp Thr Thr
                195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
                260                 265                 270

Gly Trp Arg Cys Val Asp Arg Asp Phe Cys Ala Asn Ile Leu Ser Ala
                275                 280                 285

Glu Ser Ser Asp Ser Glu Gly Phe Val Ile His Asp Gly Glu Cys Met
                290                 295                 300

Gln Glu Cys Pro Ser Gly Phe Ile Arg Asn Gly Ser Gln Ser Met Tyr
305                 310                 315                 320
```

```
Cys Ile Pro Cys Glu Gly Pro Cys Pro Lys Val Cys Glu Glu Lys
            325                 330                 335

Lys Thr Lys Thr Ile Asp Ser Val Thr Ser Ala Gln Met Leu Gln Gly
        340                 345                 350

Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
        370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
            405                 410                 415

Asn Tyr Ser Phe Tyr Val Leu Asp Asn Gln Asn Leu Gln Gln Leu Trp
        420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
        450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
            485                 490                 495

Ser Thr Thr Thr Ser Lys Asn Arg Ile Ile Thr Trp His Arg Tyr
        500                 505                 510

Arg Pro Pro Asp Tyr Arg Asp Leu Ile Ser Phe Thr Val Tyr Tyr Lys
            515                 520                 525

Glu Ala Pro Phe Lys Asn Val Thr Glu Tyr Asp Gly Gln Asp Ala Cys
        530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
            565                 570                 575

Tyr Ala Val Tyr Val Lys Ala Val Thr Leu Thr Met Val Glu Asn Asp
        580                 585                 590

His Ile Arg Gly Ala Lys Ser Glu Ile Leu Tyr Ile Arg Thr Asn Ala
            595                 600                 605

Ser Val Pro Ser Ile Pro Leu Asp Val Leu Ser Ala Ser Asn Ser Ser
        610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
            645                 650                 655

Leu Tyr Arg His Asn Tyr Cys Ser Lys Asp Lys Ile Pro Ile Arg Lys
        660                 665                 670

Tyr Ala Asp Gly Thr Ile Asp Ile Glu Glu Val Thr Glu Asn Pro Lys
            675                 680                 685

Thr Glu Val Cys Gly Gly Glu Lys Gly Pro Cys Cys Ala Cys Pro Lys
        690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
            725                 730                 735

Arg Lys Arg Arg Asp Val Met Gln Val Ala Asn Thr Thr Met Ser Ser
```

```
                        740                 745                 750
Arg Ser Arg Asn Thr Thr Ala Ala Asp Thr Tyr Asn Ile Thr Asp Pro
            755                 760                 765

Glu Leu Glu Thr Glu Tyr Pro Phe Phe Glu Ser Arg Val Asp Asn
    770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met
    850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
        915                 920                 925

Gly Tyr Glu Asn
        930

<210> SEQ ID NO 92
<211> LENGTH: 512
<212> TYPE: PRT
<213> ORGANISM: artificial
<220> FEATURE:
<223> OTHER INFORMATION: IGF-1R ECD Nterminal

<400> SEQUENCE: 92

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
```

```
            165                 170                 175
Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
            195                 200                 205

Asn Arg Cys Gln Lys Met Cys Pro Ser Thr Cys Gly Lys Arg Ala Cys
210             215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
                260                 265                 270

Gly Trp Arg Cys Val Asp Arg Asp Phe Cys Ala Asn Ile Leu Ser Ala
                275                 280                 285

Glu Ser Ser Asp Ser Glu Gly Phe Val Ile His Asp Gly Glu Cys Met
290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
                340                 345                 350

Cys Thr Ile Phe Lys Gly Asn Leu Leu Ile Asn Ile Arg Arg Gly Asn
                355                 360                 365

Asn Ile Ala Ser Glu Leu Glu Asn Phe Met Gly Leu Ile Glu Val Val
370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
                420                 425                 430

Asp Trp Asp His Arg Asn Leu Thr Ile Lys Ala Gly Lys Met Tyr Phe
                435                 440                 445

Ala Phe Asn Pro Lys Leu Cys Val Ser Glu Ile Tyr Arg Met Glu Glu
                450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Ile Thr Trp His Arg Tyr
                500                 505                 510
```

<210> SEQ ID NO 93
<211> LENGTH: 4
<212> TYPE: PRT
<213> ORGANISM: artificial
<220> FEATURE:
<223> OTHER INFORMATION: tetrapeptide (linker)

<400> SEQUENCE: 93

Gly Phe Leu Gly
1

```
<210> SEQ ID NO 94
<211> LENGTH: 4
<212> TYPE: PRT
<213> ORGANISM: artificial
<220> FEATURE:
<223> OTHER INFORMATION: tetrapeptide (linker)

<400> SEQUENCE: 94

Ala Leu Ala Leu
1

<210> SEQ ID NO 95
<211> LENGTH: 5
<212> TYPE: PRT
<213> ORGANISM: artificial
<220> FEATURE:
<223> OTHER INFORMATION: pentapeptide (linker)

<400> SEQUENCE: 95

Pro Val Gly Val Val
1               5
```

COMPOSITION FOR THE TREATMENT OF IGF-1R EXPRESSING CANCER

The present invention relates to a method for the treatment of IGF-1R expressing cancers as well as to a compositions and a kit for said traitment. From one aspect, the invention relates to the combined use of a first antibody for the determination of the IGF-1R status of a cancer and a second antibody used as an ADC for the treatment of said cancer.

BACKGROUND OF THE INVENTION

The insulin-like growth factor 1 receptor called IGF-1R (or sometimes IGF1R or IGF-IR) is a receptor with tyrosine kinase activity having 70% homology with the insulin receptor IR. IGF-1R is a glycoprotein of molecular weight approximately 350,000. It is a hetero-tetrameric receptor of which each half—linked by disulfide bridges—is composed of an extracellular α-subunit and of a transmembrane 1-subunit. IGF-1R binds IGF1 and IGF2 with a very high affinity (Kd #1 nM) but is equally capable of binding to insulin with an affinity 100 to 1000 times lower. Conversely, the IR binds insulin with a very high affinity although the IGFs only bind to the insulin receptor with a 100 times lower affinity. The tyrosine kinase domain of IGF-1R and of IR has a very high sequence homology although the zones of weaker homology respectively concern the cysteine-rich region situated on the α-subunit and the C-terminal part of the 3-subunit. The sequence differences observed in the α-subunit are situated in the binding zone of the ligands and are therefore at the origin of the relative affinities of IGF-1R and of IR for the IGFs and insulin respectively. The differences in the C-terminal part of the 3-subunit result in a divergence in the signalling pathways of the two receptors; IGF-1R mediating mitogenic, differentiation and antiapoptosis effects, while the activation of the IR principally involves effects at the level of the metabolic pathways.

The cytoplasmic tyrosine kinase proteins are activated by the binding of the ligand to the extracellular domain of the receptor. The activation of the kinases in turn involves the stimulation of different intra-cellular substrates, including IRS-1, IRS-2, Shc and Grb 10. The two major substrates of IGF-1R are IRS and She which mediate, by the activation of numerous effectors downstream, the majority of growth and differentiation effects connected with the attachment of the IGFs to this receptor. The availability of substrates can consequently dictate the final biological effect connected with the activation of the IGF-1R. When IRS-1 predominates, the cells tend to proliferate and to transform. When She dominates, the cells tend to differentiate. It seems that the route principally involved for the effects of protection against apoptosis is the phosphatidyl-inositol 3-kinases (PI 3-kinases) route.

The role of the IGF system in carcinogenesis has become the subject of intensive research in the last ten years. This interest followed the discovery of the fact that in addition to its mitogenic and antiapoptosis properties, IGF-1R seems to be required for the establishment and the maintenance of a transformed phenotype. In fact, it has been well established that an overexpression or a constitutive activation of IGF-1R leads, in a great variety of cells, to a growth of the cells independent of the support in media devoid of foetal calf serum, and to the formation of tumors in nude mice. This in itself is not a unique property since a great variety of products of overexpressed genes can transform cells, including a good number of receptors of growth factors. However, the crucial discovery which has clearly demonstrated the major role played by IGF-1R in the transformation has been the demonstration that the IGR-1R⁻ cells, in which the gene coding for IGF-1R has been inactivated, are totally refractory to transformation by different agents which are usually capable of transforming cells, such as the E5 protein of bovine papilloma virus, an overexpression of EGFR or PDGFR, the T antigen of SV40, activated ras or the combination of these two last factors.

IGF-1R is expressed in a great variety of tumors and of tumor lines and the IGFs amplify the tumor growth via their attachment to IGF-1R. Other arguments in favor of the role of IGF-1R in carcinogenesis come from studies using murine monoclonal antibodies directed against the receptor or using negative dominants of IGF-1R. Actually, murine monoclonal antibodies directed against IGF-1R inhibit the proliferation of numerous cell lines in culture and the growth of tumor cells in vivo. It has likewise been shown that a negative dominant of IGF-1R is capable of inhibiting tumor proliferation.

A large number of projects have been initiated to develop naked IGF-1R antibodies for the treatment of cancers. Nevertheless, at this date, none of these projects have been successful and there are no anti-IGF-1R antibodies on the market.

Moreover, a series of clinical trials involving anti-IGF-1R antibodies combined to anti-EGFR antibodies in order to target both EGFR and IGF-1R, have failed as none of these antibodies were able to treat KRAS mutant patients.

As a consequence, IGF-1R is not considered now as a major target and, in the research of potential therapeutic antibodies, IGF-1R is no more considered as of particular interest.

Previous attempts to develop a valuable antibody that can be used as a relevant diagnostic or prognostic tool have been reported but none of these are giving satisfaction.

As it will be apparent from the following examples, the inventors have been surprised to demonstrate that the commercially available antibodies commonly used at this day for the scoring of the IGF-1R expressing tumors seem to be not relevant as they give false positive and/or false negative. This issue has probably leaded, in part, to the failure of clinical trials with IGF-1R antibodies due to an inappropriate selection of the patients.

Moreover, first studies performed using commercial antibodies showed discrepancy between IGF-1R scoring and anti-tumoral activity of the targeted ADC therapy.

Nevertheless, it must also be noticed that endeavours to generate IGF-1R antibodies were focussed on naked antibodies, i.e. antibodies useful by their intrinsic properties. In this sense, IGF-1R is considered as a target not suitable for the generation of an ADC such as an antibody-drug-conjugate (referred as "ADC") as IGF-1R is described as a target also widely expressed by normal cells, including blood vessels. In this sense, it can be noticed that the most recent IGF-1R antibody, i.e. AVE1642, is developed as a naked antibody not armed with a drug. It is the same with the other IGF-1R antibodies currently in development and with all those which failed in clinical trials.

The present invention intends to remedy this issue by providing a novel method for the treatment of IGF-1R expressing cancers based on the use of a first IGF-1R antibody as a diagnostic antibody and a second IGF-1R antibody as a therapeutic antibody, preferentially as an ADC.

SUMMARY OF THE INVENTION

The invention relates to a method for the treatment of cancer comprising treating a subject in need thereof with an IGF-1R targeting therapy if the subject presents an IGF-1R (+) status, wherein:

the IGF-1R status of the subject has been determined from a biological sample of the subject, using a first IGF-1R antibody being:

i) an antibody, or any antigen binding fragment thereof, comprising a heavy chain with CDR-H1 of SEQ ID No. 1, CDR-H2 of SEQ ID No. 2, and CDR-H3 of SEQ ID No. 3; and a light chain with CDR-L1 of SEQ ID No. 4, CDR-L2 of SEQ ID No. 5, and CDR-L3 of SEQ ID No. 6; or ii) an antibody, or any antigen binding fragment thereof, comprising a heavy chain with CDR-H1 of SEQ ID No. 11, CDR-H2 of sequence SEQ ID No. 12 and CDR-H3 of sequence SEQ ID No. 13; and a light chain with CDR-L1 of sequence SEQ ID No. 14, CDR-L2 of sequence SEQ ID No. 15, and CDR-L3 of sequence SEQ ID No. 16;

and wherein treatment is realized with an antibody-drug-conjugate of the following formula (I):

$$Ab\text{-}(L\text{-}D)_n$$

or a pharmaceutically acceptable salt thereof, wherein

Ab is a second IGF-1R antibody, or an antigen binding fragment thereof, which binds to the human IGF-1R and which is internalized following its binding to IGF-1R;

L is a linker;

D is a drug moiety; and n is 1 to 12.

The invention also relates to a method of treating an IGF-1R(+) cancer in a subject with an antibody-drug-conjugate of the following formula (I):

$$Ab\text{-}(L\text{-}D)_n$$

or a pharmaceutically acceptable salt thereof, wherein

Ab is a second IGF-1R antibody, or an antigen binding fragment thereof, which binds to the human IGF-1R and which is internalized following its binding to IGF-1R;

L is a linker;

D is a drug moiety; and n is 1 to 12;

and wherein, prior to treatment, the subject's cancer has been determined to be IGF-1R(+) by a method using a first IGF-1R antibody being:

i) an antibody, or any antigen binding fragment thereof, comprising a heavy chain with CDR-H1 of SEQ ID No. 1, CDR-H2 of SEQ ID No. 2, and CDR-H3 of SEQ ID No. 3; and a light chain with CDR-L1 of SEQ ID No. 4, CDR-L2 of SEQ ID No. 5, and CDR-L3 of SEQ ID No. 6; or ii) an antibody, or any antigen binding fragment thereof, comprising a heavy chain with CDR-H1 of SEQ ID No. 11, CDR-H2 of sequence SEQ ID No. 12 and CDR-H3 of sequence SEQ ID No. 13; and a light chain with CDR-L1 of sequence SEQ ID No. 14, CDR-L2 of sequence SEQ ID No. 15, and CDR-L3 of sequence SEQ ID No. 16.

In another alternative mode, the invention relates to a method of diagnosing and treating cancer in a subject, wherein the method comprises:

a) diagnosing the subject's cancer as being IGF-1R(+) using a first IGF-1R antibody being:

i) an antibody, or any antigen binding fragment thereof, comprising a heavy chain with CDR-H1 of SEQ ID No. 1, CDR-H2 of SEQ ID No. 2, and CDR-H3 of SEQ ID No. 3; and a light chain with CDR-L1 of SEQ ID No. 4, CDR-L2 of SEQ ID No. 5, and CDR-L3 of SEQ ID No. 6; or ii) an antibody, or any antigen binding fragment thereof, comprising a heavy chain with CDR-H1 of SEQ ID No. 11, CDR-H2 of sequence SEQ ID No. 12 and CDR-H3 of sequence SEQ ID No. 13; and a light chain with CDR-L1 of sequence SEQ ID No. 14, CDR-L2 of sequence SEQ ID No. 15, and CDR-L3 of sequence SEQ ID No. 16; and b) treating the said subject diagnosed in step a) with an antibody-drug-conjugate of the following formula (I):

$$Ab\text{-}(L\text{-}D)_n$$

or a pharmaceutically acceptable salt thereof, wherein

Ab is a second IGF-1R antibody, or an antigen binding fragment thereof, which binds to the human IGF-1R and which is internalized following its binding to IGF-1R;

L is a linker;

D is a drug moiety; and n is 1 to 12.

The invention also relates to a composition for the treatment of cancer, or for use for the treatment of cancer, in a subject with an IGF-1R(+) status characterized in that it comprises an antibody-drug-conjugate of the following formula (I):

$$Ab\text{-}(L\text{-}D)_n$$

or a pharmaceutically acceptable salt thereof, wherein

Ab is a second IGF-1R antibody, or an antigen binding fragment thereof, which binds to the human IGF-1R and which is internalized following its binding to IGF-1R;

L is a linker;

D is a drug moiety; and n is 1 to 12;

and wherein the IGF-1R(+) status of said subject has been determined from a biological sample of the subject, using a first IGF-1R antibody being:

i) an antibody, or any antigen binding fragment thereof, comprising a heavy chain with CDR-H1 of SEQ ID No. 1, CDR-H2 of SEQ ID No. 2, and CDR-H3 of SEQ ID No. 3; and a light chain with CDR-L1 of SEQ ID No. 4, CDR-L2 of SEQ ID No. 5, and CDR-L3 of SEQ ID No. 6; or ii) an antibody, or any antigen binding fragment thereof, comprising a heavy chain with CDR-H1 of SEQ ID No. 11, CDR-H2 of sequence SEQ ID No. 12 and CDR-H3 of sequence SEQ ID No. 13; and a light chain with CDR-L1 of sequence SEQ ID No. 14, CDR-L2 of sequence SEQ ID No. 15, and CDR-L3 of sequence SEQ ID No. 16.

The invention also relates to an antibody-drug-conjugate for use in the treatment of IGF-1R expressing cancer in a subject, comprising the steps of:

A) determining the IGF-1R(+) status of said subject from a biological sample of the subject, using a first IGF-1R antibody; and B) administrating said antibody-drug-conjugate to the patient if the subject present an IGF-IR(+) status, and wherein:

said first IGF-1R antibody being:

i) an antibody, or any antigen binding fragment thereof, comprising a heavy chain with CDR-H1 of SEQ ID No. 1, CDR-H2 of SEQ ID No. 2, and CDR-H3 of SEQ ID No. 3; and a light chain with CDR-L1 of SEQ ID No. 4, CDR-L2 of SEQ ID No. 5, and CDR-L3 of SEQ ID No. 6; or ii) an antibody, or any antigen binding fragment thereof, comprising a heavy chain with CDR-H1 of SEQ ID No. 11, CDR-H2 of sequence SEQ ID No. 12 and CDR-H3 of sequence SEQ ID No. 13; and a light chain with CDR-L1 of sequence SEQ ID No. 14, CDR-L2 of sequence SEQ ID No. 15, and CDR-L3 of sequence SEQ ID No. 16; and said antibody-drug-conjugate having the following formula (I):

Ab-(L-D)$_n$ or a pharmaceutically acceptable salt thereof, wherein

Ab is a second IGF-1R antibody, or an antigen binding fragment thereof, which binds to the human IGF-1R and which is internalized following its binding to IGF-1R;

L is a linker;

D is a drug moiety; and n is 1 to 12.

According to the method, composition or kit herein described, by "an antibody, or any antigen binding fragment thereof", it is intended particularly to designate an IGF-1R antibody, or any IGF-1R binding fragment thereof.

According to the method, composition or kit herein described, the first and the second antibodies do not bind to the same IGF-1R epitope.

According to the method, composition or kit herein described, the first IGF-1R antibody is:

i) an antibody comprising a heavy chain variable domain of sequence SEQ ID No. 7, or any sequence with at least 90% of homology with the sequence SEQ ID No. 7; and/or a light chain variable domain of sequence SEQ ID No. 8, or any sequence with at least 90% of homology with the sequence SEQ ID No. 8; or ii) an antibody comprising a heavy chain variable domain of sequence SEQ ID No. 17, or any sequence with at least 90% of homology with the sequence SEQ ID No. 17; and/or a light chain variable domain of sequence SEQ ID No. 18, or any sequence with at least 90% of homology with the sequence SEQ ID No. 18.

According to the method, composition or kit herein described, the first IGF-1R antibody is:

i) the antibody 810D12 secreted by the hybridoma filed at the CNCM, Institut Pasteur, Paris, on Sep. 17, 2014, under number I-4893; or ii) the antibody 816C12 secreted by the hybridoma filed at the CNCM, Institut Pasteur, Paris, on Sep. 17, 2014, under number I-4894.

According to the method, composition or kit herein described, Ab is an IGF-1R antibody, or an antigen binding fragment thereof, selected from i) an antibody which comprises the three heavy chain CDRs of sequence SEQ ID No. 21, 22 and 23 and the three light chain CDRs of sequence SEQ ID No. 24, 25 and 26; or ii) an antibody which competes for binding to IGF-1R with the antibody of i); or iii) an antibody which binds to the same epitope of IGF-1R as the antibody of i).

According to the method, composition or kit herein described, Ab is:

a) an antibody comprising the three heavy chain CDRs of sequence SEQ ID No. 27, 22 and 23 and the three light chain CDRs of sequence SEQ ID No. 29, 25 and 31;

b) an antibody comprising the three heavy chain CDRs of sequence SEQ ID No. 27, 22 and 23 and the three light chain CDRs of sequence SEQ ID No. 30, 25 and 31;

c) an antibody comprising the three heavy chain CDRs of sequence SEQ ID No. 27, 22 and 23 and the three light chain CDRs of sequence SEQ ID No. 29, 25 and 32; or d) an antibody comprising the three heavy chain CDRs of sequence SEQ ID No. 28, 22 and 23 and the three light chain CDRs of sequence SEQ ID No. 29, 25 and 31.

According to the method, composition or kit herein described, Ab is:

a) an antibody comprising a heavy chain variable domain of sequence selected from SEQ ID Nos. 33, 39, 41, 43, 45, 47, 49, 51, 53, 55, 57 and 59 or any sequence with at least 80% identity with SEQ ID No. 33, 39, 41, 43, 45, 47, 49, 51, 53, 55, 57 or 59; and the three light chain CDRs of sequence SEQ ID Nos. 29, 25 and 31;

b) an antibody comprising a light chain variable domain of sequence selected from SEQ ID Nos. 34, 37 and 60 or any sequence with at least 80% identity with SEQ ID Nos. 34, 37 or 60; and the three heavy chain CDRs of sequences SEQ ID Nos. 27, 22 and 23; or c) an antibody comprising a heavy chain variable domain of sequence selected from SEQ ID Nos. 33, 39, 41, 43, 45, 47, 49, 51, 53, 55, 57 and 59 or any sequence with at least 80% identity with SEQ ID Nos. 33, 39, 41, 43, 45, 47, 49, 51, 53, 55, 57 or 59; and a light chain variable domain of sequence selected from SEQ ID Nos. 34, 37 and 60 or any sequence with at least 80% identity with SEQ ID Nos. 34, 37 or 60.

According to the method, composition or kit herein described, Ab comprises:

a) a heavy chain of sequence selected from SEQ ID Nos. 35, 40, 42, 44, 46, 48, 50, 52, 54, 56, 58 and 61 or any sequence with at least 80% identity with SEQ ID Nos. 35, 40, 42, 44, 46, 48, 50, 52, 54, 56, 58 or 61; and b) a light chain of sequence selected from SEQ ID Nos. 36, 38 and 62 or any sequence with at least 80% identity with SEQ ID Nos. 36, 38 or 62.

According to the method, composition or kit herein described, Ab is i) an antibody selected from the antibodies 208F2, 212A11, 214F8, 219D6 and 213B10, ii) the antibodies which compete for binding to IGF-1R with the antibodies of i); or iii) the antibodies which bind to the same epitope of IGF-1R as the antibodies of i).

According to the method, composition or kit herein described, the drug moiety D is selected from alkylating agents, anti-metabolites, anti-tumor antibiotics, mitotic inhibitors, chromatin function inhibitors, anti-angiogenesis agents, anti-estrogens, anti-androgens, chelating agents, Iron absorption stimulant, Cyclooxygenase inhibitors, Phosphodiesterase inhibitors, DNA inhibitors, DNA synthetis inhibitors, Apopstotis stimulants, Thymidylate inhibitors, T cell inhibitors, Interferon agonists, Ribonucleoside triphosphate reductase inhibitors, Aromatase inhibitors, Estrogen receptor antagonists, Tyrosine kinase inhibitors, Cell cycle inhibitors, Taxane, Tubulin inhibitors, angiogenesis inhibitors, macrophage stimulants, Neurokinin receptor antagonists, Cannabinoid receptor agonists, Dopamine receptor agonists, granulocytes stimulating factor agonists, Erythropoietin receptor agonists, somatostatin receptor agonists, LHRH agonists, Calcium sensitizers, VEGF receptor antagonists, interleukin receptor antagonists, osteoclast inhibitors, radical formation stimulants, endothelin receptor antagonists, Vinca alkaloid, anti-hormone or immunomodulators or any other drug that fullfills the activity criteria of a cytotoxic or a toxin;

According to the method, composition or kit herein described, the drug moiety D is an auristatin, a dolostatin 10, or a derivative thereof.

According to the method, composition or kit herein described, the drug moiety D is of the following formula (II):

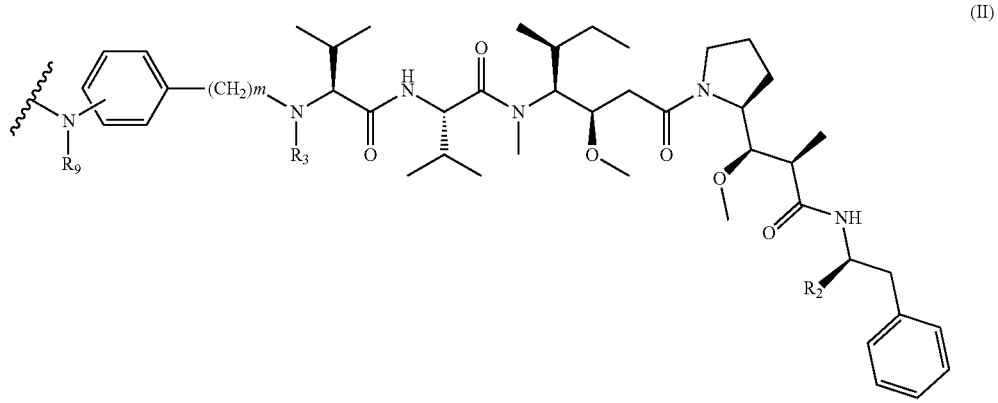

wherein:
$R_2$ is COOH, COOCH$_3$ or thiazolyl;
$R_3$ is H or (C$_1$-C$_6$)alkyl;
$R_9$ is H or (C$_1$-C$_6$)alkyl;
m is an integer comprised between 1 and 8;
the wavy line indicates the point of attachment to L.
According to the method, composition or kit herein described, L is a linker of the following formula (III):

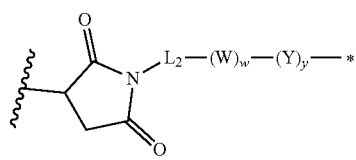

wherein
$L_2$ is (C$_4$-C$_{10}$)cycloalkyl-carbonyl, (C$_2$-C$_6$)alkyl, (C$_2$-C$_6$)alkyl-carbonyl,
W is an amino acid unit; w is an integer comprised between 0 and 5;
Y is PAB-carbonyl with PAB being

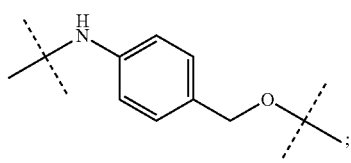

y is 0 or 1;
the asterisk indicates the point of attachment to D; and
the wavy line indicates the point of attachment to Ab.
According to the method, composition or kit herein described, the antibody-drug-conjugate is:

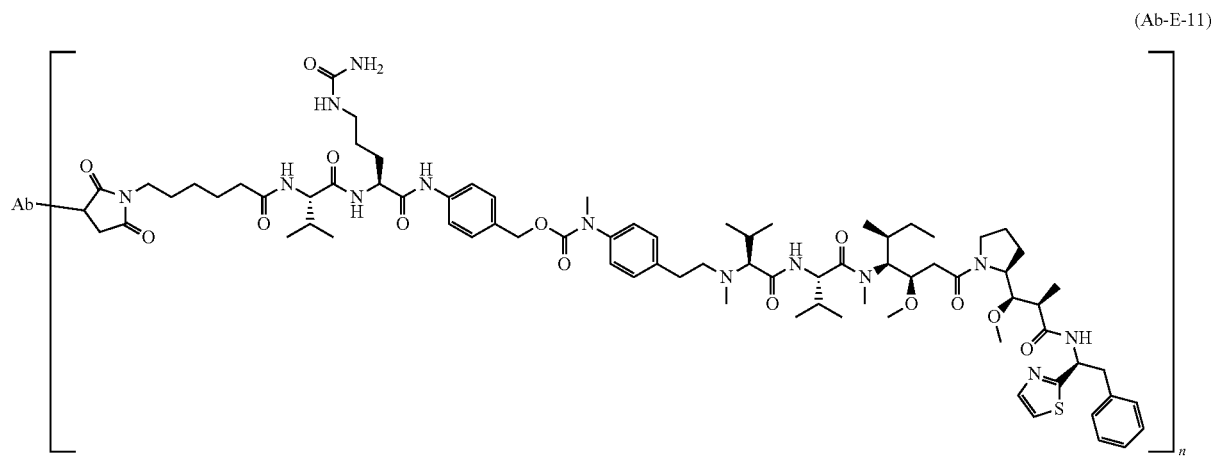

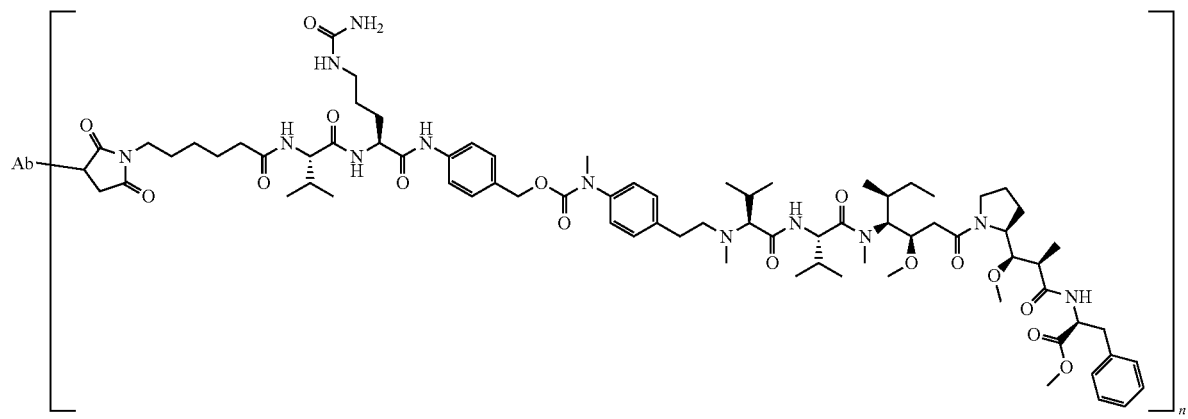
(Ab-E-12)
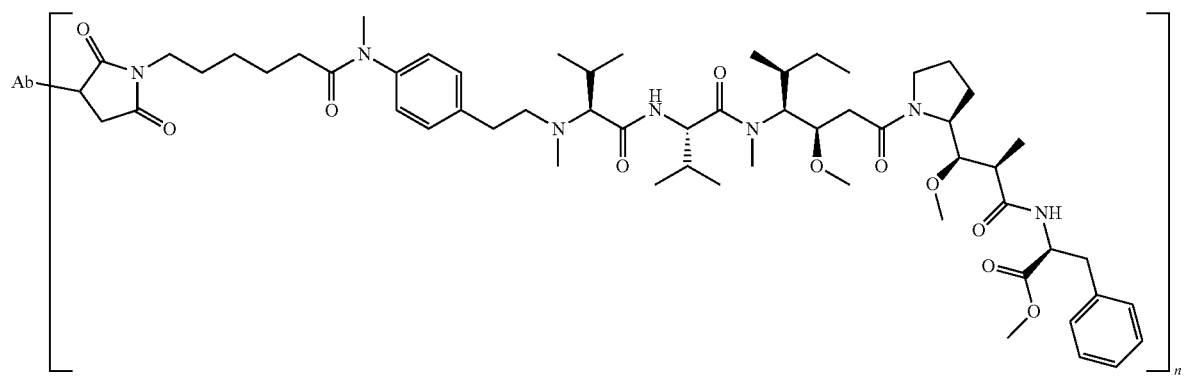
(Ab-G-12)
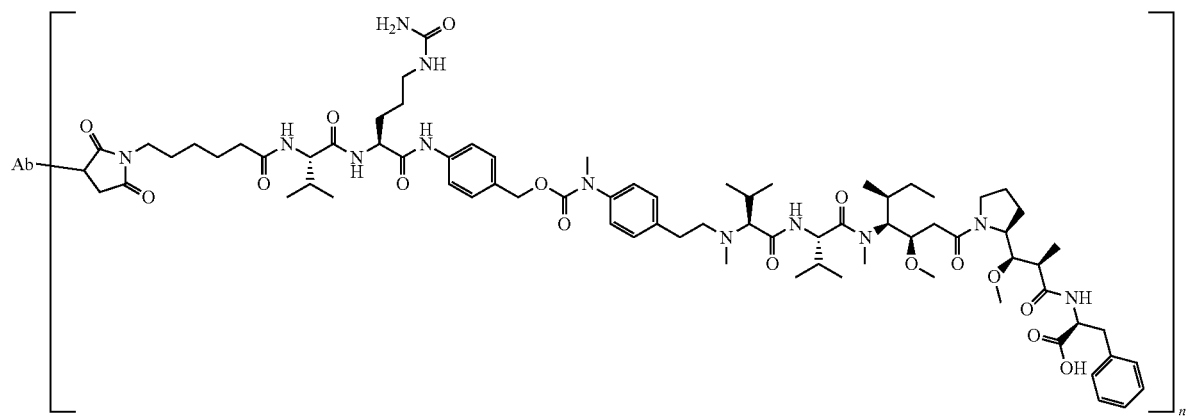
(Ab-E-13)

-continued
(Ab-F-13)
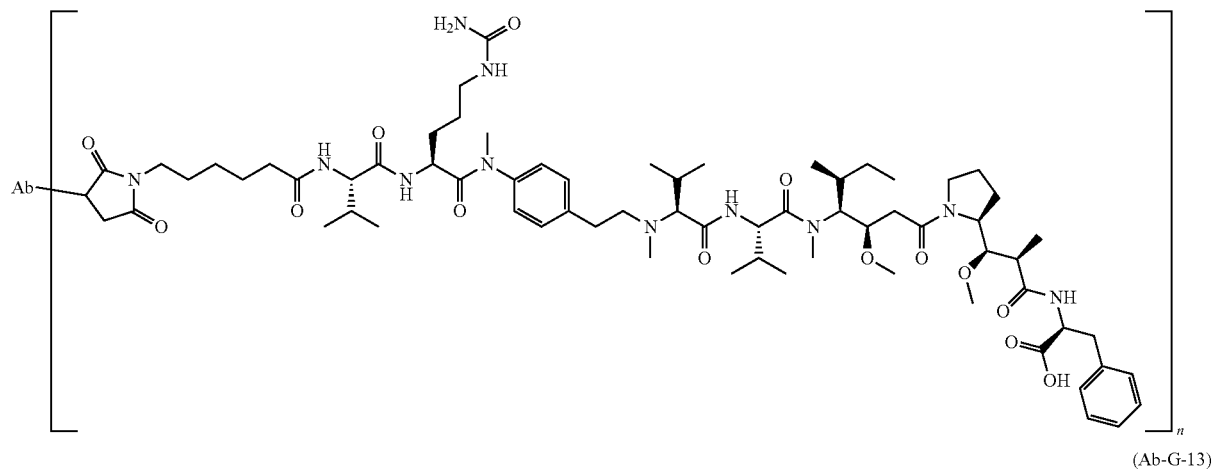
(Ab-G-13)
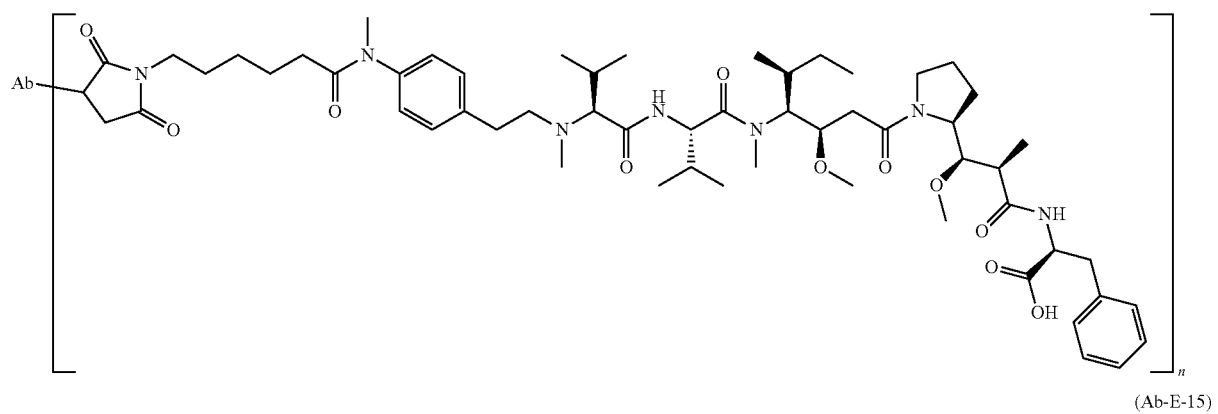
(Ab-E-15)
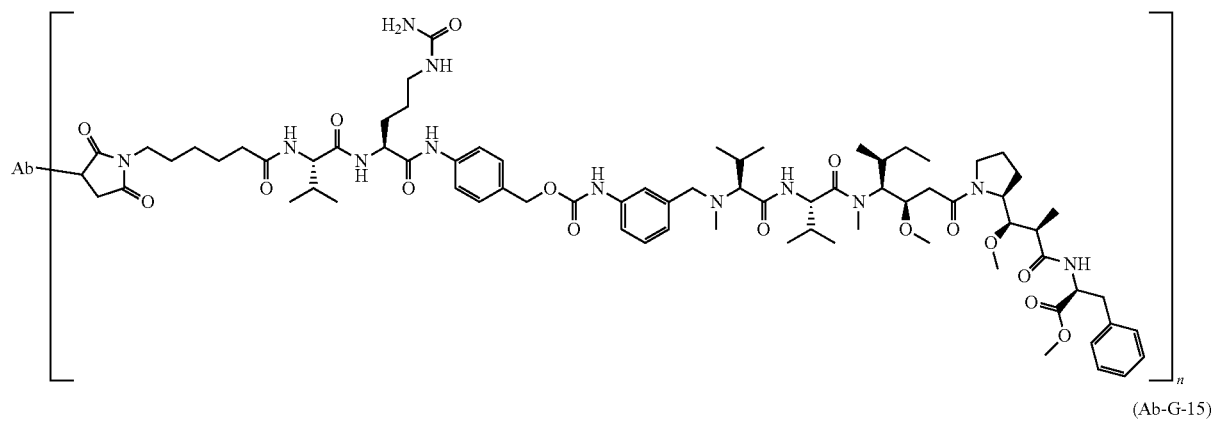
(Ab-G-15)
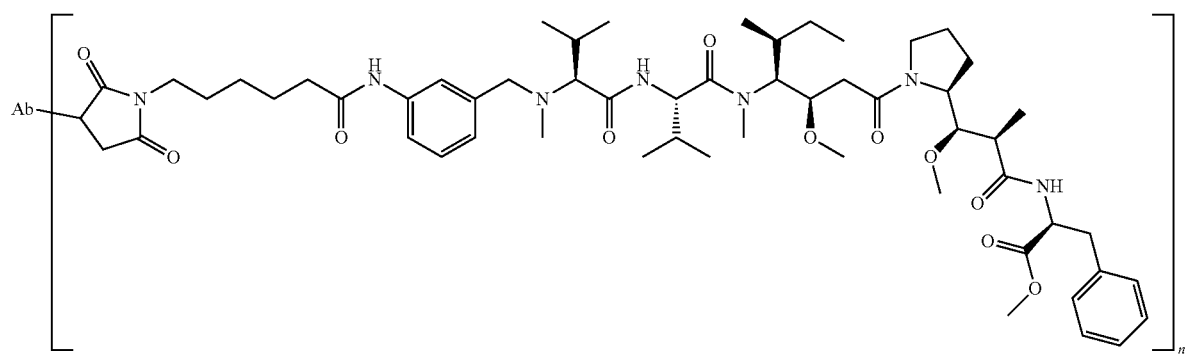

(Ab-F-61)

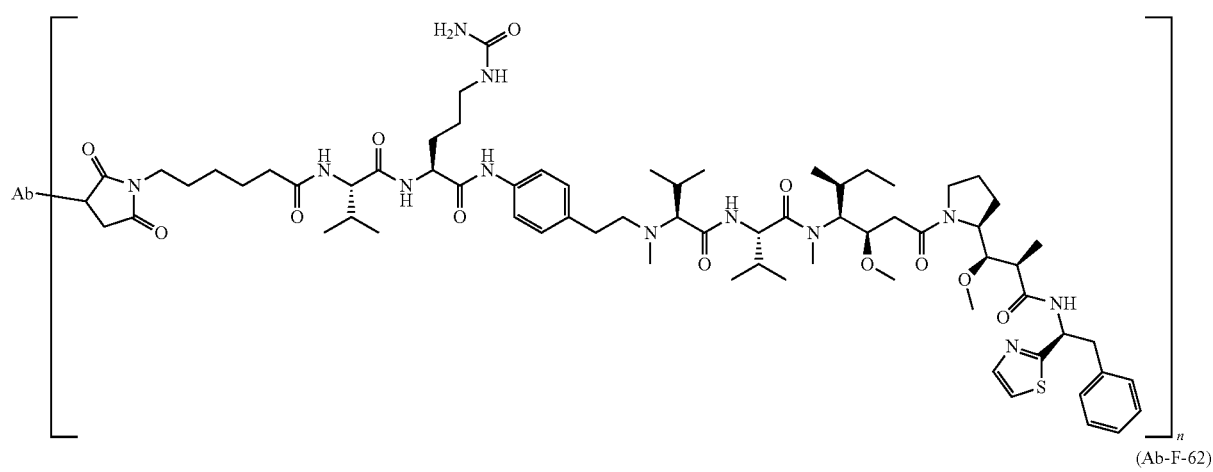

(Ab-F-62)

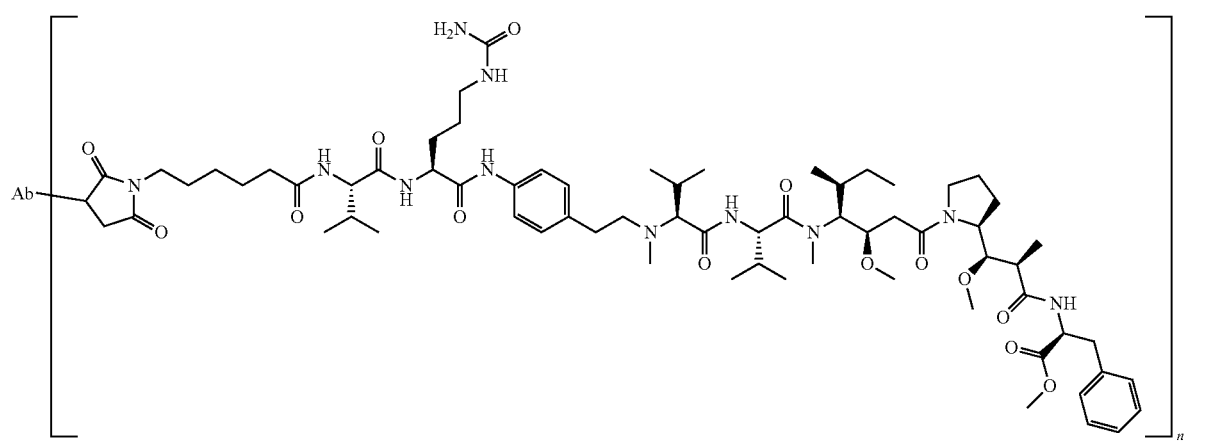

(Ab-F-63)

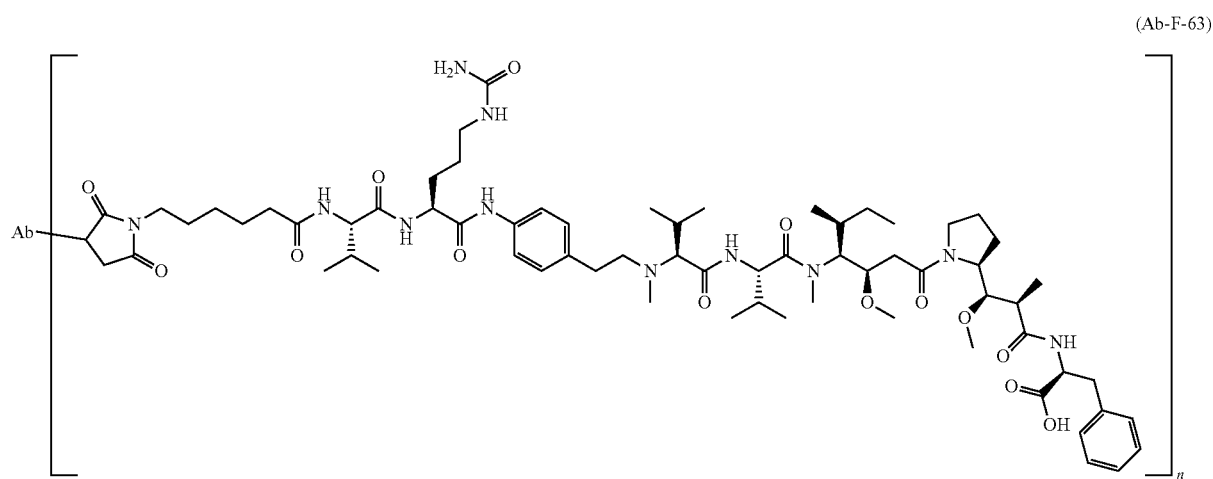

and the pharmaceutically acceptable salts thereof, wherein Ab is i) an antibody selected from the antibodies 208F2, 212A11, 214F8, 219D6 and 213B10, or ii) an antibody selected from the antibodies which compete for binding to IGF-1R with the antibodies of i); or iii) an antibody selected from the antibodies which bind to the same epitope of IGF-1R as the antibodies of i).

The invention also relates to a kit for use in the treatment of IGF-1R expressing cancer, comprising at least:

a) a first IGF-1R antibody consisting of:

i) an antibody, or any antigen binding fragment thereof, comprising a heavy chain with CDR-H1 of SEQ ID No. 1, CDR-H2 of SEQ ID No. 2, and CDR-H3 of SEQ ID No. 3;

and a light chain with CDR-L1 of SEQ ID No. 4 CDR-L2 of SEQ ID No. 5, and CDR-L3 of SEQ ID No. 6; or ii) an antibody, or any antigen binding fragment thereof, comprising a heavy chain with CDR-H1 of SEQ ID No. 11, CDR-H2 of sequence SEQ ID No. 12 and CDR-H3 of sequence SEQ ID No. 13; and a light chain with CDR-L1 of sequence SEQ ID No. 14, CDR-L2 of sequence SEQ ID No. 15, and CDR-L3 of sequence SEQ ID No. 16;

and b) an antibody-drug-conjugate of the following formula (I):

$$Ab\text{-}(L\text{-}D)_n \quad (I)$$

or a pharmaceutically acceptable salt thereof, wherein

Ab is a second IGF-1R antibody, or an antigen binding fragment thereof, capable of binding to the human IGF-1R selected from i) an antibody which comprises the three heavy chain CDRs of sequence SEQ ID No. 21, 22 and 23 and the three light chain CDRs of sequence SEQ ID No. 24, 25 and 26; or ii) an antibody which competes for binding to IGF-1R with the antibody of i); or iii) an antibody which binds to the same epitope of IGF-1R as the antibody of i);

L is a linker;

D is a drug moiety of the following formula (II):

ii) an antibody, or any antigen binding fragment thereof, comprising a heavy chain with CDR-H1 of SEQ ID No. 11, CDR-H2 of sequence SEQ ID No. 12 and CDR-H3 of sequence SEQ ID No. 13; and a light chain with CDR-L1 of sequence SEQ ID No. 14, CDR-L2 of sequence SEQ ID No. 15, and CDR-L3 of sequence SEQ ID No. 16;

and wherein treatment is realized with an antibody-drug-conjugate of the following formula (I):

$$Ab\text{-}(L\text{-}D)_n$$

or a pharmaceutically acceptable salt thereof, wherein

Ab is a second IGF-1R antibody, or an antigen binding fragment thereof, which binds to the human IGF-1R and which is internalized following its binding to IGF-1R;

L is a linker;

D is a drug moiety; and n is 1 to 12.

The invention also relates to a composition for the treatment of cancer, or for use for the treatment of cancer, in a subject with an IGF-1R(+) status characterized in that it comprises an antibody-drug-conjugate of the following formula (I):

$$Ab\text{-}(L\text{-}D)_n$$

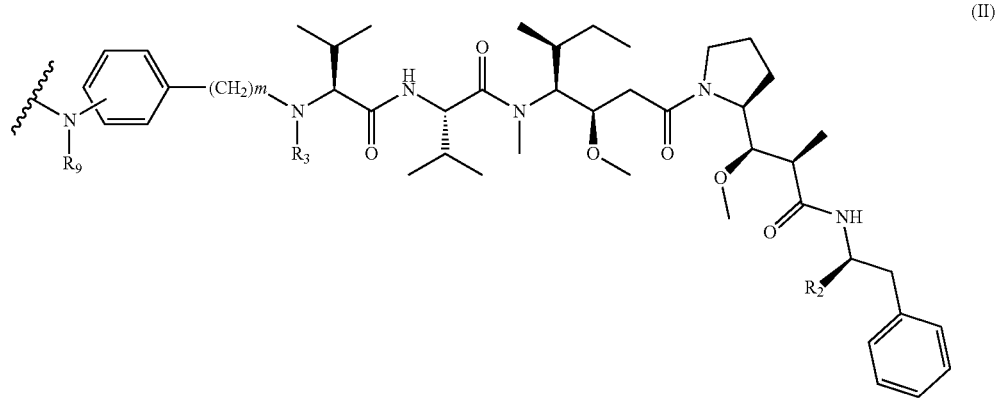

wherein:

$R_2$ is COOH, COOCH$_3$ or thiazolyl;

$R_3$ is H or $(C_1$-$C_6)$alkyl;

$R_9$ is H or $(C_1$-$C_6)$alkyl;

m is an integer comprised between 1 and 8;

the wavy line indicates the point of attachment to L; and n is 1 to 12.

DETAILED DESCRIPTION OF THE INVENTION

The invention relates to a method for the treatment of cancer comprising treating a subject in need thereof with an IGF-1R targeting therapy if the subject presents an IGF-1R (+) status, wherein:

the IGF-1R status of the subject has been determined from a biological sample of the subject, using a first IGF-1R antibody being:

i) an antibody, or any antigen binding fragment thereof, comprising a heavy chain with CDR-H1 of SEQ ID No. 1, CDR-H2 of SEQ ID No. 2, and CDR-H3 of SEQ ID No. 3; and a light chain with CDR-L1 of SEQ ID No. 4, CDR-L2 of SEQ ID No. 5, and CDR-L3 of SEQ ID No. 6; or or a pharmaceutically acceptable salt thereof, wherein Ab is a second IGF-1R antibody, or an antigen binding fragment thereof, which binds to the human IGF-1R and which is internalized following its binding to IGF-1R;

L is a linker;

D is a drug moiety; and n is 1 to 12;

and wherein the IGF-1R(+) status of said subject has been determined from a biological sample of the subject, using a first IGF-1R antibody being:

i) an antibody, or any antigen binding fragment thereof, comprising a heavy chain with CDR-H1 of SEQ ID No. 1, CDR-H2 of SEQ ID No. 2, and CDR-H3 of SEQ ID No. 3; and a light chain with CDR-L1 of SEQ ID No. 4, CDR-L2 of SEQ ID No. 5, and CDR-L3 of SEQ ID No. 6; or ii) an antibody, or any antigen binding fragment thereof, comprising a heavy chain with CDR-H1 of SEQ ID No. 11, CDR-H2 of sequence SEQ ID No. 12 and CDR-H3 of sequence SEQ ID No. 13; and a light chain with CDR-L1 of sequence SEQ ID No. 14, CDR-L2 of sequence SEQ ID No. 15, and CDR-L3 of sequence SEQ ID No. 16.

The invention also relates to an antibody-drug-conjugate for use in the treatment of IGF-1R expressing cancer in a subject, comprising the steps of:

A) determining the IGF-1R(+) status of said subject from a biological sample of the subject, using a first IGF-1R antibody; and B) administrating said antibody-drug-conjugate to the patient if the subject present an IGF-IR(+) status, and wherein:

said first IGF-1R antibody being:

i) an antibody, or any antigen binding fragment thereof, comprising a heavy chain with CDR-H1 of SEQ ID No. 1, CDR-H2 of SEQ ID No. 2, and CDR-H3 of SEQ ID No. 3; and a light chain with CDR-L1 of SEQ ID No. 4, CDR-L2 of SEQ ID No. 5, and CDR-L3 of SEQ ID No. 6; or ii) an antibody, or any antigen binding fragment thereof, comprising a heavy chain with CDR-H1 of SEQ ID No. 11, CDR-H2 of sequence SEQ ID No. 12 and CDR-H3 of sequence SEQ ID No. 13; and a light chain with CDR-L1 of sequence SEQ ID No. 14, CDR-L2 of sequence SEQ ID No. 15, and CDR-L3 of sequence SEQ ID No. 16; and said antibody-drug-conjugate having the following formula (I):

Ab-(L-D)$_n$     (I)

or a pharmaceutically acceptable salt thereof, wherein

Ab is a second IGF-1R antibody, or an antigen binding fragment thereof, which binds to the human IGF-1R and which is internalized following its binding to IGF-1R;

L is a linker;

D is a drug moiety; and n is 1 to 12.

The invention also relates to a kit for use in the treatment of IGF-1R expressing cancer, comprising at least:

a) a first IGF-1R antibody consisting of:

i) an antibody, or any antigen binding fragment thereof, comprising a heavy chain with CDR-H1 of SEQ ID No. 1, CDR-H2 of SEQ ID No. 2, and CDR-H3 of SEQ ID No. 3; and a light chain with CDR-L1 of SEQ ID No. 4 CDR-L2 of SEQ ID No. 5, and CDR-L3 of SEQ ID No. 6; or ii) an antibody, or any antigen binding fragment thereof, comprising a heavy chain with CDR-H1 of SEQ ID No. 11, CDR-H2 of sequence SEQ ID No. 12 and CDR-H3 of sequence SEQ ID No. 13; and a light chain with CDR-L1 of sequence SEQ ID No. 14, CDR-L2 of sequence SEQ ID No. 15, and CDR-L3 of sequence SEQ ID No. 16;

and b) an antibody-drug-conjugate of the following formula (I):

Ab-(L-D)$_n$     (I)

or a pharmaceutically acceptable salt thereof, wherein

Ab is a second IGF-1R antibody, or an antigen binding fragment thereof, capable of binding to the human IGF-1R selected from i) an antibody which comprises the three heavy chain CDRs of sequence SEQ ID No. 21, 22 and 23 and the three light chain CDRs of sequence SEQ ID No. 24, 25 and 26; or ii) an antibody which competes for binding to IGF-1R with the antibody of i); or iii) an antibody which binds to the same epitope of IGF-1R as the antibody of i);

L is a linker;

D is a drug moiety of the following formula (II):

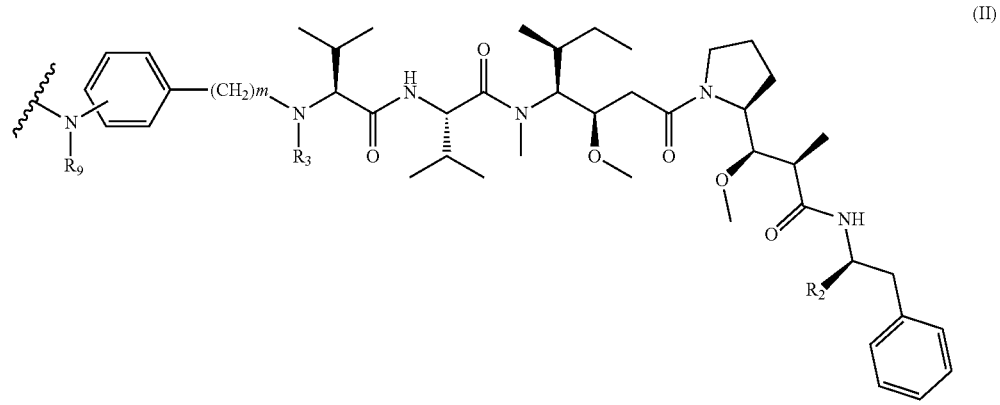

wherein:

$R_2$ is COOH, COOCH$_3$ or thiazolyl;

$R_3$ is H or (C$_1$-C$_6$)alkyl;

$R_9$ is H or (C$_1$-C$_6$)alkyl;

m is an integer comprised between 1 and 8;

the wavy line indicates the point of attachment to L; and n is 1 to 12.

I—Definitions

The terms "antibody", "antibodies" "ab", "Ab", "MAb" or "immunoglobulin" are used interchangeably in the broadest sense and include monoclonal antibodies, isolated, engineered or recombinant antibodies (e.g., full length or intact monoclonal antibodies), polyclonal antibodies, multivalent antibodies or multispecific antibodies (e.g., bispecific antibodies) and also antibody fragment thereof, so long as they exhibit the desired biological activity. More particularly, such a molecule consists of a glycoprotein comprising at least two heavy (H) chains and two light (L) chains interconnected by disulfide bonds. Each heavy chain comprises a heavy chain variable region (or domain) (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system.

As used in the present specification, the expression "IGF-1R antibody" should be interpreted as similar to "anti-IGF-1R antibody" and means an antibody capable of binding to IGF-1R.

The term "monoclonal antibody" or "Mab" as used herein refers to an antibody obtained from a population of substantially homogeneous antibodies, i.e. the individual antibodies of the population are identical except for possible naturally occurring mutations that may be present in minor amounts. Monoclonal antibodies are highly specific, being directed against a single epitope. Such monoclonal antibody may be produced by a single clone of B cells or hybridoma. Monoclonal antibodies may also be recombinant, i.e. produced by protein engineering or chemical synthesis. Monoclonal antibodies may also be isolated from phage antibody libraries. In addition, in contrast with preparations of polyclonal antibodies which typically include various antibodies directed against various determinants, or epitopes, each monoclonal antibody is directed against a single epitope of the antigen. The monoclonal antibody herein includes murine, chimeric and humanized antibody, such as described after.

The term "recombinant antibody" refers to an antibody that results from the expression of recombinant DNA within living cells. A recombinant antibody of the invention is obtained by using laboratory methods of genetic recombination, well known by a person skilled in the art, creating DNA sequences that would not be found in biological organisms.

By "antigen binding fragment" or "IGF-IR binding fragment" of an antibody of the ADC according to the invention, it is intended to indicate any peptide, polypeptide, or protein retaining the ability to bind to the target (also generally referred as antigen) of the antibody. In an embodiment, such "antigen binding fragments" are selected in the group consisting of Fv, scFv (sc for single chain), Fab, F(ab')$_2$, Fab', scFv-Fc fragments or diabodies, or any fragment of which the half-life time would have been increased by chemical modification, such as the addition of poly(alkylene) glycol such as poly(ethylene) glycol ("PEGylation") (pegylated fragments called Fv-PEG, scFv-PEG, Fab-PEG, F(ab')$_2$-PEG or Fab'-PEG) ("PEG" for Poly(Ethylene) Glycol), or by incorporation in a liposome, said fragments having at least one of the characteristic CDRs of the antibody according to the invention. Preferably, said "antigen binding fragments" will be constituted or will comprise a partial sequence of the heavy or light variable chain of the antibody from which they are derived, said partial sequence being sufficient to retain the same specificity of binding as the antibody from which it is descended and a sufficient affinity, preferably at least equal to 1/100, in a more preferred manner to at least 1/10, of the affinity of the antibody from which it is descended, with respect to the target. More preferably, said "antigen binding fragments" will be constituted of or will comprise at least the three CDRs CDR-H1, CDR-H2 and CDR-H3 of the heavy variable chain and the three CDRs CDR-L1, CDR-L2 and CDR-L3 of the light variable chain of the antibody from which they are derived.

By "binding", "binds", or the like, it is intended that the antibody, or any antigen binding fragment thereof, forms a complex with an antigen that is relatively stable under physiologic conditions. Specific binding can be characterized by an equilibrium dissociation constant of at least about $1 \times 10^{-6}$ M. Methods for determining whether two molecules bind are well known in the art and include, for example, equilibrium dialysis, surface plasmon resonance, radiolabelled assays and the like. For the avoidance of doubt, it does not mean that the said antibody could not bind or interfere, at a low level, to another antigen. Nevertheless, as an embodiment, the said antibody binds only to the said antigen.

By CDR regions or CDR(s), it is intended to indicate the hypervariable regions of the heavy and light chains of the immunoglobulins as defined by IMGT. The IMGT unique numbering has been defined to compare the variable domains whatever the antigen receptor, the chain type, or the species [Lefranc M.-P., Immunology Today 18, 509 (1997)/ Lefranc M.-P., The Immunologist, 7, 132-136 (1999)/ Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering, the conserved amino acids always have the same position, for instance cystein 23 (1st-CYS), tryptophan 41 (CONSERVED-TRP), hydrophobic amino acid 89, cystein 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering is used in 2D graphical representations, designated as IMGT Colliers de Perles [Ruiz, M. and Lefranc, M.-P., Immunogenetics, 53, 857-883 (2002)/Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

It must be understood that, without contradictory specification in the present specification, complementarity-determining regions or CDRs, mean the hypervariable regions of the heavy and light chains of immunoglobulins as defined according to the IMGT numbering system. Nevertheless, CDRs can also be defined according to the Kabat numbering system (Kabat et al., Sequences of proteins of immunological interest, 5$^{th}$ Ed., U.S. Department of Health and Human Services, NIH, 1991, and later editions). There are three heavy-chain CDRs and three light-chain CDRs. Here, the terms "CDR" and "CDRs" are used to indicate, depending on the case, one or more, or even all, of the regions containing the majority of the amino acid residues responsible for the antibody's binding affinity for the antigen or epitope it recognizes. In order to simplify the reading of the present application, the CDRs according to Kabat are not defined. Nevertheless, it would be obvious for the person skilled in that art, using the definition of the CDRs according to IMGT, to define the CDRs according to Kabat.

The term half maximal effective concentration (EC$_{50}$) corresponds to the concentration of a drug, antibody or toxicant which induces a response halfway between the baseline and maximum after some specified exposure time. It is commonly used as a measure of drug's potency. The $EC_{50}$ of a graded dose response curve therefore represents the concentration of a compound where 50% of its maximal effect is observed. The $EC_{50}$ of a quantal dose response curve represents the concentration of a compound where 50% of the population exhibits a response, after specified exposure duration. Concentration measures typically follow a sigmoidal curve, increasing rapidly over a relatively small change in concentration. This can be determined mathematically by derivation of the best-fit line.

The term "epitope" is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

In the sense of the present invention, the "identity" or "percentage identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444] or by means of computer software using these algorithms (GAP, BESTFIT, FASTA and TFASTA in the Wisconsin Genetics Software Package, Genetics Computer Group, 575 Science Dr., Madison, Wis., or by the comparison software BLAST NR or BLAST P). Percentage identity is calculated by determining the number of positions at which the amino acid nucleotide or residue is identical between the two sequences, preferably between the two complete sequences, dividing the number of identical positions by the total number of positions in the alignment window and multiplying the result by 100 to obtain the percentage identity between the two sequences. For example, the BLAST program, "BLAST 2 sequences" (Tatusova et al., "Blast 2 sequences—a new tool for comparing protein and nucleotide sequences", FEMS Microbiol., 1999, Lett. 174:247-250) available on the site ncbi.nlm.nih.gov, can be used with the default parameters (notably for the parameters "open gap penalty": 5, and "extension gap penalty": 2; the selected matrix being for example the "BLOSUM 62" matrix proposed by the program); the percentage identity between the two sequences to compare is calculated directly by the program. For the amino acid sequence exhibiting at least 80%, preferably 85%, 90%, 95% and 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below. Equivalent amino acids can be determined either on their structural homology with the amino acids for which they are substituted or on the results of comparative tests of biological activity between the various antibodies likely to be generated. As a non-limiting example, table 1 below summarizes the possible substitutions likely to be carried out without resulting in a significant modification of the biological activity of the corresponding modified antibody; inverse substitutions are naturally possible under the same conditions. In a more preferred embodiment, for the amino acid sequence exhibiting at least 80%, preferably 85%, 90%, 95% and 98% identity with a reference amino acid sequence of an antibody containing CDR(s), preferred examples include at least the non-modified CDR(s) contained in the reference sequence.

TABLE 1

| Original residue | Substitution(s) |
| --- | --- |
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (E) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, defining a fragment or a region of a nucleic acid, containing unnatural nucleotides or not, and being either a double-strand DNA, a single-strand DNA or transcription products of said DNAs.

As used herein, phrases such as "a subject that would benefit from administration of an IGF-1R therapy" and "a subject susceptible to be treated with an IGF-1R therapy" includes subjects, such as mammalian subjects, that would benefit from administration of a IGF-1R therapy, e.g., for detection of IGF-1R(e.g., for a diagnostic procedure) and/or from treatment, i.e., palliation or prevention of a disease such as cancer, with a, IGF-1R binding molecule which binds to IGF-1R. As described in more detail herein, the IGF-1R binding molecule can be used in unconjugated form or can be conjugated, e.g., to a drug, prodrug, or an isotope.

By "IGF-1R expressing cancers", it is meant any cancer which express, over-express, or abnormally express IGF-1R.

In certain embodiments it comprises the precancerous lesion, abnormal cell growth, benign tumor, malignant tumor, or "cancer" comprises cells which express, overexpress, or abnormally express IGF-1R.

"Diagnosing" a disease as used herein refers to the process of identifying or detecting the presence of a pathological hyperproliferative oncogenic disorder associated with or mediated by expression of IGF-1R, monitoring the progression of the disease, and identifying or detecting cells or samples that are indicative of a disorder associated with the expression of IGF-1R.

"Prognosis" as used herein means the likelihood of recovery from a disease or the prediction of the probable development or outcome of a disease. For example, if a sample from a subject is negative for staining with the IGF-1R antibody, then the "prognosis" for that subject is better than if the sample is positive for IGF-1R staining. Samples may be scored for IGF-1R expression levels on an appropriate scale as it will be more detailed hereinafter.

A "biological sample" may be any sample that may be taken from a subject. Such a sample must allow for the determination of the expression levels of the biomarker of the invention. The nature of the sample will thus be dependent upon the nature of the tumor. Preferred biological samples include samples such as a blood sample, a plasma sample, or a lymph sample, if the cancer is a liquid tumor. Preferred biological samples include samples such as a biopsy sample or a sample taken from a surgical resection therapy, if the cancer is a solid tumor. Preferably, the biological sample is a biological fluid, such as serum, whole blood cells, a tissue sample or a biopsy of human origin. The sample may for example include, biopsied tissue, which can be conveniently assayed for the presence of a pathological oncogenic disorder associated with expression of IGF-1R.

"IGF-1R status" within the meaning of the invention, relates to the classification of tumor to a IGF-1R positive [IGF-1R (+)] or IGF-1R negative [IGF-1R (−)] class based on the determination of the expression level of the IGF-1R as measured by any methods such as immunohistochemistry (IHC), Fluorescence Activated Cell Sorting FACS, or other methods known by the person skilled in the art.

II—The First IGF-1R Antibody

In an embodiment of the invention, the first IGF-1R antibody, or any antigen binding fragment thereof, comprises:

i) a heavy chain with CDR-H1 of sequence SEQ ID No. 1, CDR-H2 of sequence SEQ ID No. 2 and CDR-H3 of sequence SEQ ID No. 3; and ii) a light chain with CDR-L1 of sequence SEQ ID No. 4, CDR-L2 of sequence SEQ ID No. 5 and CDR-L3 of sequence SEQ ID No. 6.

The first IGF-1R antibody is characterized in that it comprises a heavy chain variable domain of sequence SEQ ID No. 7, or any sequence with at least 90% of homology with the sequence SEQ ID No. 7.

The first IGF-1R antibody is characterized in that it comprises a light chain variable domain of sequence SEQ ID No. 8, or any sequence with at least 90% of homology with the sequence SEQ ID No. 8.

According to said embodiment, the first IGF-1R antibody referred as 810D12, is characterized in that it comprises a heavy-chain variable domain sequence comprising the amino acid sequence SEQ ID No. 7 or a sequence with at least 80%, preferably 85%, 90%, 95% and 98% of homology after optimal alignment with sequence SEQ ID No. 7; and/or in that it comprises a light-chain variable domain sequence comprising the amino acid sequence SEQ ID No. 8 or a sequence with at least 80%, preferably 85%, 90%, 95% and 98% of homology after optimal alignment with sequence SEQ ID No. 8.

In another embodiment of the invention, the first IGF-1R antibody, or any antigen binding fragment thereof, comprises:

i) a heavy chain with CDR-H1 of sequence SEQ ID No. 11, CDR-H2 of sequence SEQ ID No. 12 and CDR-H3 of sequence SEQ ID No. 13; and ii) a light chain with CDR-L1 of sequence SEQ ID No. 14, CDR-L2 of sequence SEQ ID No. 15 and CDR-L3 of sequence SEQ ID No. 16.

The first IGF-1R antibody is characterized in that it comprises a heavy chain variable domain of sequence SEQ ID No. 17, or any sequence with at least 90% of homology with the sequence SEQ ID No. 17.

The first IGF-1R antibody is characterized in that it comprises a light chain variable domain of sequence SEQ ID No. 18, or any sequence with at least 90% of homology with the sequence SEQ ID No. 18.

According to said embodiment, the first IGF-1R antibody referred as 810D12, is characterized in that it comprises a heavy-chain variable domain sequence comprising the amino acid sequence SEQ ID No. 17 or a sequence with at least 80%, preferably 85%, 90%, 95% and 98% of homology after optimal alignment with sequence SEQ ID No. 17; and/or in that it comprises a light-chain variable domain sequence comprising the amino acid sequence SEQ ID No. 18 or a sequence with at least 80%, preferably 85%, 90%, 95% and 98% of homology after optimal alignment with sequence SEQ ID No. 18.

A particular aspect of the invention is that the first IGF-1R antibody, or any antigen binding fragment thereof, does not bind to the Insulin receptor (IR).

In another embodiment, the first IGF-1R antibody of the invention consists of a monoclonal antibody.

In another embodiment, the first IGF-1R antibody of the invention consists of a recombinant antibody.

In another embodiment, the antibody of the invention consists of a chemically synthesized antibody.

"IGF-1R antibody" includes (without contrary specification) the murine, the chimeric and the humanized versions of the said IGF-1R antibody.

For more clarity, the following table 2 illustrates the sequences of the antibodies 810D12 (Table 2a) and 816C12 (Table 2b), defined according to IMGT.

TABLE 2a

| Antibody | CDR numbering | Heavy chain | Light chain | SEQ ID NO. |
|---|---|---|---|---|
| 810D12 I-4893 | IMGT | CDR-H1 | | 1 |
| | | CDR-H2 | | 2 |
| | | CDR-H3 | | 3 |
| | | | CDR-L1 | 4 |
| | | | CDR-L2 | 5 |
| | | | CDR-L3 | 6 |
| | | variable domain | | 7 |
| | | | variable domain | 8 |

TABLE 2b

| Antibody | CDR numbering | Heavy chain | Light chain | SEQ ID NO. |
|---|---|---|---|---|
| 816C12 I-4894 | IMGT | CDR-H1 | | 11 |
| | | CDR-H2 | | 12 |
| | | CDR-H3 | | 13 |
| | | | CDR-L1 | 14 |
| | | | CDR-L2 | 15 |
| | | | CDR-L3 | 16 |
| | | variable domain | | 17 |
| | | | variable domain | 18 |

In one embodiment, the monoclonal antibody herein includes murine, chimeric and humanized antibody.

The first IGF-1R antibody can be derived from an hybridoma of murine origin filed within the French collection for microorganism cultures (CNCM, Pasteur Institute, Paris, France), said hybridoma being obtained by the fusion of Balb/C immunized mice splenocytes/lymphocytes and cells of the myeloma Sp 2/O—Ag 14 cell line. Said hybridoma can be selected from i) the hybridoma of murine origin deposited at the CNCM, Institut Pasteur, Paris, France, on Sep. 17, 2014, under the number I-4893 or ii) the hybridoma of murine origin deposited at the CNCM, Institut Pasteur, Paris, France, on Sep. 17, 2014, under the number I-4894.

The first IGF-1R monoclonal antibody, here referred as 810D12, or any antigen binding fragment thereof, being secreted by the said hybridoma I-4893 obviously may be used in the present invention.

The first IGF-1R monoclonal antibody, here referred as 816C12, or any antigen binding fragment thereof, being secreted by the said hybridoma I-4894 obviously may be used in the present invention.

In another embodiment, the said first IGF-1R antibody may be encoded by the following nucleotide sequences:
  i) SEQ ID No. 9 for the heavy chain variable domain and/or SEQ ID No. 10 for the light chain variable domain;
  ii) SEQ ID No. 19 for the heavy chain variable domain and/or SEQ ID No. 20 for the light chain variable domain.

Table 3 below summarizes the various nucleotide sequences concerning the antibody 810D12 (Table 3a) and the antibody 816C12 (Table 3b).

TABLE 3a

| Antibody | Heavy chain | Light chain | SEQ ID NO. |
|---|---|---|---|
| 810D12 I-4893 | variable domain | | 9 |
| | | variable domain | 10 |

TABLE 3b

| Antibody | Heavy chain | Light chain | SEQ ID NO. |
|---|---|---|---|
| 816C12 I-4894 | variable domain | | 19 |
| | | variable domain | 20 |

The use of the first IGF-1R antibody of the invention as biomarker is also disclosed. The methods may be used for detecting or diagnosing various hyperproliferative oncogenic disorders associated with expression of IGF-1R exemplified by, but not limited to, prostate cancer, osteosarcomas, lung cancer, breast cancer, endometrial cancer, glioblastoma, colon, cancer, gastric cancer, renal cancer, pancreas cancer, head and neck cancer or any other cancer associated with expression of IGF-1R. As would be recognized by one of ordinary skill in this art, the level of antibody expression associated with a particular disorder will vary depending on the nature and/or the severity of the pre-existing condition.

The IGF-1R status determination can be done by any method or technics known or currently used by the person skilled in the Art (generally based on the determination of the expression level of IGF-1R). Nevertheless, some non limitative examples are described below.

Stage determination has potential prognosis value and provides criteria for designing optimal therapy. Simpson et al., J. Clin. Oncology 18:2059 (2000). For example, treatment selection for solid tumors is based on tumor staging, which is usually performed using the Tumor/Node/Metastasis (TNM) test from the American Joint Committee on Cancer (AJCC). It is commonly acknowledged that, while this test and staging system provides some valuable information concerning the stage at which solid cancer has been diagnosed in the patient, it is imprecise and insufficient. In particular, it fails to identify the earliest stages of tumor progression.

In an embodiment, a method for determining in vitro or ex vivo the IGF-1R scoring of tumoral cells in a subject, may comprises the steps of:
  (a) contacting a biological sample from the said subject with the first IGF-1R antibody, or an antigen-binding fragment thereof, as above described;
  (b) quantifying by Fluorescence Activated Cell Sorting (FACS) or immunohistochemistry (IHC) the level of binding of the said first IGF-1R antibody, or an antigen-binding fragment thereof, to IGF-1R in the said biological sample; and
  (c) scoring the tumoral cells by comparing the quantified level obtained in step (b) to an appropriate scale based on two parameters which are the intensity of the staining and the percentage of positive cells.

In an embodiment, the first IGF-1R antibody is capable of binding IGF-1R when tissue samples are, formalin fixed-, formol substituted fixed-, Glyco-fixx fixed-, paraffin embedded and/or frozen.

Any conventional hazard analysis method may be used to estimate the prognostic value of IGF-1R. Representative analysis methods include Cox regression analysis, which is a semiparametric method for modeling survival or time-to-event data in the presence of censored cases (Hosmer and Lemeshow, 1999; Cox, 1972). In contrast to other survival analyses, e.g. Life Tables or Kaplan-Meyer, Cox allows the inclusion of predictor variables (covariates) in the models. Using a convention analysis method, e.g., Cox one may be able to test hypotheses regarding the correlation of IGF-1R expression status of in a primary tumor to time-to-onset of either disease relapse (disease-free survival time, or time to metastatic disease), or time to death from the disease (overall survival time). Cox regression analysis is also known as Cox proportional hazard analysis. This method is standard for testing the prognostic value of a tumor marker on patient survival time. When used in multivariate mode, the effect of several covariates are tested in parallel so that individual covariates that have independent prognostic value can be identified, i.e. the most useful markers. The term negative or positive "IGF-1R status" can also be referred as [IGF-1R (−)] or [IGF-1R (+)].

A sample may be "scored" during the diagnosis or monitoring of cancer. In its simplest form, scoring may be categorical negative or positive as judged by visual examination of samples by immunohistochemistry. More quantitative scoring involves judging the two parameters intensity of staining and the proportion of stained ("positive") cells that are sampled.

In an embodiment, to ensure standardization, samples may be scored for IGF-1R expression levels on different scales, most of them being based on an assessment of the intensity of the reaction product and the percentage of positive cells (Payne et al., Predictive markers in breast cancer—the present, Histopathology 2008, 52, 82-90).

In another embodiment, said scoring comprises using an appropriate scale based on the intensity of the staining and the percentage of positive cells.

As a first example, by analogy with the Quick Allred scoring for IHC assessment of oestrogen receptor and progesterone receptor, samples may be scored for IGF-1R expression levels on a global scale from 0 to 8 combining scores for intensity of reactivity and for the proportion of cells stained (Harvey J M, Clarck G M, Osborne C K, Allred D C; J. Clin. Oncol. 1999; 17; 1474-1481). More particularly, the first criteria of intensity of reactivity is scored on a scale from 0 to 3, 0 corresponding to "No reactivity" and 3 corresponding to "Strong reactivity". The second criteria of proportion reactive is scored on a scale from 0 to 5, 0 corresponding to "No reactivity" and 5 to "67-100% proportion reactive". The intensity of the reactivity score and the proportion reactive score are then summed to produce total score of 0 through 8. A total score of 0-2 is regarded as negative while a total score of 3-8 is regarded as positive.

According to this scale, the terms negative or positive "IGF-1R status" of tumors used in the present description refers to levels of expression of IGF-1R that correspond to scores 0-2 or 3-8 on the Allred scale, respectively.

Table 4 hereinafter illustrates the guidelines for interpreting IHC results according to Allred method.

TABLE 4

| Intensity of immunoreactivity | Score 1 | Proportion reactive | Score 2 |
|---|---|---|---|
| No reactivity | 0 | No reactivity | 0 |
| Weak reactivity | 1 | <1% | 1 |
| Moderate reactivity | 2 | 1-10% | 2 |
| Strong reactivity | 3 | 11-33% | 3 |
| — | | 34-66% | 4 |
| — | | 67-100% | 5 |

| Total Score (Score 1 + Score 2) | Interpretation |
|---|---|
| 0-2 | Negative |
| 3-8 | Positive |

According to the invention, the said appropriate scale may be a scale of 0 to 8 wherein no reactivity is scored 0, and a strong reactivity in a proportion of 67-100% proportion reactive is scored 8

In other words, it is described a process of determining in vitro or ex vivo the status of a tumor from a subject, wherein said process comprises the steps of (a) scoring a tumor from a subject according to the Allred scale; and (b) determining that the status of the tumor is [IGF-1R(+)] with an Allred score of 3 to 8; or (c) determining that the status of the tumor is [IGF-1R(−)] with an Allred score of 0 to 2.

In a particular aspect of the invention, a tumor is [IGF-1R (+)] with an Allred score of 3.

In a particular aspect of the invention, a tumor is [IGF-1R (+)] with an Allred score of 4.

In a particular aspect of the invention, a tumor is [IGF-1R (+)] with an Allred score of 5.

In a particular aspect of the invention, a tumor is [IGF-1R (+)] with an Allred score of 6.

In a particular aspect of the invention, a tumor is [IGF-1R (+)] with an Allred score of 7.

In a particular aspect of the invention, a tumor is [IGF-1R (+)] with an Allred score of 8.

In another particular aspect of the invention, a tumor is [IGF-1R (+)] with an Allred score of 3 to 8.

Another particular method herein described for determining in vitro or ex vivo the IGF-1R status of tumoral cells in a subject, is characterized in that it comprises the steps of:
(a) scoring IGF-1R tumoral cells as above described; and
(b) determining that the IGF-1R status of tumoral cells is [IGF-1R(+)] with a score of 3 to 8; or
(c) determining that the IGF-1R status of tumoral cells is [IGF-1R(−)] with a score of 0 to 2.

As a second example, by analogy with the conventional scoring for IHC assessment of HER-2 receptor for example, samples may be scored for IGF-1R expression levels on a somewhat simpler scoring method integrating the intensity of staining (preferentially membranous staining) and the proportion of cells that display staining into a combined scale from 0 to 3+.

In this scale, referred as the simplified scale, 0 and 1+ are negative whereas 2+ and 3+ represents positive staining. Nevertheless, scores 1+-3+ can be recoded as positive because each positive score may be associated with significantly higher risk for relapse and fatal disease when compared to score 0 (negative), but increasing intensity among the positive scores may provide additional risk reduction.

Generally speaking, the terms negative or positive "IGF-1R status" of tumors used in the present description refers to levels of expression of IGF-1R that correspond to scores 0-1+ or 2+-3+ on the simplified scale, respectively. Only complete circumferential membranous reactivity of the invasive tumor should be considered and often resembled a "chicken wire" appearance. Under current guidelines, samples scored as borderline (score of 2+ or 3+) for IGF-1R are required to undergo further assessment. The IHC analysis should be rejected, and either repeated or tested by FISH or any other method if, as non limitative example, controls are not as expected, artifacts involve most of the sample and the sample has strong membranous positivity of normal breast ducts (internal controls) suggesting excessive antigen retrieval.

For more clarity, table 5 hereinafter summarizes these parameters.

TABLE 5

| IGF-1R status | IHC description |
|---|---|
| 0 | No reactivity or membranous reactivity in less than 10% of tumour cells |
| 1+ | Faint/barely perceptible membranous reactivity is detected in more than 10% of tumour cells. The cells are immunoreactive only in part of the membrane. |
| 2+ | Weak to moderate complete membranous reactivity is seen in more than 10% of tumour cells. |
| 3+ | Strong complete reactivity is seen in more than 10% of tumour cells. |

The appropriate scale may be a scale of 0 to 3+ wherein no membranous reactivity of tumor cells is scored 0 and strong complete reactivity in more than 10% of tumor cells is scored 3+.

In more details, as above described, said appropriate scale is a scale of 0 to 3 wherein no membranous reactivity of tumor cells is scored 0; faint perceptible membranous reactivity in more than 10% of tumor cells is scored 1+; weak to moderate complete membranous reactivity in more than 10% of tumor cells is scored 2+; and strong complete reactivity in more than 10% of tumor cells is scored 3+.

In other words, it is described a process of determining in vitro or ex vivo the status of a tumor from a subject, wherein said process comprises the steps of (a) scoring a tumor from a subject according to the simplified scale as above described; and (b) determining that the status of the tumor is [IGF-1R(+)] with a score of 2+ or 3+; or (c) determining that the status of the tumor is [IGF-1R(−)] with a score of 0 or 1+.

In a particular aspect of the invention, a tumor is [IGF-1R (+)] with a score of 2+.

In a particular aspect of the invention, a tumor is [IGF-1R (+)] with a score of 3+.

In another particular aspect of the invention, a tumor is [IGF-1R (+)] with a score of 2+ or 3+.

In another embodiment, the method for determining in vitro or ex vivo the IGF-1R status tumoral cells in a subject may comprise the steps of:

(a) scoring IGF-1R tumoral cells from the said subject according to the method described before; and (b) determining that the IGF-1R status of tumoral cells is [IGF-1R(+)] with a score of $2^+$ or 3+; or (c) determining that the IGF-1R status of tumoral cells is [IGF-1R(−)] with a score of 0 or $1^+$.

Generally, the results of a test or assay can be presented in any of a variety of formats. The results can be presented qualitatively. For example, the test report may indicate only whether or not a particular polypeptide was detected, perhaps also with an indication of the limits of detection. The results may be displayed as semi-quantitative. For example, various ranges may be defined, and the ranges may be assigned a score (e.g., 0 to 3+ or 0 to 8 depending on the used scale) that provides a certain degree of quantitative information. Such a score may reflect various factors, e.g., the number of cells in which IGF-1R is detected, the intensity of the signal (which may indicate the level of expression of IGF-1R or IGF-1R-bearing cells), etc. The results may be displayed in a quantitative way, e.g., as a percentage of cells in which IGF-1R is detected, as a protein concentration, etc.

As will be appreciated by one of ordinary skill in the art, the type of output provided by a test will vary depending upon the technical limitations of the test and the biological significance associated with detection of the polypeptide. For example, in the case of certain polypeptides a purely qualitative output (e.g., whether or not the polypeptide is detected at a certain detection level) provides significant information. In other cases a more quantitative output (e.g., a ratio of the level of expression of the polypeptide in the sample being tested versus the normal level) is necessary.

In another aspect of the invention, the IGF-1R status determination may be done for the monitoring of IGF-1R expression in response to the administration of a therapy targeting the IGF-1R pathway. Such a monitoring can be very useful when the said therapy triggers the downregulation and/or the degradation of IGF-1R.

It is also an object of the invention to describe a method for determining whether an oncogenic disorder is susceptible to treatment with an IGF-1R targeting therapy, said method comprising the steps of:

(a) determining in vitro or ex vivo the IGF-1R status of tumoral cells of a subject according to the method above described, and (b) determining that, if the IGF-1R status of tumoral cells is IGF-1R(+), the oncogenic disorder is susceptible to treatment with an antibody drug targeting the IGF-1R pathway.

In particular, monitoring IGF-1R expression on the cell surface could be a critical tool for evaluating the efficacy of the treatment during clinical trials and "personalized" therapies.

An increase or a decrease in the level of IGF-1R is indicative of the evolution of a cancer associated with IGF-1R. Thus, by measuring an increase in the number of cells expressing IGF-1R or changes in the concentration of IGF-1R present in various tissues or cells, it is possible to determine whether a particular therapeutic regime aimed at ameliorating a malignancy associated with IGF-1R is effective.

Another object of the invention is also a method for determining in vitro or ex vivo the efficacy of a therapeutic regimen designed to alleviate an oncogenic disorder associated with IGF-1R in a subject suffering from said disorder, said method comprising the steps of:

(a) determining a first expression level of IGF-1R as above described in a first biological sample, said first biological sample corresponding to first time point of the said treatment;

(b) determining a second expression level of IGF-1R as above described in a second biological sample, said second biological sample corresponding to a second, later time point of the said treatment;

(c) calculating the ratio of the said first expression level obtained in step (a) to the said second expression level obtained in step (b); and (d) determining that the efficacy of said therapeutic regime is high when the ratio of step (c) is greater than 1; or determining that the efficacy of said therapeutic regime is low when the ratio of step (c) is inferior or equal to 1.

In a preferred embodiment, the said therapeutic regime designed to alleviate an oncogenic disorder associated with IGF-1R in a subject suffering from said disorder includes the administration of a therapy targeting the IGF-1R pathway to the said subject.

It is also an object of the invention to provide an in vivo method of imaging an oncogenic disorder associated with expression of IGF-1R. Such a method is useful for localizing in vivo the tumoral cells, as well as monitoring their invasiveness. Likewise, the method is useful for monitoring the progression and/or the response to treatment in patients previously diagnosed with a IGF-1R-mediated cancer.

An embodiment is a method for detecting the location of IGF-1R expressing tumoral cells in a subject, said method comprising the steps of:

a) administering the first IGF-1R antibody, or a antigen-binding fragment thereof, to the subject; and b) detecting binding of said first IGF-1R antibody, wherein said binding indicates the presence of the tumoral cells.

As for the detection of the presence of an expressing tumor, many techniques known by the person skilled in the art can be used. Nevertheless, preferred means are IHC and FACS.

III—The Antibody Drug Conjugate (ADC)

III.1—the Second IGF-1R Antibody (Ab)

In an embodiment, the second IGF-1R antibody Ab consists of a recombinant antibody.

In another embodiment, the second IGF-1R antibody Ab consists of a chemically synthesized antibody.

In an embodiment of the present application, the epitope of the second IGF-1R antibody Ab is preferentially localized into the extracellular domain of the human IGF-1R (also referred as IGF-1R ECD).

In a particular embodiment, the second IGF-1R antibody Ab, or any antigen binding fragment thereof, is capable of binding to IGF-1R with an $EC_{50}$ comprised between $10 \times 10^{-10}$ to $1 \times 10^{-10}$, and more preferentially between $8 \times 10^{-10}$ to $2 \times 10^{-10}$.

As a preferred embodiment, the $EC_{50}$, determined in the present invention, characterizes the potency of antibody to bind on the IGF-1R ECD exposed on human tumor cells. The $EC_{50}$ parameter is determined using FACS analysis. The $EC_{50}$ parameter reflects the antibody concentration for which 50% of the maximal binding on the human IGF-IR expressed on human tumor cells is obtained. Each $EC_{50}$ value was calculated as the midpoint of the dose response curve using a four-parameter regression curve fitting program (Prism Software). This parameter has been selected as to be representative of physiological/pathological conditions.

The competition for binding to IGF-1R can be determined by any methods or techniques known by the person skilled in the art such as, without limitation, radioactivity, Biacore, ELISA, Flow cytometry, etc. As "which competes for binding to IGF-1R" it is meant a competition of at least 20%, preferentially at least 50% and more preferentially at least 70%.

The determination of the binding to the same epitope can be determined by any methods or techniques known by the person skilled in the art such as, without limitation, radioactivity, Biacore, ELISA, Flow cytometry, etc. As "which bind to the same epitope of IGF-1R, it is meant a competition of at least 20%, preferentially at least 50% and more preferentially at least 70%.

As above mentioned, and contrary to the general knowledge, the present invention focuses on specific IGF-1R antibodies presenting a high ability to be internalized following IGF-1R binding. As used herein, an antibody that "is internalized" or that "internalized" (the two expressions being similar) is one that is taken up by (meaning it "enters") the cell upon binding to IGF-1R on a mammalian cell. Such an antibody is interesting as part of the ADC, so it addresses or directs the linked cytotoxic into the targeted cancer cells. Once internalized the cytotoxic triggers cancer cell death.

Surprisingly, the second IGF-1R antibodies Ab according to the invention are all presenting the same sequences for the CDR-H2, CDR-H3 and CDR-L2, the other 3 CDRs being different. This observation seems coherent as it is part of the general knowledge that, regarding the binding specificity of an antibody, the CDR-H3 is described as being the most important and the most implicated with the recognition of the epitope.

Important keys to success with ADC therapy are thought to be the target antigen specificity and the internalization of the antigen-antibody complexes into the cancer cells. Obviously non-internalizing antigens are less effective than internalizing antigens to delivers cytotoxic agents. Internalization processes are variable across antigens and depend on multiple parameters that can be influenced by antibodies.

In the ADC, the cytotoxic confers the cytotoxic activity and the used antibody is responsible for the specificity against cancer cells, as well as a vector for entering within the cells to correctly address the cytotoxic. Thus to improve the ADC, the antibody can exhibit high ability to internalize into the targeted cancer cells. The efficiency of the antibody mediated internalisation differs significantly depending on the epitope targeted. Selection of potent internalizing IGF-1R antibodies requires various experimental data studying not only IGF-1R downregulation but also following IGF-1R antibody internalization into the cells.

In an embodiment, the internalization of the second IGF-1R Ab can be evaluated by immunofluorescence or FACS (Flow Cytometry) (as exemplified hereinafter in the present application) or any method or process known by the person skilled in the art specific for the internalization mechanism. In a preferred embodiment, the antibody od the ADC according to the invention can induce internalization after binding to IGF-1R of at least 30%, preferentially 50% and more preferentially 80%.

The complex IGF-1R/second IGF-1R antibody Ab is internalized after binding of the second IGF-1R antibody Ab to the ECD of said IGF-1R, and a reduction in the quantity of IGF-1R at the surface of the cells is induced. This reduction can be quantified by any method known by the person skilled in the art such as non limitative examples western-blot, FACS, and immunofluorescence.

In one embodiment, this reduction, thus reflecting the internalization, can be preferably measured by FACS and expressed as the difference or delta between the Mean Fluorescence Intensity (MFI) measured at 4° C. with the MFI measured at 37° C. after 4 hours incubation with the second IGF-1R antibody Ab.

As non limitative example, this delta is determined based on MFIs obtained with untreated cells and cells treated with the second IGF-1R antibody Ab using i) breast cancer cells MCF7 after a 4 hour incubation period with the second IGF-1R antibody Ab and ii) a secondary antibody labelled with Alexa488. This parameter is defined as calculated with the following formula: $\Delta(MFI_{4° C.}-MFI_{37° C.})$.

This difference between MFIs reflects the IGF-1R downregulation as MFIs are proportional to IGF-1R expressed on the cell-surface.

In an advantageous aspect, the antibodies consist of antibodies triggering a $\Delta(MFI_{4° C.}-MFI_{37° C.})$ on MCF-7 of at least 280, preferably of at least 400.

In more details, the above mentioned delta can be measured according to the following process, which must be considered as an illustrative and non limitative example:
 a) Treating and incubating tumor cells of interest with the second IGF-1R antibody Ab in either cold (4° C.) or warm (37° C.) complete culture medium;
 b) Treating the treated cells of step a) and, in parallel, untreated cells with a secondary antibody;
 c) Measuring the MFI (representative of the quantity of IGF-1R present at the surface) for the treated and the non treated cells with a secondary labeled antibody capable of binding to the antibody of the invention; and
 d) Calculating the delta as the subtraction of the MFI obtained with the treated cells from the MFI obtained with the non treated cells.

From this delta MFI, an internalization percentage can be determined as: $100 \times (MFI_{4° C.}-MFI_{37° C.})/MFI_{4° C.}$ The second IGF-1R antibodies Ab of the ADC, preferably, on MCF7 an internalization percentage comprised between 50% and 99%, 70% and 90%, preferentially between 75% and 87%.

A particular advantage of the second IGF-1R antibodies Ab relies on their rate of internalization.

It is generally known that, for an ADC, it is desirable that the used antibodies exhibit a rapid rate of internalization, preferably within 24 hours from administration of the antibody and, more preferably within 12 hours and, even more preferably within 6 hours.

In the present invention, the internalization rate, also referred as cell surface bound antibody decrease or cell surface antibody decay, is expressed as t½ (half life) and corresponds as the time necessary to obtain a decrease of 50% of the ΔMFI (this aspect will be clearly understood regarding the following examples).

A particular advantage is that the second IGF-1R antibodies Ab have a t½ comprised between 5 and 25 minutes, and preferentially between 10 and 20 minutes.

The second IGF-1R antibody Ab, or any antigen binding fragment thereof, may comprise three heavy chain CDRs with CDR-H2 of sequence SEQ ID No. 22 and CDR-H3 of sequence SEQ ID No. 23, and three light chain CDRs with CDR-L2 of sequence SEQ ID No. 25.

The second IGF-1R antibody Ab, or any antigen binding fragment thereof, may comprise the three heavy chain CDRs of sequences SEQ ID Nos. 21, 22 and 23 and the three light chain CDRs of sequences SEQ ID Nos. 24, 25 and 26.

In an embodiment, the second IGF-1R antibody Ab, or any antigen binding fragment thereof, may comprise the three heavy chain CDRs comprising or consisting of the sequences SEQ ID Nos. 21, 22 and 23, or any sequence exhibiting at least 80%, preferably 85%, 90%, 95% and 98% identity with SEQ ID Nos. 21, 22 or 23; and the three light chain CDRs comprising or consisting of the sequences SEQ ID Nos. 24, 25 and 26, or any sequence exhibiting at least 80%, preferably 85%, 90%, 95% and 98% identity with SEQ ID Nos. 24, 25 or 26.

In another embodiment, the second IGF-1R antibody Ab, or any antigen binding fragment thereof, comprises the three heavy chain CDRs comprising the sequences SEQ ID Nos. 21, 22 and 23; and the three light chain CDRs comprising the sequences SEQ ID Nos. 24, 25 and 26.

According to a particular aspect, the second IGF-1R antibody Ab, does not bind to the Insulin receptor (IR). This aspect is of interest as the antibody herein described will not have any negative impact on the IR, meaning the Insulin metabolism.

In another embodiment, still another advantageous aspect of the second IGF-1R antibody Ab is capable of binding not only to the human IGF-1R but also to the monkey IGF-1R, and more particularly to the cynomolgus IGF-1R. This aspect is also of interest as it will facilitate the toxicity assessment required for clinical trials.

In still another embodiment, the second IGF-1R antibody Ab consists of a monoclonal antibody.

The second IGF-1R antibody Ab is preferably derived from an hybridoma of murine origin filed within the French collection for microorganism cultures (CNCM, Pasteur Institute, 25 rue du Docteur Roux, 75724 Paris Cedex 15, France), said hybridoma being obtained by the fusion of Balb/C immunized mice splenocytes/lymphocytes and cells of the myeloma Sp 2/O—Ag 14 cell line.

Said murine hybridoma may be selected from the hybridoma I-4757, I-4773, I-4775, I-4736 and I-4774 deposited at the CNCM, Institut Pasteur France on the 30 May 2013, 26 Jun. 2013, 26 Jun. 2013, 24 Apr. 2013 and 26 Jun. 2013, respectively.

In a particular aspect, the second IGF-1R antibody Ab may be an antibody selected from i) an antibody produced by the hybridoma I-4757, I-4773, I-4775, I-4736 or I-4774 deposited at the CNCM, Institut Pasteur France on the 30 May 2013, 26 Jun. 2013, 26 Jun. 2013, 24 Apr. 2013 and 26 Jun. 2013, respectively, or ii) an antibody which competes for binding to IGF-1R with the antibody of i); or iii) an antibody which binds to the same epitope of IGF-1R as does the antibody of i).

In an embodiment, the second IGF-1R antibody Ab of the invention consists of a murine antibody, then referred as m[name of the antibody].

In an embodiment, the second IGF-1R antibody Ab consists of a chimeric antibody, then referred as c[name of the antibody].

In an embodiment, the second IGF-1R antibody Ab consists of a humanized antibody, then referred as hz[name of the antibody].

For the avoidance of doubt, in the following specification, the expressions "IGF-1R antibody" and "[name of the antibody]" are similar and include (without contrary specification) the murine, the chimeric and the humanized versions of the said IGF-1R antibody or of the said "[name of the antibody]". When necessary, the prefix m- (murine), c-(chimeric) or hz-(humanized) is used.

For more clarity, the following table 6a illustrates the CDR sequences, defined according to IMGT, for the preferred second IGF-1R antibodies Ab. Any other antibody presenting the same characteristics may be comprised in the scope of the present invention.

TABLE 6a

|  | Heavy chain | Light chain | SEQ ID No. |
| --- | --- | --- | --- |
| Consensus | CDR-H1 |  | 21 |
|  | CDR-H2 |  | 22 |
|  | CDR-H3 |  | 23 |
|  |  | CDR-L1 | 24 |
|  |  | CDR-L2 | 25 |
|  |  | CDR-L3 | 26 |
| 208F2 | CDR-H1 |  | 27 |
|  | CDR-H2 |  | 22 |
|  | CDR-H3 |  | 23 |
|  |  | CDR-L1 | 29 |
|  |  | CDR-L2 | 25 |
|  |  | CDR-L3 | 31 |
| 212A11 | CDR-H1 |  | 27 |
|  | CDR-H2 |  | 22 |
|  | CDR-H3 |  | 23 |
|  |  | CDR-L1 | 30 |
|  |  | CDR-L2 | 25 |
|  |  | CDR-L3 | 31 |
| 214F8 & 213B10 | CDR-H1 |  | 27 |
|  | CDR-H2 |  | 22 |
|  | CDR-H3 |  | 23 |
|  |  | CDR-L1 | 29 |
|  |  | CDR-L2 | 25 |
|  |  | CDR-L3 | 32 |
| 219D6 | CDR-H1 |  | 28 |
|  | CDR-H2 |  | 22 |
|  | CDR-H3 |  | 23 |
|  |  | CDR-L1 | 29 |
|  |  | CDR-L2 | 25 |
|  |  | CDR-L3 | 31 |

It will be obvious for the Person skilled in the art that any combination of 6 CDRs as above described should be considered as part of the present invention.

As can be observed from this table 6a, all the second IGF-1R antibodies Ab herein described have the same sequences for the CDR-H2, CDR-H3 and CDR-L2, this property being of particular interest as above described.

In a given aspect, the second IGF-1R antibody Ab is a murine (m) antibody.

In another aspect, the second IGF-1R antibody Ab is a chimeric (c) antibody.

A chimeric antibody is one containing a natural variable region (light chain and heavy chain) derived from an antibody of a given species in combination with constant regions of the light chain and the heavy chain of an antibody of a species heterologous to said given species.

The chimeric antibodies can be prepared by using the techniques of recombinant genetics. For example, the chimeric antibody could be produced by cloning recombinant DNA containing a promoter and a sequence coding for the variable region of a nonhuman monoclonal antibody, notably murine, and a sequence coding for heterologous species antibody constant region, preferably human. A chimeric antibody of the ADC according to the invention coded by one such recombinant gene could be, for example, a mouse-human chimera, the specificity of this antibody being determined by the variable region derived from the murine DNA and its isotype determined by the constant region derived from human DNA.

For more clarity, the following table 6b illustrates non limitative examples of sequences of the VH and VL (variable domain and full length) for different variants of the chimeric second IGF-1R antibodies.

TABLE 6b

| | Heavy Chain | Light chain | SEQ ID No. |
|---|---|---|---|
| c208F2 | Variable domain (VH) | | 63 |
| | | Variable domain (VL) | 68 |
| | Full length | | 73 |
| | | Full length | 78 |
| c212A11 | Variable domain (VH) | | 64 |
| | | Variable domain (VL) | 69 |
| | Full length | | 74 |
| | | Full length | 79 |
| c214F8 | Variable domain (VH) | | 65 |
| | | Variable domain (VL) | 70 |
| | Full length | | 75 |
| | | Full length | 80 |
| c219D6 | Variable domain (VH) | | 66 |
| | | Variable domain (VL) | 71 |
| | Full length | | 76 |
| | | Full length | 81 |
| c213B10 | Variable domain (VH) | | 67 |
| | | Variable domain (VL) | 72 |
| | Full length | | 77 |
| | | Full length | 82 |

In still another aspect, the second IGF-1R antibody Ab is a humanized antibody.

"Humanized antibodies" means an antibody that contains CDR regions derived from an antibody of nonhuman origin, the other parts of the antibody molecule being derived from one (or several) human antibodies. In addition, some of the skeleton segment residues (called FR) can be modified to preserve binding affinity.

The humanized antibodies or fragments of same can be prepared by techniques known to a person skilled in the art. Such humanized antibodies are preferred for their use in methods involving in vitro diagnoses or preventive and/or therapeutic treatment in vivo. Other humanization techniques, also known to a person skilled in the art, such as, for example, the "CDR grafting" technique described by PDL in patents EP 0 451 216, EP 0 682 040, EP 0 939 127, EP 0 566 647 or U.S. Pat. Nos. 5,530,101, 6,180,370, 5,585,089 and 5,693,761. U.S. Pat. Nos. 5,639,641 or 6,054,297, 5,886,152 and 5,877,293 can also be cited.

As a particular embodiment of the invention, but not limitative, it is herein described a second IGF-1R antibody Ab consisting of the hz208F2. Such humanization can also be applied to the other antibodies part of the present invention.

In an embodiment, the second IGF-1R antibody Ab comprises a heavy chain variable domain (VH) having:
  i) the CDR-H1, CDR-H2 and CDR-H3 of sequences SEQ ID Nos. 27, 22 and 23, respectively, and
  ii) the FR1, FR2 and FR3 derived from the human germline IGHV1-46*01 (SEQ ID No. 86), and
  iii) the FR4 derived from the human germline IGHJ4*01 (SEQ ID No. 88).

In a preferred embodiment, the second IGF-1R antibody Ab comprises a light chain variable domain (VL) having:
  i) the CDR-L1, CDR-L2 and CDR-L3 of sequences SEQ ID Nos. 29, 25 and 31, respectively, and
  ii) the FR1, FR2 and FR3 derived from the human germline IGKV1-39*01 (SEQ ID No. 87), and
  iii) the FR4 derived from the human germline IGKJ4*01 (SEQ ID No. 89).

In a preferred, but not limitative, embodiment of the invention, the second IGF-1R antibody Ab comprises:
  a) a heavy chain having CDR-H1, CDR-H2 and CDR-H3 of sequences SEQ ID Nos. 27, 22 and 23, respectively, and FR1, FR2 and FR3 derived from the human germline IGHV1-46*01 (SEQ ID No. 86), and the FR4 derived from the human germline IGHJ4*01 (SEQ ID No. 88); and
  b) a light chain having CDR-L1, CDR-L2 and CDR-L3 of sequences SEQ ID Nos. 29, 25 and 31, respectively, and FR1, FR2 and FR3 derived from the human germline IGKV1-39*01 (SEQ ID No. 87), and the FR4 derived from the human germline IGKJ4*01 (SEQ ID No. 89).

In another embodiment, the second IGF-1R antibody Ab is selected from:
  a) an antibody comprising a heavy chain variable domain of sequence selected from SEQ ID Nos. 33, 39, 41, 43, 45, 47, 49, 51, 53, 55, 57 and 59 or any sequence with at least 80%, preferably 85%, 90%, 95% and 98% identity with SEQ ID No. 33, 39, 41, 43, 45, 47, 49, 51, 53, 55, 57 or 59; and the three light chain CDRs of sequences SEQ ID Nos. 29, 25 and 31;
  b) an antibody comprising a light chain variable domain of sequence selected from SEQ ID Nos. 34, 37 and 60 or any sequence with at least 80%, preferably 85%, 90%, 95% and 98% identity with SEQ ID Nos. 34, 37 or 60; and the three heavy chain CDRs of sequences SEQ ID Nos. 27, 22 and 23; and
  c) an antibody comprising a heavy chain variable domain of sequence selected from SEQ ID Nos. 33, 39, 41, 43, 45, 47, 49, 51, 53, 55, 57 and 59 or any sequence with at least 80%, preferably 85%, 90%, 95% and 98% identity with SEQ ID Nos. 33, 39, 41, 43, 45, 47, 49, 51, 53, 55 or 57; and a light chain variable domain of sequence selected from SEQ ID Nos. 34, 37 and 60 or any sequence with at least 80%, preferably 85%, 90%, 95% and 98% identity with SEQ ID Nos. 34, 37 or 60.

In another embodiment, the second IGF-1R antibody Ab is selected from:
  a) an antibody comprising a heavy chain of sequence selected from SEQ ID Nos. 33, 39, 41, 43, 45, 47, 49, 51, 53, 55 and 57, or any sequence exhibiting at least 80% identity with SEQ ID No. 33, 39, 41, 43, 45, 47, 49, 51, 53, 55 or 57, and a light chain of sequence SEQ ID No. 34 or any sequence exhibiting at least 80% identity with SEQ ID No. 34;
  b) an antibody comprising a heavy chain of sequence selected from SEQ ID Nos. 33, 41, 45 and 55 or any sequence exhibiting at least 80% identity with SEQ ID No. 33, 41, 45 or 55 and a light chain of sequence SEQ ID No. 37, or any sequence exhibiting at least 80% identity with SEQ ID No. 37; and
  c) an antibody comprising a heavy chain of sequence SEQ ID No. 59 or any sequence exhibiting at least 80% identity with SEQ ID No. 59 and a light chain of sequence SEQ ID No. 60, or any sequence exhibiting at least 80% identity with SEQ ID No. 60.

Still in another embodiment, the second IGF-1R antibody Ab is an antibody selected from:

a) an antibody comprising or consisting of a heavy chain of sequence SEQ ID No. 35 or any sequence exhibiting at least 80% identity with SEQ ID No. 35 and a light chain of sequence SEQ ID No. 36 or any sequence exhibiting at least 80% identity with SEQ ID No. 36;

b) an antibody comprising or consisting of a heavy chain of sequence SEQ ID No. 35 or any sequence exhibiting at least 80% identity with SEQ ID No. 35 and a light chain of sequence SEQ ID No. 38 or any sequence exhibiting at least 80% identity with SEQ ID No. 38;

c) an antibody comprising or consisting of a heavy chain of sequence SEQ ID No. 40 or any sequence exhibiting at least 80% identity with SEQ ID No. 40 and a light chain of sequence SEQ ID No. 36 or any sequence exhibiting at least 80% identity with SEQ ID No. 36;

d) an antibody comprising or consisting of a heavy chain of sequence SEQ ID No. 42 or any sequence exhibiting at least 80% identity with SEQ ID No. 42 and a light chain of sequence SEQ ID No. 36 or any sequence exhibiting at least 80% identity with SEQ ID No. 36;

e) an antibody comprising or consisting of a heavy chain of sequence SEQ ID No. 42 or any sequence exhibiting at least 80% identity with SEQ ID No. 42 and a light chain of sequence SEQ ID No. 38 or any sequence exhibiting at least 80% identity with SEQ ID No. 38;

f) an antibody comprising or consisting of a heavy chain of sequence SEQ ID No. 44 or any sequence exhibiting at least 80% identity with SEQ ID No. 44 and a light chain of sequence SEQ ID No. 36 or any sequence exhibiting at least 80% identity with SEQ ID No. 36;

g) an antibody comprising or consisting of a heavy chain of sequence SEQ ID No. 46 or any sequence exhibiting at least 80% identity with SEQ ID No. 46 and a light chain of sequence SEQ ID No. 36 or any sequence exhibiting at least 80% identity with SEQ ID No. 36;

h) an antibody comprising or consisting of a heavy chain of sequence SEQ ID No. 46 or any sequence exhibiting at least 80% identity with SEQ ID No. 46 and a light chain of sequence SEQ ID No. 38 or any sequence exhibiting at least 80% identity with SEQ ID No. 38;

i) an antibody comprising or consisting of a heavy chain of sequence SEQ ID No. 48 or any sequence exhibiting at least 80% identity with SEQ ID No. 48 and a light chain of sequence SEQ ID No. 36 or any sequence exhibiting at least 80% identity with SEQ ID No. 36;

j) an antibody comprising or consisting of a heavy chain of sequence SEQ ID No. 50 or any sequence exhibiting at least 80% identity with SEQ ID No. 50 and a light chain of sequence SEQ ID No. 36 or any sequence exhibiting at least 80% identity with SEQ ID No. 36;

k) an antibody comprising or consisting of a heavy chain of sequence SEQ ID No. 52 or any sequence exhibiting at least 80% identity with SEQ ID No. 52 and a light chain of sequence SEQ ID No. 36 or any sequence exhibiting at least 80% identity with SEQ ID No. 36;

l) an antibody comprising or consisting of a heavy chain of sequence SEQ ID No. 54 or any sequence exhibiting at least 80% identity with SEQ ID No. 54 and a light chain of sequence SEQ ID No. 36 or any sequence exhibiting at least 80% identity with SEQ ID No. 36;

m) an antibody comprising or consisting of a heavy chain of sequence SEQ ID No. 56 or any sequence exhibiting at least 80% identity with SEQ ID No. 56 and a light chain of sequence SEQ ID No. 36 or any sequence exhibiting at least 80% identity with SEQ ID No. 36;

n) an antibody comprising or consisting of a heavy chain of sequence SEQ ID No. 56 or any sequence exhibiting at least 80% identity with SEQ ID No. 56 and a light chain of sequence SEQ ID No. 38 or any sequence exhibiting at least 80% identity with SEQ ID No. 38;

o) an antibody comprising or consisting of a heavy chain of sequence SEQ ID No. 58 or any sequence exhibiting at least 80% identity with SEQ ID No. 58 and a light chain of sequence SEQ ID No. 36 or any sequence exhibiting at least 80% identity with SEQ ID No. 36; and p) an antibody comprising or consisting of a heavy chain of sequence SEQ ID No. 61 or any sequence exhibiting at least 80% identity with SEQ ID No. 61 and a light chain of sequence SEQ ID No. 62 or any sequence exhibiting at least 80% identity with SEQ ID No. 62.

In other words, the invention relates to a method wherein the second IGF-1R antibody Ab is an antibody comprising:

a) a heavy chain of sequence selected from SEQ ID Nos. 35, 40, 42, 44, 46, 48, 50, 52, 54, 56, 58 and 61, or any sequence with at least 80% identity with SEQ ID Nos. 35, 40, 42, 44, 46, 48, 50, 52, 54, 56, 58 or 61; and b) a light chain of sequence selected from SEQ ID Nos. 36, 38 and 62 or any sequence with at least 80% identity with SEQ ID Nos. 36, 38 and 62.

For more clarity, the following table 6c illustrates non limitative examples of sequences of the VH and VL (variable domain and full length) for different variants of the humanized antibody hz208F2.

TABLE 6c

|  | Heavy Chain | Light chain | SEQ ID No. |
|---|---|---|---|
| hz208F2 H037/L018 | Variable domain (VH) |  | 33 |
|  |  | Variable domain (VL) | 34 |
|  | Full length |  | 35 |
|  |  | Full length | 36 |
| Hz208F2 H037/L021 | Variable domain (VH) |  | 33 |
|  |  | Variable domain (VL) | 37 |
|  | Full length |  | 35 |
|  |  | Full length | 38 |
| Hz208F2 H047/L018 | Variable domain (VH) |  | 39 |
|  |  | Variable domain (VL) | 34 |
|  | Full length |  | 40 |
|  |  | Full length | 36 |
| Hz208F2 H049/L018 | Variable domain (VH) |  | 41 |
|  |  | Variable domain (VL) | 34 |
|  | Full length |  | 42 |
|  |  | Full length | 36 |
| Hz208F2 H049/L021 | Variable domain (VH) |  | 41 |
|  |  | Variable domain (VL) | 37 |
|  | Full length |  | 42 |
|  |  | Full length | 38 |
| Hz208F2 H051/L018 | Variable domain (VH) |  | 43 |
|  |  | Variable domain (VL) | 34 |
|  | Full length |  | 44 |
|  |  | Full length | 36 |
| Hz208F2 H052/L018 | Variable domain (VH) |  | 45 |
|  |  | Variable domain (VL) | 34 |
|  | Full length |  | 46 |
|  |  | Full length | 36 |
| Hz208F2 H052/L021 | Variable domain (VH) |  | 45 |
|  |  | Variable domain (VL) | 37 |
|  | Full length |  | 46 |
|  |  | Full length | 38 |

TABLE 6c-continued

| Heavy Chain | Light chain | | SEQ ID No. |
|---|---|---|---|
| Hz208F2 H057/L018 | Variable domain (VH) | | 47 |
| | Variable domain (VL) | | 34 |
| | Full length | | 48 |
| | | Full length | 36 |
| Hz208F2 H068/L018 | Variable domain (VH) | | 49 |
| | Variable domain (VL) | | 34 |
| | Full length | | 50 |
| | | Full length | 36 |
| Hz208F2 H070/L018 | Variable domain (VH) | | 51 |
| | Variable domain (VL) | | 34 |
| | Full length | | 52 |
| | | Full length | 36 |

TABLE 6c-continued

| Heavy Chain | Light chain | | SEQ ID No. |
|---|---|---|---|
| Hz208F2 H071/L018 | Variable domain (VH) | | 53 |
| | Variable domain (VL) | | 34 |
| | Full length | | 54 |
| | | Full length | 36 |
| Hz208F2 H076/L018 | Variable domain (VH) | | 55 |
| | Variable domain (VL) | | 34 |
| | Full length | | 56 |
| | | Full length | 36 |
| Hz208F2 H076/L021 | Variable domain (VH) | | 55 |
| | Variable domain (VL) | | 37 |
| | Full length | | 56 |
| | | Full length | 38 |
| Hz208F2 H077/L018 | Variable domain (VH) | | 57 |
| | Variable domain (VL) | | 34 |
| | Full length | | 58 |
| | | Full length | 36 |
| hz208F2 H026/L024 | Variable domain (VH) | | 59 |
| | Variable domain (VL) | | 60 |
| | Full length | | 61 |
| | | Full length | 62 |

III-2—the Drug (D)

The drug moiety D can be selected from alkylating agents, anti-metabolites, anti-tumor antibiotics, mitotic inhibitors, chromatin function inhibitors, anti-angiogenesis agents, anti-estrogens, anti-androgens, chelating agents, Iron absorption stimulant, Cyclooxygenase inhibitors, Phosphodiesterase inhibitors, DNA inhibitors, DNA synthetis inhibitors, Apopstotis stimulants, Thymidylate inhibitors, T cell inhibitors, Interferon agonists, Ribonucleoside triphosphate reductase inhibitors, Aromatase inhibitors, Estrogen receptor antagonists, Tyrosine kinase inhibitors, Cell cycle inhibitors, Taxane, Tubulin inhibitors, angiogenesis inhibitors, macrophage stimulants, Neurokinin receptor antagonists, Cannabinoid receptor agonists, Dopamine receptor agonists, granulocytes stimulating factor agonists, Erythropoietin receptor agonists, somatostatin receptor agonists, LHRH agonists, Calcium sensitizers, VEGF receptor antagonists, interleukin receptor antagonists, osteoclast inhibitors, radical formation stimulants, endothelin receptor antagonists, Vinca alkaloid, anti-hormone or immunomodulators or any other drug that fullfills the activity criteria of a cytotoxic or a toxin and D is preferentially an auristatin, a dolostatin 10, or a derivatives thereof.

In a preferred embodiment, the drug moiety according to the method and composition of the invention has the following formula (II)

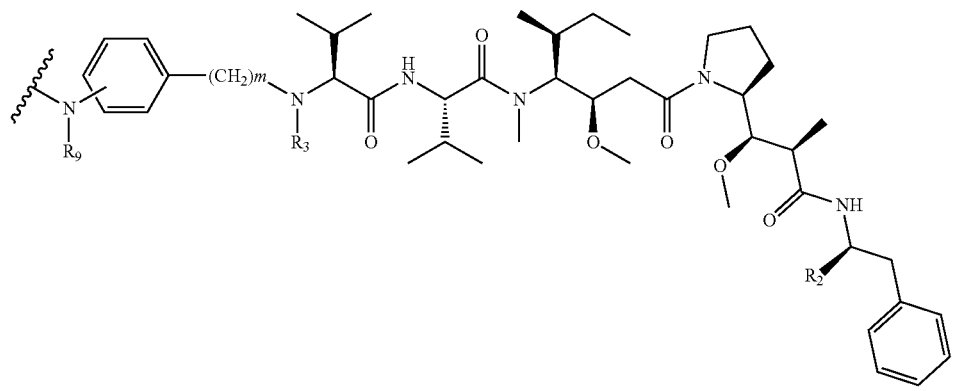

where:

$R_2$ is COOH, COOCH$_3$ or thiazolyl (such as thiazol-2-yl), $R_3$ is H or a $(C_1$-$C_6)$alkyl (such as methyl), in particular a $(C_1$-$C_6)$alkyl group, $R_9$ is H or $(C_1$-$C_6)$alkyl (such as methyl), m is an integer comprised between 1 and 8, and the wavy line indicates the point of attachment to L.

By "alkyl" in the present invention is meant a straight-chain or branched, saturated hydrocarbon chain. For example, mention can be made of methyl, ethyl, propyl, isopropyl, butyl, isobutyl, sec-butyl, tert-butyl, pentyl or hexyl groups.

By "$(C_x$-$C_y)$alkyl" in the present invention is meant an alkyl chain such as defined above comprising x to y carbon atoms. Therefore, a $(C_1$-$C_6)$alkyl group is an alkyl chain having 1 to 6 carbon atoms.

The $(C_1$-$C_6)$alkyl is advantageously a $(C_1$-$C_4)$alkyl, preferably a $(C_1$-$C_2)$alkyl.

Among the compounds of the invention, one particularly appreciated class of drug moieties corresponds to the formula (II) drug moieties in which $R_2$ represents a COOH group.

Another particularly appreciated class of moieties corresponds to the formula (II) moieties in which $R_2$ is a thiazole (in particular a thiazol-2-yl group).

Another class of particularly appreciated moieties corresponds to the formula (II) moieties in which $R_2$ is COOMe.

According to one particular embodiment of the present invention, $R_2$ is more particularly a COOH, COOMe or thiazol-2-yl group.

According to a first preferred embodiment, $R_2$ is COOH.

According to a second preferred embodiment, $R_2$ is COOMe.

$R_3$ particularly represents a $(C_1-C_6)$alkyl, advantageously a methyl group.

m is an integer comprised between 1 and 8, in particular between 1 and 6, advantageously between 1 and 4, preferably is 1 or 2.

In a preferred embodiment, $R_2$ is COOH, $R_3$ is a methyl group and m is 1 or 2.

Among the drug moieties of the invention, one particularly appreciated class of drug moieties corresponds to the formula (II) drug moieties in which $R_9$ is a methyl group or a hydrogen.

In a preferred embodiment:
- $R_2$ is COOH, $R_3$ is a methyl group, $R_9$ is a methyl group and m is 1 or 2, or
- $R_2$ is COOH, $R_3$ is a methyl group, $R_9$ is a hydrogen and m is 1 or 2.

According to a preferred embodiment, the $NR_9$ group is located on the phenyl ring in a para position in relation to the $(CH_2)_m$ group.

Advantageously, the drug moiety is chosen from among the following moieties:

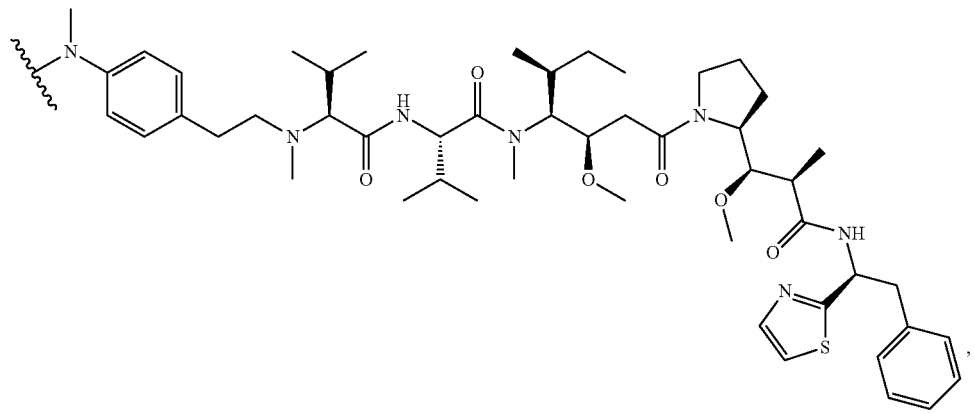

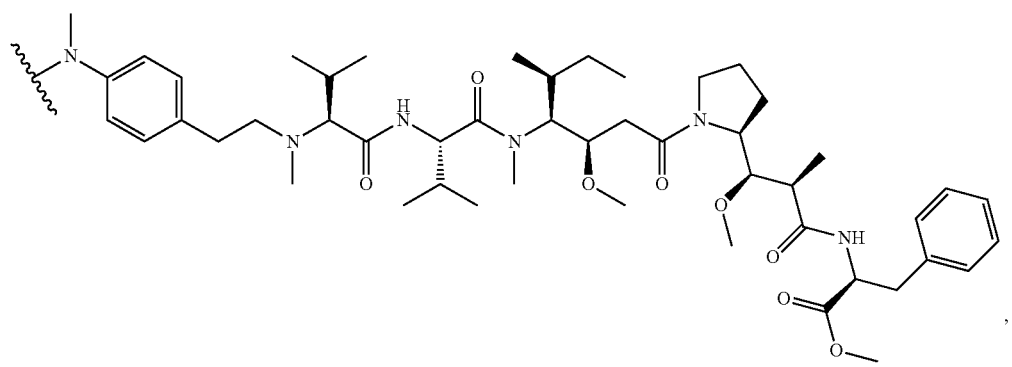

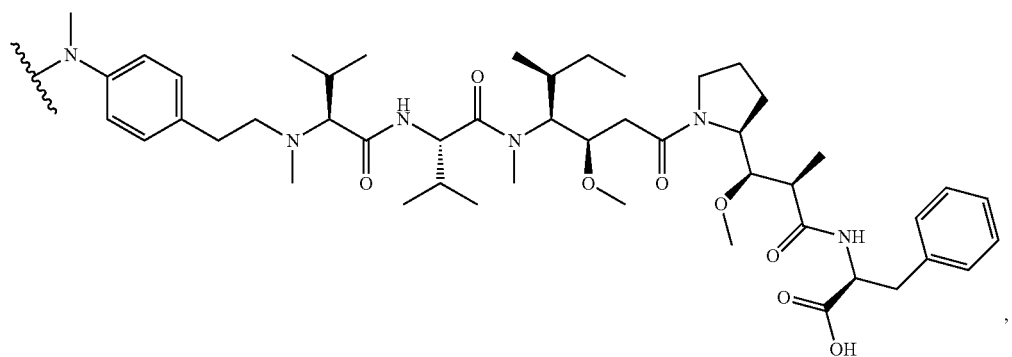

-continued
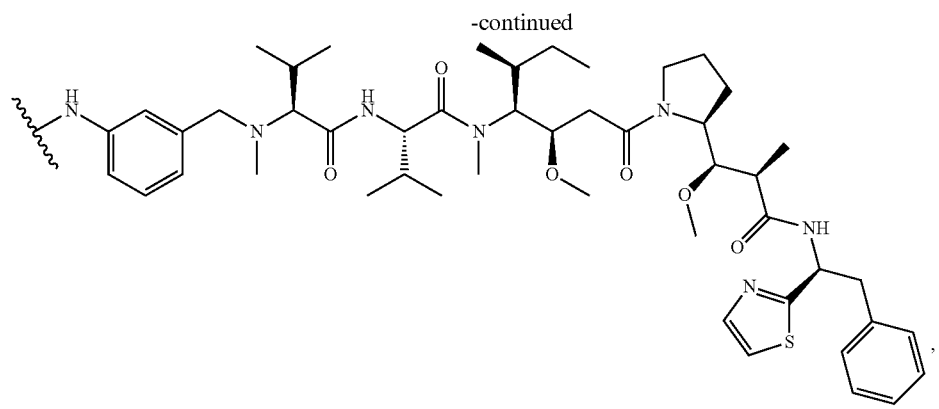
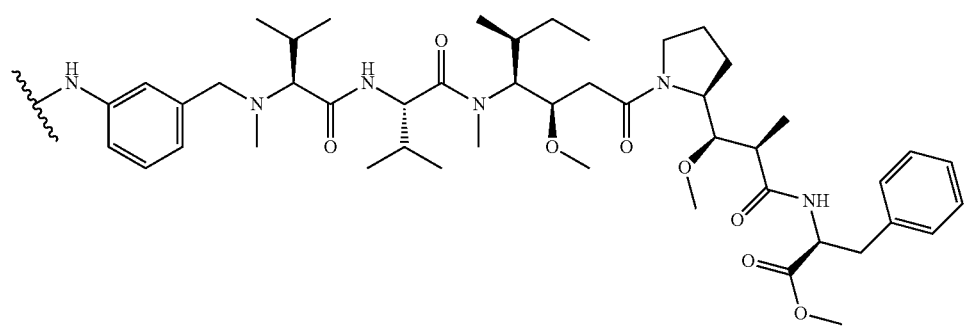
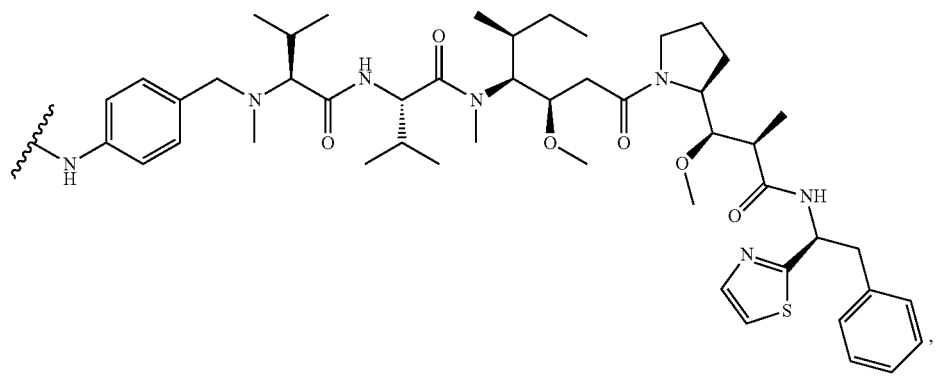
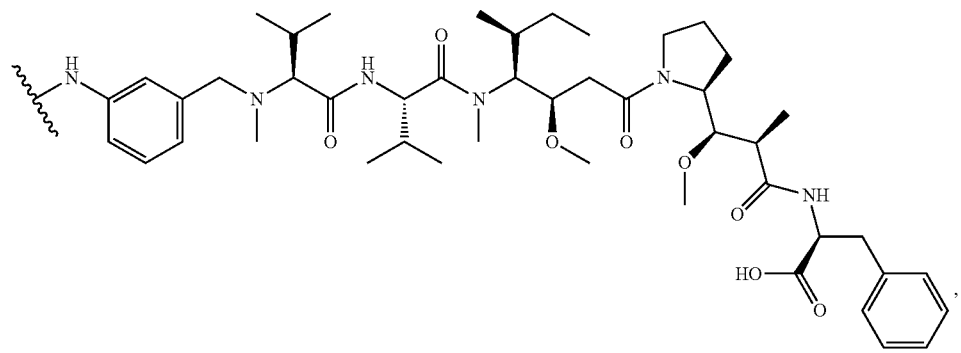

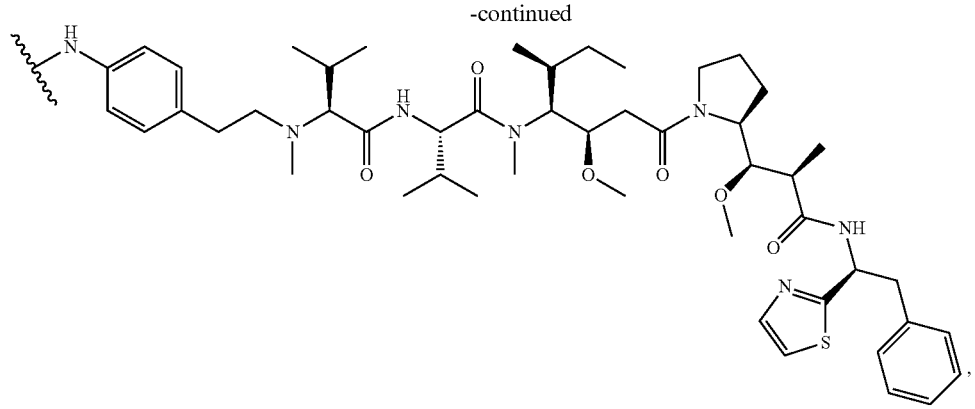
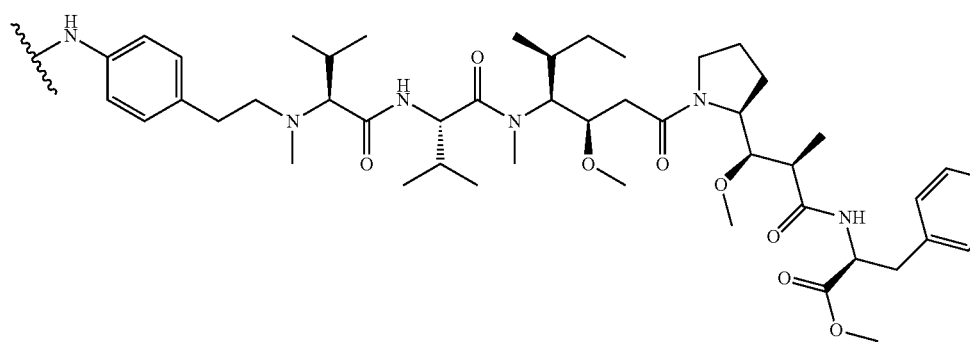
, and
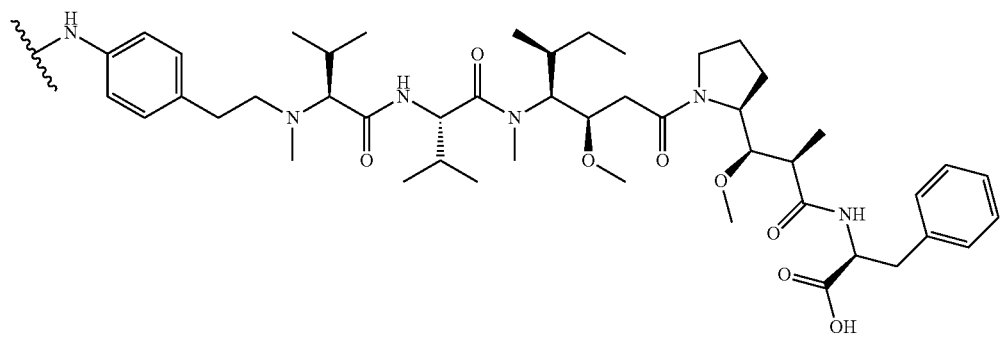
Preparation of the Drug (of Formula DH):
The drug can be prepared using the general methods described in the following synthesis schemes, optionally supplemented by any standard operation when needed that is described in the literature or well known to persons skilled in the art, or described in the examples in the experimental part hereof.
Scheme 1
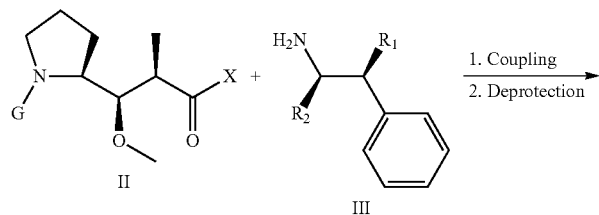

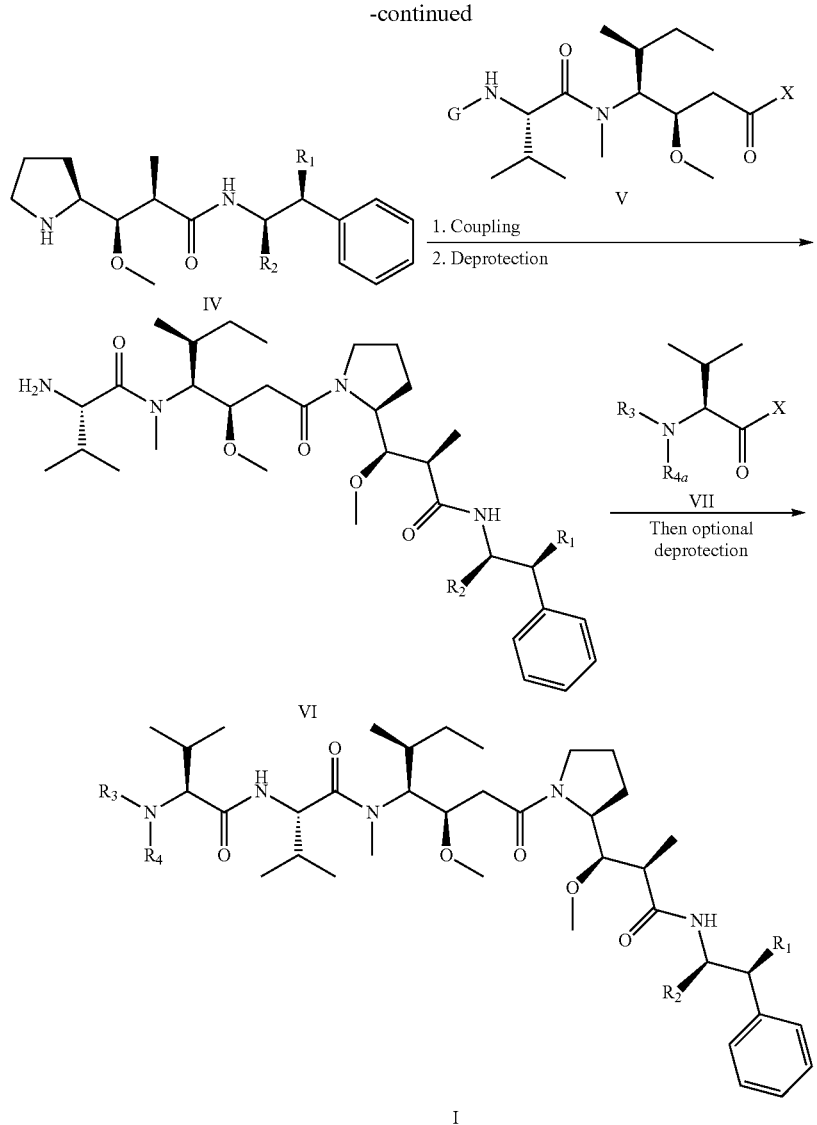

Scheme 1 illustrates the first general method which can be used to prepare the drug. In the above general formulas, $R_1$=H, $R_2$ and $R_3$ are such as previously defined for formula II, $R_4$ represents

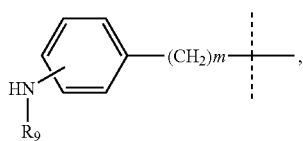

$R_{4a}$ represents a $R_4$ group such as previously defined optionally in protected form and G is a protective group.

The first step consists of the condensing of compound (II), protected on its amine function by a protective group G, with compound (III). X may represent a leaving group such as a chlorine. In this case the first step consists of the reaction between an acid chloride and an amine. This reaction can be conducted using methods and techniques well known to those skilled in the art. In one particularly appreciated method, the two entities are caused to react in the presence of an organic or inorganic base e.g. $Et_3N$, $iPr_2NEt$, pyridine, NaH, $Cs_2CO_3$, $K_2CO_3$ in a solvent such as THF, dichloromethane, DMF, DMSO, at a temperature notably between −20° C. and 100° C. X may also be a hydroxyl (OH). In this case, the first step is a condensation reaction between the carboxylic acid (II) and the amine (III). This reaction can be performed following methods and techniques well known to skilled persons. In one particularly appreciated method, these two entities are caused to react in the presence of a coupling agent such as 1-(3-dimethylaminopropyl)-3-ethylcarbodiimide (EDC), 3-hydroxy-1,2,3-benzotriazin-4(3H)-one, a tertiary amine such as diisopropylethylamine, in a polar aprotic solvent such as dichloromethane or DMF, at a temperature notably between −15° C. and 40° C. In another particularly appreciated method, these two entities are caused to react in the presence of diethyl phosphorocyanidate (DEPC), a tertiary amine such as triethylamine, in a polar aprotic solvent such as dichloromethane or DMF, at a temperature of between −15° C. and 40° C. Another particularly appreciated method consists of causing these two entities to react in the presence of O-(7-azabenzotriazol-1- yl)-1,1,3,3-tetramethyl-uroniumhexafluorophosphate (HATU), a tertiary amine such as diisopropylethylamine, in a polar aprotic solvent such as dichloromethane or DMF, at a temperature of between −15° C. and 100° C.

After deprotection of the intermediate using techniques well known to those skilled in the art («Protective Groups in Organic Synthesis», T. W. Greene, John Wiley & Sons, 2006 and «Protecting Groups», P. J. Kocienski, Thieme Verlag, 1994), compound (IV) can be condensed with compound (V) following the methods and techniques described above to lead to compound (VI) after a deprotection step. This compound can then, after condensation with the intermediate (VII) and optional deprotection, lead to the formation of the drug. Compound (VI) can also be coupled with a compound (VII') in which R'$_3$ is a precursor of R$_3$, in particular an R$_3$ group protected by a protective group. Coupling followed by deprotection of group R'$_3$ to lead to R$_3$ can be carried out following the same procedures as described previously.

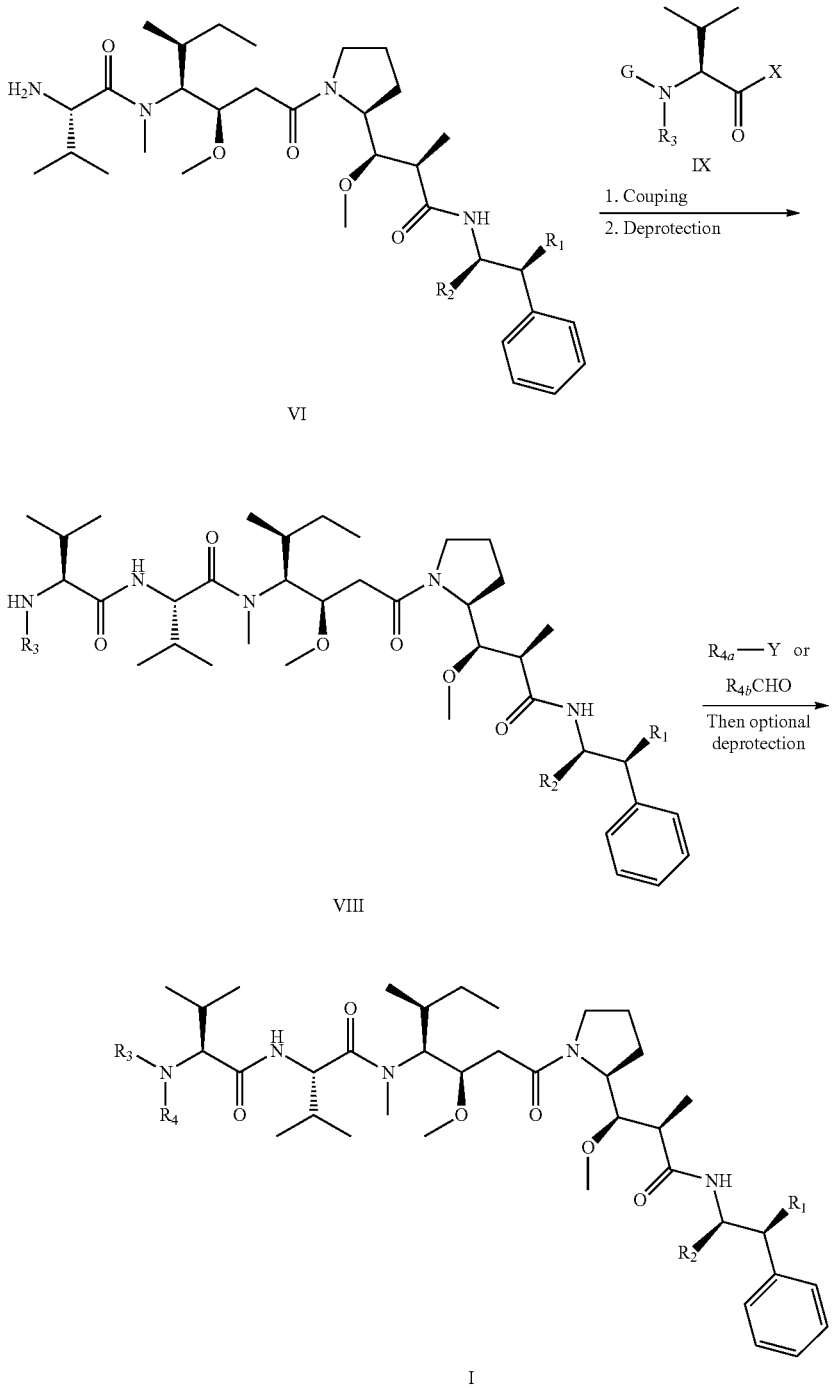

Scheme 2 illustrates the second general method which can be used to prepare the drug. In the above general formulas, G is a protective group, $R_1$=H, $R_2$, $R_3$ and $R_{4a}$ are such as previously defined, and $R_{4b}$ represents

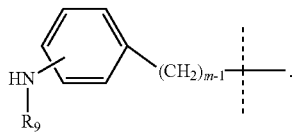

At the first step, compound (IX) protected on its amine function by a protective group G is condensed with compound (VI). X may represent a leaving group e.g. a chlorine. In this case, the first step consists of the reaction between an acid chloride and an amine. This reaction can be performed using methods and techniques well known to persons skilled in the art. In one particularly appreciated method the two entities are caused to react in the presence of an organic or inorganic base such as $Et_3N$, $iPr_2NEt$, pyridine, NaH, $Cs_2CO_3$, $K_2CO_3$ in a solvent such as THF, dichloromethane, DMF, DMSO at a temperature notably between −20° and 100° C. X may also represent a hydroxyl. In this case, the first step is a condensation reaction between the carboxylic acid (IX) and the amine (VI). This reaction can be conducted following methods and techniques well known to skilled persons. In one particularly appreciated method, the two entities are caused to react in the presence of 1-(3-dimethylaminopropyl)-3-ethyl-carbodiimide (EDC), 3-hydroxy-1,2,3-benzotriazin-4(3H)-one, a tertiary amine such as diisopropylethylamine, in a polar aprotic solvent such as dichloromethane or DMF, at a temperature notably between −15° C. and 40° C. In another particularly appreciated method, these two entities are caused to react in the presence of diethyl phosphorocyanidate (DEPC), a tertiary amine such as triethylamine, in a polar aprotic solvent such as dichloromethane or DMF, at a temperature notably between −15° C. and 40° C.

After deprotection of the intermediate, using techniques well known to skilled persons, the obtained compound (VIII) can lead to the drug after reaction with $R_4Y$. In this case, Y is a leaving group such as Cl, Br, I, $OSO_2CH_3$, $OSO_2CF_3$ or O-Tosyl. The reaction is conducted in the presence of an organic or inorganic base such as $Et_3N$, $iPr_2NEt$, NaH, $Cs_2CO_3$, $K_2CO_3$, in a polar anhydrous solvent such as dichloromethane, THF, DMF, DMSO at a temperature notably between −20° and 100° C. In another particularly appreciated method, compound (VIII) is caused to react with an aldehyde of formula $R_{4b}$—CHO where $R_{4b}$ corresponds to a precursor of $R_4$. In this case, the reaction is a reductive amination in the presence of a reducing agent such as $NaBH_4$, $NaBH_3CN$, $NaBH(OAc)_3$, in a polar solvent such as 1,2-dichloroethane, dichloromethane, THF, DMF, MeOH, in the optional presence of titanium isopropoxide (IV), at a pH which can be controlled by the addition of an acid such as acetic acid at a temperature notably between −20° C. and 100° C.

In the foregoing synthesis schemes, a drug may lead to another drug after an additional reaction step such as saponification for example using methods well known to skilled persons whereby an $R_2$ group representing an ester (COOMe), is changed to an $R_2$ group representing a carboxylic acid (COOH).

If it is desired to isolate a drug containing at least one base function in the state of an acid addition salt, this is possible by treating the free base of the drug (containing at least one base function) with a suitable acid, preferably in equivalent quantity. The suitable acid may in particular be trifluoroacetic acid.

III.3—the Linker (L)

"Linker", "Linker Unit", "L" or "link" means, in the present invention, a chemical moiety comprising a covalent bond or a chain of atoms that covalently attaches an antibody to at least one drug.

Linkers may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Carbon-14-labeled 1-isothiocyanatobenzyl-3-methyldiethylene triaminepentaacetic acid (MX-DTPA) is an exemplary chelating agent for conjugation of cyctotoxic agents to the addressing system. Other cross-linker reagents may be BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

The linker may be a "non cleavable" or "cleavable".

In a preferred embodiment, it consists in a "cleavable linker" facilitating release of the drug in the cell. For example, an acid-labile linker, peptidase-sensitive linker, photolabile linker, dimethyl linker or disulfide-containing linker may be used. The linker is, in a preferred embodiment, cleavable under intracellular conditions, such that cleavage of the linker releases the drug from the antibody in the intracellular environment.

For example, in some embodiments, the linker is cleavable by a cleaving agent that is present in the intracellular environment (e.g., within a lysosome or endosome or caveolea). The linker can be, for example, a peptidyl linker that is cleaved by an intracellular peptidase or protease enzyme, including, but not limited to, a lysosomal or endosomal protease. Typically, the peptidyl linker comprises at least two successive amino acids or at least three successive amino acids or is at least two amino acids long or at least three amino acids long. Cleaving agents can include cathepsins B and D and plasmin, all of which are known to hydrolyze dipeptide drug derivatives resulting in the release of active drug inside target cells. For example, a peptidyl linker that is cleavable by the thiol-dependent protease cathepsin-B, which is highly expressed in cancerous tissue, can be used (e.g., a linker comprising or being Phe-Leu or Gly-Phe-Leu-Gly). In specific embodiments, the peptidyl linker cleavable by an intracellular protease comprises or is Val-Cit or Phe-Lys. One advantage of using intracellular proteolytic release of the drug is that the drug is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the drug via an acylhydrazone bond).

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene).

In certain preferred embodiments, the linker unit may have the following general formula:

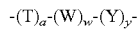

wherein:
T is a stretcher unit;
a is 0 or 1;
W is an amino acid unit;
w is an integer ranging from 0 to 12;
Y is a spacer unit;
y is 0, 1 or 2.

The stretcher unit (T), when present, links the second IGF-1R antibody Ab to an amino acid unit (W) when present, or to the spacer unit when present, or directly to the drug. Useful functional groups that can be present on the second IGF-1R antibody Ab, either naturally or via chemical manipulation, include sulfhydryl, amino, hydroxyl, the anomeric hydroxyl group of a carbohydrate, and carboxyl. Suitable functional groups are sulfhydryl and amino. Sulfhydryl groups can be generated by reduction of the intramolecular disulfide bonds of the second IGF-1R antibody Ab, if present. Alternatively, sulfhydryl groups can be generated by reaction of an amino group of a lysine moiety of the second IGF-1R antibody Ab with 2-iminothiolane or other sulfhydryl generating reagents. In specific embodiments, the second IGF-1R antibody Ab is engineered to carry one or more lysines. More preferably, the second IGF-1R antibody Ab can be engineered to carry one or more Cysteines (cf. ThioMabs).

In certain specific embodiments, the stretcher unit forms a bond with a sulfur atom of the second IGF-1R antibody Ab. The sulfur atom can be derived from a sulfhydryl (—SH) group of a reduced antibody.

In certain other specific embodiments, the stretcher unit is linked to the second IGF-1R antibody Ab via a disulfide bond between a sulfur atom of the antibody and a sulfur atom of the stretcher unit.

In other specific embodiments, the reactive group of the stretcher contains a reactive site that can be reactive to an amino group of the second IGF-1R antibody Ab. The amino group can be that of an arginine or a lysine. Suitable amine reactive sites include, but are not limited to, activated esters (such as succinimide esters, 4-nitrophenyl esters, pentafluorophenyl esters), anhydrides, acid chlorides, sulfonyl chlorides, isocyanates and isothiocyanates.

In yet another aspect, the reactive function of the stretcher contains a reactive site that is reactive to a modified carbohydrate group that can be present on the second IGF-1R antibody Ab. In a specific embodiment, the second IGF-1R antibody Ab is glycosylated enzymatically to provide a carbohydrate moiety or is naturally glycosylated. The carbohydrate may be mildly oxidized with a reagent such as sodium periodate and the resulting carbonyl unit of the oxidized carbohydrate can be condensed with a stretcher that contains a functionality such as a hydrazide, an oxime, a reactive amine, a hydrazine, a thiosemicarbazide, a hydrazine carboxylate, or an arylhydrazide.

According to a particular embodiment, the stretcher unit has the following formula:

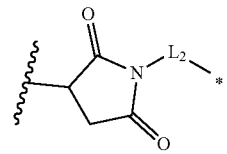

wherein
$L_2$ is $(C_4-C_{10})$cycloalkyl-carbonyl, $(C_2-C_6)$alkyl or $(C_2-C_6)$alkyl-carbonyl (the cycloalkyl or alkyl moieties being linked to the nitrogen atom of the maleimide moiety),
the asterisk indicates the point of attachment to the amino acid unit, if present, to the spacer unit, if present, or to the drug D, and
the wavy line indicates the point of attachment to the second IGF-1R antibody Ab.

By "$(C_4-C_{10})$cycloalkyl" in the present invention is meant a hydrocarbon cycle having 4 to 10 carbon atoms including, but not limited to, cyclopentyl, cyclohexyl and the like.

$L_2$ can be advantageously $(C_2-C_6)$alkyl-carbonyl such as a pentyl-carbonyl of the following formula:

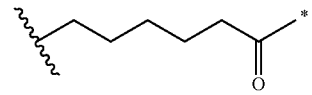 [SMILES: *CCCCCC(C)=O]

wherein
the asterisk indicates the point of attachment to the amino acid unit, if present, to the spacer unit, if present, or to the drug D; and
the wavy line indicates the point of attachment to the nitrogen atom of the maleimide moiety.

The amino acid unit (W), when present, links the stretcher unit (T) if present, or otherwise the second IGF-1R antibody Ab to the spacer unit (Y) if the spacer unit is present, or to the drug if the spacer unit is absent.

As above mentioned, $(W)_w$ is absent (w=0) or may be a dipeptide, tripeptide, tetrapeptide, pentapeptide, hexapeptide, heptapeptide, octapeptide, nonapeptide, decapeptide, undecapeptide or dodecapeptide unit, wherein the amino acids forming the peptides can be different from one another.

Thus $(W)_w$ can be represented by the following formula: $(W1)_{w1}(W2)_{w2}(W3)_{w3}(W4)_{w4}(W5)_{w5}$, wherein each W1 to W5 represents, independently from one another, an amino acid unit and each w1 to w5 is 0 or 1.

In some embodiments, the amino acid unit $(W)_w$ may comprise amino acid residues such as those occurring naturally, as well as minor amino acids and non-naturally occurring amino acid analogs, such as citrulline.

The amino acid residues of the amino acid unit $(W)_w$ include, without limitation, alanine, valine, leucine, isoleucine, methionine, phenylalanine, tryptophan, proline, lysine protected or not with acetyl or formyl, arginine, arginine protected or not with tosyl or nitro groups, histidine, ornithine, ornithine protected with acetyl or formyl, and citrulline. Exemplary amino acid linker components include preferably a dipeptide, a tripeptide, a tetrapeptide or a pentapeptide, notably a dipeptide or a tripeptide.

Exemplary dipeptides include: Val-Cit, Ala-Val, Ala-Ala, Val-Ala, Lys-Lys, Cit-Cit, Val-Lys, Ala-Phe, Phe-Lys, Ala-Lys, Phe-Cit, Leu-Cit, Ile-Cit, Trp-Cit, Phe-Ala, Phe-$N^9$-tosyl-Arg, Phe-$N^9$-Nitro-Arg.

Exemplary tripeptides include: Val-Ala-Val, Ala-Asn-Val, Val-Leu-Lys, Ala-Ala-Asn, Phe-Phe-Lys, Gly-Gly-Gly, D-Phe-Phe-Lys, Gly-Phe-Lys.

Exemplary tetrapeptide include: Gly-Phe-Leu-Gly (SEQ ID NO. 93), Ala-Leu-Ala-Leu (SEQ ID NO. 94).

Exemplary pentapeptide include: Pro-Val-Gly-Val-Val (SEQ ID NO. 95).

According to a particular embodiment, $(W)_w$ can be a dipeptide (i.e. w=2) such as Val-Cit, or the linker lacks an amino acid unit (w=0). When the linker lacks an amino acid unit, preferably it lacks also a spacer unit.

According to a preferred embodiment, w=0 (i.e. $(W)_w$ is a single bond) or w=2 (i.e. $(W)_w$ is a dipeptide) and $(W)_w$ can thus be selected from:

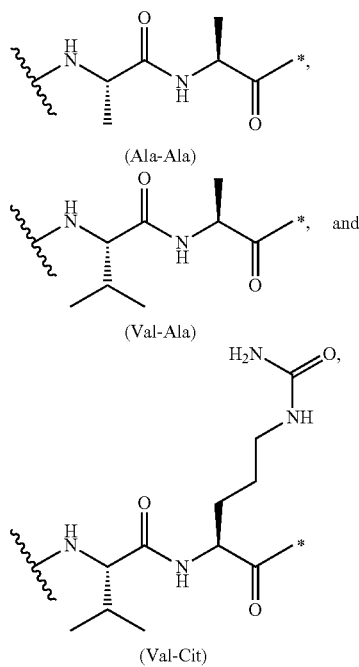

(Ala-Ala)

(Val-Ala)

(Val-Cit)

and in particular is Val-Cit,
wherein
the asterisk indicates the point of attachment to the spacer unit if present, or to the drug D; and
the wavy line indicates the point of attachment to $L_2$.

Amino acid linker components can be designed and optimized in their selectivity for enzymatic cleavage by a particular enzyme, for example, a tumor-associated protease, cathepsin B, C and D, or a plasmin protease.

The amino acid unit of the linker can be enzymatically cleaved by an enzyme including, but not limited to, a tumor-associated protease to liberate the drug.

The amino acid unit can be designed and optimized in its selectivity for enzymatic cleavage by a particular tumor-associated protease. The suitable units are those whose cleavage is catalyzed by the proteases, cathepsin B, C and D, and plasmin.

The spacer unit (Y), when present, links an amino acid unit if present, or the stretcher unit if present, or otherwise the antibody to the drug. Spacer units are of two general types: self-immolative and non self-immolative. A non self-immolative spacer unit is one in which part or all of the spacer unit remains bound to the drug after enzymatic cleavage of an amino acid unit from the antibody-drug conjugate. Examples of a non self-immolative spacer unit include, but are not limited to a (glycine-glycine) spacer unit and a glycine spacer unit. To liberate the drug, an independent hydrolysis reaction should take place within the target cell to cleave the glycine-drug unit bond.

In a particular embodiment, a non self-immolative the spacer unit (Y) is Gly.

Alternatively, an antibody-drug conjugate containing a self-immolative spacer unit can release the drug without the need for a separate hydrolysis step. In these embodiments, (Y) is a residue of p-aminobenzyl alcohol (PAB) unit that is linked to $(W)_w$ via the nitrogen atom of the PAB group, and connected directly to the drug via a ester, carbonate, carbamate or ether group.

Other examples of self-immolative spacers include, but are not limited to, aromatic compounds that are electronically equivalent to the PAB group such as residues of 2-aminoimidazol-5-methanol derivatives and ortho or para-aminobenzylacetals. Spacers can be used that undergo facile cyclization upon amide bond hydrolysis, such as substituted and unsubstituted 4-aminobutyric acid amides, appropriately substituted bicyclo[2.2.1] and bicyclo[2.2.2] ring systems and 2-aminophenylpropionic acid amides.

In an alternate embodiment, the spacer unit is a branched bis(hydroxymethyl)styrene (BHMS) unit, which can be used to incorporate additional drugs.

In a particular embodiment, the spacer unit (Y) is PAB-carbonyl with PAB being

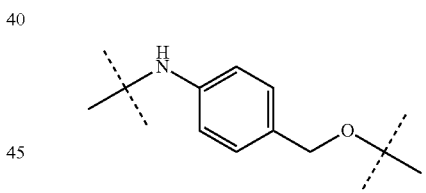

(the oxygen of the PAB unit being linked to the carbonyl), and y=1 or the linker lacks a spacer unit (y=0).

In a particular embodiment, the linker has the following formula (III):

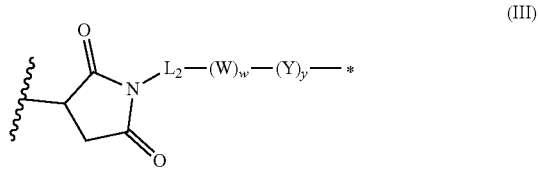

(III)

wherein
$L_2$ is $(C_4$-$C_{10})$cycloalkyl-carbonyl, $(C_2$-$C_6)$alkyl or $(C_2$-$C_6)$alkyl-carbonyl (the carbonyl of these moieties, when present, being linked to $(W)_w$), W represents an amino acid unit, with w representing an integer comprised between 0 and 5, Y is PAB-carbonyl, with PAB being

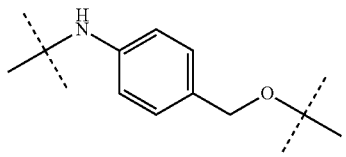

(the oxygen of the PAB unit being linked to the carbonyl), and y is 0 or 1 (preferably y is 0 when w is 0 and y is 0 or 1 when w is comprised between 1 and 5), the asterisk indicates the point of attachment to the drug D, and the wavy line indicates the point of attachment to the second IGF-1R antibody Ab.

Advantageously, $L_2$ is $(C_2-C_6)$alkyl-carbonyl such as a pentyl-carbonyl of the following formula:

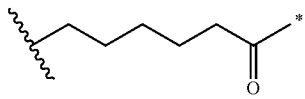 [SMILES: *CCCCCC(C)=O]

wherein the asterisk indicates the point of attachment to $(W)_w$; and the wavy line indicates the point of attachment to the nitrogen atom of the maleimide moiety.

According to a preferred embodiment, the linker L is selected from:

may be prepared by any method known by the person skilled in the art such as, without limitation, i) reaction of a nucleophilic group of the second IGF-1R antibody Ab with a bivalent linker reagent followed by reaction with a nucleophilic group of the drug or ii) reaction of a nucleophilic group of the drug with a bivalent linker reagent followed by reaction with a nucleophilic group of the second IGF-1R antibody Ab.

Nucleophilic groups on the second IGF-1R antibody Ab include, without limitation, N-terminal amine groups, side chain amine groups (e.g. lysine), side chain thiol groups, and sugar hydroxyl or amino groups when the second IGF-1R antibody Ab is glycosylated.

Nucleophilic groups on the drug include, without limitation, amine, thiol, and hydroxyl groups, and preferably amine groups.

Amine, thiol, and hydroxyl groups are nucleophilic and capable of reacting to form covalent bonds with electrophilic groups on linker moieties and linker reagents including, without limitation, active esters such as NHS esters, HOBt esters, haloformates, and acid halides; alkyl and benzyl halides such as haloacetamides; aldehydes; ketones; carboxyl; and maleimide groups. The antibody may have reducible interchain disulfides, i.e. cysteine bridges. The antibody may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into the antibody through any reaction known by the person skilled in the art. As non limitative example, reactive thiol groups may be introduced into the second IGF-1R antibody Ab by introducing one or more cysteine residues.

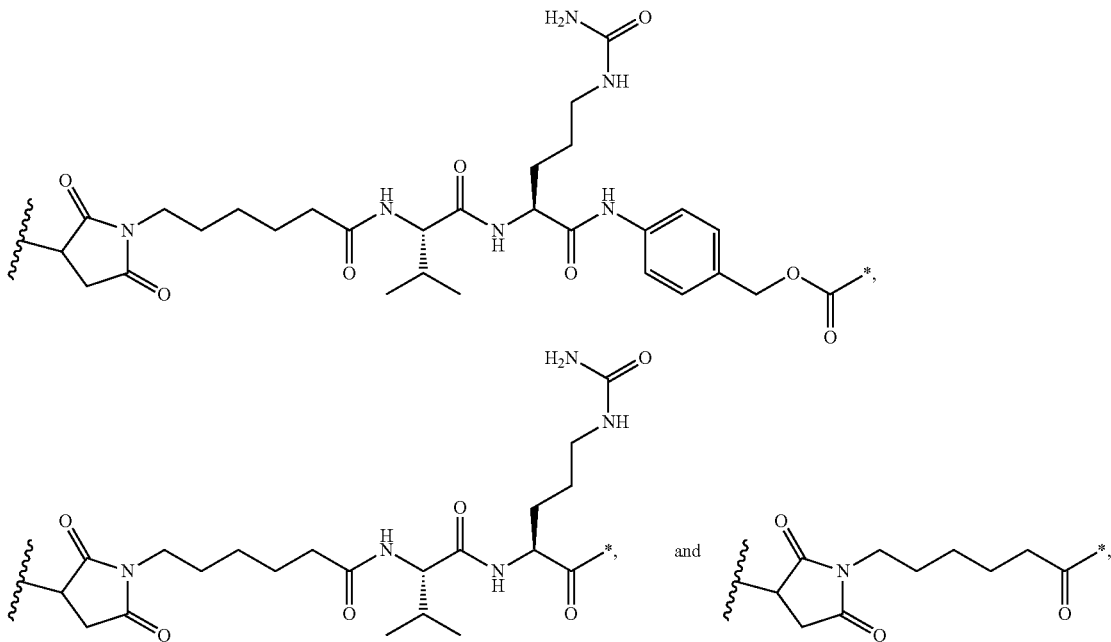

wherein the asterisk indicates the point of attachment to the drug D, and the wavy line indicates the point of attachment to the second IGF-1R antibody Ab.

III.4—the Antibody-Drug-Conjugate (ADC)

In a preferred embodiment, the antibody-drug conjugate (ADC) used in the method or composition of the invention ADC may also be produced by modification of the second IGF-1R antibody Ab to introduce electrophilic moieties, which can react with nucleophilic substituents on the linker reagent. The sugars of glycosylated antibody may be oxidized to form aldehyde or ketone groups which may react with the amine group of linker reagents or drug. The resulting imine Schiff base groups may form a stable linkage, or may be reduced to form stable amine linkages. In one embodiment, reaction of the carbohydrate portion of a glycosylated second IGF-1R antibody Ab with either galactose oxidase or sodium meta-periodate may yield carbonyl (aldehyde and ketone) groups in the protein that can react with appropriate groups on the drug. In another embodiment, proteins containing N-terminal serine or threonine residues can react with sodium meta-periodate, resulting in production of an aldehyde in place of the first amino acid.

In a preferred embodiment, the ADC is prepared by preparation of the drug-linker moiety followed by coupling between a nucleophilic group of the second IGF-1R antibody Ab (for ex. the SH group of a cysteine moiety) and an electrophilic group of the drug-linker moiety (for ex. a maleimide).

1. Drug-Linker

The Drug-Linker moiety can be prepared by coupling:
the linker with the drug,
a part of the linker with the drug before completing the synthesis of the linker,
the linker with a part or a precursor of the drug before completing the synthesis of the drug, or
a part of the linker with a part or a precursor of the drug before completing the synthesis of the linker and the drug.

The coupling reactions are well known reactions for the one skilled in the art between a nucleopilic group and an electrophilic group.

The nucleophilic group can be in particular an amine, thiol or hydroxyl group. In a preferred embodiment it is a primary or secondary amine group.

The electrophilic group can be a carboxylic acid group (COOH) optionally in an activated form or an activated carbonate ester moiety.

By "activated form" of a carboxylic acid is meant a carboxylic acid in which the OH moiety of the COOH function has been replaced with an activated leaving group (LG) enabling coupling of the activated carboxylic acid group with an amino group in order to form an amide bond and release the compound LG-H. Activated forms may be activated esters, activated amides, anhydrides or acyl halides such as acyl chlorides. Activated esters include derivatives formed by reaction of the carboxylic acid group with N-hydroxybenzotriazole or N-hydroxysuccinimide.

By "activated carbonate ester" is meant a carbonate ester comprising a —OC(O)OR moiety in which OR represents a good leaving group enabling coupling of the activated carbonate ester with an amino group in order to form a carbamate moiety and release the compound ROH. The R group of the activated carbonate ester includes, without limitation, the p-nitro-phenyl, pentafluorophenyl, 2,5-dioxo-2,5-dihydro-1H-pyrrol-1-yl and benzyl groups, preferably the p-nitro-phenyl and pentafluorophenyl groups.

When the linker has the following formula (III):

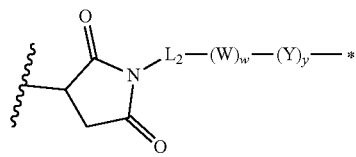

(III)

the Drug-Linker moiety has the following formula (IV):

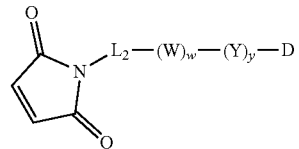

(IV)

and the last step of the synthesis of the Drug-Linker moiety is generally the coupling between a compound of the following formula (V):

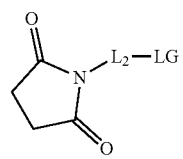

(V)

where $L_2$ is as defined previously and LG represents a leaving group notably a halide such as a chloride or a group derived from N-hydroxysuccinimide, and a compound of the following formula (VI):

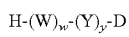

H-$(W)_w$-$(Y)_y$-D     (VI).

When y=1 and Y=PAB-carbonyl, the compound of formula (VI) can be prepared by the coupling between the drug (DH) and a compound of the following formula (VII), preferably a protected form thereof:

G-$(W)_w$-PAB-CO—OR     (VII)

where W and w are as defined previously and R is as defined in the definition of the "activated carbonate ester", and G is H or a protecting group.

When the compound of formula (VII) is in a protected form, final step of deprotection is necessary.

When y=0, the compound (VI) has the formula H-$(W)_w$-D, wherein $(W)_w$ and preferably D are composed of amino acid units. Consequently, the compound (VI) can be prepared in this case by a conventional peptide synthesis method well known to the one skilled in the art.

2. Ab-Linker-Drug

An embodiment according to the invention consists of a coupling between a cysteine present on the second IGF-1R antibody Ab and an electrophilic group of the Drug-Linker moiety, preferably with a maleimide moiety present on the Drug-Linker moiety.

The maleimide-cysteine coupling can be performed by methods well known to the person skilled in the art.

Generally, antibodies do not contain many, if any, free and reactive cysteine thiol groups which can be linked to a drug moiety. Most cysteine thiol residues in antibodies exist as disulfide bridges and must be reduced with a reducing agent such as dithiothreitol (DTT) or TCEP, under partial or total reducing conditions. The loading (drug/antibody ratio) of an ADC may be controlled in several different manners, including: (i) limiting the molar excess of drug-linker intermediate (D-L) or linker reagent relative to antibody, (ii) limiting the conjugation reaction time or temperature, and (iii) partial or limited reducing conditions for cysteine thiol modification.

The disulfide bond structure of human IgGs is now well established (reviewed in Liu and May, mAbs 4 (2012):

17-23). There are in fact many similarities and some differences with regard to the disulfide bond structures of the 4 human IgG subclasses, namely IgG1, IgG2, IgG3 and IgG4. All IgG subclasses contain invariably 12 intra-chain disulfide bridges and the differences reside in their inter-chain disulfide bonds formed between heavy and light chains. Each intra-chain disulfide bond is associated with an individual IgG domain, i.e. variable (VL and VH) and constant (CL, CH1, CH2 and CH3) domains. The 2 heavy chains are linked in their hinge region by a variable number of disulfide bridges: 2 for IgG1 and IgG4, 4 for IgG2 and 11 for IgG3. The heavy and light chains of the IgG1 are connected by a disulfide bond between the last cysteine residue of the light chain and the fifth residue of the heavy chain, whereas for the other subclasses, IgG2, IgG3 and IgG4, the light chain is linked to the heavy chain by a disulfide bond between the last cysteine residue of the light chain and the third cysteine residue of the heavy chain, which is located at the interface of VH and CH1 domains. Disulfide bond structures other than these classical structures have been described for IgG2 and IgG4 (reviewed in Liu and May, mAbs 4 (2012): 17-23). Inter-chain disulfide bonds are highly solvent exposed and are consequently much more reactive than the intra-chain disulfide bonds, which are buried in anti-parallel beta-sheet structures within each domain and are not solvent exposed. For these reasons, whatever the antibody isotype, coupling will take place on inter-chain exposed cysteine residues after mild reduction. Each inter-chain disulfide bridge can thus form, theoretically, two sites of conjugation.

Additional nucleophilic groups can be introduced into antibodies through the reaction of lysines with 2-iminothiolane (Traut's reagent) resulting in the conversion of an amine into a thiol. Reactive thiol groups may also be introduced into the antibody (or fragment thereof) by engineering one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114 (13):2721-2729; U.S. Pat. Nos. 7,521,541; 7,723,485; WO2009/052249). The engineered cysteine thiols may react with linker reagents or the drug-linker reagents of the present invention which have thiol-reactive, electrophilic groups such as maleimide or alpha-halo amides to form ADC with cysteine engineered antibodies and the drug moieties. The location of the drug moiety can thus be designed, controlled, and known. The drug loading can be controlled since the engineered cysteine thiol groups typically react with thiol-reactive linker reagents or drug-linker reagents in high yield. Engineering an IgG antibody to introduce a cysteine amino acid by substitution at a single site on the heavy or light chain gives two new cysteines on the symmetrical antibody. A drug loading near 2 can be achieved with near homogeneity of the conjugation product ADC.

Where more than one nucleophilic or electrophilic group of the antibody reacts with a drug-linker intermediate, or linker reagent followed by drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody.

For some ADC, drug ratio may be limited by the number of attachment sites on the antibody. High drug loading, e.g. drug ratio >5, may cause aggregation, insolubility, toxicity, or loss of cellular permeability of certain ADC. Typically, less drug moieties than the theoretical maximum are conjugated to an antibody during a conjugation reaction.

The drug loading also referred as the Drug-Antibody ratio (DAR) is the average number of drugs per cell binding agent.

In the case of antibody IgG1 and IgG4 isotypes, where the drugs are bound to cysteines after partial antibody reduction, drug loading may range from 1 to 8 drugs (D) per antibody, i.e. where 1, 2, 3, 4, 5, 6, 7, and 8 drug moieties are covalently attached to the antibody.

In the case of an antibody IgG2 isotype, where the drugs are bound to cysteines after partial antibody reduction, drug loading may range from 1 to 12 drugs (D) per antibody, i.e. where 1, 2, 3, 4, 5, 6, 7, 8, 9, 10, 11 and 12 drug moieties are covalently attached to the antibody.

Compositions of ADC include collections of cell binding agents, e.g. antibodies, conjugated with a range of drugs, from 1 to 8 or 1 to 12.

The average number of drugs per antibody in preparations of ADC from conjugation reactions may be characterized by conventional means such as UV, reverse phase HPLC, HIC, mass spectrometry, ELISA assay, and electrophoresis.

As non limitative embodiment, it is presented herein the conjugation with the second IGF-1R antibody hz208F2. In this case, the drug is coupled to at least one cysteine selected from i) for the light chain of sequence SEQ ID No. 36, 38 or 62, the residue Cys. in position 214 and ii) for the heavy chain of sequence SEQ ID No. 35, 40, 42, 44, 46, 48, 50, 52, 54, 56, 58 or 61, the residues Cys. in position 223, 229 and 232.

As non limitative embodiment, it is presented herein the conjugation with the second IGF-1R antibody hz208F2. In this case, the drug is coupled to two, three or four, cysteines selected from i) for the light chain of sequence SEQ ID No. 36, 38 or 62, the residue Cys. in position 214 and ii) for the heavy chain of sequence 35, 40, 42, 44, 46, 48, 50, 52, 54, 56, 58 and 61, the residues Cys. in positions 223, 229 and 232.

An alternative consists of lysine coupling. An antibody may contain, for example, many lysine residues that do not react with the drug-linker intermediate (D-L) or linker reagent. Only the most reactive lysine groups may react with an amine-reactive linker reagent. Also, only the most reactive cysteine thiol groups may react with a thiol-reactive linker reagent.

Where the compounds of the invention are bound to lysines, drug loading may range from 1 to 80 drugs (D) per cell antibody, although an upper limit of 40, 20, 10 or 8 may be preferred. Compositions of ADC include collections of cell binding agents, e.g. antibodies, conjugated with a range of drugs, from 1 to 80, 1 to 40, 1 to 20, 1 to 10 or 1 to 8.

The ADC of formula (I) according to the invention can be in the form of a pharmaceutically acceptable salt.

In the present invention by "pharmaceutically acceptable" is meant that which can be used in the preparation of a pharmaceutical composition which is generally, safe nontoxic and neither biologically nor otherwise undesirable, and which is acceptable for veterinary use as well as for human pharmaceutical use.

By "pharmaceutically acceptable salt" of a compound is meant a salt which is pharmaceutically acceptable as defined herein and which has the desired pharmacological activity of the parent compound.

Pharmaceutically acceptable salts notably comprise:

(1) the addition salts of a pharmaceutically acceptable acid formed with pharmaceutically acceptable inorganic acids such as hydrochloric, hydrobromic, phosphoric, sulfuric and similar acids; or formed with pharmaceutically acceptable organic acids such as acetic, trifluoroacetic, propionic, succinic, fumaric, malic, tartaric, citric, ascorbic, maleic, glutamic, benzoic, salicylic, toluenesulfonic, methanesulfonic, stearic, lactic and similar acids; and (2) the addition salts of a pharmaceutically acceptable base formed when an acid proton present in the parent compound is either replaced by a metallic ion e.g. an alkaline metal ion, an alkaline-earth metal ion or an aluminium ion; or coordinated with a pharmaceutically acceptable organic base such as lysine, arginine and similar; or with a pharmaceutically acceptable inorganic base such as sodium hydroxide, potash, calcium hydroxide and similar.

These salts can be prepared from the compounds of the invention containing a base or acid function, and the corresponding acids or bases using conventional chemical methods.

IV—Treatment

The present invention also concerns a method for treating cancer comprising the administration to a person in need thereof of an effective amount of a formula (I) compound such as defined above.

Cancers can be preferably selected through IGF-1R-expressing cancers including tumoral cells expressing or over-expressing whole or part of the protein IGF-1R at their surface.

More particularly, said cancers are breast cancer, colon cancer, esophageal carcinoma, hepatocellular cancer, gastric cancer, glioma, lung cancer, melanoma, osteosarcoma, ovarian cancer, prostate cancer, rhabdomyosarcoma, renal cancer, thyroid cancer, uterine endometrial cancer, schwannoma, neuroblastoma, oral squamous cancer, mesothelioma, leiomyosarcoma and any drug resistance phenomena or cancers.

The method according to the invention is useful for treating cancer, in particular, drug resistant or refractory cancers, in a patient. In some embodiments, the patient has a refractory or drug-resistant cancer, where the patient has failed at least one prior treatment with a chemotherapeutic agent.

For the avoidance of doubt, by drug resistance or refractory cancers, it is meant any resistant IGF-1R-expressing cancers, i.e. not only resistant cancers which initially express IGF-1R but also cancers which initially do not express or overexpress IGF-1R but which express IGF-1R once they have become resistant to a previous treatment.

Other particular types of cancers that can be treated include, but are not limited to, refractory or drug resistant forms of carcinomas, lymphomas, blastomas, sarcomas, leukemias, lymphoid malignancies, and other cancers, cell proliferative disorders and tumors.

Another object of the invention is a pharmaceutical composition comprising the ADC as described in the specification.

More particularly, the invention relates to a pharmaceutical composition comprising the ADC of the invention with at least an excipient and/or a pharmaceutical acceptable vehicle.

In the present description, the expression "pharmaceutically acceptable vehicle" or "excipient" is intended to indicate a compound or a combination of compounds entering into a pharmaceutical composition not provoking secondary reactions and which allows, for example, facilitation of the administration of the active compound(s), an increase in its lifespan and/or in its efficacy in the body, an increase in its solubility in solution or else an improvement in its conservation. These pharmaceutically acceptable vehicles and excipients are well known and will be adapted by the person skilled in the art as a function of the nature and of the mode of administration of the active compound(s) chosen.

The active ingredient can be administered in unit forms of administration, in a mixture with conventional pharmaceutical carriers, to animals or to human beings. Suitable unit forms of administration comprise forms via oral route and forms for administration via parenteral route (subcutaneous, intradermal, intramuscular or intravenous).

As solid compositions, for oral administration, use can be made of tablets, pills, powders (hard or soft gelatine capsules) or granules. In these compositions, the active ingredient of the invention is mixed with one or more inert diluents such as starch, cellulose, sucrose, lactose or silica, in a stream of argon. These compositions may also comprise substances other than diluents, for example one or more lubricants such as magnesium stearate or talc, a colouring agent, a coating (coated tablets) or a varnish.

The sterile compositions for parenteral administration may preferably be aqueous or non-aqueous solutions, suspensions or emulsions. As solvent or vehicle, use can be made of water, propylene glycol, a polyethylene glycol, vegetable oils, in particular olive oil, injectable organic esters e.g. ethyl oleate or other suitable organic solvents. These compositions may also contain adjuvants, in particular wetting, isotonic, emulsifying, dispersing and stabilising agents. Sterilisation can be performed in several manners, for example by sanitising filtration, by incorporating sterilising agents into the composition, by radiation or by heating. They can also be prepared in the form of solid sterile compositions which can be dissolved at the time of use in sterile water or any other injectable sterile medium.

Preferably, these ADCs will be administered by the systemic route, in particular by the intravenous route, by the intramuscular, intradermal, intraperitoneal or subcutaneous route, or by the oral route. In a more preferred manner, the composition comprising the ADCs according to the invention will be administered several times, in a sequential manner.

The invention concerns thus also a kit comprising at least i) an antibody-drug-conjugate according to the invention and/or a pharmaceutical composition according to the invention and ii) a syringe or vial or ampoule in which the said antibody-drug-conjugate and/or pharmaceutical composition is disposed.

Their modes of administration, dosages and optimum pharmaceutical forms can be determined according to the criteria generally taken into account in the establishment of a treatment adapted to a patient such as, for example, the age or the body weight of the patient, the seriousness of his/her general condition, the tolerance to the treatment and the secondary effects noted.

Other characteristics and advantages of the invention appear in the continuation of the description with the examples and the figures whose legends are represented below.

FIGURE LEGENDS

Figure 1B:
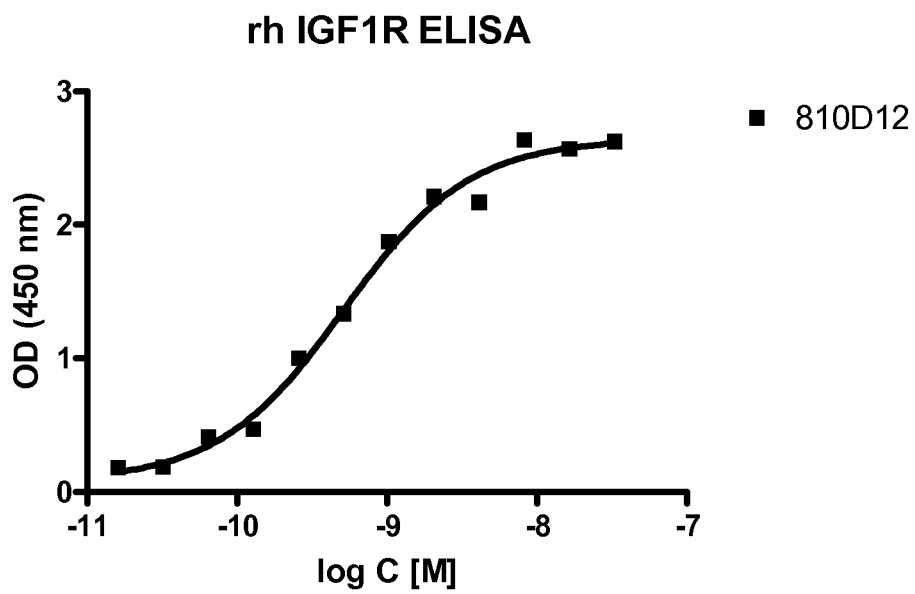

FIGS. 1A and 1B: Graphic representation of OD values obtained with first IGF-1R antibodies 816C12 (A) and 810D10 (B) in the rhIGF1R ELISA. Data fitting and $EC_{50}$ determination are determined using Prism application.

FIGS. 2A-2D: Immunohistochemistry (IHC) patterns of recognition of paraffin embedded tumor MCF-7 with the first IGF-1R antibody 816C12 (2A), with the first IGF-1R antibody 810D12 (2B), with G11 anti-IGF-1R antibody (Roche Ventana) (2C) or AF-305 (R&D system) anti-IGF-1R antibody (2D).

Figure 3:
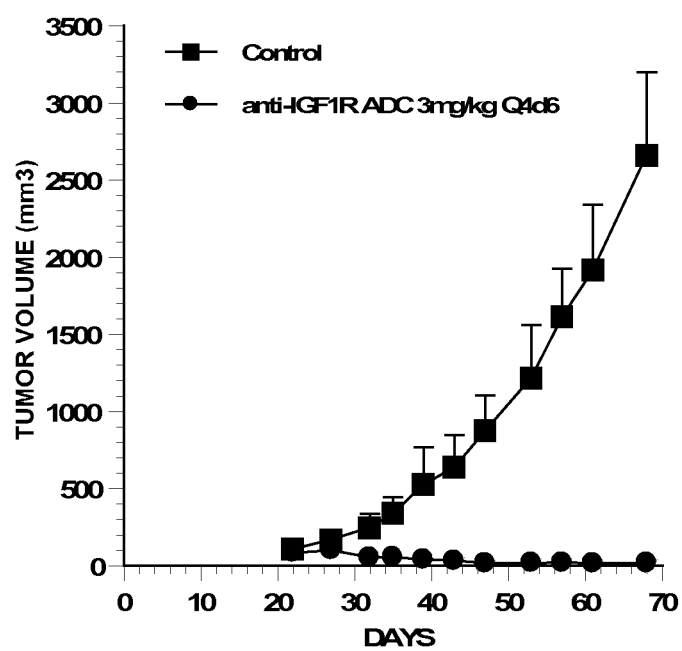

FIG. 3 In vivo activity of an anti-IGF-1R ADC in the MCF-7 xenograft model.

FIGS. 4A-4D: Immunohistochemistry (IHC) patterns of recognition of paraffin embedded tumor SBC-5 with the first IGF-1R antibody 816C12 (4A), with the first IGF-1R antibody 810D12 (4B), with G11 anti-IGF-1R antibody (Roche Ventana) (4C) or AF-305 (R&D system) anti-IGF-1R antibody (4D).

Figure 5:
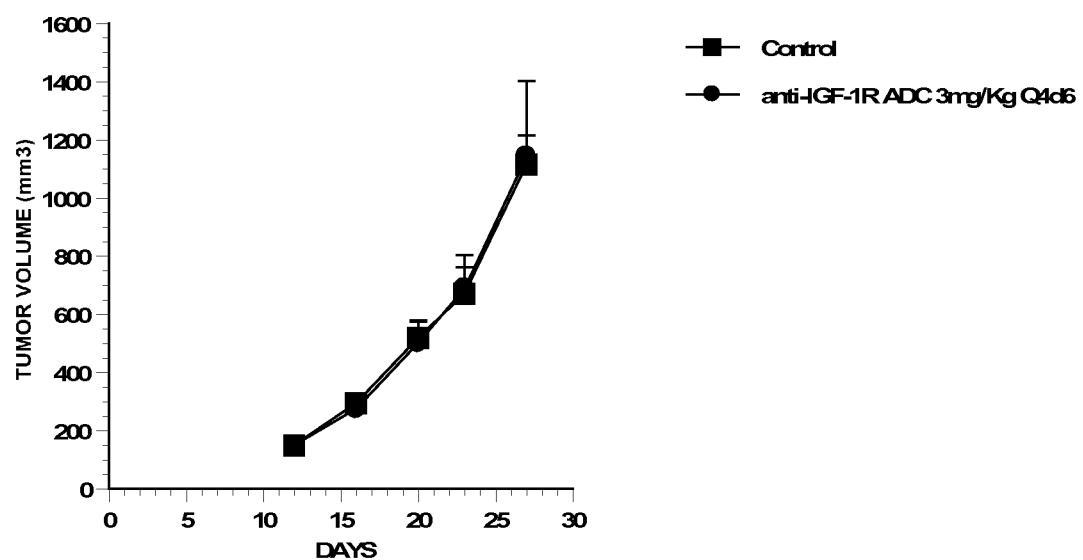

FIG. 5: In vivo activity of an anti-IGF-1R ADC in the SBC-5 xenograft model.

Figure 6:
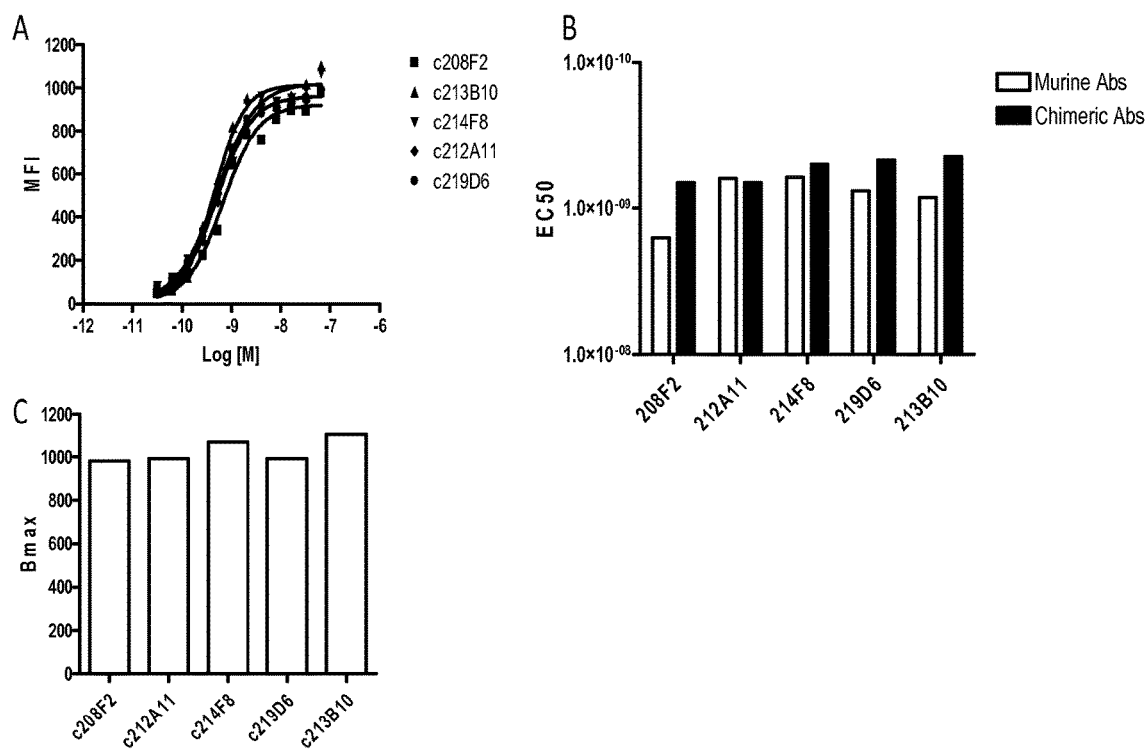

FIGS. 6A-6C: Antibody binding to the human native IGF-1R by FACS analyses. FIG. 6A represents the titration curve, on MCF-7 cell line. MFI represents the mean of fluorescent intensity. FIG. 6B represents the $EC_{50}$ of both murine and chimeric anti-IGF-1R antibodies on the MCF-7 cell line. FIG. 6C represents the $B_{max}$ of chimeric anti-IGF-1R antibodies on MCF-7 cell line.

Figure 7:
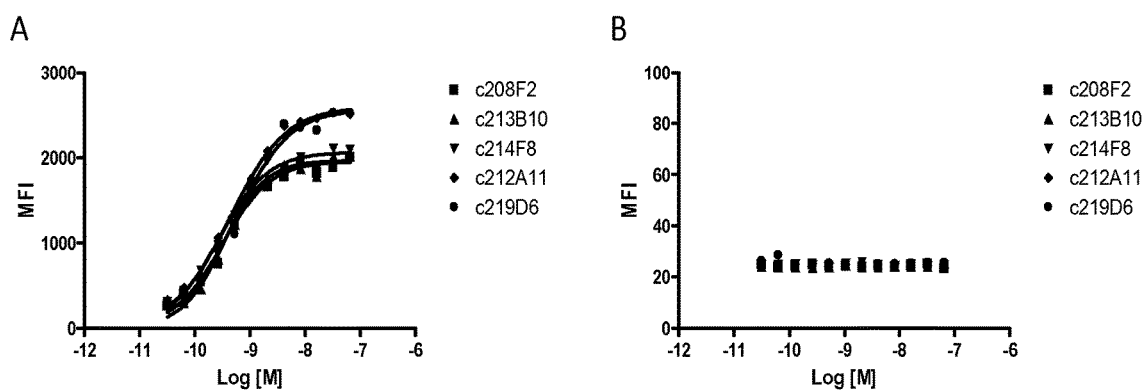

FIGS. 7A-7B: Evaluation of hIGF-1R recognition using transfected vs non transfected cells. FIG. 7A) Represents titration curves of one chimeric anti-IGF-1R Ab on IGF-1R$^+$ cell line. MFI represents the mean of fluorescent intensity. FIG. 7B represents the binding of chimeric anti-IGF-1R Abs on the human IGF-1R cell line.

Figure 8:
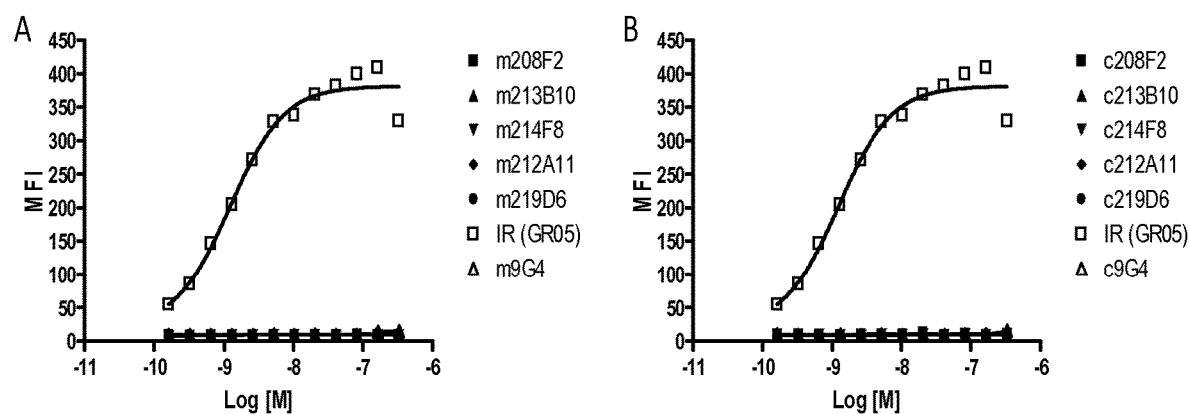

FIGS. 8A-8B: Evaluation of the specificity of Abs to IGF-1R vs hIR using transfected cells. FIG. 8A represents the binding of murine anti-IGF-1R Ab on the hIR$^+$ transfected cell line. FIG. 8B represents the binding of chimeric anti-IGF-1R Ab on the IR+ cell line. MFI represents the mean of fluorescent intensity. GRO5 anti-hIR Mab (Calbiochem) was introduced as a positive control.

Figure 9:
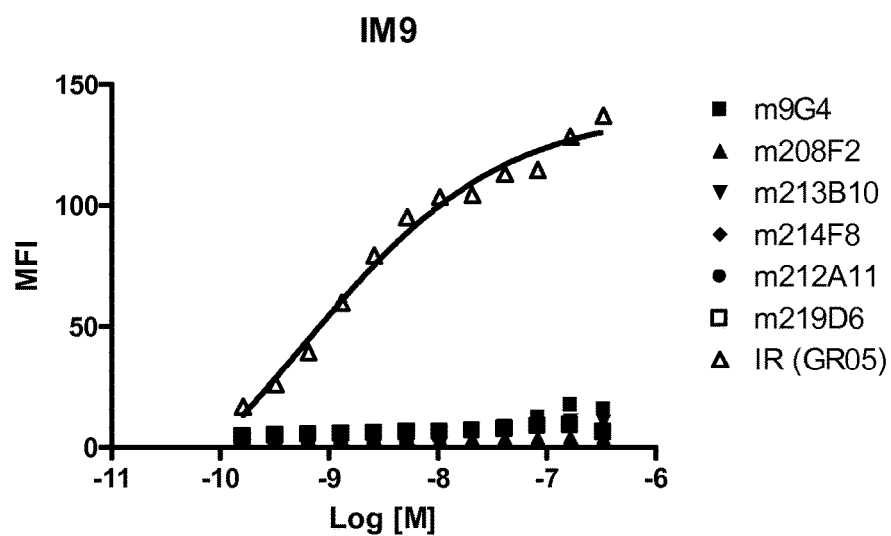

FIG. 9: Binding of murine anti-IGF-1R Ab on the IM-9 cell line. MFI represents the mean of fluorescent intensity. GRO5 anti-hIR Mab was introduced as a positive control.

Figure 10:
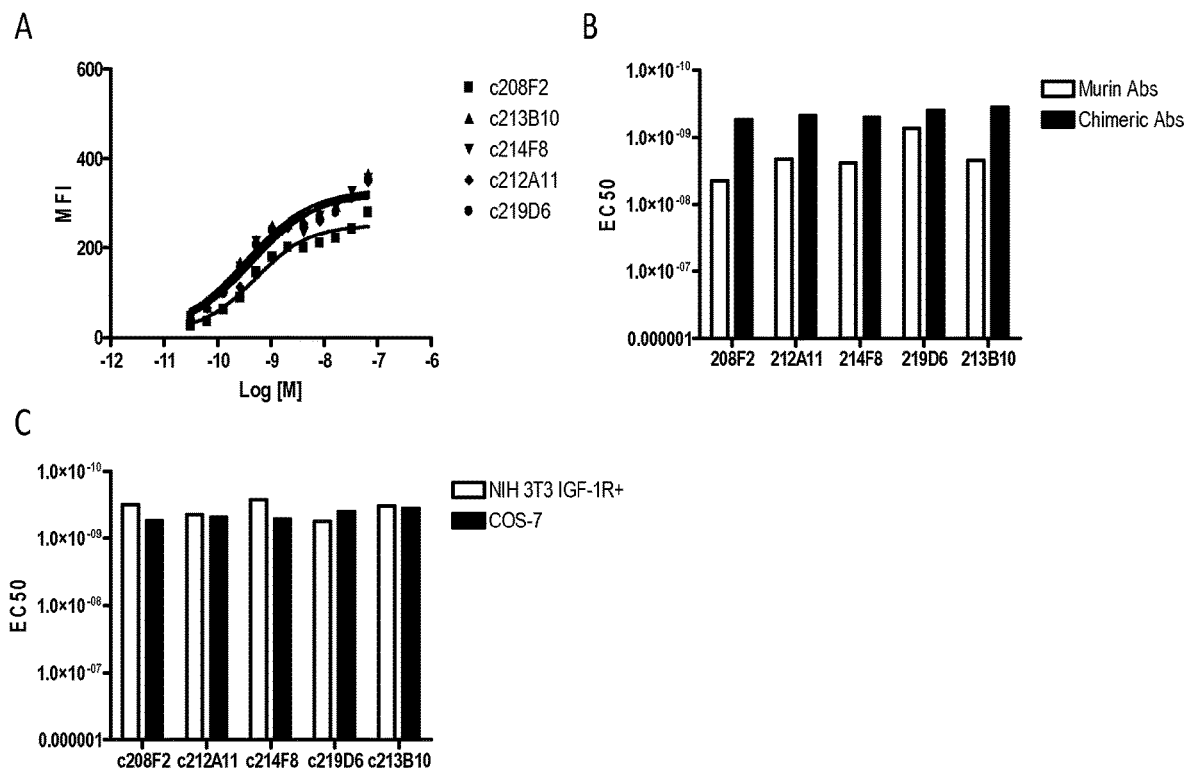

FIGS. 10A-10C: Evaluation of recognition of the monkey IGF-1R. FIG. 10A represents the titration curves of chimeric anti-IGF-1R Ab on the COS-7 cell line. MFI represents the mean of fluorescent intensity. FIG. 10B represents the $EC_{50}$ of both murine and chimeric anti-IGF-1R antibodies on COS-7 cell line. FIG. 10C represents the $EC_{50}$ of chimeric anti-IGF-1R antibodies on both NIH 3T3 transfected cells hIGF-1R+ and COS-7 cell lines.

Figure 11:
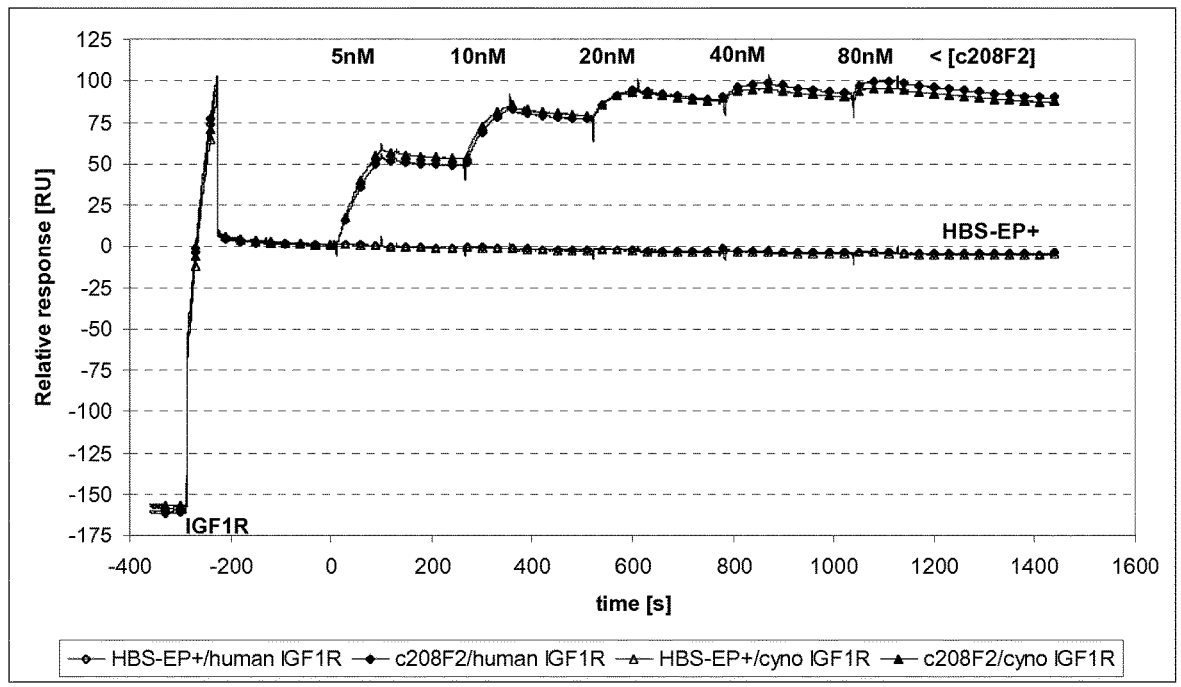

FIG. 11: Sensorgrams obtained on a SPR technology based Biacore X100 using a CM5 sensorchip activated with more the 11000 RU of mouse anti-Tag His antibody chemically grafted to the carboxymethyl dextran matrix. The experiment was run at a flow rate of 30 μl/min at 25° C. using the HBS-EP+ as the running and samples diluting buffer. The figure showed the superposition of 4 independent sensorgrams aligned on the x-axis at the beginning of the first injection of the analytes and on the y-axis by the baseline defined just before this first injection. The sensorgrams obtained with the capture of the human based sequence of the recombinant soluble IGF1R are marked by diamonds. The sensorgrams obtained with the capture of the cynomolgus based sequence of the recombinant soluble IGF-1R are marked by triangles. White symbols correspond to the blank cycles (5 injections of the running buffer) and black symbols correspond to the injections of the growing range of concentrations of c208F2 (5, 10, 20, 40 and 80 nM).

Figure 12:
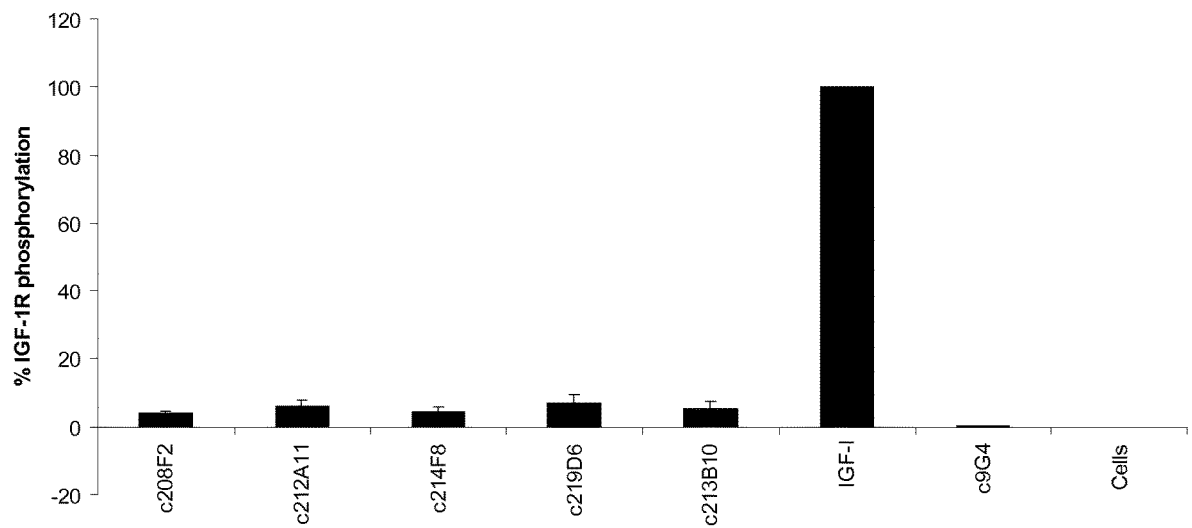

FIG. 12: Evaluation of the intrinsic effect of anti-hIGF-1R antibodies on the receptor phosphorylation compared to IGF1.

Figure 13:
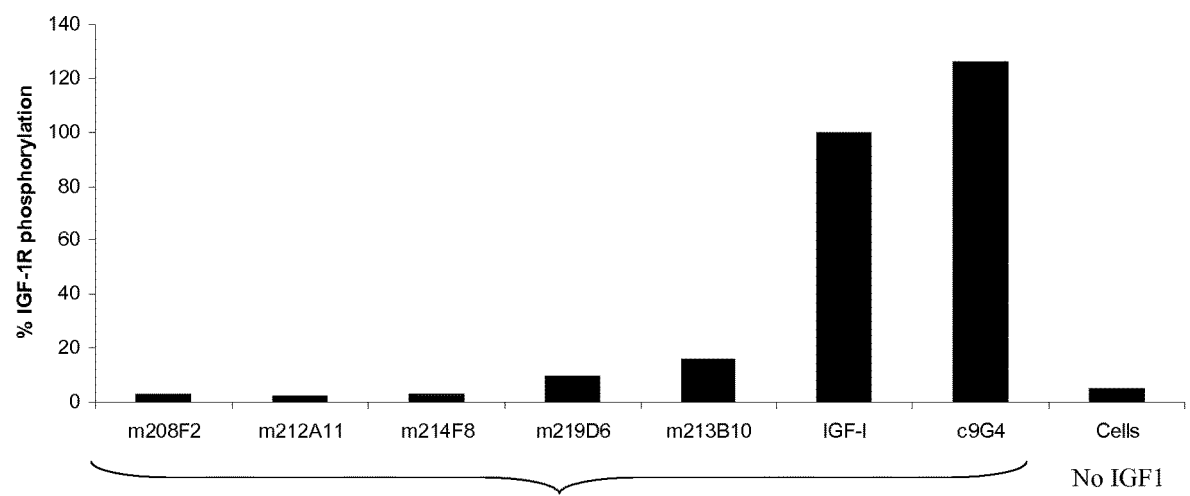
Figure 14:
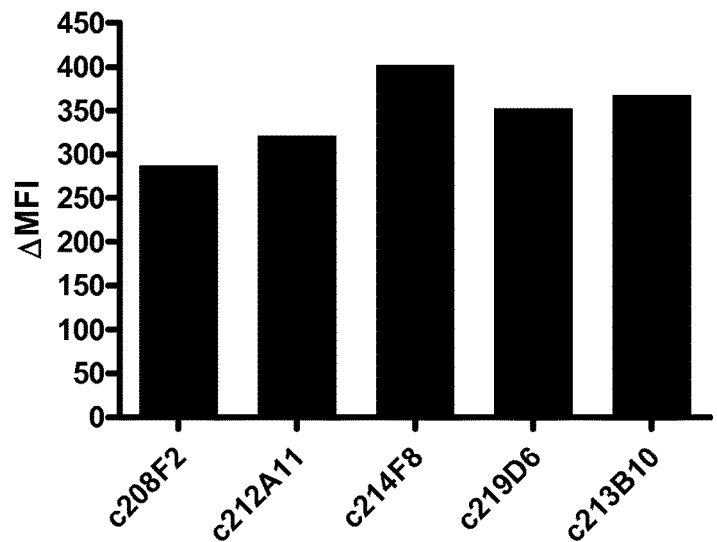

FIG. 13: Inhibition of IGF-1R phosphorylation in response to IGF-1 by murine anti-hIGF-1R FIG. 14: Cell surface signal intensity of anti-IGF-1R antibodies is down-regulated after cell incubation at 37° C. MCF-7 cells were incubated at 4° C. or 37° C. for 4 h with 10 μg/ml of Abs. The figure represents the ΔMFI.

FIGS. 15A-15B: Antibody surface decay. Cell surface bound antibody was assessed after 10, 20, 30, 60 and 120 min at 37° C. FIG. 15A represents the % of remaining IGF-1R in comparison to the signal intensity measured at 4° C. FIG. 15B represents Half Life calculation usinf Prims Software and using exponential decay fitting.

Figure 16:
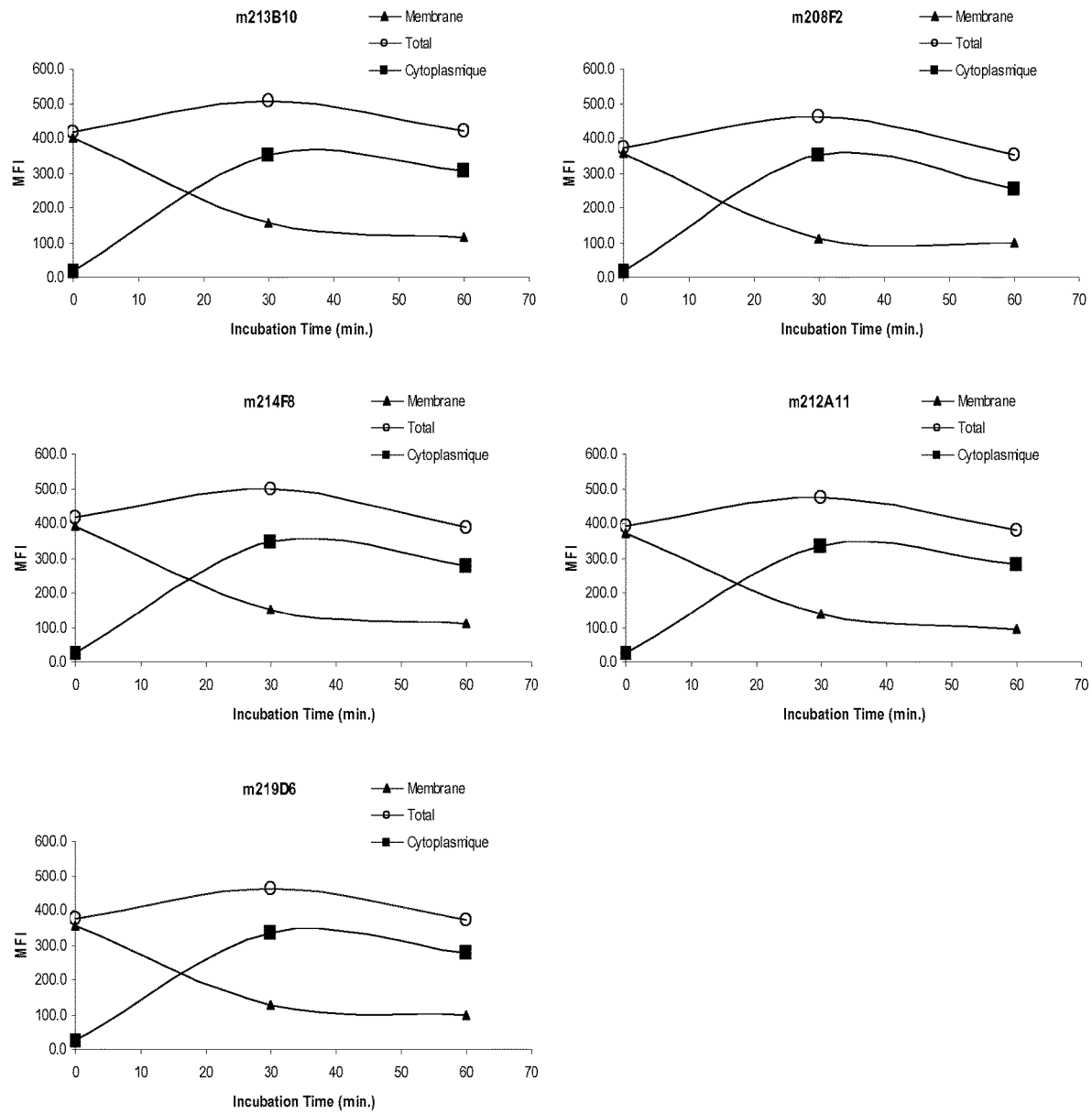

FIG. 16: Anti-hIGF-1R Abs are internalized. Cells were incubated with 10 μg/ml of murine Abs for 0, 30 or 60 min at 37° C. Cells were permeabilized or not and incubated with a secondary anti-mouse IgG-Alexa 488. Membrane corresponds to the signal intensity w/o permeabilization. Total correspond to the signal intensity after cell permeabilization and cytoplasmic corresponds to internalized Ab. The name of each evaluated antibody is depicted on the top of each graph.

Figure 17A:
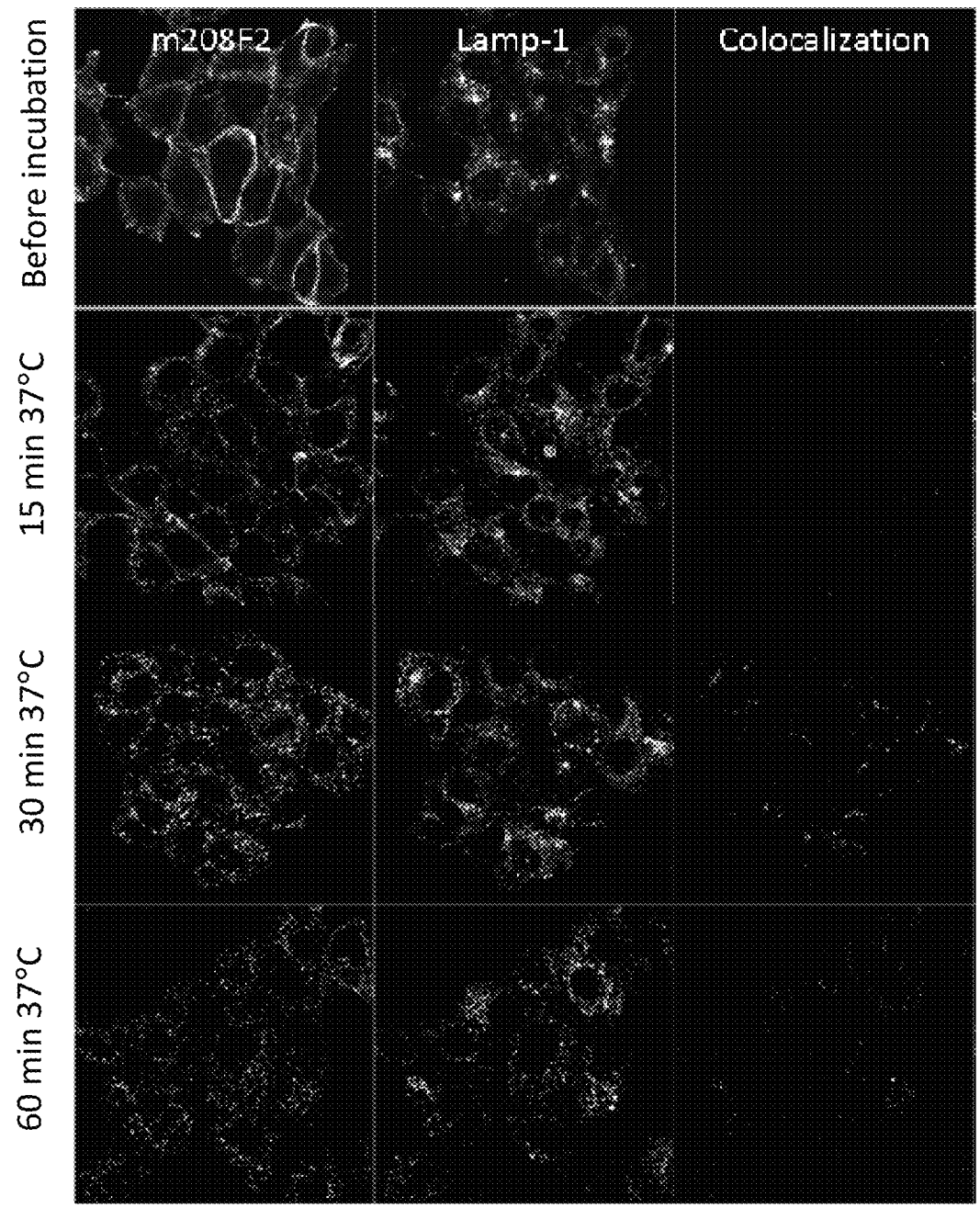
Figure 17B:
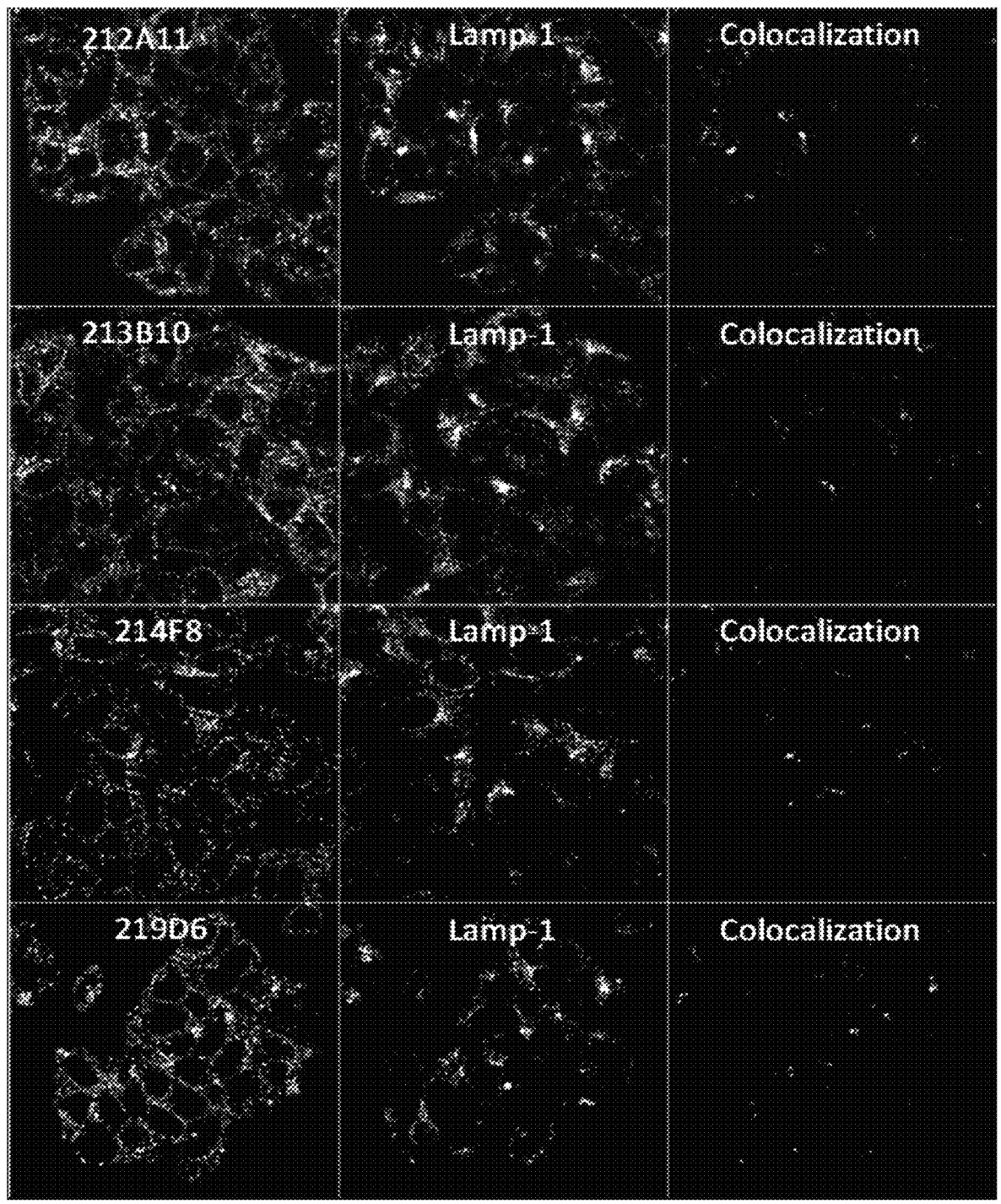

FIGS. 17A-17B: Imaging Ab internalization. FIG. 17A: MCF-7 cells incubated with m208F2 for 20 min. at 4° C. and washed before incubation (W) at 37° C. for 15 (X), 30 (Y) and 60 (Z) min. Cells were fixed and permeabilized. The m208F2 Ab was revealed using an anti-mouse IgG Alexa488 and Lamp-1 using a rabbit anti-Lamp-1 antibody and with a secondary anti-rabbit IgG Alexa 555. FIG. 17B: MCF-7 cells were incubated for 30 minutes at 37° C. with anti-hIGF-1R murine antibodies and stained as described above. Colocalization was identified using the colocalization highliter plug-in of the ImageJ software.

Figure 18:
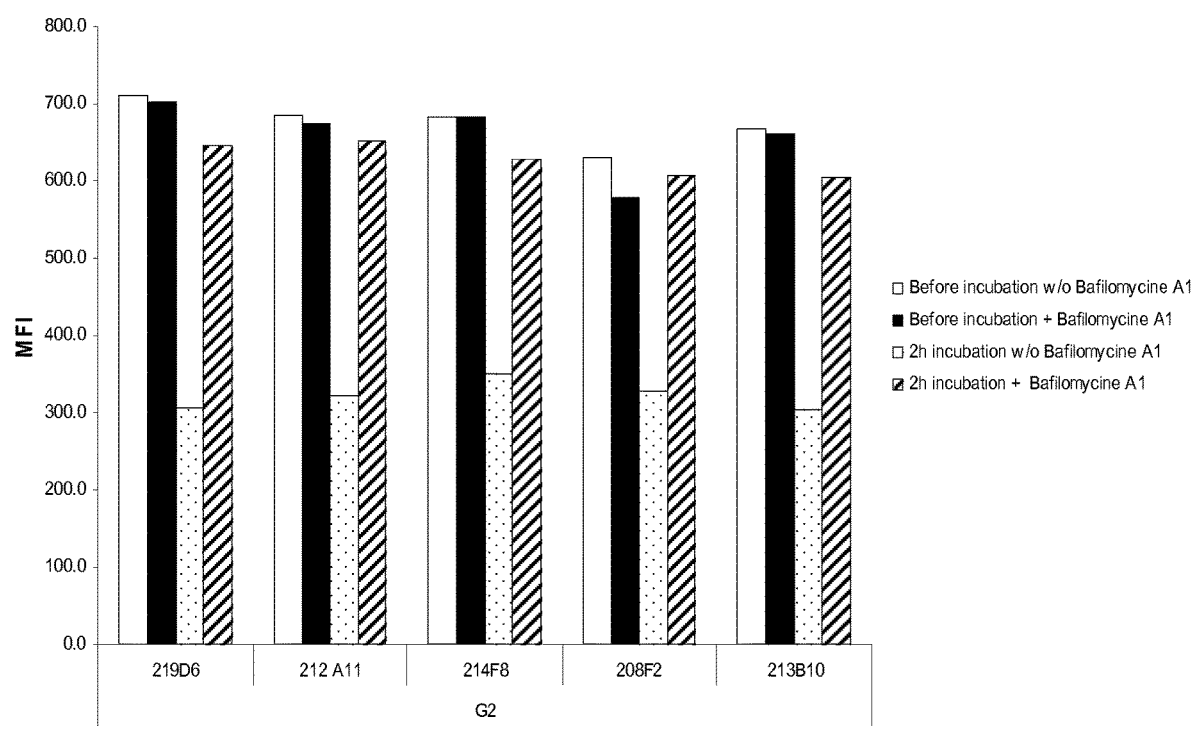

FIG. 18: Involvement of the lysosome pathway in antibody degradation

Figure 19:
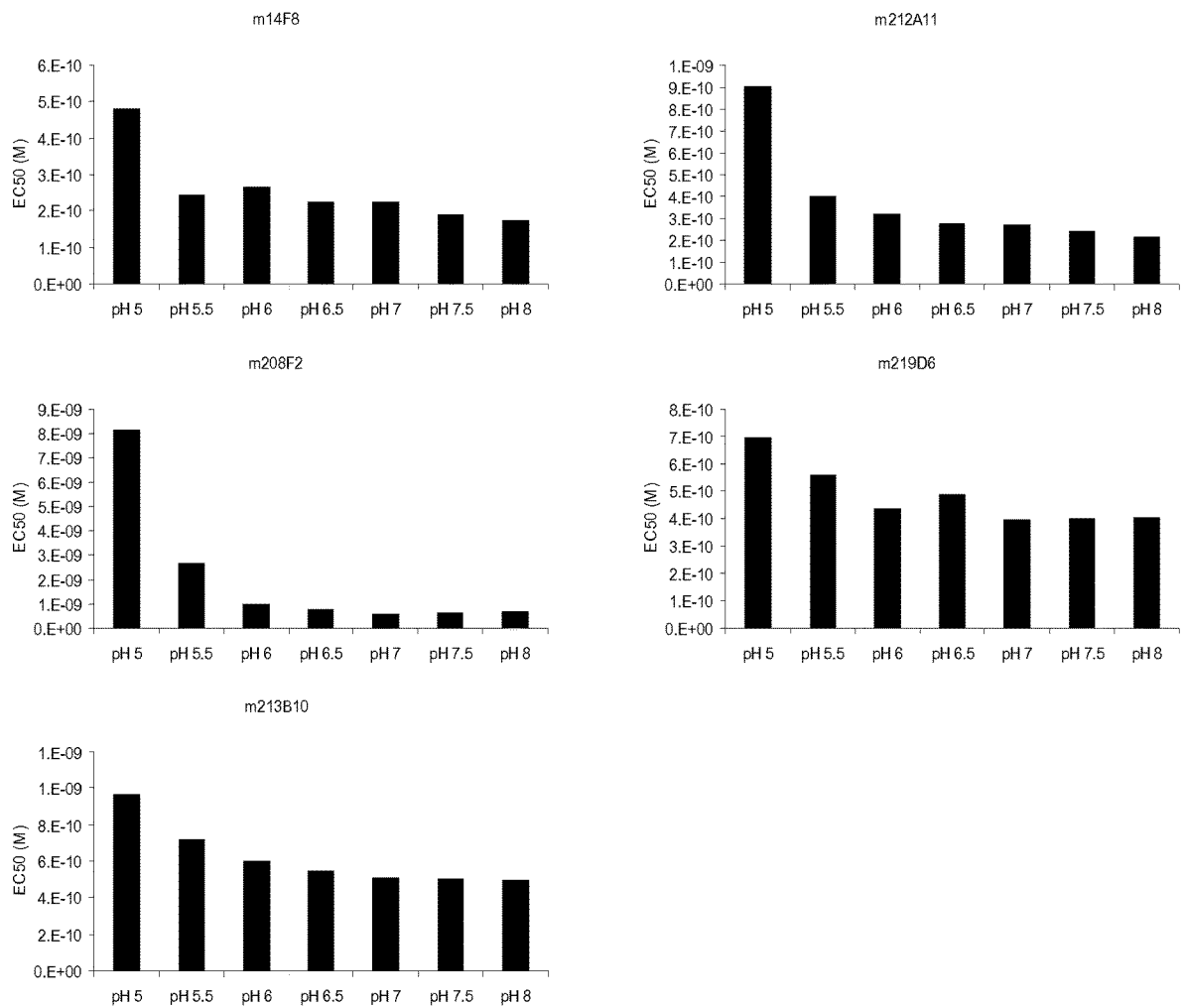

FIG. 19: Acidic pH decreases binding capacity of the five murine anti-IGF-1R antibodies.

FIGS. 20A-20D: Binding characteristic of the first humanized form of the c208F2 Mab. Binding properties of the hz208F2 mAb was evaluated on the human cell line MCF-7 (A), on the monkey cell line COS-7 (B) and on the transfected murine cell line expressing the human insulin receptor (C). The binding of both the murine and the chimeric 208F2 mAbs was evaluated in parallel. The anti-hIR antibody clone GRO5 was used to verify the expression of the hIR on the transefected cell line (D).

Figure 21:
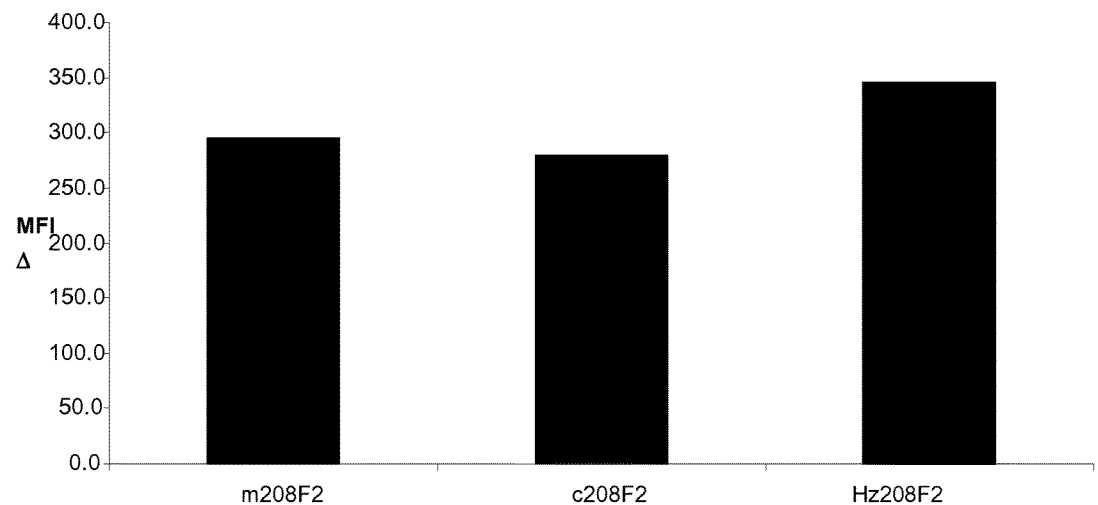

FIG. 21: hz208F2 antibody surface decay

Figure 22:
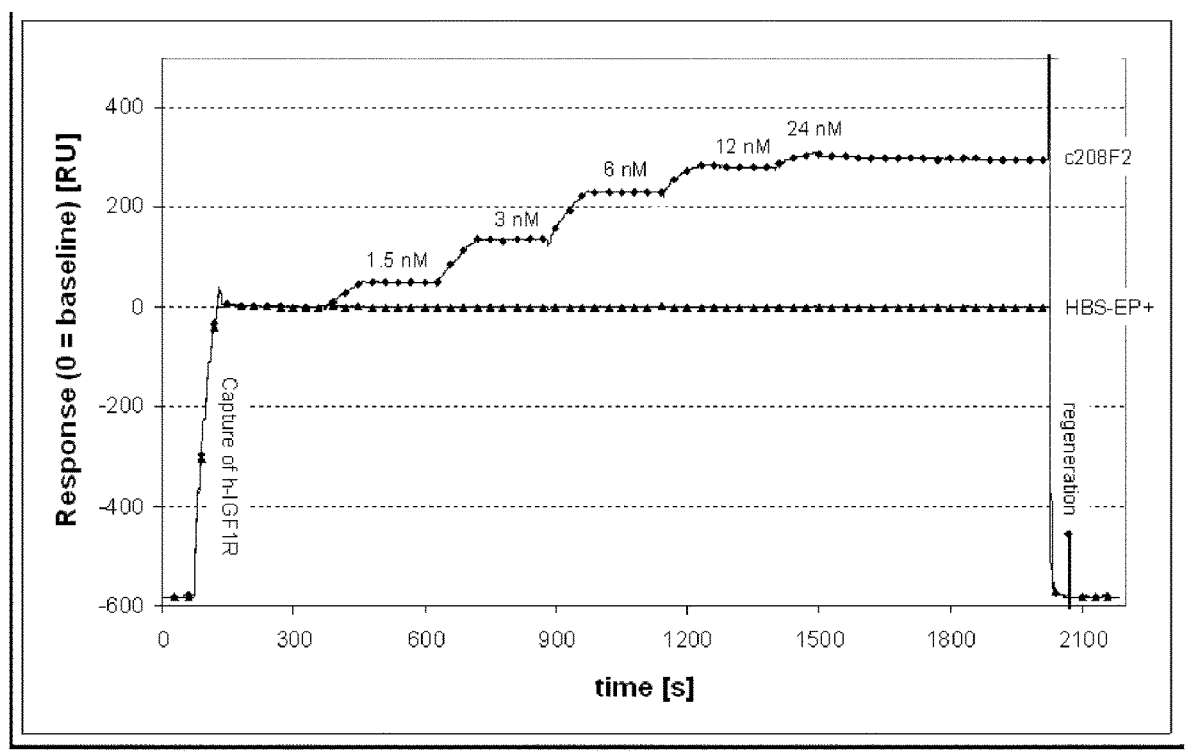

FIG. 22: Superposition of to sensorgrammes obtained with a SPR based Biacore X100 device at a temperature of 25° C. with a CM5 sensor chip activated on both flowcells with aroud 12.000 RU of a mouse anti-TagHis monoclonal antibodies chemically grafted to the carboxymethyldextran matrix using a HBS-EP+ as the running buffer at a flow rate of 30 μl/min. Each sensorgrammes (the first one marked by triangles and the second one marked by diamonds) correspond to a complete cycle:

1—Injection during one minute of a solution of recombinant h-IGF-1R (10 µg/ml) on the second flowcell.
2—For the first sensorgramme: 5 injections of running buffer during 90 s each
For the second sensorgramme: five injections in the growing range of concentrations of the anti-IGF-1R c208F2 antibody solutions during 90 s each.
3—A delay of 300 s for the determination of the dissociation kinetic rates.
4—A regeneration of the surface by an injection during 45 s of a 10 mM Glycine, HCl pH 1.5 buffer.

Figure 23:
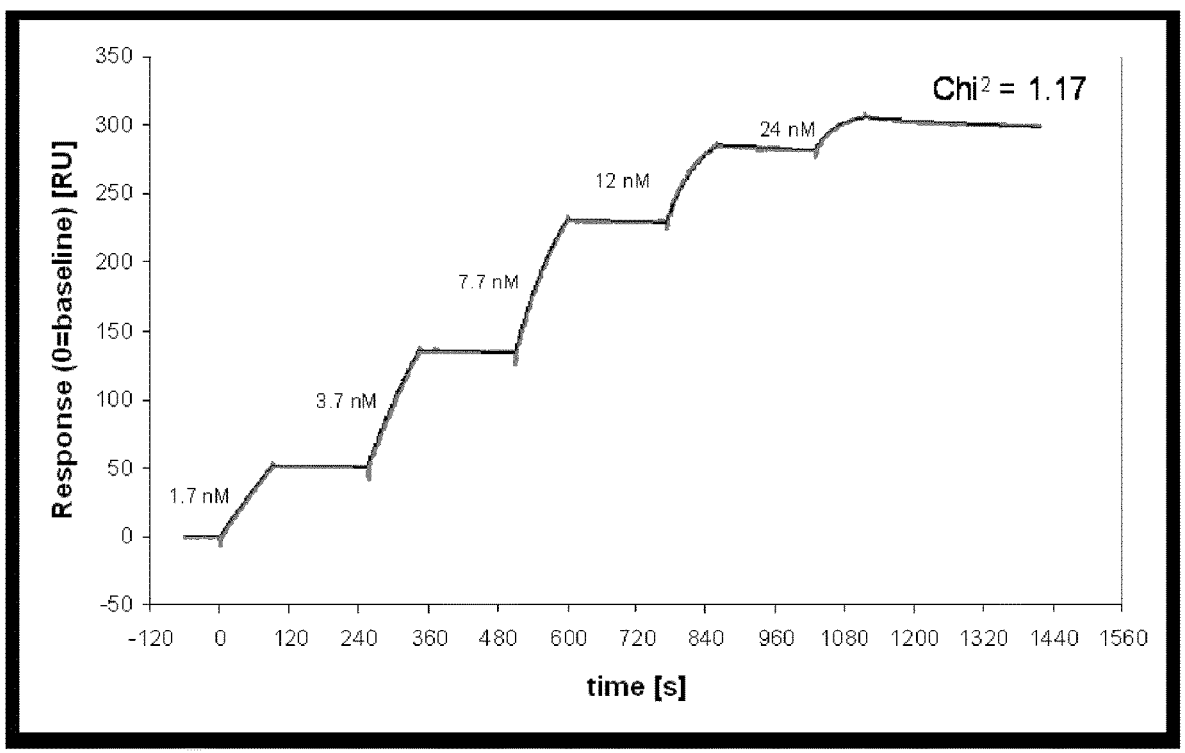

FIG. 23: The sensorgramme corresponding to the subtraction of the blank sensorgramme (5 injections of HBS-EP+) to the sensorgramme obtained with the growing range of concentrations of the anti-IGF-1R c208F2 solutions is presented in grey. The theoretical sensorgramme corresponding to the 1:1 model with the following parameters: $k_{on}=(1.206\pm0.036)\times10^6$ $M^{-1}\cdot s^{-1}$, $k_{off}=(7.81\pm0.18)\times10^{-5}$ $s^{-1}$, Rmax=307.6±0.3 RU is presented by a thin black line. The calculated concentrations of c208F2 are reported on the graph: only the highest concentration (24 nM) is considered as a constant).

Figure 24:
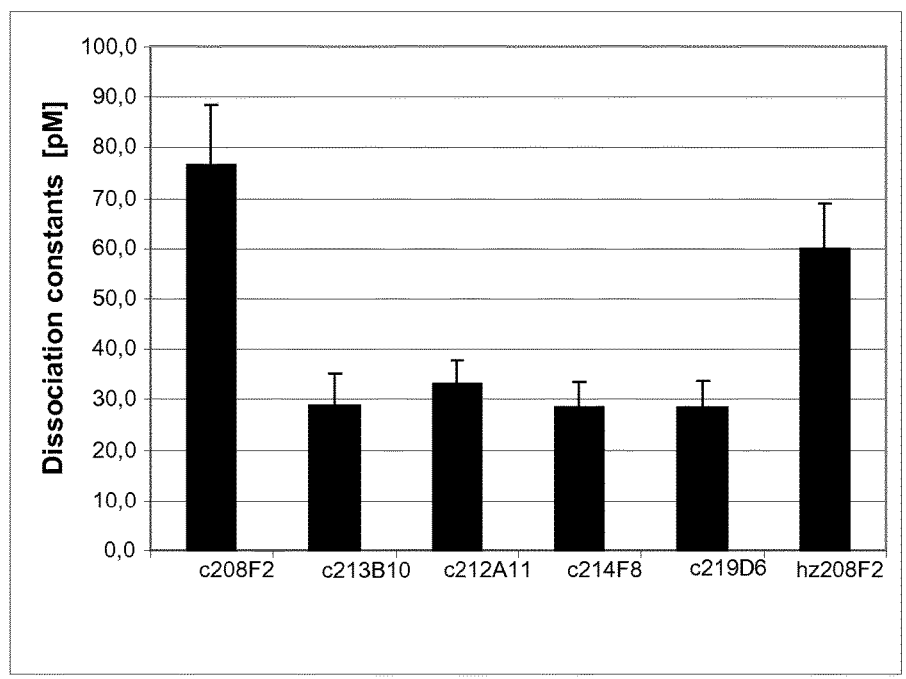

FIG. 24: The dissociation constants correspond to the mean of the four experiments run for each antibody and correspond to the ratio: $k_{off}/k_{on}\times10^{12}$ to be express in the pM unit. The error bars correspond to the standard error (n=4).

Figure 25:
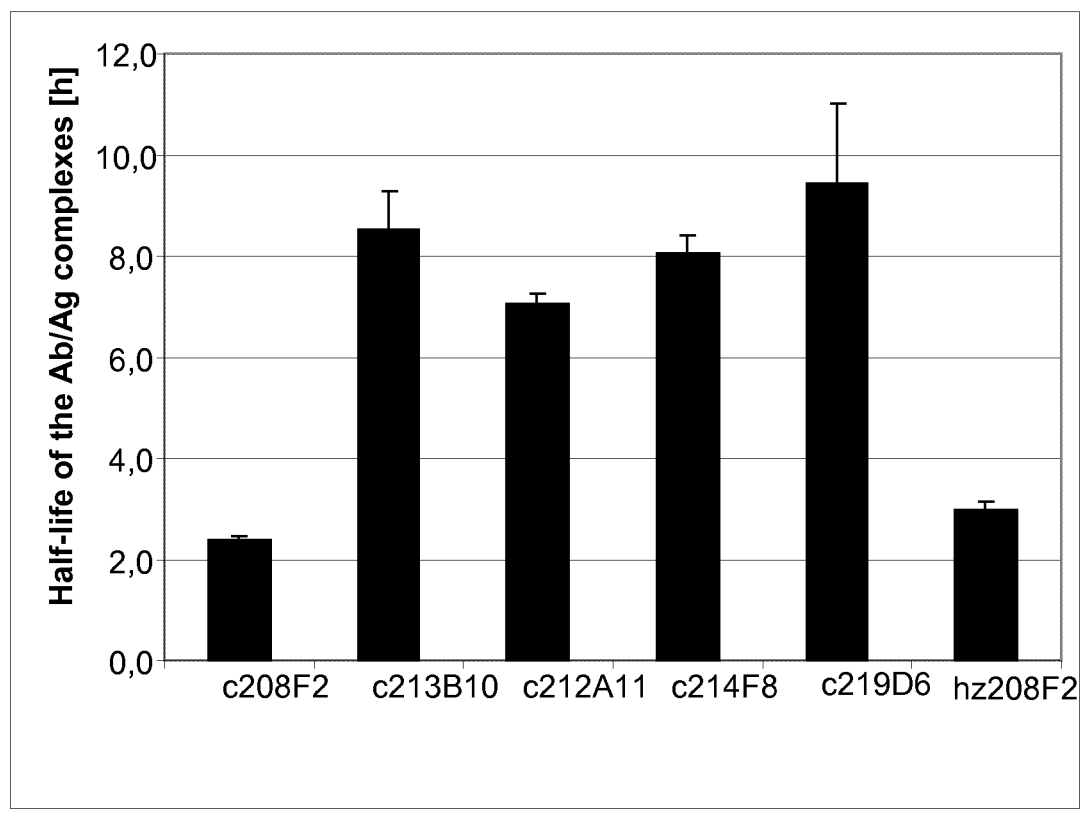

FIG. 25: the half-lives correspond to the mean of the four experiments run for each antibody and correspond to the ratio: $Ln(2)/k_{off}/3600$ to be express in the h unit. The error bars correspond to the standard error (n=4).

Figure 26:
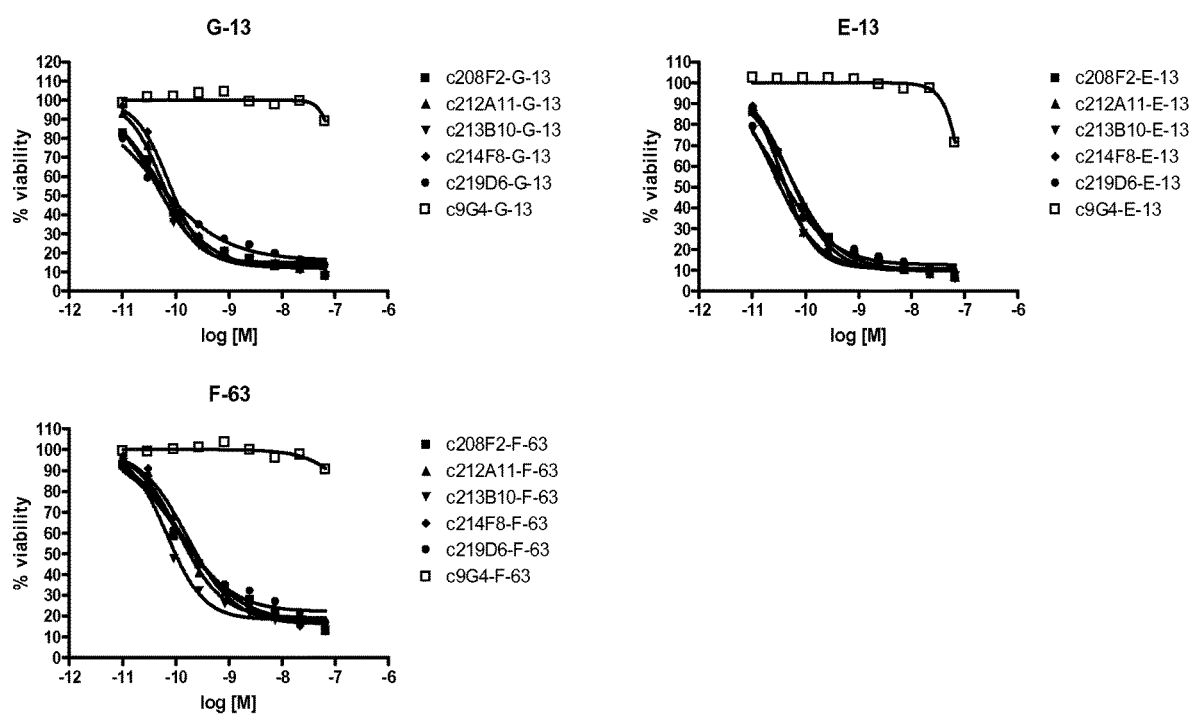

FIG. 26: Cell cytotoxicity of anti-IGF-1R coupled with three different compounds. Five chimeric antibodies anti-IGF-1R were coupled with either E-13, G-13 or F-63. An irrelevant antibody c9G4 was also coupled with the same compounds.

Figure 27A:
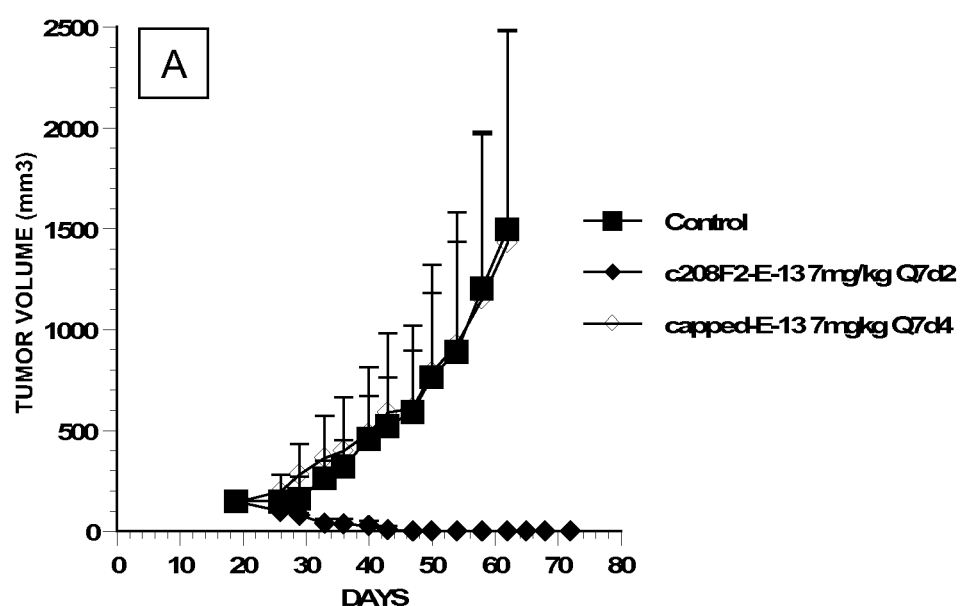
Figure 27B:
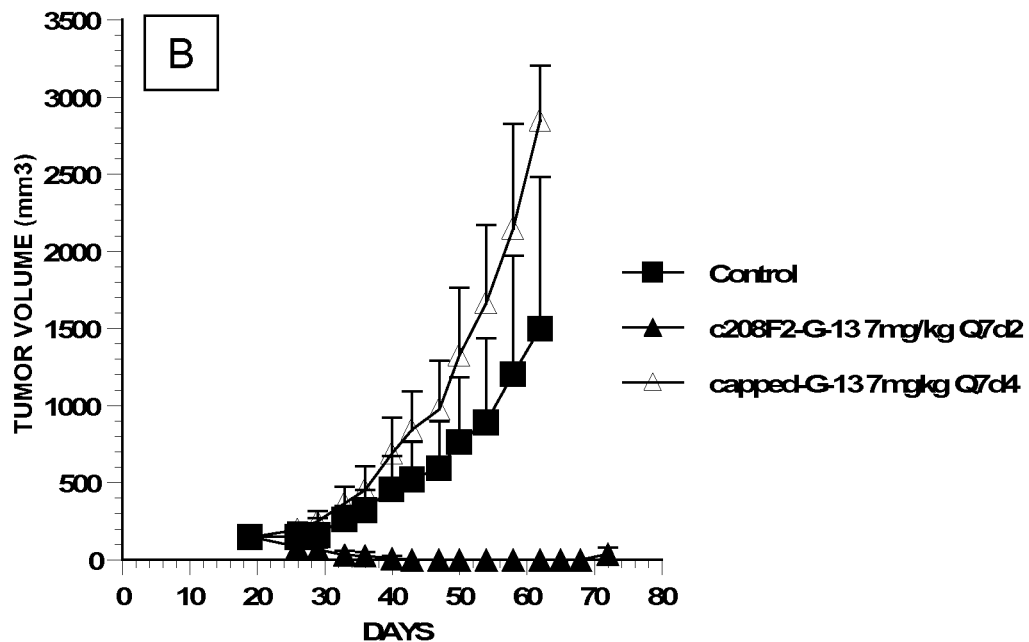
Figure 27C:
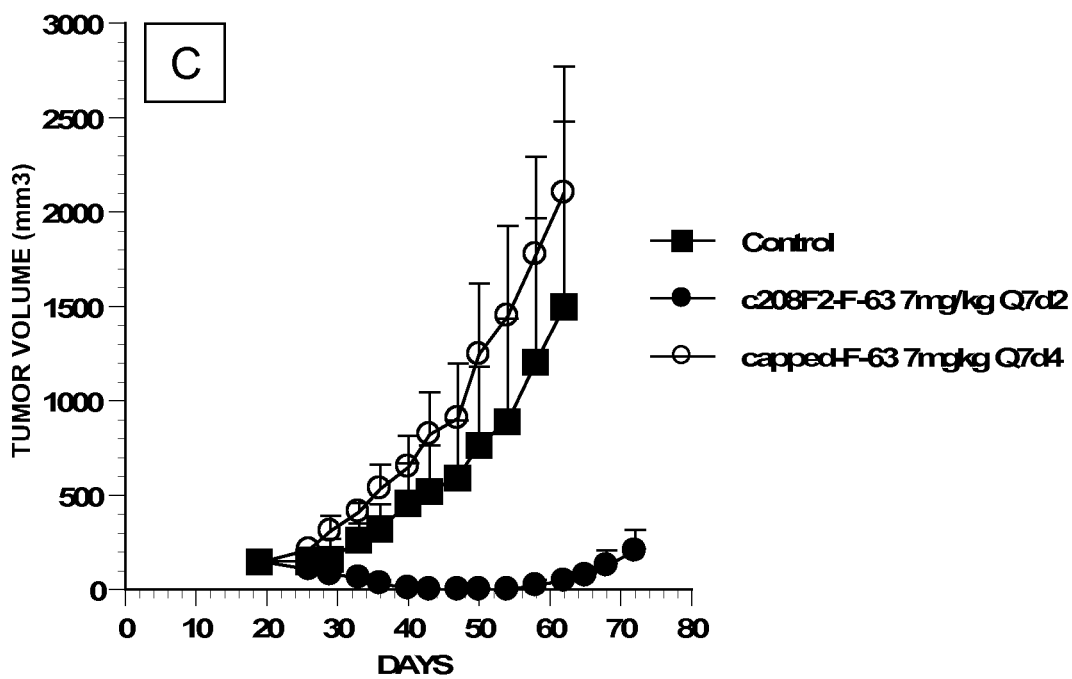

FIGS. 27A-27C: In vivo evaluation of c208F2-E-13 (FIG. 27A), c208F2-G-13 (FIG. 27B) and c208F2-F-63 (FIG. 27C) in the MCF-7 xenograft model.

Figure 28A:
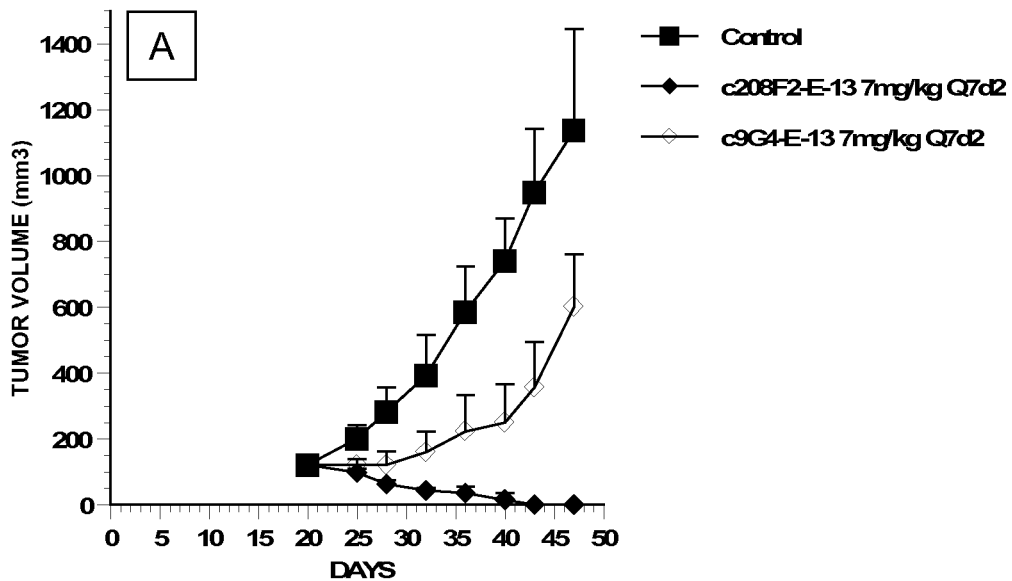
Figure 28B:
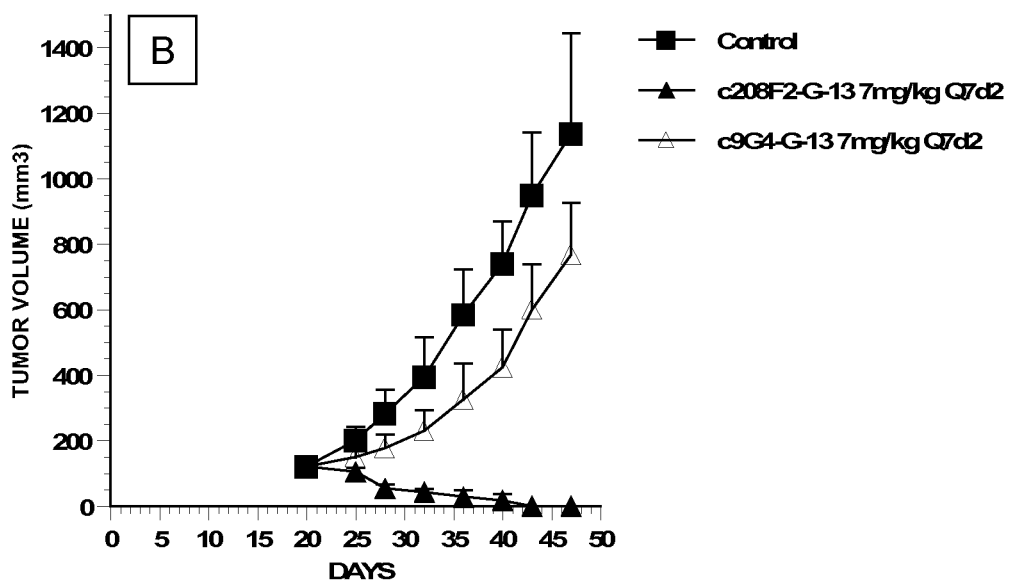

FIGS. 28A-28B: in vivo evaluation of both c208F2-E-13 (FIG. 28A) and c208F2-G-13 (FIG. 28B) compared to ADCs control (c9G4-E13 and c9G4-G-13) in the MCF-7 xenograft model.

FIGS. 29A-29B: Acidic pH decreases binding capacity of the humanized IGF-1R antibodies hz208F2 H026/L024 (A) and hz208F2 (H077/L018 (B).

Figure 30:
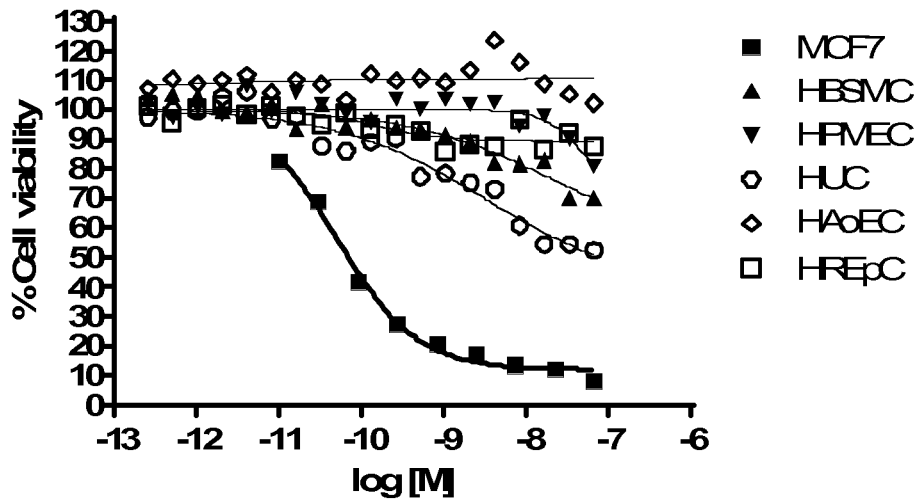

FIG. 30: Evaluation of the cytotoxicity of c208F2-G-13 on normal cells.

Figure 31:
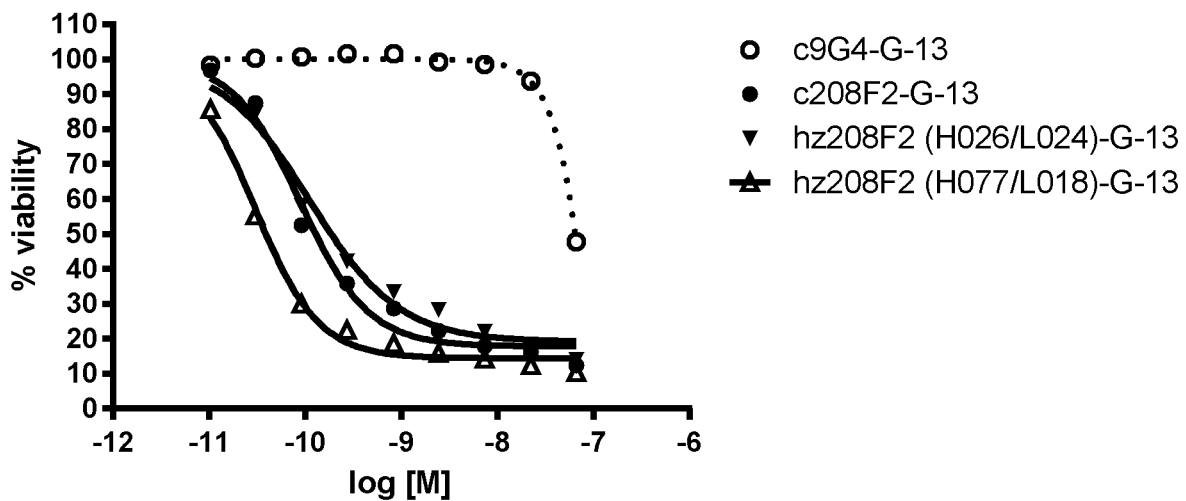

FIG. 31: Cell cytotoxicity of the humanized variants of hz208F2 coupled with G-13. An irrelevant antibody c9G4 was also coupled with the same compound.

Figure 32:
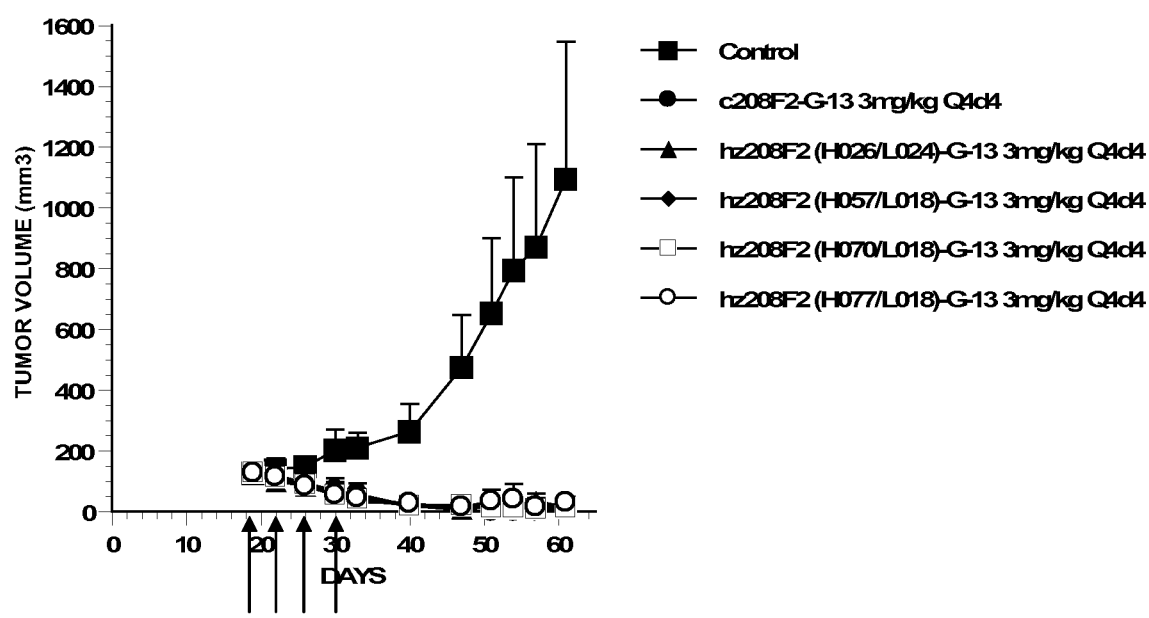

FIG. 32: in vivo evaluation of humanized forms of 208F2-G-13 vs c208F2-G-13 in the MCF-7 xenograft model.

Figure 33:
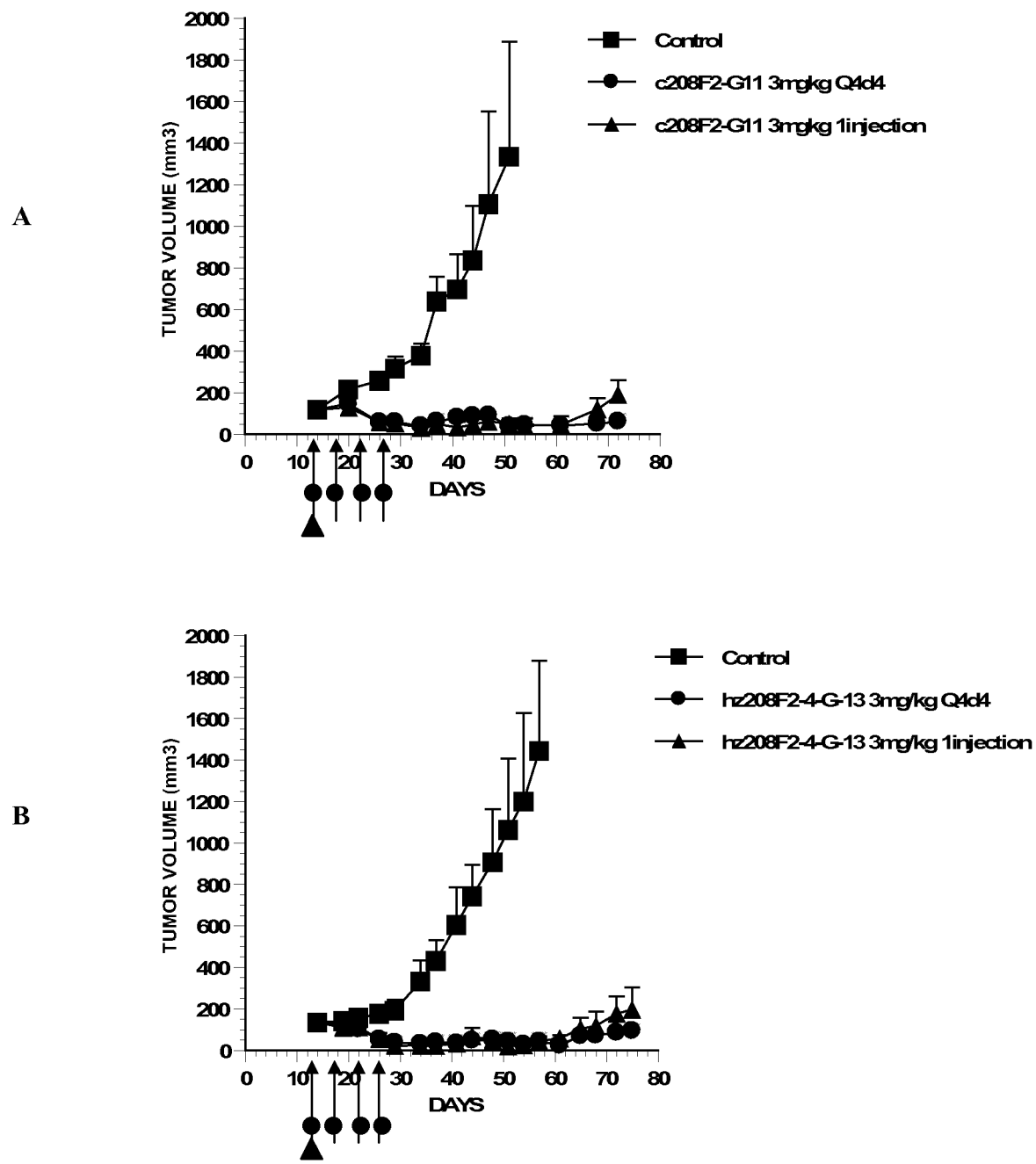

FIGS. 33A and 33B: in vivo evaluation of either c208F2-G-13 (33A) or hz208F2-4-G-13 (33B) injected 4 times compared to one injection in the MCF-7 xenograft model.

Figure 34:
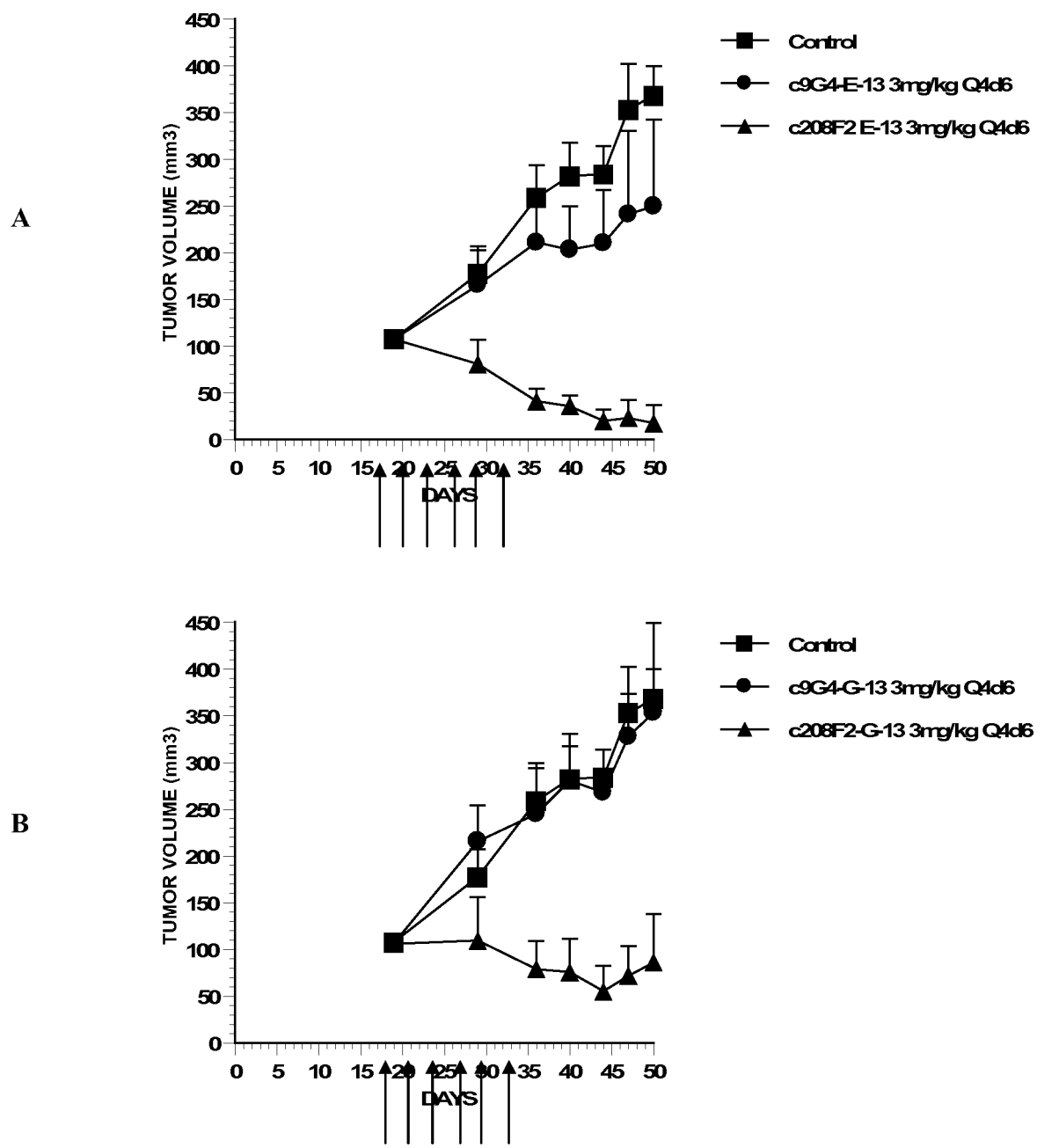

FIGS. 34A and 34B: in vivo evaluation of c208F2-E-13 (34A) and c208F2-G-13 (34B) in the CaOV-3 xenograft model.

FIGS. 35A-35D: 4 Sensorgrams corresponding to the capture of a soluble form of h-IGF1R (30 µg/ml) captured on a CM5 activated by more than 12000 RU of an anti-poly Histidine mouse monoclonal antibody chemically linked to the carboxymethyldextran matrix.

This injection is followed by the injection as Ac1 of either the running buffer (HBS-EP+) (A and C) or the Hz208F2-4 (B and C) used at the concentration of 50 µg/ml. This injection is followed by the injection of the Ac2 Hz208F2-4 at the concentration of 50 µg/ml (A and B) or m810C12 at 50 µg/ml too (C and D). The experiment is run on a Biacore X100 at 25° C. at a flow rate of 10 l/min.

Figure 36:
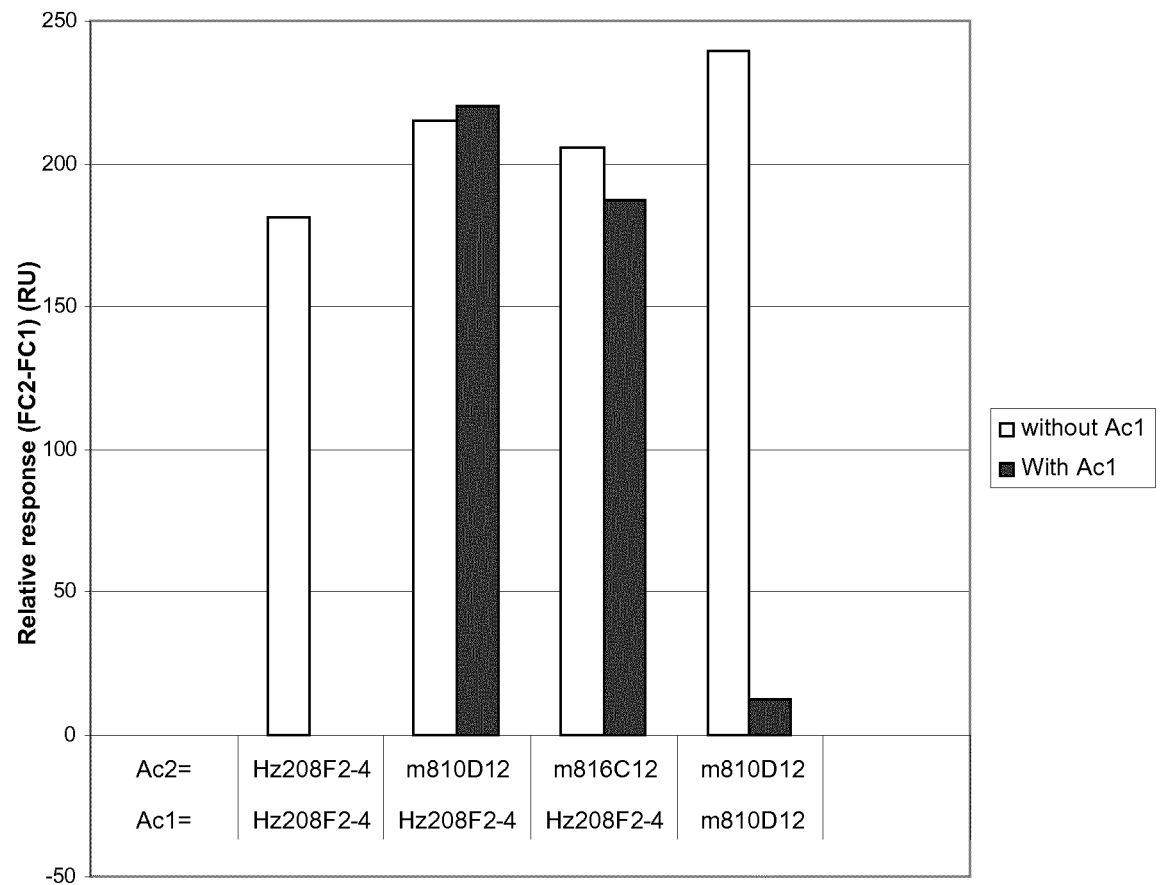

FIG. 36: Binding level of the Ac2 at 20 s after the end of the injection without Ac1 (white bars) or in presence of Ac1 (black bars).

Figure 37:
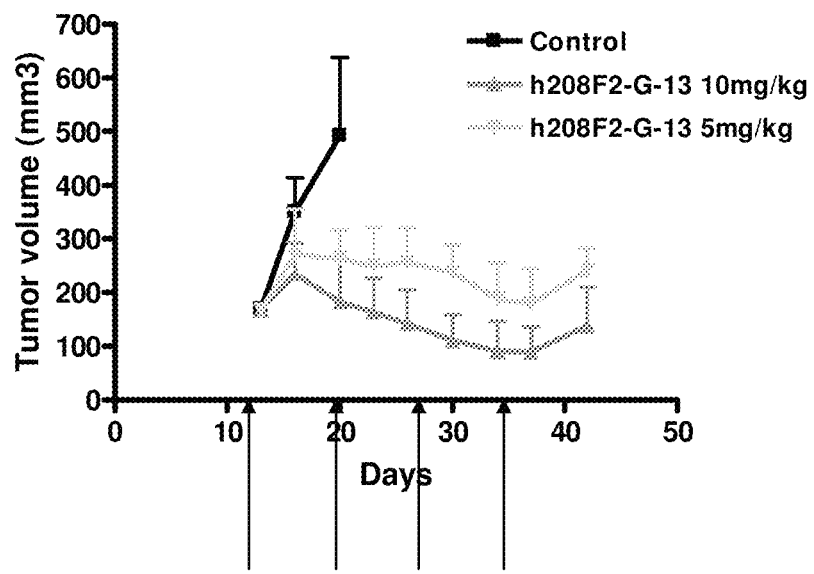

FIG. 37: In vivo activity of the 208F2 antibody conjugated to G-13 compounds in the 2+ NCI-H2122 xenograft model.

Figure 38:
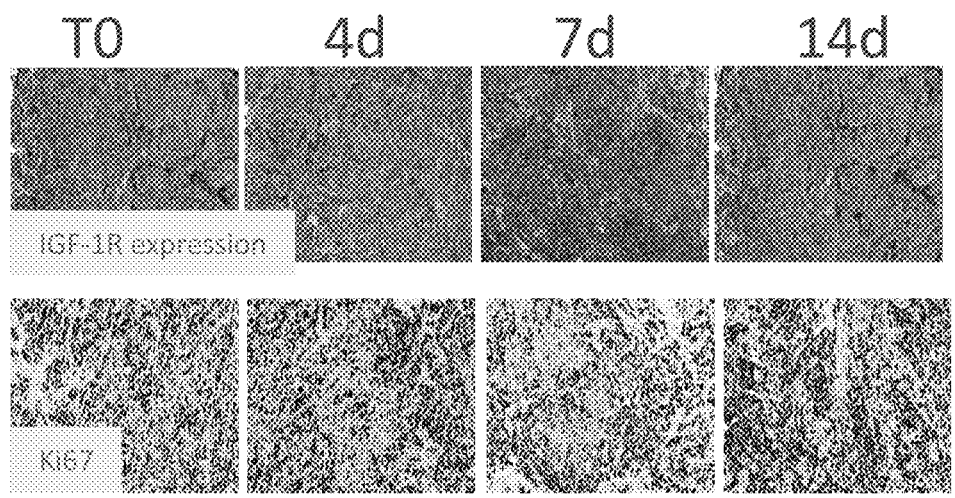

FIG. 38: IGF-1R and Ki67 staining levels in MCF7 tumor before injection of 208F2-G-13.

Figure 39:
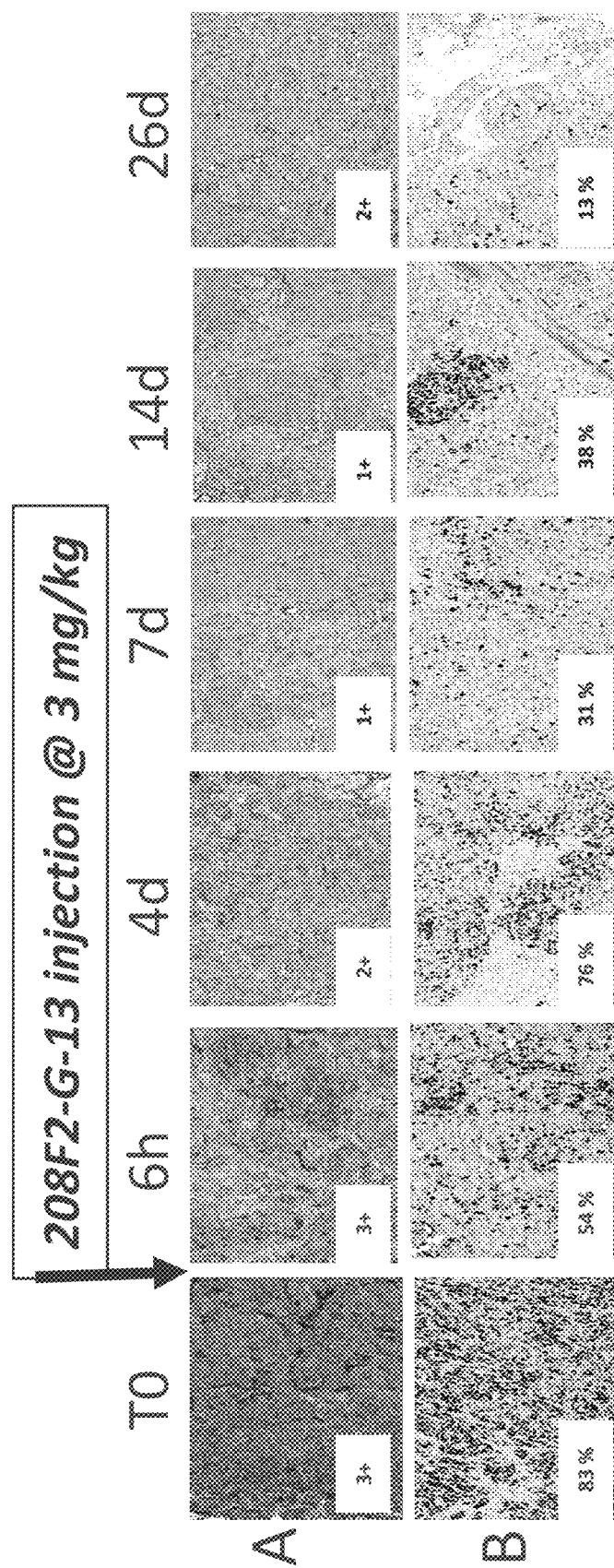

FIG. 39: IGF-1R and Ki67 staining levels in MCF7 tumor after injection of 208F2-G-13.

EXAMPLES

Example 1: First IGF-1R Antibodies Generation and Selection

Mabs 816C12 and 810D12 were produced and selected as described bellow.

Female Balb/C mice were immunized by subcutaneous injection with 10 µg of recombinant human IGF-1R protein (R and D Systems, 391-GR) with Freund Adjuvant. Immunisation was repeated three times at 2 weeks intervals. The fourth injection was made by intraperitoneal injection in presence of adjuvant.

Three days later spleen cells were fused with SP2OAg14 myeloma cells with PEG 50%. After 14 days of HAT metabolic selection, hybridoma supernatants were tested by FACS using human MCF7 breast cancer cells. Only MCF7 binding antibodies were kept.

Antibodies of interest were then cloned by limit dilution. Eight days after cloning, supernatants were selected once again by FACS using MCF7 cells. Three positive clones were kept for each hybridoma. Isotyping of the secreted antibodies is determined using SBA clonotyping system-HRP kit from Southern Biotechnologies (Cat: 5300-05). Finally, one clone is expanded and frozen.

Further characterizations of 816C12 and 810D12 were then performed using hybridoma supernatant such as rhIGF-1R or rmIGF-1R or rhIR ELISA. In all direct ELISAs, proteins of interest were immobilized (1 µg/ml) to the bottom of each well. After saturation, hybridoma supernatants were added to the wells. After a 1-hour incubation period and a washing step, a solution of goat anti-mouse IgG—HRP labelled polyclonal antibody was used for detection, prior to the addition of the TMB substrate. The reaction was stopped with a 1M $H_2SO_4$ solution before reading the OD with a spectrophotometer at a 450 nm wavelength. Data are presented in Table 7.

TABLE 7

| | OD values obtained at 5 µg/ml by ELISA | | |
| --- | --- | --- | --- |
| | rhIGF-1R coating | rmIGF-1R coating | rhIR coating |
| 816C12 | 2.622 | 0.065 | 0.055 |
| 810D12 | 2.136 | 1.293 | 0.048 |
| Positive CTRL | 2.338 | 1.293 | 1.077 |
| Negative CTRL | 0.055 | 0.065 | 0.048 |

The dose response curves for the second IGF-1R antibodies on rhIGF-1R coating are presented in FIG. 1 for the 816C12 and in FIG. 1B for the 810D12. The values of the $EC_{50}$ are determined using Prism application.

Data showed that the 816C12 antibody only recognizes the rh IGF-1R with an $EC_{50}$ of 0.41 nM and that the 810D12 antibody only recognize the rh IGF-1R with an $EC_{50}$ of 0.51 nM. They both do not bind to the murine form of the IGF-1R nor the human IR.

Example 2: Evaluation of the Correlation of the Staging with the First IGF-1R Antibody of the Invention and the Activity of an ADC Targeting IGF-1R in the MCF-7 Xenograft Model In order to correlate the grading of tumors with the pharmacology, the tumors have been graded (section 2.1) and then in vivo experiments on MCF-7 xenograft model have been made with an ADC comprising a second IGF-1R antibody moiety targeting the IGF-1R known to be internalized and a drug moiety consisting of an auristatin (section 2.2).

2.1: Immunohistochemistry Detection of the IGF-1R Expression on the MCF-7 Xenograft Model Sections of tissue from MCF-7 xenograft were deparaffinized, rehydrated, and placed in Target Retrieval Buffer 1× (Dako S1699) in a boiling bath pre-warm at 98° C. for heat-induced epitope retrieval at 98° C. for 40 minutes then 20 additional minutes in the Target Retrieval Buffer. After 3 washes in Tris Buffer Saline-0.05% tween 20 (TBS-T) (Dako S3006) the Endogenous peroxidase activity was blocked using Peroxidase Blocking Reagent (Dako K4007) for five minutes. Sections were washed with TBS-T and incubated a blocking reagent (UltraV block-TA-125UB-LabVision) for 5 minutes before incubation with either the 816C12 monoclonal antibody (at 5 µg/ml) or mouse IgG1/kappa (5 µg/ml, X0931, Dako) as negative control for 1 hours at room temperature. Sections were washed with TBS-T and incubated with Envision (Dako) for 30 minutes. Diaminobenzidine was used for development of a brown reaction product (Dako K3468). The slides were immersed in hematoxylin for 2 minutes to counterstain (Dako S3309).

Figure 2A:
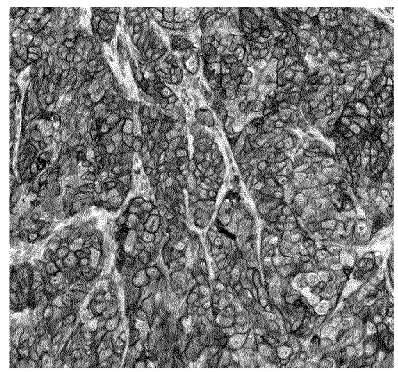
Figure 2B:
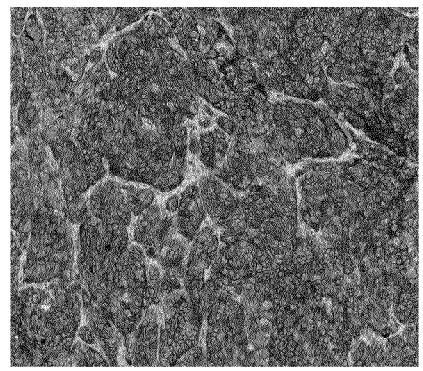
Figure 2C:
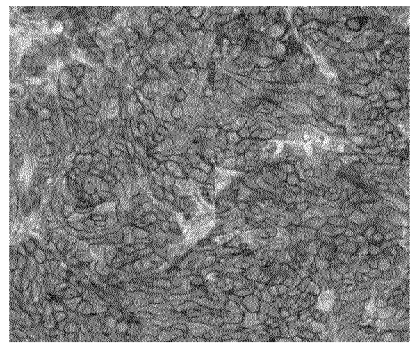
Figure 2D:
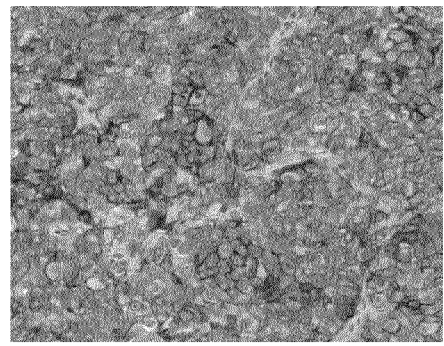

First IGF-1R antibody 816C12 and 810D12 differentially stain the cell membrane of MCF-7. In this IHC procedure, the brown reaction product correlates to positive staining of the cell membrane and lack of brown reaction product correlates to negative staining and no visualization of the cell membrane. Using membranous algorithm, the scoring for the staining of MCF-7 tumor cells was 3+(FIG. 2A for 816C12 and FIG. 2B for 810D12). Using G11 antibody (Roche Ventana) or AF-305 (R&D system) anti-IGF-1R antibodies, section of the same tumor were scored 2+(FIGS. 2C and 2D respectively).

2.2: In Vivo Activity of an Anti-IGF-1R ADC in the MCF-7 Xenograft Model.

Anti-IGF-1R ADC, comprising a seconf IGF-1R moiety, has been evaluated in vivo, in the MCF-7 xenograft model.

All animal procedures were performed according to the guidelines of the 2010/63/UE Directive on the protection of animals used for scientific purposes. The protocol was approved by the Animal Ethical Committee of the Pierre Fabre Institute. Five millions MCF-7 cells were injected subcutaneous into 7 weeks old Swiss/Nude mice. Prior to cell injection, oestrogen pellets (Innovative Research of America) were implanted to the left flank to mice in order to release estrogens necessary to the in vivo growth of MCF-7 tumors.

Twenty days after MCF-7 cell implantation, when tumors reached an average size of 120-150 mm$^3$, the animals were divided into groups of 6 mice according to tumor size and aspect. Anti-IGF-1R ADC was inoculated by intraperitoneal injections for a 6 injection cycle every four days (Q4d4). The health status of animals was monitored daily. Tumor volume was measured twice a week with an electronic calliper until study end. Tumor volume is calculated with the following formula: $\pi/6 \times length \times width \times height$. Toxicity was evaluated following the weight of animals three times per week. Statistical analyses were performed at each measure using a Mann-Whitney test.

Injection of anti-IGF-1R ADC significantly inhibited and even induced a complete tumor growth regression (FIG. 3) as expected for a tumor graded 3+ but not for a tumor graded 2+.

Example 3: Evaluation of the Correlation of the Staging with the First IGF-1R Antibody of the Invention and the Activity of an ADC Targeting IGF-1R in the SBC-5 Xenograft Model In order to correlate the grading of tumors with the pharmacology, the tumors have been graded (section 3.1) and then in vivo experiments on SBC-5 xenograft model have been made with an ADC comprising an antibody moiety targeting the IGF-1R and a drug moiety consisting of an auristatin (section 3.2).

3.1 Immunohistochemistry Detection of the IGF-1R Expression on the SBC-5 Xenograft Model.

Level of IGF-1R was analyzed using the same protocol described in section 2.1 of the example 2 before.

Figure 4A:
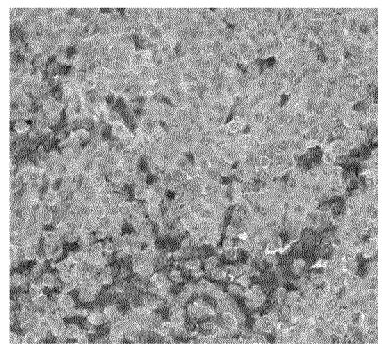
Figure 4B:
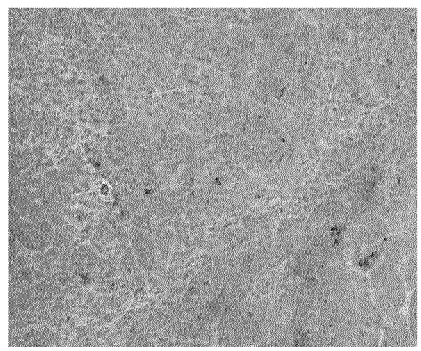
Figure 4C:
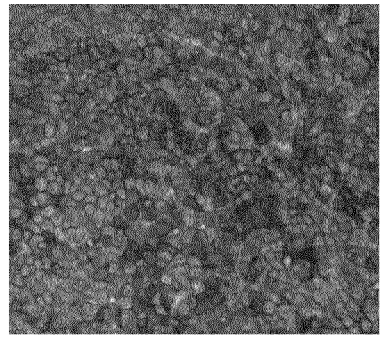
Figure 4D:
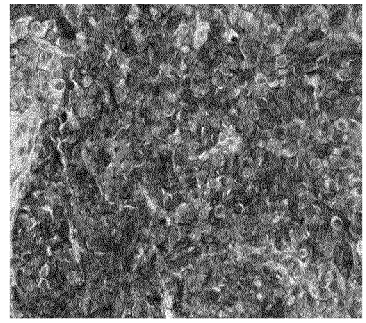

When IGF-1R was detected with the 816C12 and the 810D12, low levels were detected (1+) (FIG. 4A for the 816C12 and 4B for the 810D12). When IGF-1R was detected with G11 antibody (Roche Ventana) or AF-305 (R&Dsystem) anti-IGF-1R antibodies, sections from the same tumor were scored 3+(FIGS. 4C and 4D respectively).

3.2: In Vivo Activity of an Anti-IGF-1R ADC in the SBC-5 Xenograft Model.

Anti-IGF-1R ADC has been evaluated in vivo, in the SBC-5 xenograft model.

All animal procedures were performed according to the guidelines of the 2010/63/UE Directive on the protection of animals used for scientific purposes. The protocol was approved by the Animal Ethical Committee of the Pierre Fabre Institute. Five millions SBC-5 cells were injected subcutaneous into 7 weeks old Athymic mice. Twelve days after cell implantation, when tumors reached an average size of 150 mm$^3$, the animals were divided into groups of 6 mice according to tumor size and aspect. Anti-IGF-1R ADC was inoculated by intraperitoneal injections for a 6 injection cycle every four days (Q4d6). The health status of animals was monitored daily. Tumor volume was measured twice a week with an electronic calliper until study end. Tumor volume is calculated with the following formula: $\pi/6 \times length \times width \times height$. Toxicity was evaluated following the weight of animals three times per week. Statistical analyses were performed at each measure using a Mann-Whitney test.

Tumor progression of SBC-5 tumoral cells was not affected by injection of anti-IGF-1R ADC comprising a second IGF-1R antibody (FIG. 5) as expected for a tumor graded 1+ but not for a tumor graded 3+.

Example 4: Generation of Murine Second IGF-1R Antibodies Ab Raised Against IGF-1R ECD To generate murine monoclonal antibodies (Mabs) against human extracellular domain (ECD) of the human IGF-1 receptor (hIGF-1R), 5 BALB/c mice were immunized 3-times s.c. with 10 µg of the rhIGF-1R protein (R&D Systems, Cat N° 391-GR). As an alternative, three additional immunizations with 10 μg of the murine extracellular domain (ECD) of IGF-1R (R&D Systems, Cat N° 6630-GR/Fc) were performed on some animals. The first immunization was done in presence of Complete Freund Adjuvant (Sigma, St Louis, Md., USA). Incomplete Freund adjuvant (Sigma) was added for following immunizations. Three days prior to the fusion, immunized mice were boosted with 10 μg of the rhIGF-1R protein. Then splenocytes and lymphocytes were prepared by perfusion of the spleen and by mincing of the proximal lymph nodes, respectively, harvested from 1 out of the 5 immunized mice (selected after sera titration of all mice) and fused to SP2/0-Ag14 myeloma cells (ATCC, Rockville, Md., USA). The fusion protocol is described by Kohler and Milstein (Nature, 256:495-497, 1975). Fused cells are then subjected to HAT selection. In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988). Approximately 10 days after the fusion, colonies of hybrid cells were screened. For the primary screen, supernatants of hybridomas were evaluated for the secretion of Mabs raised against the IGF-1R ECD protein by FACS analysis using human breast MCF7 tumor cells (ATCC) and/or monkey COS7 cells (African green monkey kidney-SV40 transformed) which express monkey IGF-1R on their cell surface. More precisely, for the selection by flow cytometry, $10^5$ cells (either MCF7 or COS7) were plated in each well of a 96 well-plate in PBS containing 1% BSA and 0.01% sodium azide (FACS buffer) at 4° C. After a 2 min centrifugation at 2000 rpm, the buffer was removed and hybridoma supernatants to be tested were added. After 20 min of incubation at 4° C., cells were washed twice and an Alexa 488-conjugated goat anti-mouse antibody 1/500° diluted in FACS buffer (#A11017, Molecular Probes Inc., Eugene, USA) was added and incubated for 20 min at 4° C. After a final wash with FACS buffer, cells were analyzed by FACS (Facscalibur, Becton-Dickinson) after addition of propidium iodide to each tube at a final concentration of 40 μg/ml. Wells containing cells alone and cells incubated with the secondary Alexa 488-conjugated antibody were included as negative controls. Isotype controls were used in each experiment (Sigma, ref M90351MG). At least 5000 cells were assessed to calculate the mean value of fluorescence intensity (MFI).

Additionally an internalization assay was performed in order to select only internalizing second IGF-1R antibodies Ab. For this assay, MCF7 tumor cell line was cultured in RMPI 1640 without phenol red with 1% L-glutamine and 10% of FACS for 3 days before experiment. Cells were then detached using trypsin and 100 μl of a cell suspension at $4.10^5$ cell/ml are plated in 96-multiwell plates in RPMI1640 without phenol red with 1% L-glutamine and 5% FBS. After a 2 min centrifugation at 2000 rpm, cells were resupended in 50 μl of either hybridoma supernatants or control antibody solutions (positive and isotype controls at 1 μg/ml). After a 20 min incubation time at 4° C., cells were centrifuged 2 min at 2000 rpm and resuspended in either cold (4° C.) or warm (37° C.) complete culture medium. Cells were then incubated for 2 hours either at 37° C. or at 4° C. Then cells were washed three times with FACS buffer. An Alexa 488-labeled goat anti-mouse IgG antibody was incubated for 20 minutes and cells were washed three times before FACS analysis on propidium iodide negative cell population.

Following the FACS analysis, two parameters were determined: (i) the difference of the fluorescent signal detected on the surface of cells incubated at 4° C. with those obtained with the cells incubated at 37° C. with one hybridoma supernatant and (ii) the percentage of remaining IGF-1R on the cell surface.

The percentage of remaining hIGF 1R is calculated as follows: % remaining IGF-1R=(MFI$_{Ab\ 37°\ C.}$/MFI$_{Ab\ 4°\ C.}$)× 100.

In addition three ELISAs were performed (either before or after cloning) to study the binding of second IGF-1R antibodies Ab on the recombinant human (hIGF-1R) and murine (mIGF-1R) proteins, and on the recombinant human Insulin Receptor (hIR) protein. Hybridoma secreting antibody showing binding on rh- and/or rm-IGF-1R and no binding on rhIR were retained. Briefly, 96-well ELISA plates (Costar 3690, Corning, N.Y., USA) were coated 100 μl/well of either the rhIGF-1R protein (R&D Systems, cat N° 391-GR) at 0.6 μg/ml or rmIGF-1R protein (R&D Systems, cat N° 6630-GR/Fc) at 1 μg/ml or rhIR protein (R&D Systems, cat N° 1544-IR/CF) at 1 μg/ml in PBS overnight at 4° C. The plates were then blocked with PBS containing 0.5% gelatin (#22151, Serva Electrophoresis GmbH, Heidelberg, Germany) for 2 h at 37° C. Once the saturation buffer discarded by flicking plates, 100 μl of each supernatant dilution were added to each well (either undiluted hybridoma supernatant either supernatant serial dilutions) and incubated for 1 h at 37° C. After three washes, 100 μl horseradish peroxidase-conjugated polyclonal goat anti-mouse IgG (#115-035-164, Jackson Immuno-Research Laboratories, Inc., West Grove, Pa., USA) was added at a 1/5000 dilution in PBS containing 0.1% gelatin and 0.05% Tween 20 (w:w) for 1 h at 37° C. Then, ELISA plates were washed 3-times and the TMB (#UP664782, Uptima, Interchim, France) substrate is added. After a 10 min incubation time at room temperature, the reaction was stopped using 1 M sulfuric acid and the optical density at 450 nm is measured.

Hybridoma secreting second IGF-1R antibodies Ab of interest were expanded and cloned by limit dilution. Once isotyped, one clone of each code was expanded and frozen. Each second IGF-1R antibody Ab of interest was produced in in vitro production systems named CellLine (Integra Biosciences) for further characterization.

Additional assays to address binding specificity FACS analyses were performed on IM9 cells (human IR expressing B lymphoblasts) as well as on hIGF-1R transfected cells versus non transfected cells.

All the data corresponding to the selected second IGF-1R antibodies Ab were summarized in Table 8 and demonstrated that the five selected second IGF-1R antibodies Ab strongly recognize the native human IGF-1R expressed either on MCF-7 breast cancer cells or on transfected cells. They also recognize monkey IGF-1R on COS-7 cells. These second IGF-1R antibodies Ab do not cross react with the human insulin receptor highly expressed on IM9 cells. It has to be noticed that these second IGF-1R antibodies Ab poorly recognize the rhIGF-1R ECD protein when directly coated to ELISA plates.

| hybridoma name | Isotype | CNCM | ELISA (SNT at 5 µg/ml) D.O 450 nm | | | MCF7 Internalisation Assay (SNT ay 5 µg/ml) | | | | FACS (SNT at 5 µg/ml MFI) | | | |
|---|---|---|---|---|---|---|---|---|---|---|---|---|---|
| | | | rh IGF1R | rm IGF1R | rh Insulin R | MFI 4° C. | MFI 37° C. | % remaining rh IGF1R | Δ (MFI 4° C.- MFI 37° C.) | IM9 (hIR⁺) | Cos-7 (monkey IGF1R⁺) | Tf hIGF1R⁺ | Non Tf cells (hIGF1R⁻) |
| 208F2 | IgG1 K | I-4757 | 0.163 | 0.999 | 0.140 | 355 | 94 | 27 | 261 | 4 | 106 | 2197 | 22 |
| 212A11 | IgG1 K | I-4773 | 0.232 | 0.102 | 0.141 | 390 | 106 | 27 | 284 | 7 | 125 | 2187 | 23 |
| 213B10 | IgG1 K | I-4774 | 0.399 | 0.127 | 0.110 | 386 | 115 | 30 | 271 | 7 | 122 | 2055 | 23 |
| 214F8 | IgG1 K | I-4775 | 0.349 | 0.102 | 0.115 | 386 | 111 | 29 | 275 | 7 | 132 | 2137 | 20 |
| 219D6 | IgG1 K | I-4736 | 0.329 | 0.112 | 0.106 | 349 | 108 | 30 | 243 | 7 | 114 | 2110 | 21 |

Example 5: Second IGF-1R Antibody Ab Binding to the Human Native IGF-1R by FACS Analyses The five murine second IGF-1R antibodies Ab were chimerized. The binding properties of both the murine and the chimeric second IGF-1R antibodies Ab were evaluated0 by FACS analyses on the human MCF-7 breast adenocarcinoma cell line (ATCC#HTB-22) using increasing antibody concentrations. For that purpose, cells (1×10⁶ cells/ml) were incubated with IGF-1R antibodies for 20 min. at 4° C. in FACS buffer (PBS, 0.1% BSA, 0.01% NaN₃). They were then washed 3 times and incubated with the appropriate secondary antibody coupled with Alexa 488 for 20 additional minutes at 4° C. in the dark before being washed 3 times in FACS buffer. The binding of the second IGF-1R antibodies Ab was immediately performed on viable cells which were identified using propidium iodide (that stains dead cells). The maximum of signal intensity obtained with each antibody was designed as $B_{max}$ and expressed in mean of fluorescence intensity (MFI). The $EC_{50}$ of binding expressed in molarity (M) was calculated using a nonlinear regression analysis (GraphPad Prims 4.0).

The titration curve of each murine or chimeric seconf IGF-1R antibodies Ab demonstrated that all generated antibodies are capable to recognize the native IGF-1R form with a typical saturation profile (FIG. 6A). In order to rank second IGF-1R antibodies Ab and to compare the binding properties of both murine and chimeric Ab, the binding $EC_{50}$ of each compound was determined using a non linear regression analysis. The comparison of the $EC_{50}$ of each murine Ab with its corresponding chimeric form showed that the 2 forms displayed the same binding properties demonstrating that the second IGF-1R antibodies Ab chimerization did not affect IGF-1R recognition (FIGS. 6B-C). $EC_{50}$ and $B_{max}$ values of chimeric antibodies were summarized in Table 9.

TABLE 9

| AC | $B_{max}$ | $EC_{50}$ |
|---|---|---|
| c208F2 | 981 | 6.7E-10 |
| c212A11 | 991 | 6.7E-10 |
| c214F8 | 1069 | 5.0E-10 |
| c219D6 | 993 | 4.7E-10 |
| c213B10 | 1103 | 4.4E-10 |

Example 6: Confirmation of Second IGF-1R Antibody Ab Specificity by Using Either IGF-1R or IR Transfected Cells or IM9 Cells that Express Significant Levels of IR In order to confirm the specificity of the generated second IGF-1R antibodies Ab for IGF-1R versus IR, stable transfectants expressing either hIGF-1R or hIR were evaluated by FACS analyses. Briefly, increasing concentrations of chimeric second IGF-1R antibodies Ab were incubated with cells for 20 min at 4° C. in FACS buffer (PBS, 0.1% BSA, 0.01% NaN₃). Cells were then washed 3 times and incubated with the appropriate secondary antibody coupled with Alexa 488 before being incubated for 20 additional minutes at 4° C. in the dark and then washed 3 times in FACS buffer. The binding of second anti-IGF-1R antibodies Ab was immediately performed on viable cells which were identified using propidium iodide (that stains dead cells). The binding $EC_{50}$ expressed in molarity (M) was calculated using a nonlinear regression analysis (GraphPad Prims 4.0).

Titration curves obtained on the hIGF-1R transfected cell line (FIG. 7A) versus untransfected cells (FIG. 7B) confirmed the binding specificity of chimeric second IGF-1R antibodies Ab for the human IGF-1R. $EC_{50}$ and $B_{max}$ values were summarized in Table 10.

TABLE 10

| Ac | $B_{max}$ | $EC_{50}$ (M) |
|---|---|---|
| c208F2 | 2008 | 3.2E-10 |
| c212A11 | 2513 | 4.4E-10 |
| c214F8 | 2094 | 2.7E-10 |
| c219D6 | 2521 | 5.5E-10 |
| c213B10 | 2029 | 3.3E-10 |

In order to verify the absence of binding of both murine and chimeric second IGF-1R antibodies Ab on hIR, a stable cell line expressing the human IR (hIR) was used. The recognition of human cell surface hIR by both murine and chimeric second IGF-1R antibodies Ab was performed by FACS analyses. Increasing concentration of either the murine or the chimeric Ab were incubated on the hIR⁺ transfected cell line for 20 minutes at 4° C. in FACS buffer (PBS, 0.1% BSA, 0.01% NaN₃). Cells were then washed 3 times and incubated with the appropriate secondary antibody coupled with Alexa 488 before being incubated for 20 additional minutes at 4° C. in the dark and then washed 3 times in FACS buffer. The binding of second IGF-1R antibodies Ab was immediately performed on viable cells which were identified using propidium iodide (that stains dead cells). The binding $EC_{50}$ expressed in molarity (M) was calculated using a nonlinear regression analysis (GraphPad Prims 4.0). The anti-hIR antibody clone GRO5 was used as positive controls. The murine and chimeric 9G4 antibodies were introduced as irrelevant antibodies.

The high level of expression of hIR on cell surface of the transfected cells was confirmed using the commercial anti-hIR antibody GRO5 (FIGS. 8A and 8B). Even using high concentrations of either the murine (FIG. 8A) or the chimeric (FIG. 8B) second IGF-1R antibodies Ab, no binding on cell surface of hIR+ transfected cells was observed. These results demonstrated that neither murine nor chimeric second IGF-1R antibody Ab did recognized the hIR.

This specificity of recognition of hIGF-1R versus IR has also been demonstrated, by FACS analyses, using IM9 cells, a B-lymphoma cell line that expresses hIR (FIG. 9). For this FACS analyses, the protocol was the same as the one described above and murine second IGF-1R antibodies Ab were used in order to prevent the cross reactivity of the secondary anti-human Ab (IM9 cells express human Ig on their cell surface). Results presented in FIG. 9 demonstrated once again that the expected signal was observed using the GRO5 anti-hIR antibody while none of the murine second IGF-1R antibody Ab evaluated displayed any significant binding signal on this cell line.

Example 7: Second IGF-1R Antibody Ab Binding to the Monkey Native IGF-1R by FACS and Biacore Analyses One of the first pre-requisite for regulatory toxicology studies is to find a relevant animal specie in order to evaluate the selected compound. As the series of antibodies described herein is not able to recognize murine IGF-1R, the most likely specie for toxicological evaluation is the non human primate (NHP).

In order to evaluate the binding of second IGF-1R antibodies Ab on monkey IGF-1R, the binding of both murine and chimeric second IGF-1R antibodies Ab was first evaluated by FACS analyses on COS-7 cell line using increasing antibody concentrations. Cells ($1 \times 10^6$ cells/ml) were incubated with second IGF-1R antibodies Ab for 20 minutes at 4° C. in FACS buffer (PBS, 0.1%, BSA, 0.01% $NaN_3$). Then, cells were washed 3 times and incubated with the appropriate secondary antibody coupled with Alexa 488 before being incubated for 20 additional minutes at 4° C. in the dark and finally washed 3 times in FACS buffer. The binding of second IGF-1R antibodies Ab was immediately evaluated on viable cells identified using propidium iodide (that stains dead cells). The binding $EC_{50}$ expressed in molarity (M) was calculated using a nonlinear regression analysis (GraphPad Prims 4.0).

The titration curves obtained on the COS-7 monkey cell line showed that, all the second IGF-1R antibodies Ab recognized specifically the IGF-1R expressed on the surface of the monkey cell line (FIG. 5A). Determination of the, $EC_{50}$ for each murine and chimeric second IGF-1R antibody Ab showed that the 2 forms compared well regarding to their binding properties on monkey IGF-1R (FIG. 10B). Those results showed that all the generated second IGF-1R antibodies Ab recognized the monkey IGF-1R.

A comparison of binding $EC_{50}$ on COS-7 cells versus transfected IGF-1R cells was performed in order to verify the magnitude of chimeric antibody recognition on human versus monkey IGF-1R. Results shown in FIG. 10C demonstrated a similar recognition of human and monkey IGF-1Rs by all second IGF-1R antibodies Ab.

In order to confirm the recognition on another type of monkey, cells were transfected with the IGF-1R form Cynomolgus monkey to produce soluble monkey IGF-1R ECD and Biacore experiments were performed with one of the chimeric second IGF-1R antibodies (c208F2) in order to compare its binding properties either the hIGF-1R or the Cynomolgus IGF-1R.

The recognition experiments were run on a Biacore X100 device using a CM5 sensor chip activated by an anti-Tag His antibody (His capture kit GE Healthcare catalogue number 28-9950-56). More than 11000 RU of antibodies are chemically grafted on the carboxymethyldextan matrix using the amine kit chemistry. The experiments were carried out at 25° C. with a flow rate of 30 µl/min using the HBS-EP buffer (GE Healthcare) as the running and sample dilution buffer. The single cycle kinetic scheme was used to defined the kinetic parameters of the binding of the chimeric form of the 208F2 second IGF-1R antibody (c208F2) on hIGF-1R compared to Macaca IGF-1R A solution of a soluble recombinant version of the IGF-1R hetero-tetramere composed of 2a chains and the extracellular domains of 2β chains expressed with an additional C-terminal 10-His tag, based either on the sequence of the human (R&D Systems catalogue number 305-GR-50) or of the one of cynomolgus (produced in house) was injected 1 minute on the second flowcell at a dilution defined to capture around 160 RU of antigen. After the capture phase, either the running buffer was injected 5 times (90 s each injection) or a growing range of 5 concentrations of c208F2 were injected (90 s each injection) on both flowcells. At the end of the fifth injection the running buffer was passed in order to define the dissociation rate.

The surface was then regenerated with an injection of a 10 mM Glycine, HCl pH 1.5 buffer during 30 s.

The computed signal corresponds to the difference between the response of the flowcell 2 (with captured IGF-1R) and the response of the flowcell 1 (without any IGF-1R molecules) (FIG. 11).

For each IGF-1R molecule (human or cyno), the signal due to the injections of the growing range of concentrations of c208F2 was corrected by subtraction of the signal obtained with the 5 injections of the buffer (double reference). The resulting sensorgrams were analysed using the Biaevaluation software with a 1:1 model. The kinetic rates are evaluated either independently (2 kinetics rates of the binding of c208F2 on each IGF-1R) or commonly (the same kinetic rates of the binding of c208F2 on the human and the cynomolgus IGF-1R). The quality of the fitting was assessed by a Chi2/Rmax ratio lower than 0.05 RU.

The kinetics rates of the binding (see Table 11) defined separately for each IGF-1R are close and a fitting of both sensorgrams with the same kinetic rates is of good quality.

The c208F2 antibody recognizes as well the recombinant human and cynomolgus IGF-1Rs with a dissociation constant (KD) about 0.2 nM. The affinities defined in tis study correspond to the functional affinities (avidities) of the antibodies for a level of captured human and cynomolgus IGF-1R around 160 RU.

TABLE 11

| IGF1R | kon [1/M.s] | koff [1/s] | Kd [nM] | Chi2/Rmax |
|---|---|---|---|---|
| human | 1.52E+06 | 3.40E−04 | 0.23 | 0.045 |
| cynomogus | 1.85E+06 | 3.10E−04 | 0.17 | 0.032 |
| Hum. & Cyno. | 1.52E+06 | 3.33E−04 | 0.22 | 0.039 |

Example 8: Intrinsic Effect of Generated Second IGF-1R Antibodies Ab on IGF-1R Phosphorylation It is well known that antibodies could induce an agonistic effect when they bind to tyrosine kinase receptors. As we would not like to select such agonist antibodies, the evaluation of hIGF-1R phosphorylation was studied using the chimeric second IGF-1R antibodies Ab.

For that purpose, MCF-7 cells were incubated in serum-free medium overnight. Then, either IGF-1 (100 nM) or second IGF-1R antibodies Ab to be tested were added (10 µg/ml) for 10 minutes at 37° C. Medium was discarded and cells were scraped in a lysis buffer (pH 7.5) containing 10 mM Tris HCl buffer (pH 7.5), 15% NaCl (1 M), 10% detergent mix (10 mM Tris-HCl, 10% Igepal lysis buffer) (Sigma Chemical Co.), 5% sodium deoxycholate (Sigma Chemical Co.), 1 protease inhibitor cocktail complete TM tablet (Roche), 1% phosphatase inhibitor Cocktail Set II (Calbiochem), for 90 min at 4° C. The lysates were clarified by centrifugation at 4° C., heated for 5 min at 100° C. and kept at −20° C. or directly loaded on 4-12% SDS-PAGE gels. Incubation of the primary antibody was performed for 2 hr at room temperature and then incubation with HRP-linked secondary antibodies was done for 1 hr at room temperature. Membranes were washed in TBST prior to visualization of proteins with ECL. Blots were quantified using Image J software. Phospho-protein values were normalized with GAPDH. Phosphorylation of hIGF-1R in response to IGF-1 was considered as 100% of stimulation. The effect of second IGF-1R antibodies Ab on the phosphorylation of hIGF-1R was determined as % of phosphorylation induced by IGF-1.

The results described in FIG. 12 represent the mean of the % of pIGF-1R in response to the chimeric second IGF-1R antibodies of 3 independent experiments+/−S.D. compared to IGF-1. As illustrated no significant or minor (<10%) phosphorylation of hIGF-1R was detected when MCF-7 cells were incubated with 10 µg of anti-IGF-1R Abs.

Example 9: Inhibition of IGF-1R Phosphorylation in Response to IGF-1 by Murine Second IGF-1R Antibodies Ab In order to characterize the selected second IGF-1R antibodies Ab, their ability to inhibit IGF1-induced phosphorylation was studied. For that purpose, MCF-7 cells were incubated in serum-free medium overnight. Then, cells were incubated for 5 minutes with murine second IGF-1R antibodies before addition of IGF-1 for 2 minutes at 37° C. Medium was discarded and cells were scraped in a lysis buffer (pH 7.5) containing 10 mM Tris HCl buffer (pH 7.5), 15% NaCl (1 M), 10% detergent mix (10 mM Tris-HCl, 10% Igepal lysis buffer) (Sigma Chemical Co.), 5% sodium deoxycholate (Sigma Chemical Co.), 1 protease inhibitor cocktail complete TM tablet (Roche), 1% phosphatase inhibitor Cocktail Set II (Calbiochem), for 90 min at 4° C. The lysates were clarified by centrifugation at 4° C., heated for 5 min at 100° C. and kept at −20° C. or directly loaded on 4-12% SDS-PAGE gels. Incubation of the primary antibody was performed for 2 h at room temperature and then incubation with HRP-linked secondary antibodies was performed for 1 hr at room temperature. Membranes were washed in TBST prior to visualization of proteins with ECL. Blots were quantified using Image J software. Phospho-protein values were normalized with GAPDH. Phosphorylation of hIGF-1R in response to IGF-1 was considered as 100% of stimulation. The effect of anti-hIGF-1R Abs on the phosphorylation of hIGF-1R was determined as % of phosphorylation induced by IGF-1.

All second IGF-1R antibodies Ab inhibited strongly hIGF-1R phosphorylation in response to IGF-1 (decrease >80%) (FIG. 13). The best inhibitors of IGF1-induced phosphorylation of hIGF-1R are the m208F2, m212A11 and m214F8 Mabs.

Example 10: Study of IGF-1R Internalization after Binding of the Generated Second IGF-1R Antibodies by FACS Analyses MCF-7 cells were incubated with 10 µg/ml of chimeric antibodies at 4° C. for 20 min. Then, cells were washed and incubated at 4° C. or 37° C. for 4 h. The quantity of cell-surface bound antibody was determined using a secondary antibody. The ΔMFI defined as the difference between MFI measured at 4° C. and MFI measured at 37° C. after a 4 hour incubation time corresponded to the quantity of internalized second IGF-1R antibodies Ab. The ΔMFI was presented in FIG. 14 and Table 12. The percentage of internalization at 10 µg/ml of Ab were calculated as followed 100*(MFI at 4° C.-MFI at 37° C.)/MFI at 4° C. and presented in Table 12.

TABLE 12

| Abs | % Internalization | ΔMFI | ΔMFI_EC$_{50}$ |
|---|---|---|---|
| c208F2 | 83 | 288 | 1.8E−10 |
| c212A11 | 80 | 322 | 2.7E−10 |
| c214F8 | 87 | 403 | 2.2E−10 |
| c219D6 | 80 | 353 | 4.4E−10 |
| c231B10 | 85 | 369 | 2.3E−10 |

In order to determine whether the second IGF-1R antibodies that also recognized the monkey IGF-1R were able to internalize this receptor, the same internalization experiment was performed. Results summarized in Table 13 demonstrated that all tested antibodies were able to mediate monkey IGF-1R internalization.

TABLE 13

| | Murine Abs | | Chimeric Abs | |
|---|---|---|---|---|
| Abs | ΔMFI | % internalisation | ΔMFI | % internalisation |
| 208F2 | 53 | 74 | 52 | 67 |
| 212A11 | 83 | 73 | 98 | 75 |
| 214F8 | 76 | 71 | 98 | 72 |
| 219D6 | 80 | 71 | 102 | 74 |
| 213B10 | 84 | 74 | 101 | 73 |

Figure 15:
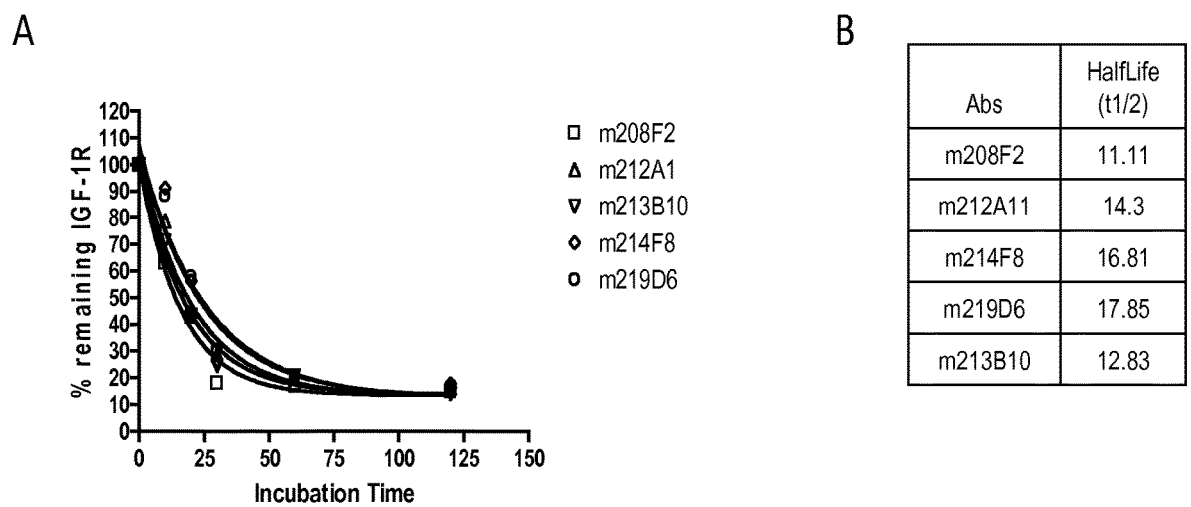

The kinetic of cell surface bound antibody decrease was further evaluated. For that purpose, MCF-7 cells were seeded in 96-well plates and incubated with 10 µg/ml of murine for 20 min at 4° C. Cells were then washed to remove unbound antibody and in media at 37° C. for 10, 20, 30, 60 or 120 min. At each time point, cells were centrifuged and then surface labeled on ice with a secondary anti-mouse IgG-Alexa488 to determine the amount of antibody remaining on the cell surface. The fluorescence intensity for each murine Ab and for each time point was normalized by the signal at 4° C. (% remaining IGF-1R) and fitted to an exponential decay to determine the half life (t1/2). t1/2 was considered as the time needed to obtain a decrease of 50% of the signal. As illustrated in FIG. 15, the surface level of all murine Abs dropped rapidly over the first 30 min and the decrease was almost maximum after 60 min of incubation (FIG. 15A). The calculated half life was comprised between 10 to 18 min according to the murine Ab (FIG. 15B).

In order to validate that the decrease of the cell surface signal was due to second IGF-1R antibodies Ab internalization and not due to receptor shedding, cells were incubated with murine Abs for 0, 30 and 60 min a 37° C. (FIG. 16). Cells were then fixed and permeabilized or not in order to determine cell surface bound antibody (w/o permeabilization) and total antibody signal corresponding to cell-surface bound+internalized second IGF-1R antibodies Ab (with permeabilization). The quantity of internalized second IGF-1R antibodies Ab (cytoplasmic) was determined as follow: MFI after permabilization—MFI w/o permeabilization. This experiment showed that the decrease of cell-surface bound second IGF-1R antibodies Ab was due to an increase of cytoplasmic Abs demonstrating that Abs were internalized (FIG. 16). In addition, the degradation of the Abs started after 1 h of incubation as indicated by the decrease of the signal after permeabilization (Total).

Example 11: Study of IGF-1R Internalization after Binding of the Generated Second IGF-1R Antibodies by Confocal Analyses To further confirm second IGF-1R antibodies Ab internalization, confocal microscopy was done to assess the subcellular distribution of antibodies following cellular trafficking. Cells were incubated with anti-hIGF-1R Abs 37° C., fixed and permeabilized. Therefore, cells were stained using a secondary antibody Alexa-488 and with rabbit anti-Lamp-1 antibody that was revealed using a secondary anti-Rabbit IgG Alexa 555. Before incubation at 37° C., the murine 208F2 Ab was localized on the membrane of MCF-7 cells (FIG. 17A). No colocalization with the lysosome marker, lamp-1 was noted using the colocalization highliter plug-in of the Image J software. The cell surface bound antibody decreased dramatically after 15 min of incubation at 37° C. Concomitantly to the decrease of the cell surface bound antibody, intracellular antibody was detected into vesicles. Rare colocalization with lamp-1 could be observed. After 30 min of incubation, the cell surface bound antibody was hardly detected. However, the colocalization of the Ab into lysosome increased. After 1 h of incubation, the intracellular Ab staining decreased as well as the number of colocalization with lamp-1. This kinetic of cell surface bound antibody and its intracellular accumulation correlated with the kinetic of antibody surface decay measure by FACS. In addition, as already described with FACS studies, the degradation of murine Abs started after 1 h of incubation by confocal microscopy.

The internalization of all other second IGF-1R murine antibodies Ab and their colocalization with Lamp-1 was also assessed (FIG. 17B). After 30 min of incubation at 37° C., intracellular antibody was detected and colocalization with lamp-1 could be observed indicating that all selected anti-IGF-1R antibodies were effectively internalized into lysosomes.

Example 12: Inhibition of Second IGF-1R Antibodies Abs Degradation Using Lysosome Inhibitor, Bafilomycin A1

In order to confirm that second IGF-1R antibodies Ab reached the lysosome were they are degraded, cells were treated or not with bafilomycine A1, a potent inhibitor of lysosome functions. Cells were then incubated with 10 μg/ml of Ab to be tested at 4° C., washed and incubated for 2 h at 37° C. The internalized Ab was detected after cell permeabilisation using a secondary anti-mouse IgG-Alexa 488 Ab. Addition of bafilomycine A1 prevented the degradation of intracellular Ab (FIG. 18) indicating that Abs were effectively internalized and degraded into lysosomes.

Example 13: Effect of pH on Second IGF-1R Antibody Ab-IGF-1R Binding

As second IGF-1R antibodies Ab were selected on the bases of their internalizing potential and shown above to co-localize with early endosomes before entering into the lysosomal compartment, an interesting approach consisted in selecting antibodies for which the stability of the Ab/hIGF-1R binding was modulated regarding to pH environment and preferentially antibodies that dissociated preferentially from IGF-1R when the pH environment became acid. Indeed, the primary difference between early endosomes and lysosomes is their luminal pH: in the endosome compartment the pH is approximately 6 while in the lysosomal compartment the pH is about 4.5.

It is well known that once internalized after ligand binding (IGF1), hIGF-1R returns back to the cell surface through a recycling pathway.

Without being link by a theory, an hypothesis herein described is that antibodies more prone to be released from their target early at acidic pH will probably favour target recycling to the membrane and consequently could be considered as better candidates for ADC approaches.

In order to investigate whether some of generated second IGF-1R antibodies Ab display such a property and to correlate this property to cytotoxic activity, the binding of the murine second IGF-1R antibodies Ab on MCF-7 cell line was done in buffers at different pH. Increasing concentrations of murine mAbs were incubated on MCF-7 cell line for 20 min at 4° C. in different pH ranging from 5 to 8. Cells were then washed 3 times and incubated with the appropriate secondary antibody coupled with Alexa 488 in FACS buffer. Cells were incubated for 20 additional minutes at 4° C. in the dark and then washed 3 times in FACS buffer. The binding of anti-hIGF-1R antibodies was immediately performed on viable cells which were identified using propidium iodide that stained dead cells. The binding $EC_{50}$ expressed in molarity (M) was calculated using a nonlinear regression analysis (GraphPad Prims 4.0). All murine second IGF-1R antibodies Ab selected showed a lower binding capacity at acidic pH as illustrated in FIG. 19.

Figure 29:
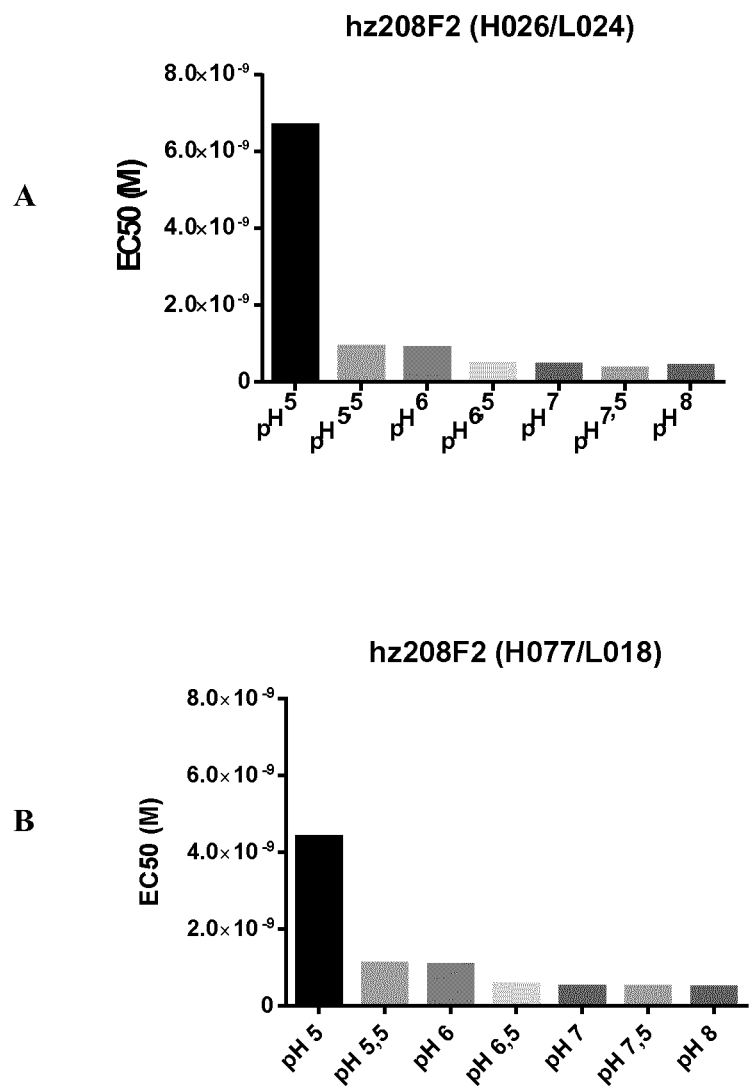

The binding of the humanized second IGF-1R antibodies Ab on MCF-7 cell line was done in buffers at different pH. Increasing concentrations of humanized mAbs were incubated on MCF-7 cell line for 20 min at 4° C. in different pH ranging from 5 to 8. Cells were then washed 3 times and incubated with the appropriate secondary antibody coupled with Alexa 488 in FACS buffer. Cells were incubated for 20 additional minutes at 4° C. in the dark and then washed 3 times in FACS buffer. The binding of humanized second IGF-1R antibodies Ab was immediately performed on viable cells which were identified using propidium iodide that stained dead cells. The binding $EC_{50}$ expressed in molarity (M) was calculated using a nonlinear regression analysis (GraphPad Prims 4.0). The humanized second IGF-1R antibodies showed a lower binding capacity at acidic pH as illustrated in FIG. 29.

Example 14: Evaluation of a Humanized Form of the 208F2 Mab 14.1 Evaluation of the Binding and Internalization of the Humanized Form hz208F2 H026/L024 (Also Sometimes Referred as VH3/VL3 or Variant 3)

Figure 20:
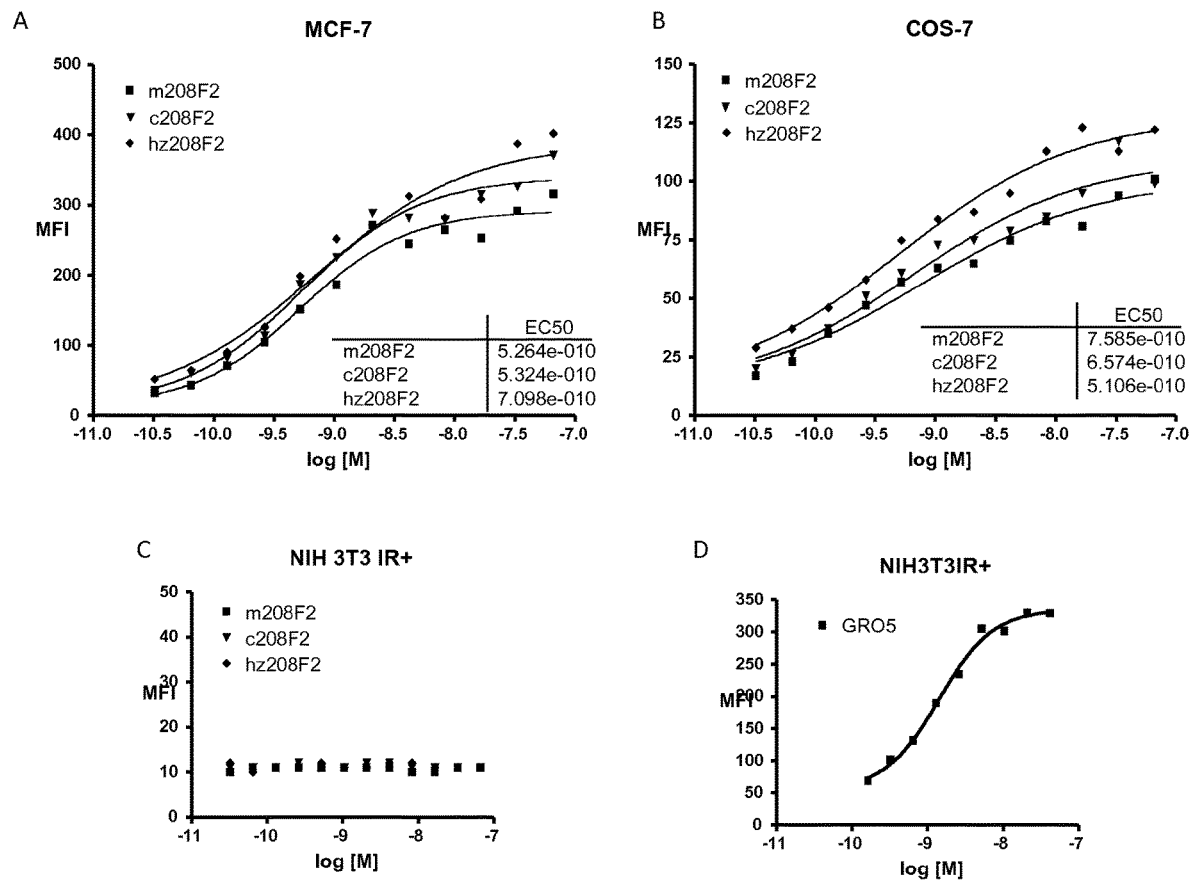

The binding of the humanized form of the c208F2 mAb was evaluated on MCF-7, COS-7 and NIH 3T3 IR+ cell lines. Increasing concentrations of m208F2, c208F2 or hz208F2 VH3VL3 were added on each cell line for 20 min. at 4° C. Cells were then washed and the binding of the tested mAb was revealed using the corresponding secondary antibody. In order to validate the expression of the human IR on the transfected cell line, the commercial anti-hIR antibody clone GRO5 was used and its recognition profile exemplified on (FIG. 20D).

Comparison of the humanized form with either murine or chimeric ones on MCF-7 (FIG. 20A) or monkey COS-7 (FIG. 20B) cells showed close profiles for the 3 tested forms. The humanisation process did not modify the specificity of recognition of the antibody that is perfectly comparable to the murine and chimeric forms regarding to the absence of cross reactivity on the human insulin receptor (FIG. 20C).

The calculated $EC_{50}$ s of the first humanized form of 208F2 on the human cell line MCF-7 and the monkey cell line COS-7 were similar to the one determined with either the murine or the chimeric form of the mAb 208F2.

The capacity of the mAb hz208F2 H026/L024 to be internalized was assessed by flow cytometry. MCF-7 cells were incubated with 10 µg/ml of antibodies at 4° C. for 20 min. Then, cells were washed and incubated at 4° C. or 37° C. for 4 h. The quantity of cell-surface bound antibody was determined using a secondary antibody. The ΔMFI defined as the difference between MFI measured at 4° C. and MFI measured at 37° C. after a 4 hour incubation time corresponded to the quantity of internalized Ab. The ΔMFI was presented in FIG. 21 and Table 14a. The percentage of internalization at 10 µg/ml of Ab were calculated as followed 100*(MFI at 4° C.-MFI at 37° C.)/MFI at 4° C. and presented in Table 14a. Therefore, the humanized hz208F2 H026/L024 (referred VH3/VL3 in the following table) had similar binding and internalization properties as the one measured with the corresponding murine and chimeric 208F2 antibodies.

TABLE 14a

|  | ΔMFI | % internalization |
|---|---|---|
| m208F2 | 294 | 88 |
| c208F2 | 278 | 82 |
| Hz208F2 VH3/VL3 | 344 | 87 |

14.2 Evaluation of the Binding of Subsequent hz208F2 Humanized Forms

The second IGF-1R antibody 208F2 was humanized and the binding properties of sixteen humanized variants (including the first form described in 12.1) were evaluated. The binding properties of the humanized variants were evaluated by FACS analyses on the human MCF-7 breast adenocarcinoma cell line and the monkey cell line Cos-7 using increasing antibody concentrations. For that purpose, cells (1×10⁶ cells/ml) were incubated with anti-IGF-1R antibodies for 20 min. at 4° C. in FACS buffer (PBS, 0.1% BSA, 0.01% NaN3). They were then washed 3 times and incubated with the appropriate secondary antibody coupled with Alexa 488 for 20 additional minutes at 4° C. in the dark before being washed 3 times in FACS buffer. The binding of anti-IGF-1R antibodies was immediately performed on viable cells which were identified using propidium iodide (that stains dead cells). The $EC_{50}$ of binding expressed in molarity (M) was calculated using a nonlinear regression analysis (GraphPad Prims 4.0).

The $EC_{50}$ of humanized variants showed that all the humanized variants displayed the equivalent binding properties on both human and monkey cell lines.

$EC_{50}$ of humanized antibodies were summarized in Table 14b.

TABLE 14b

|  |  | EC50 (M) | |
|---|---|---|---|
|  |  | MCF-7 | Cos-7 |
| Humanized variants | hz208F2 H026/L024 | 7.09E−10 | 5.1E−10 |
|  | hz208F2 H037/L018 | 4.9E−10 | 7.4E−10 |
|  | hz208F2 H047/L018 | 7.7E−10 | 9.2E−10 |
|  | hz208F2 H049/L018 | 4.9E−10 | 6.9E−10 |
|  | hz208F2 H051/L018 | 5.7E−10 | 7.2E−10 |
|  | hz208F2 H052/L018 | 8.4E−10 | 9.9E−10 |
|  | hz208F2 H057/L018 | 5.8E−10 | 8.3E−10 |
|  | hz208F2 H068/L018 | 1.1E−09 | 1.2E−09 |
|  | hz208F2 H070/L018 | 4.6E−10 | 7.3E−10 |
|  | hz208F2 H071/L018 | 5.5E−10 | 1.1E−09 |
|  | hz208F2 H076/L018 | 6.5E−10 | 1.1E−09 |
|  | hz208F2 H077/L018 | 7.7E−10 | 1.1E−09 |
|  | hz208F2 H037/L021 | 4.8E−10 | 8.2E−10 |
|  | hz208F2 H049/L021 | 6.6E−10 | 8.5E−10 |
|  | hz208F2 H052/L021 | 5.7E−10 | 1.2E−09 |
|  | hz208F2 H076/L021 | 5.8E−10 | 1.1E−09 |

14.3 Evaluation of the Internalization of Another hz208F2 Humanized Form

MCF-7 cells were incubated with 10 µg/ml of humanized antibodies at 4° C. for 20 min. Then, cells were washed and incubated at 4° C. or 37° C. for 4 h. The quantity of cell-surface bound antibody was determined using a secondary antibody on a FacsCalibur Flow cytometer (Becton Dickinson). The ΔMFI defined as the difference between MFI measured at 4° C. and MFI measured at 37° C. after a 4 hour incubation time corresponded to the quantity of internalized Ab. The ΔMFI was presented in Table 14c. The percentage of internalization at 10 µg/ml of Ab was calculated as followed 100*(MFI at 4° C.-MFI at 37° C.)/MFI at 4° C. The humanized second IGF-1R antibody hz208F2 H077/L018 is able to induce a significant internalization of IGF-1R.

TABLE 14c

|  | ΔMFI | % Internalization |
|---|---|---|
| hz208F2 H077/L018 | 468 | 88 |

Example 15: Definition of the Dissociation Constant ($K_D$) of the Binding of Five Chimeric Anti-IGF-1R Antibodies (c208F2, c213B10, c212A11, c214F8 and c219D6) and a Humanized Version (H026/L024) of the 208F2 Antibody on a Soluble Recombinant Human IGF-1R The dissociation constants ($K_D$) of the binding of the antibodies on a recombinant soluble human-IGF-1R were defined by the ratio between the dissociation rate ($k_{off}$) and the association rate ($k_{on}$). The kinetic experiments were run on a Biacore X100 device using a CM5 sensor chip activated by a mouse anti-Tag His monoclobnal antibody. Around 12000 RU of antibodies are chemically grafted on the carboxymethyldextan matrix using the amine kit chemistry.

The experiments were carried out at 25° C. with a flow rate of 30 µl/min using the HBS-EP+ buffer (GE Healthcare) as the running and sample dilution buffer.

The single cycle kinetic scheme was used to define the kinetic parameters of the binding of the anti-IGF-1R antibodies on a soluble recombinant human IGF-1R captured by its two C-terminal 10 Histidine-tag.

1—A solution of a soluble recombinant version of the human IGF-1R hetero-tetramere: 2α chains and the extracellular domains of 2β chains expressed with an additional C-terminal 10-His tag (R&D Systems catalogue number 305-GR-50) was injected during one minute on the second flowcell at a concentration of 10 µg/ml. A mean of 587 RU (with a standard deviation 24 RU) of the soluble receptor were captured at each of the 24 cycles realised for this study.

2—After the capture phase, either the running buffer was injected 5 times (90 s each injection) or a growing range of 5 concentrations of one of the six antibodies was injected (90 s each injection) on both flowcells. At the end of the fifth injection the running buffer was passed during 5 minutes in order to define the dissociation rate.

3—The surface was then generated with an injection of a 10 mM Glycine, HCl pH 1.5 buffer during 45 s.

The computed signal corresponds to the difference between the response of the flowcell 2 (with captured IGF-1R) and the response of the flowcell 1 (without any IGF-1R molecules).

For each IGF-1R the signal due to the injections the growing range of concentrations of one antibody was corrected by subtraction of the signal obtained with the 5 injections of the buffer (double reference) see FIG. 22.

The resulting sensorgrams were analysed by the Biaevaluation software with a 1:1 model.

Four experiences were run for each antibody using two different ranges of concentrations: 40, 20, 10, 5 and 2.5 nM for the two first experiments and: 24, 12, 6, 3 and 1.5 nM for the two last experiments run for each second IGF-1R antibody.

For the 6 second IGF-1R antibodies tested in this experiment the experimental data fitted well with an 1:1 model with significant $k_{off}$ values when the higher concentration was defined as a constant and the other four concentrations are calculated (see FIG. 23).

The dissociation constants ($K_D$) calculated as the ratio: $k_{off}/k_{on}$ and the half-live of the complexes calculated as the ratio: $Ln(2)/k_{off}$ are represented in the FIGS. 24 and 25. They correspond to the mean of the four independent experiments run for each second IGF-1R antibodies. The error bars correspond to the standard errors (n=4) of the values.

The dissociation constants are in the range of 10 to 100 pM. The c208F2 antibody presents the weaker affinity (higher dissociation constant value) for the h-IGF-1R (with a $K_D$ around 75 pM) and its humanized version is at least as good as the chimeric version (with a $K_D$ around 60 pM). The four other second IGF-1R chimeric antibodies present a quite similar affinity for the hIGF1-R (with a $K_D$ around 30 pM). The difference of the affinities is principally linked to the dissociation rate or the resultant half life of the complexes. With 208F2 the half-life of the complex is between 2 and 3 hour with the second IGF-1R chimeric and the humanized versions. For the four other second IGF-1R chimeric antibodies the means half lives are between 7.0 and 9.4 h.

These very slow dissociation kinetics are clearly linked to the bivalent structure of the antibodies which are able to bind simultaneously by both of their Fab arms to two adjacent h-IGF-1R molecules. In this case the level of captured IGF-1R molecules may have an impact on the dissociation rate. The affinities defined in this study correspond to the functional affinities (or avidities) of the antibodies for a level of captured h-IGF-1R around 600 RU. The 3 fold difference of KD observed between data shown above (table 11) and values presented in example 13 is linked to a change of the level of capture of hIGF-1R (600RU versus 160 RU in example 7).

Example 16: Synthesis of the Drugs of the Invention

The following abbreviations are used in the following examples:
aq. aqueous
ee enantiomeric excess
equiv equivalent
ESI Electrospray ionisation
LC/MS Liquid Chromatography coupled with Mass Spectrometry
HPLC High Performance Liquid Chromatography
NMR Nuclear Magnetic Resonance
sat. saturated
UV ultraviolet Reference Compound 1

(S)-2-((S)-2-((3-aminopropyl)(methyl)amino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethylbutanamide, bis trifluoroacetic acid

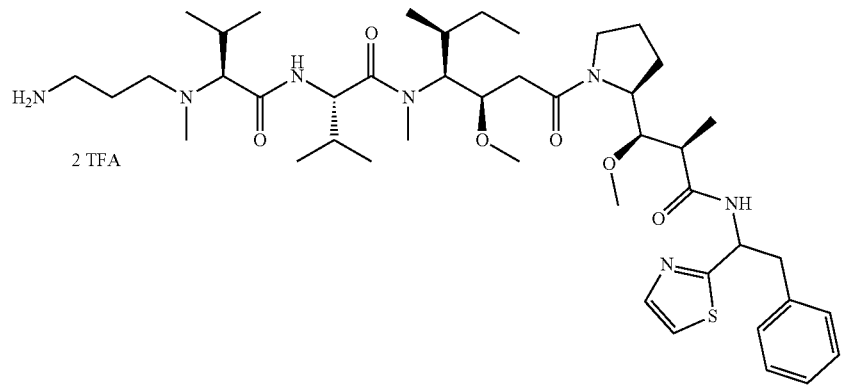 [SMILES: CC[C@H](C)[C@@H]([C@@H](CC(=O)N1CCC[C@H]1[C@H](OC)[C@@H](C)C(=O)NC(Cc1ccccc1)c1nccs1)OC)N(C)C(=O)[C@@H](NC(=O)[C@H](C(C)C)N(C)CCCN)C(C)C]

Compound 1A: (4R,5S)-4-methyl-5-phenyl-3-propanoyl-1,3-oxazolidin-2-one

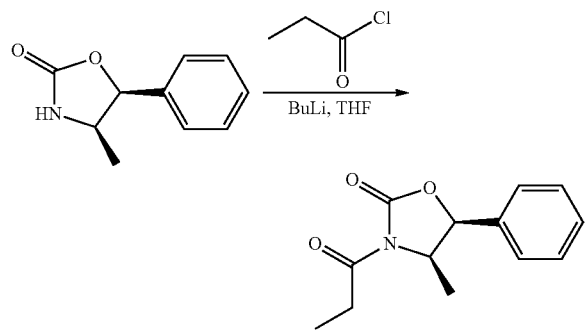

(4R,5S)-4-methyl-5-phenyl-1,3-oxazolidin-2-one (5.8 g, 32.7 mmol, 1.00 equiv) was dissolved in tetrahydrofuran (THF, 120 mL) in an inert atmosphere. The mixture was cooled to −78° C. and n-butyllithium (14.4 mL) was added drop-wise. After agitation for 30 minutes at −78° C., propanoyl chloride (5.7 mL) was added. Agitation was continued for 30 minutes at −78° C. then overnight at ambient temperature. The reaction mixture was concentrated then re-dissolved in 200 mL of water. The pH of the solution was adjusted to 7 with sodium bicarbonate saturated aqueous solution. This aqueous phase was extracted 3 times with 100 mL of ethyl acetate (EtOAc). The organic phases were combined, dried over sodium sulfate, filtered and concentrated to yield 6.8 g (89%) of compound 1A in the form of a yellow oil.

Compound 1B: tert-butyl (2S)-2-[(1R,2R)-1-hydroxy-2-methyl-3-[(4R,5S)-4-methyl-2-oxo-5-phenyl-1,3-oxazolidin-3-yl]-3-oxopropyl]pyrrolidine-1-carboxylate

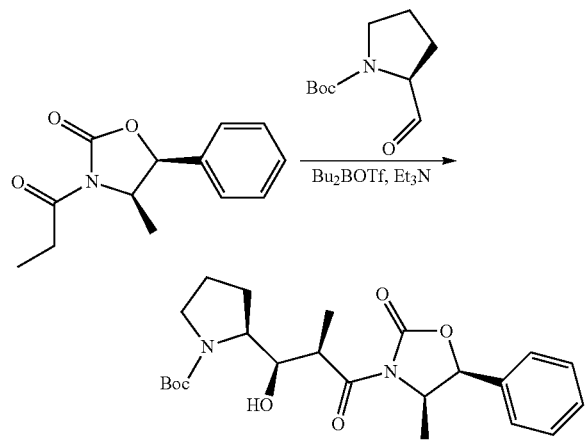

Compound 1A (17.6 g, 75.45 mmol, 1.00 equiv) was dissolved in dichloromethane (DCM, 286 mL) in an inert atmosphere. This solution was cooled with an ice bath. Triethylamine (TEA, 12.1 mL, 1.15 equiv) and Bu₂BOTf (78.3 mL, 1.04 equiv) were added drop-wise whilst holding the temperature of the reaction mixture below 2° C. Agitation was continued at 0° C. for 45 minutes, after which the reaction was cooled to −78° C. A solution of tert-butyl (2S)-2-formylpyrrolidine-1-carboxylate (8.5 g, 42.66 mmol, 0.57 equiv) in DCM (42 mL) was added drop-wise. Agitation was continued for 2 hours at −78° C., then for 1 hour at 0° C. and finally 1 hour at ambient temperature. The reaction was neutralised with 72 mL of phosphate buffer (pH=7.2-7.4) and 214 mL methanol, and cooled to 0° C. A solution of 30% hydrogen peroxide in methanol (257 mL) was added drop-wise whilst maintaining the temperature below 10° C. Agitation was continued for 1 hour at 0° C. The reaction was neutralised with 142 mL of water, then concentrated under reduced pressure. The resulting aqueous solution was extracted 3 times with 200 mL EtOAc. The organic phases were combined, dried over sodium sulfate, filtered and concentrated. The residue was purified on a silica column with a mixture of EtOAc and petroleum ether (EtOAc:PE=1:8) to yield 13.16 g (40%) of compound 1B in the form of a colourless oil.

Compound 1C: (2R,3R)-3-[(2S)-1-[(tert-butoxy)carbonyl]pyrrolidin-2-yl]-3-hydroxy-2-methylpropanoic Acid

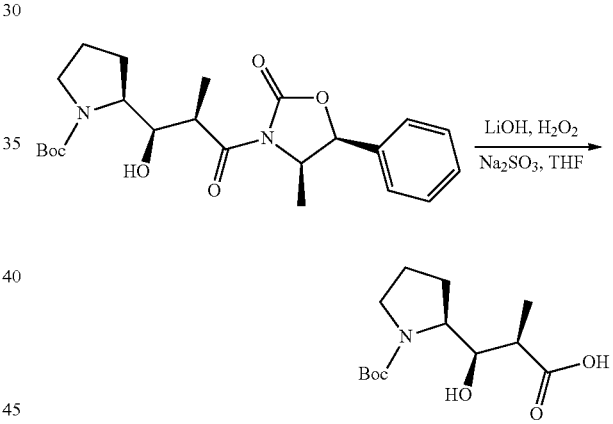

Compound 1B (13.16 g, 30.43 mmol, 1.00 equiv) was dissolved in THF (460 mL) in the presence of hydrogen peroxide (30% in water, 15.7 mL), then cooled with an ice bath. An aqueous solution of lithium hydroxide (0.4 mol/L, 152.1 mL) was added drop-wise whilst holding the reaction temperature below 4° C. The reaction mixture was agitated 2.5 hours at 0° C. An aqueous solution of Na₂SO₃ (1 mol/L, 167.3 mL) was added drop-wise whist holding the temperature at 0° C. The reaction mixture was agitated 14 hours at ambient temperature, then neutralised with 150 mL of cold sodium bicarbonate saturated solution and washed 3 times with 50 mL of DCM. The pH of the aqueous solution was adjusted to 2-3 with a 1M aqueous solution of KHSO₄. This aqueous solution was extracted 3 times with 100 mL of EtOAc. The organic phases were combined, washed once with saturated NaCl solution, dried over sodium sulfate, filtered and concentrated to yield 7.31 g (88%) of compound 1C in the form of a colourless oil.

Compound 1D: (2R,3R)-3-[(2S)-1-[(tert-butoxy)carbonyl]pyrrolidin-2-yl]-3-methoxy-2-methylpropanoic Acid

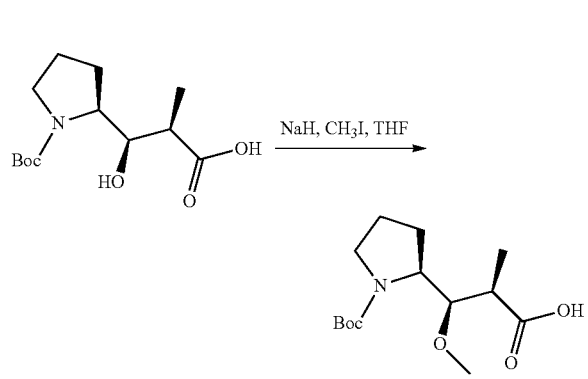

Compound 1C (7.31 g, 26.74 mmol, 1.00 equiv) was dissolved in an inert atmosphere in THF (135 mL) in the presence of iodomethane (25.3 mL). The reaction medium was cooled with an ice bath after which NaH (60% in oil, 4.28 g) was added in portions. The reaction was left under agitation 3 days at 0° C. and then neutralised with 100 mL of sodium bicarbonate saturated aqueous solution and washed 3 times with 50 mL ether. The pH of the aqueous solution was adjusted to 3 with 1M aqueous $KHSO_4$ solution. This aqueous solution was extracted 3 times with 100 mL of EtOAc. The organic phases were combined, washed once with 100 mL of $Na_2S_2O_3$ (5% in water), once with NaCl-saturated solution, then dried over sodium sulfate, filtered and concentrated to yield 5.5 g (72%) of compound 1D in the form of a colourless oil.

Compound 1E: N-methoxy-N-methyl-2-phenylacetamide

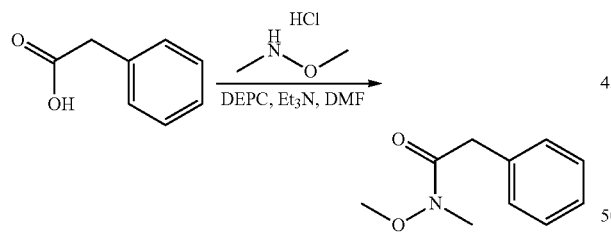

2-phenylacetic acid (16.2 g, 118.99 mmol, 1.00 equiv) was dissolved in dimethylformamide (DMF, 130 mL) then cooled to −10° C. Diethyl phosphorocyanidate (DEPC, 19.2 mL), methoxy(methyl)amine hydrochloride (12.92 g, 133.20 mmol, 1.12 equiv) and triethylamine (33.6 mL) were added. The reaction mixture was agitated 30 minutes at −10° C. then 2.5 hours at ambient temperature. It was then extracted twice with 1 litre of EtOAc. The organic phases were combined, washed twice with 500 mL of $NaHCO_3$ (sat.), once with 400 mL of water, then dried over sodium sulfate, filtered and concentrated. The residue was purified on a silica column with an EtOAc and PE mixture (1:100 to 1:3) to yield 20.2 g (95%) of compound 1E in the form of a yellow oil.

Compound 1F: 2-phenyl-1-(1,3-thiazol-2-yl)ethan-1-one

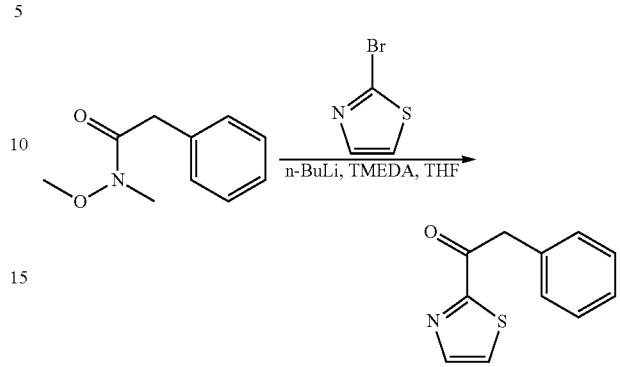

Tetramethylethylenediamine (TMEDA, 27.2 mL) was dissolved in THF 300 mL) in an inert atmosphere, then cooled to −78° C. before the drop-wise addition of n-BuLi (67.6 mL, 2.5 M). 2-bromo-1,3-thiazole (15.2 mL) was added drop-wise and agitation was continued 30 minutes at −78° C. Compound 1E (25 g, 139.50 mmol, 1.00 equiv) dissolved in THF (100 mL) was added drop-wise. Agitation was continued for 30 minutes at −78° C. then 2 hours at −10° C. The reaction was neutralised with 500 mL of $KHSO_4$ (sat.), then extracted 3 times with 1 litre of EtOAc. The organic phases were combined, washed twice with 400 mL water and twice with 700 mL of NaCl (sat.), then dried over sodium sulfate, filtered and concentrated. The residue was purified on a silica column with a mixture of EtOAc and PE (1:100 to 1:10) to yield 25 g (88%) of compound 1F in the form of a yellow oil.

Compound 1 G: (1R)-2-phenyl-1-(1,3-thiazol-2-yl)ethan-1-ol

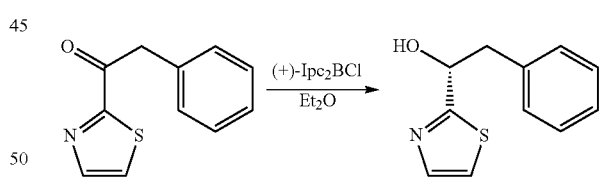

In an inert atmosphere, a solution of compound 1F (15 g, 73.8 mmol, 1.00 equiv.) in ether (300 mL) was added drop-wise to (+)-B-chlorodiisopinocampheylborane ((+)-$Ipc_2BCl$, 110.8 mL). The reaction mixture was agitated 24 hours at 0° C., then neutralised with 300 mL of a (1:1) mixture of NaOH (10% in water) and $H_2O_2$ (30% in water), and finally extracted three times with 500 mL of EtOAc. The organic phases were combined, washed twice with 300 mL of $K_2CO_3$ (sat.) and once with 500 mL of NaCl (sat.), then dried over sodium sulfate, filtered and concentrated. The residue was purified on a silica column with a mixture of EtOAc and PE (1:20 to 1:2) to yield 6.3 g (42%) of compound 1G in the form of a white solid.

Compound 1H: 2-[(1S)-1-azido-2-phenylethyl]-1,3-thiazole

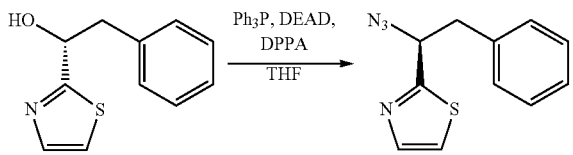 [SMILES: O[C@H](Cc1ccccc1)c1nccs1 ; [N-]=[N+]=N[C@@H](Cc1ccccc1)c1nccs1 ; "THF"]

Compound 1G (6 g, 29.23 mmol, 1.00 equiv.) was dissolved in an inert atmosphere in THF (150 mL) in the presence of triphenylphosphine (13 g, 49.56 mmol, 1.70 equiv.), then cooled to 0° C. Diethylazodicarboxylate (DEAD, 7.6 mL) was added drop-wise, followed by diphenylphosphorylazide (DPPA, 11 mL), the cold bath was then removed and the solution was left under agitation 48 hours at ambient temperature. The medium was concentrated under reduced pressure. The residue was purified on a silica column with a mixture of EtOAc and PE (1:100 to 1:30) to yield 8 g of partly purified compound 1H in the form of a yellow oil. Compound 1H was used as such in the following step.

Compound 1I: tert-butyl N-[(1 S)-2-phenyl-1-(1,3-thiazol-2-yl)ethyl]carbamate

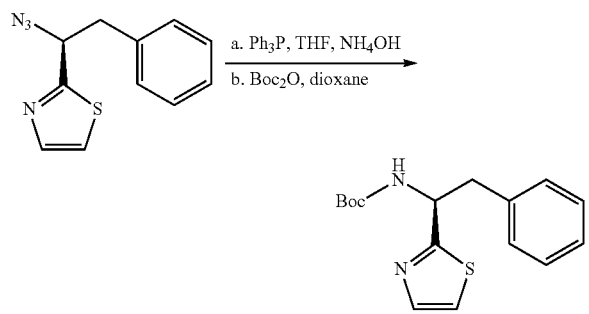

Compound 1H (6.5 g, 28.2 mmol, 1.00 equiv) was dissolved in an inert atmosphere in THF (100 mL) in the presence of triphenylphosphine (6.5 g, 33.9 mmol, 1.20 equiv.), and heated to 50° C. for 2 hours. Ammonia (70 mL) was then added and heating was continued for 3 hours. The reaction was cooled, neutralised with 500 mL water, then extracted 3 times with 500 mL of EtOAc. The organic phases were combined and extracted twice with 500 mL of 1N HCl. The aqueous phases were combined, brought to pH 8-9 by adding a sodium hydroxide solution (10% in water), then extracted 3 times with 500 mL of DCM. The organic phases were combined, dried over sodium sulfate, filtered and concentrated to yield 4.8 g (83%) of (1S)-2-phenyl-1-(1,3-thiazol-2-yl)ethan-1l-amine in the form of a yellow oil. This compound was then protected with a Boc group ((tert-butoxy)carbonyl) so that it could be purified. It was dissolved in an inert atmosphere in 1,4-dioxane (40 mL), then cooled to 0° C. (Boc)₂O (10.26 g, 47.01 mmol, 2.00 equiv) diluted in 20 mL of 1,4-dioxane was added drop-wise. The cold bath was removed and the solution left under agitation overnight at ambient temperature before being neutralised with 300 mL of water and extracted twice with 500 mL of EtOAc. The organic phases were combined, dried over sodium sulfate, filtered and concentrated. The residue was purified on a silica column with a mixture of EtOAc and PE (1:100 to 1:20, ee=93%). It was then recrystallized in a hexane/acetone mixture (~5-10/1, 1 g/10 mL) to yield 6 g (84%) of compound 11 in the form of a white solid (ee>99%).

Compound 1J: tert-butyl (2S)-2-[(1R,2R)-1-methoxy-2-methyl-2-[[(1S)-2-phenyl-1-(1,3-thiazol-2-yl)ethyl]carbamoyl]ethyl]pyrrolidine-1-carboxylate

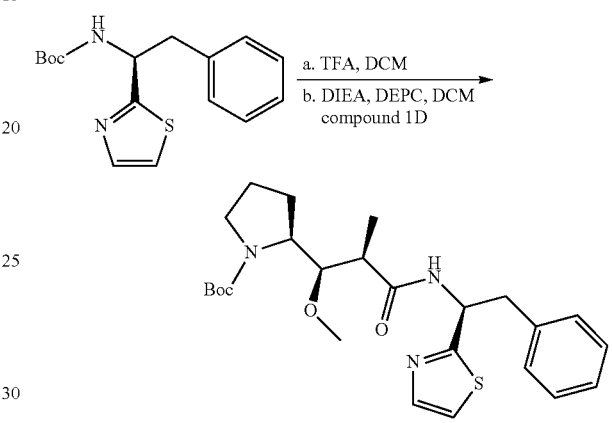

Compound 11 (3 g, 9.86 mmol, 1.00 equiv) was dissolved in an inert atmosphere in 10 mL DCM. Trifluoroacetic acid (TFA, 10 mL) was added and the solution left under agitation overnight at ambient temperature, then concentrated under reduced pressure to yield 2.0 g (64%) of (1S)-2-phenyl-1-(1,3-thiazol-2-yl)ethan-1l-amine; trifluoroacetic acid in the form of a yellow oil. This intermediate was re-dissolved in 20 mL of DCM after which compound 1D (1.8 g, 6.26 mmol, 1.05 equiv), DEPC (1.1 g, 6.75 mmol, 1.13 equiv) and diisopropylethylamine (DIEA, 1.64 g, 12.71 mmol, 2.13 equiv) were added. The reaction mixture was left under agitation overnight at ambient temperature, then concentrated under reduced pressure. The residue was purified on a silica column with a mixture of EtOAc and PE (1:100 to 1:3) to yield 2.3 g (81%) of compound 1J in the form of a pale yellow solid.

Compound 1K: (2R,3R)-3-methoxy-2-methyl-N-[(1S)-2-phenyl-1-(1,3-thiazol-2-yl)ethyl]-3-[(2S)-pyrrolidin-2-yl]propanamide; trifluoroacetic Acid

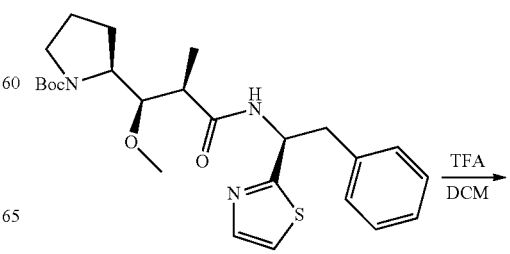

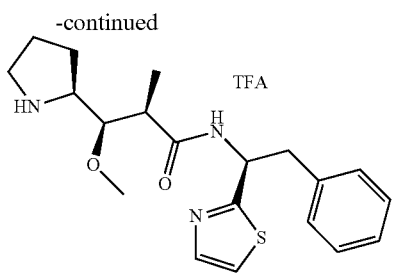

Compound 1J (2.25 g, 4.75 mmol, 1.00 equiv) was dissolved in an inert atmosphere in 10 mL of DCM. TFA (10 mL) was added and the solution left under agitation overnight at ambient temperature, then concentrated under reduced pressure to yield 2.18 g (94%) of compound 1K in the form of a yellow oil.

Compound 1L: (2S,3 S)-2-(benzylamino)-3-methylpentanoic Acid

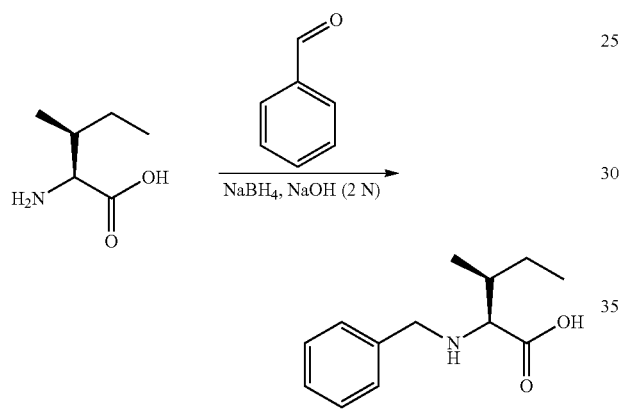

(2S,3S)-2-amino-3-methylpentanoic acid (98.4 g, 750 mmol, 1.00 equiv) was added at ambient temperature and in portions to a 2N sodium hydroxide solution (375 mL). Benzaldehyde (79.7 g, 751.02 mmol, 1.00 equiv) was quickly added and the resulting solution was agitated 30 minutes. Sodium borohydride (10.9 g, 288.17 mmol, 0.38 equiv) was added in small portions, whilst holding the temperature at between 5 and 15° C. Agitation was continued for 4 hours at ambient temperature. The reaction mixture was diluted with 200 mL of water, then washed twice with 200 mL of EtOAc. The pH of the aqueous solution was adjusted to 7 with a 2N hydrochloric acid solution. The formed precipitate was collected by filtering and gave 149.2 g (90%) of compound 1L in the form of a white solid.

Compound 1M: (2S,3 S)-2-[benzyl(methyl)amino]-3-methylpentanoic Acid

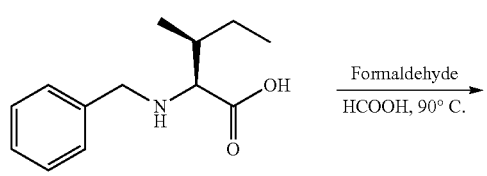

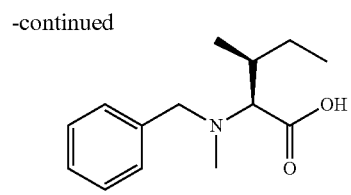

Compound 1L (25 g, 112.97 mmol, 1.00 equiv) was dissolved in an inert atmosphere in formic acid (31.2 g) in the presence of formaldehyde (36.5% in water, 22.3 g). The solution was agitated 3 hours at 90° C. then concentrated under reduced pressure. The residue was triturated in 250 mL of acetone, then concentrated. This trituration/evaporation operation was repeated twice with 500 mL of acetone to yield 21.6 g (81%) of compound 1M in the form of a white solid.

Compound 1N: (2S,3S)-2-[benzyl(methyl)amino]-3-methylpentan-1-ol

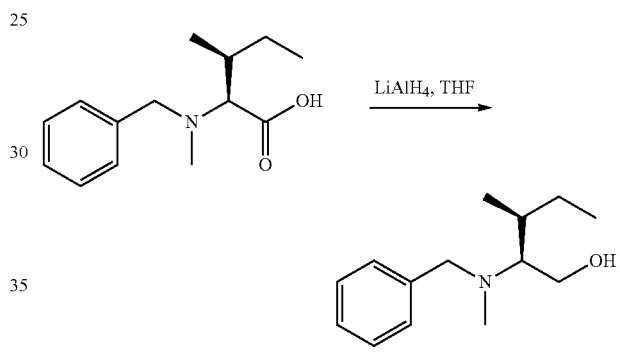

LiAlH$_4$ (0.36 g) was suspended in 10 mL of THF in an inert atmosphere at 0° C. Compound 1M (1.5 g, 6.37 mmol, 1.00 equiv) was added in small portions whilst holding the temperature at between 0 and 10° C. The reaction mixture was agitated 2 hours at 65° C., then again cooled to 0° C. before being neutralised with successive additions of 360 μL of water, 1 mL of 15% sodium hydroxide and 360 μL of water. The aluminium salts which precipitated were removed by filtering. The filtrate was dried over sodium sulfate, filtered and concentrated. The residue was purified on a silica column with a mixture of EtOAc and PE (1:50) to yield 820 mg (58%) of compound 1N in the form of a pale yellow oil.

Compound 1O: (2S,3S)-2-[benzyl(methyl)amino]-3-methylpentanal

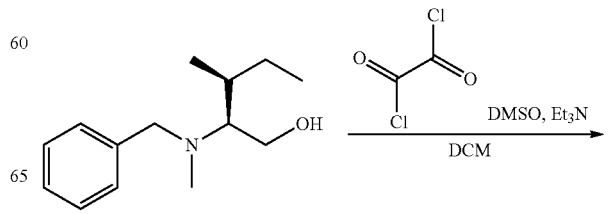

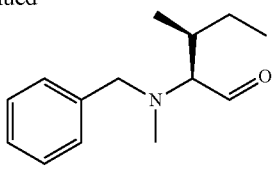

Oxalyl chloride (0.4 mL) was dissolved in DCM (15 mL) in an inert atmosphere. The solution was cooled to −70° C. and a solution of dimethylsulfoxide (DMSO (0.5 mL) in DCM (10 mL) was added drop-wise for 15 minutes. The reaction mixture was agitated 30 minutes after which a solution of compound 1N (820 mg, 3.70 mmol, 1.00 equiv) in DCM (10 mL) was added drop-wise for 15 minutes. The reaction mixture was agitated a further 30 minutes at low temperature, then triethylamine (2.5 mL) was slowly added. The reaction mixture was agitated 1 hour at −50° C., the cold bath was then removed and the reaction neutralised with 25 mL of water whilst allowing the temperature to return to normal. The solution was washed once with 30 mL of NaCl-saturated aqueous solution, then dried over sodium sulfate, filtered and concentrated. The residue was purified on a silica column with a mixture of EtOAc and PE (1:200) to yield 0.42 g (52%) of compound 1O in the form of a yellow oil.

Compound 1P: (2S,3S)—N-benzyl-1,1-dimethoxy-N,3-dimethylpentan-2-amine

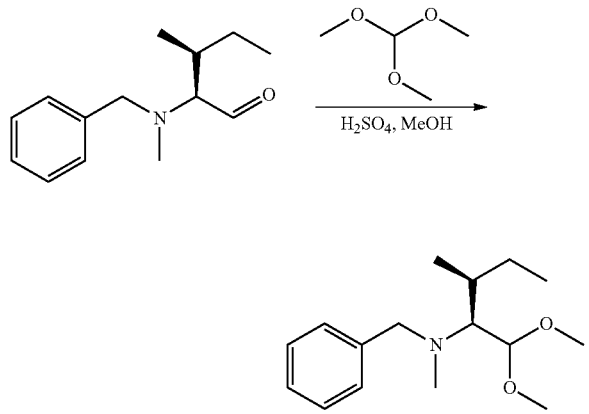

Compound 1O (4.7 g, 21.43 mmol, 1.00 equiv) was dissolved in 20 mL of methanol at 0° C. Concentrated sulfuric acid (4.3 mL) was added drop-wise and agitation was continued for 30 minutes at 0° C. Trimethyl orthoformate (21.4 mL) was added, the cold bath removed and the reaction medium left under agitation for 3 hours at ambient temperature. The reaction medium was diluted with 200 mL of EtOAc, successively washed with 100 mL of 10% Na₂CO₃ and 200 mL of saturated NaCl, then dried over sodium sulfate, filtered and concentrated under reduced pressure to yield 3.4 g (60%) of compound 1P in the form of a pale yellow oil.

Compound 1Q: [[1-(tert-butoxy)ethenyl]oxy](tert-butyl)dimethylsilane

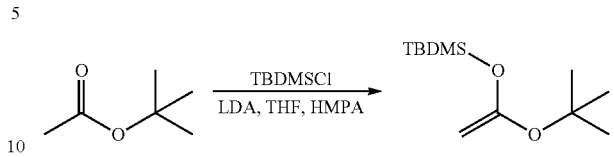

Diisopropylamine (20 g, 186.71 m mol, 1.08 equiv) was dissolved in 170 mL of THF in an inert atmosphere and cooled to −78° C. nBuLi (2.4 M, 78.8 mL) was added drop-wise and the solution agitated 30 minutes at low temperature (to give LDA-lithium diisopropylamide) before adding tert-butyl acetate (20 g, 172.18 mmol, 1.00 equiv). The reaction mixture was agitated 20 minutes at −78° C. before adding hexamethylphosphoramide (HMPA, 25.8 mL) and a solution of tertbutyldimethylchlorosilane (TBDMSCl, 28 g, 185.80 mmol, 1.08 equiv) in 35 mL of THF. Agitation was continued for 20 additional minutes at low temperature, and the cold bath was then removed. The solution was concentrated under reduced pressure. The residue was re-dissolved in 100 mL of water and extracted 3 times with 100 mL of PE. The organic phases were combined, washed once with 500 mL of NaCl-saturated aqueous solution, dried over sodium sulfate, filtered and concentrated. The residue was purified by distillation to yield 16.6 g (83%) of compound 1Q in the form of a colourless oil.

Compound 1R: tert-butyl (3R,4S,5S)-4-[benzyl(methyl)amino]-3-methoxy-5-methyl heptanoate

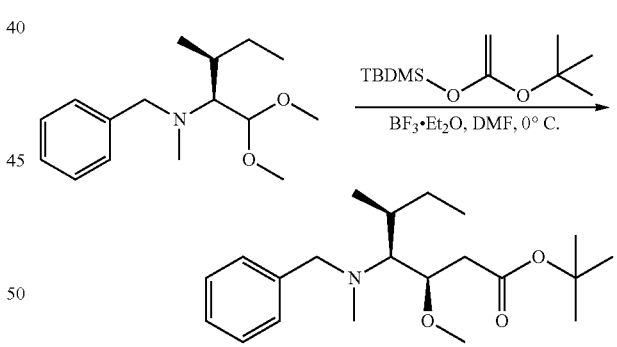

Compound 1P (2.0 g, 7.54 mmol, 1.00 equiv) and compound 1Q (2.6 g, 11.28 mmol, 1.50 equiv) were dissolved in 33 mL of DCM in an inert atmosphere. The solution was cooled to 0° C. DMF (1.2 g) was added drop-wise together with a solution of BF₃.Et₂O (2.1 g) in 7.5 mL of DCM. Agitation was continued for 24 hours at 0° C. The reaction medium was washed once with 30 mL of sodium carbonate (10%) and twice with 50 mL of NaCl-saturated aqueous solution, then dried over sodium sulfate, filtered and concentrated. The residue was purified on a silica column with a mixture of EtOAc and PE (1:100) to yield 1.82 g (91%) of compound 1R in the form of a yellow oil.

Compound 1S: (3R,4S,5 S)-3-methoxy-5-methyl-4-(methylamino)heptanoate hydrochloride

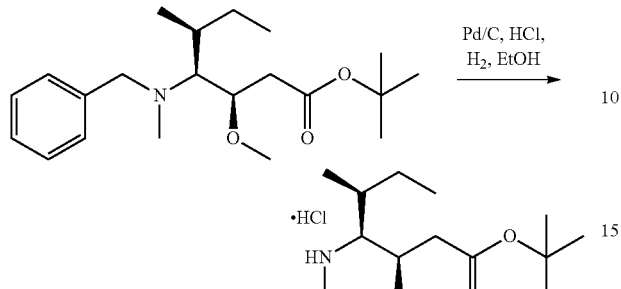

Compound 1R (2.4 g, 6.87 mmol, 1.00 equiv) was dissolved in an inert atmosphere in 35 mL of ethanol in the presence of Pd/C (0.12 g) and concentrated hydrochloric acid (0.63 mL). The nitrogen atmosphere was replaced by a hydrogen atmosphere and the reaction medium was left under agitation 18 hours at ambient temperature. The reaction medium was filtered and concentrated under reduced pressure. The residue was triturated in 50 mL of hexane and the supernatant removed which, after drying under reduced pressure, gave 1.66 g (82%) of compound 1S in the form of a white solid.

Compound 1T: tert-butyl (3R,4S,5 S)-4-[(2S)-2-[[(benzyloxy)carbonyl]amino]-N,3-dimethylbutanamido]-3-methoxy-5-methylheptanoate

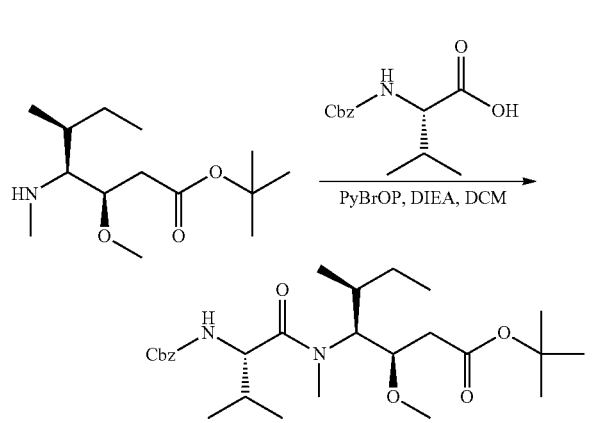

(2S)-2-[[(benzyloxy)carbonyl]amino]-3-methylbutanoic acid (15 g, 0.40 mmol, 1.00 equiv) was dissolved in 300 mL of DCM in the presence of DIEA (38.3 mL) and bromotripyrrolidinophosphonium hexafluorophosphate (PyBrOP, 32.3 g). The solution was agitated 30 minutes at ambient temperature before adding compound 1S (15.99 g, 0.42 mmol, 1.07 equiv). The reaction medium was agitated 2 hours and then concentrated. The residue was purified in reverse phase (C18) with a mixture of acetonitrile (ACN) and water (30:70 to 100:0 in 40 minutes) to yield 17 g (58%) of compound 1T in the form of a colourless oil.

Compound 1U: tert-butyl (3R,4S,5S)-4-[(2S)-2-amino-N,3-dimethylbutanamido]-3-methoxy-5-methylheptanoate

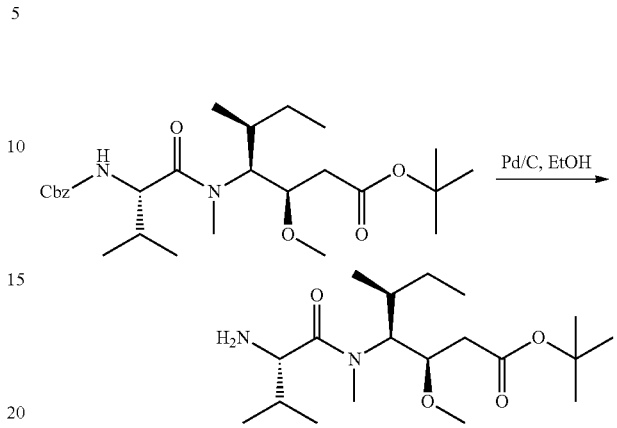

Compound 1T (76 mg, 0.15 mmol, 1.00 equiv) was dissolved in an inert atmosphere in 10 mL of ethanol in the presence of Pd/C (0.05 g). The nitrogen atmosphere was replaced by a hydrogen atmosphere and the reaction agitated 2 hours at ambient temperature. The reaction medium was filtered and concentrated under reduced pressure to yield 64 mg of compound 1U in the form of a colourless oil.

Compound 1V: (3R,4S,5 S)-4-[(2S)-2-[[(9H-fluoren-9-ylmethoxy)carbonyl]amino]-N,3-dimethylbutanamido]-3-methoxy-5-methylheptanoate

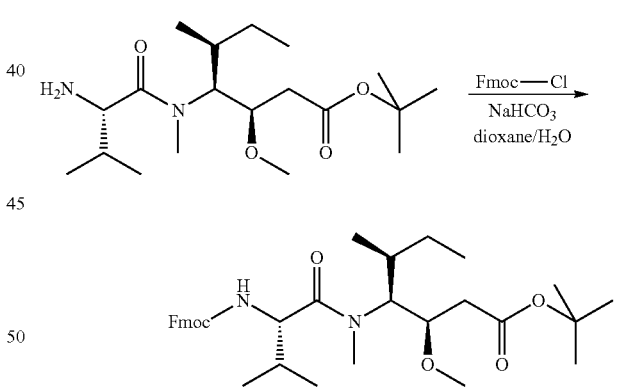

Compound 1U (18.19 g, 50.74 mmol, 1.00 equiv) was dissolved in 400 mL of a 1,4-dioxane/water mixture (1:1) in the presence of sodium bicarbonate (12.78 g, 152 mmol, 3.00 equiv) and 9H-fluoren-9-ylmethyl chloroformate (Fmoc-Cl, 19.69 g, 76 mmol, 1.50 equiv), then agitated 2 hours at ambient temperature. The reaction medium was then diluted with 500 mL of water and extracted 3 times with 200 mL of EtOAc. The organic phases were combined, washed once with 200 mL of NaCl-saturated aqueous solution, dried over sodium sulfate, filtered and concentrated to yield 40 g of partly purified compound 1V in the form of a pale yellow oil.

Compound 1W: (3R,4S,5S)-4-[(2S)-2-[[(9H-fluoren-9-ylmethoxy)carbonyl]amino]-N,3-dimethylbutanamido]-3-methoxy-5-methylheptanoic Acid

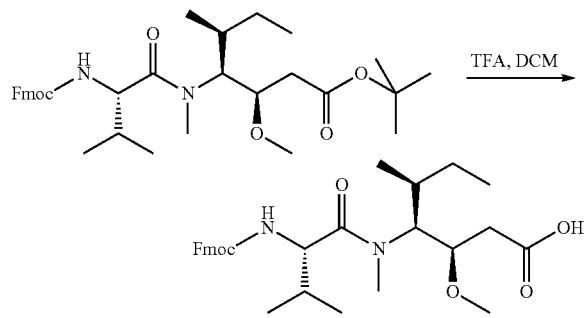

Compound 1V (40 g, 68.88 mmol, 1.00 equiv) was dissolved in a neutral atmosphere in 600 mL of DCM. TFA (300 mL) was added. The solution was agitated 2 hours at ambient temperature, then concentrated under reduced pressure. The residue was purified on a silica column with a mixture of methanol and DCM (1:10) to yield 23.6 g (65%) of compound 1W in colourless oil form.

Compound 1X: 9H-fluoren-9-ylmethyl N-[(1S)-1-[[(3R,4S,5S)-3-methoxy-1-[(2S)-2-[(1R,2R)-1-methoxy-2-methyl-2-[[(1S)-2-phenyl-1-(1,3-thiazol-2-yl)ethyl]carbamoyl]ethyl]pyrrolidin-1-yl]-5-methyl-1-oxoheptan-4-yl](methyl) carbamoyl]-2-methylpropyl]carbamate

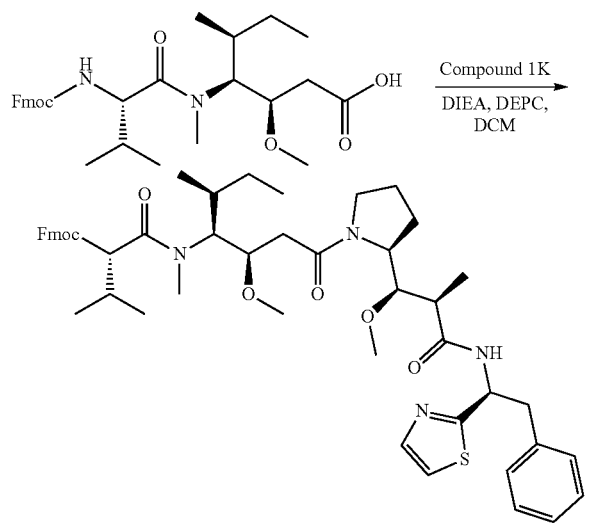

Compound 1W (2.53 g, 4.82 mmol, 1.08 equiv) was dissolved in 20 mL of DCM in the presence of compound 1K (2.18 g, 4.47 mmol, 1.00 equiv), DEPC (875 mg, 5.37 mmol, 1.20 equiv) and DIEA (1.25 g, 9.67 mmol, 2.16 equiv). The reaction mixture was left under agitation overnight at ambient temperature, then successively washed with 50 mL of saturated KHSO₄ and 100 mL of water, dried over sodium sulfate, filtered and concentrated. The residue was purified on a silica column with a mixture of methanol and DCM (1:200 to 1:40) to yield 2.8 g (71%) of compound 1X in the form of a pale yellow solid.

Compound 1Y: (2S)-2-amino-N-[(3R,5 S)-3-methoxy-1-[(2S)-2-[(1R,2R)-1-methoxy-2-methyl-2-[[(1 S)-2-phenyl-1-(1,3-thiazol-2-yl)ethyl]carbamoyl]ethyl]pyrrolidin-1-yl]-5-methyl-1-oxoheptan-4-yl]-N,3-dimethylbutanamide

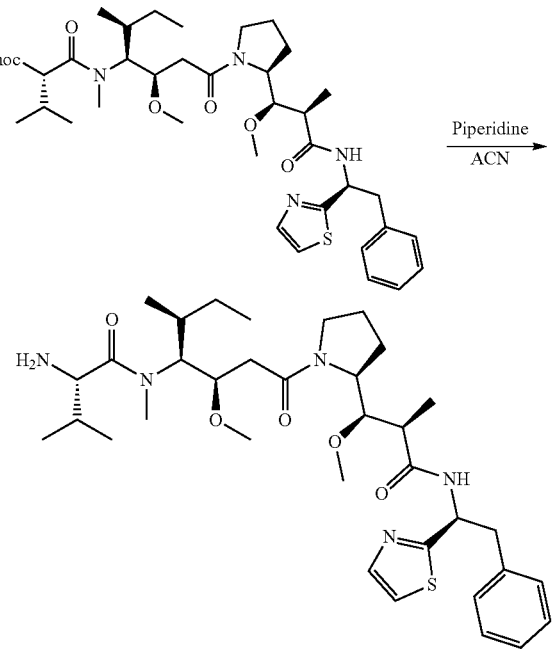

Compound 1X (2.8 g, 3.18 mmol, 1.00 equiv) was dissolved in acetonitrile (ACN, 12 mL) in the presence of piperidine (3 mL) and left under agitation 18 hours at ambient temperature. The reaction was neutralised with 50 mL of water, then extracted twice with 100 mL of DCM. The organic phases were combined, dried over sodium sulfate, filtered and concentrated. The residue was purified on a silica column with a mixture of methanol and DCM (1:100 to 1:40) to yield 1.2 g (57%) of compound 1Y in the form of a yellow solid.

Compound 1ZA: (2S)-2-[[(tert-butoxy)carbonyl](methyl)amino]-3-methyl butanoic Acid

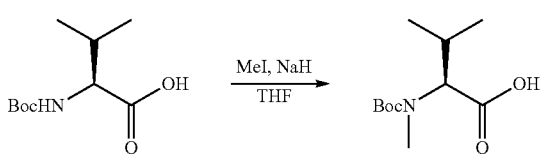 [SMILES: CC(C)[C@H](NC(=O)OC(C)(C)C)C(=O)O ; CC(C)[C@@H](C(=O)O)N(C)C(=O)OC(C)(C)C ; "THF"]

(2S)-2-[[(tert-butoxy)carbonyl]amino]-3-methylbutanoic acid (63 g, 289.97 mmol, 1.00 equiv) was dissolved in an inert atmosphere in THF (1000 mL) in the presence of iodomethane (181 mL). The solution was cooled to 0° C. before adding sodium hydride (116 g, 4.83 mol, 16.67 equiv) in small portions. The reaction mixture was agitated for 1.5 hours at 0° C., the cold bath was then removed and agitation continued for 18 hours. The reaction was neutralised with 200 mL of water and then concentrated under reduced pressure. The residual aqueous phase was diluted with 4 litres of water, washed once with 200 mL of EtOAc and its pH adjusted to between 3 and 4 with a 1N solution of hydrochloric acid. The mixture obtained was extracted 3 times with 1.2 L of EtOAc. The organic phases were combined, dried over sodium sulfate, filtered and concentrated to yield 60 g (89%) of compound 1ZA in the form of a yellow oil.

Compound 1ZB: benzyl (2S)-2-[[(tert-butoxy)carbonyl](methyl)amino]-3-methylbutanoate

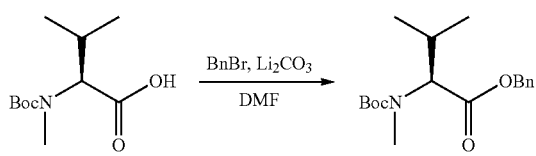

Compound 1ZA (47 g, 203.21 mmol, 1.00 equiv) was dissolved in DMF (600 mL) in the presence of $Li_2CO_3$ (15.8 g, 213.83 mmol, 1.05 equiv). The solution was cooled to 0° C. then benzyl bromide (BnBr 57.9 g, 338.53 mmol, 1.67 equiv) was added drop-wise. The reaction mixture was left under agitation overnight before being neutralised with 400 mL of water and filtered. The solution obtained was extracted twice with 500 mL of EtOAc. The organic phases were combined, dried over sodium sulfate, filtered and concentrated. The residue was purified on a silica column with a mixture of EtOAc and PE (1:100 to 1:20) to yield 22.5 g (34%) of compound 1ZB in the form of a yellow oil.

Compound 1ZC: benzyl (2S)-3-methyl-2-(methylamino)butanoate hydrochloride

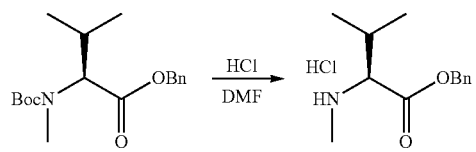

Compound 1ZB (22.5 g, 70.00 mmol, 1.00 equiv) was dissolved in 150 mL of DCM. Gaseous hydrochloric acid was bubbled. The reaction was agitated 1 hour at ambient temperature and then concentrated under reduced pressure to yield 17 g (94%) of compound 1ZC in the form of a yellow solid.

Compound 1ZD: tert-butyl N-(3,3-diethoxypropyl)carbamate

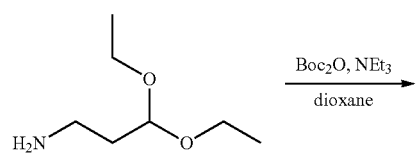

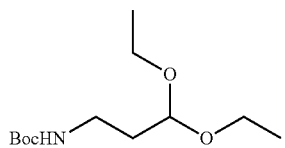

3,3-diethoxypropan-1l-amine (6 g, 40.76 mmol, 1.00 equiv) was dissolved in 1,4-dioxane (30 mL) in the presence of TEA (4.45 g, 43.98 mmol, 1.08 equiv), then cooled to 0° C. $(Boc)_2O$ (9.6 g, 43.99 mmol, 1.08 equiv) diluted in 20 mL of 1,4-dioxane was added drop-wise. The solution was agitated 2 hours at 0° C. then overnight at ambient temperature before being neutralised with 10 mL of water. The pH was adjusted to 5 with HCl (1%). The solution was extracted 3 times with 50 mL of EtOAc. The organic phases were combined, dried over sodium sulfate, filtered and concentrated to yield 8.21 g (81%) of compound 1ZD in the form of a pale yellow oil.

Compound 1ZE: tert-butyl N-(3-oxopropyl)carbamate

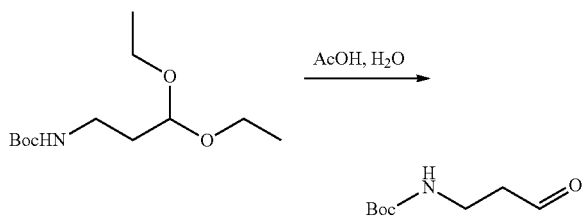

Compound 1ZD (8.20 g, 33.15 mmol, 1.00 equiv) was dissolved in 18.75 mL of acetic acid and left under agitation overnight at ambient temperature. The reaction medium was then extracted 3 times with 30 mL of EtOAc. The organic phases were combined, washed 3 times with 30 mL of saturated NaCl solution, dried over sodium sulfate, filtered and concentrated to yield 5 g (87%) of compound 1ZE in the form of a dark red oil.

Compound 1ZF: (2S)-2-[(3-[[(tert-butoxy)carbonyl]amino]propyl)(methyl) amino]-3-methylbutanoic Acid

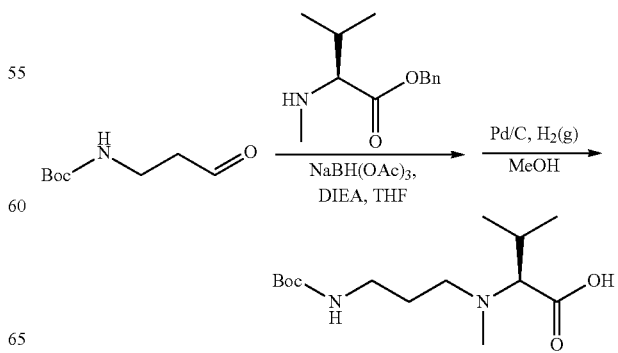

Compound 1ZE (2.4 g, 13.86 mmol, 1.00 equiv) was dissolved in 50 mL of THF in the presence of compound 1ZC (3.56 g, 13.81 mmol, 1.00 equiv) and DIEA (9.16 mL, 4.00 equiv). The reaction mixture was agitated 30 minutes at ambient temperature before adding sodium triacetoxyborohydride (5.87 g, 27.70 mmol, 2.00 equiv). Agitation was continued overnight, then the reaction was neutralised with 100 mL of water and extracted 3 times with 50 mL of EtOAc. The organic phases were combined, dried over sodium sulfate, filtered and concentrated. The residue was partly purified on a silica column with a mixture of EtOAc and PE (1:4). The crude product obtained was re-dissolved in 20 mL of methanol in the presence of Pd/C (1.2 g) and hydrogenated for 20 minutes at normal temperature and pressure. The reaction medium was filtered and concentrated under reduced pressure to yield 200 mg (5%) of compound 1ZF in the form of a white solid.

Compound 1ZG: tert-butyl N-(3-[[(1S)-1-[[(1S)-1-[[(3R,4S,5S)-3-methoxy-1-[(2S)-2-[(1R,2R)-1-methoxy-2-methyl-2-[[(1 S)-2-phenyl-1-(1,3-thiazol-2-yl)ethyl]carbamoyl]thyl]pyrrolidin-1-yl]-5-methyl-1-oxoheptan-4yl](methyl) carbamoyl]-2-methylpropyl]carbamoyl]-2-methylpropyl](methyl) amino]propyl) carbamate

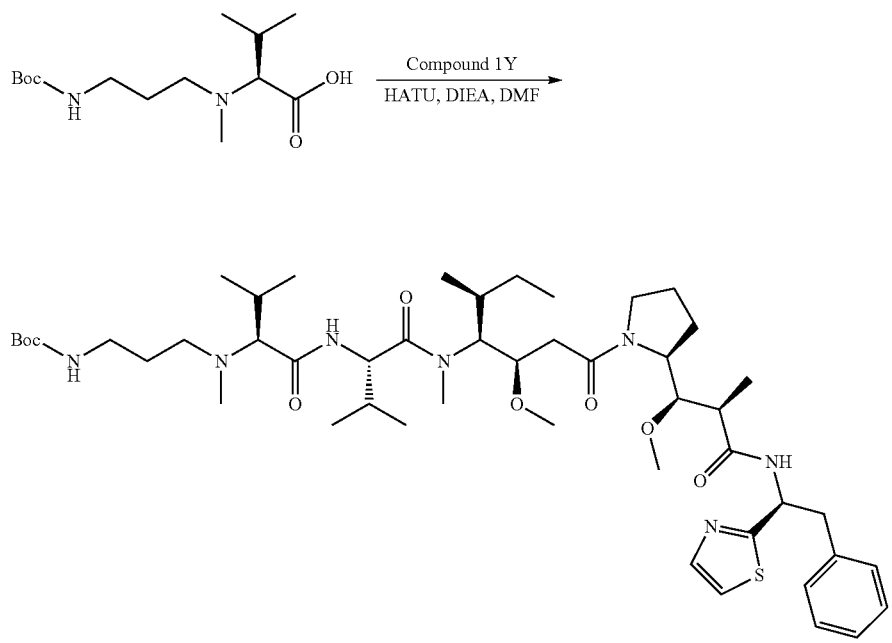

Compound 1Y (50 mg, 0.08 mmol, 1.00 equiv) was dissolved in 2 mL of DMF in the presence of compound 1ZF (26.2 mg, 0.09 mmol, 1.20 equiv), DIEA (37.7 mL) and O-(7-azabenzotriazol-1-yl)-N,N,N',N'-tetramethyluronium hexafluorophosphate (HATU, 43.3 mg, 0.11 mmol, 1.50 equiv). The reaction was left under agitation overnight at ambient temperature, then diluted with 10 mL of water and extracted 3 times with 5 mL of EtOAc. The organic phases were combined, dried over sodium sulfate, filtered and concentrated to yield 100 mg of compound 1ZG in the form of a partly purified colourless oil.

Compound 1ZG (90 mg, 0.10 mmol, 1.00 equiv) was dissolved in a neutral atmosphere in 2 mL of DCM and the solution was cooled with an ice bath. TFA (1 mL) was added and the reaction agitated for 2 hours at ambient temperature, then concentrated under reduced pressure. The residue was purified by preparative HPLC (Pre-HPLC-001 SHIMADZU, SunFire Prep C18 OBD column, 5 μm, 19×150 mm; Eluting phase: water/ACN buffered with 0.05% of TFA; Gradient of 18% to 31% ACN in 7 minutes then 31% to 100% ACN in 2 minutes; Waters 2489 UV Detector at 254 nm and 220 nm). Compound 1 was obtained with a yield of 25% (23 mg) in the form of a white solid.

LC/MS/UV (Atlantis T3 column, 3 μm, 4.6×100 mm; 35° C.; 1 mL/min, 30% to 60% ACN in water (20 mM ammonium acetate in 6 minutes); ESI ($C_{44}H_{73}N_7O_6S$, exact masse 827.53) m/z: 829 (MH$^+$), 5.84 min (93.7%, 254 nm).

$^1$H NMR (300 MHz, CD$_3$OD, ppm): δ (Presence of rotamers) 7.85-7.80 (m, 1H); 7.69-7.66 (m, 1H), 7.40-7.10 (m, 5H), 5.80-5.63 (m, 1H), 4.80-4.65 (m, 2H), 4.22-4.00 (m, 1H), 3.89-0.74 (m, 58H).

Reference Compound 2

(S)-2-((S)-2-(((2-aminopyridin-4-yl)methyl)(methyl)amino)-3-methylbutanamido)-N-((3R,4S,5S)-1-((S)-2-((1R,2R)-3-(((1 S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethylbutanamide, trifluoroacetic Acid

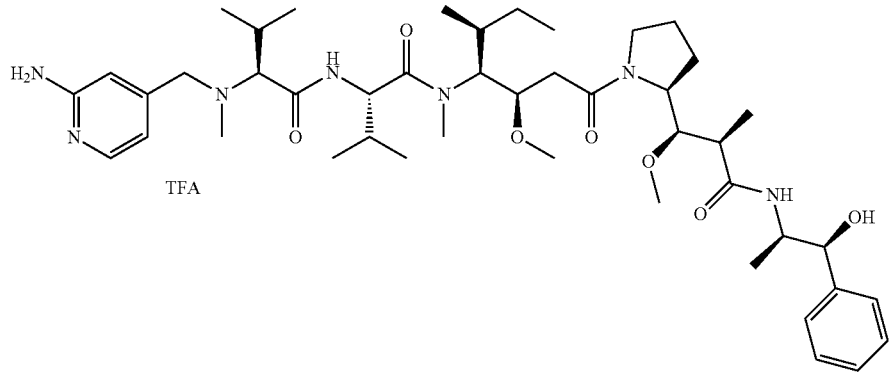 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)Cc1ccnc(N)c1)C(C)C]

Compound 2A: tert-butyl (S)-2-((1R,2R)-3-(((1S,2R)-1-hydroxy-1-phenylpropan-2-yl)amino)-1-methoxy-2-methyl-3-oxopropyl)pyrrolidine-1-carboxylate

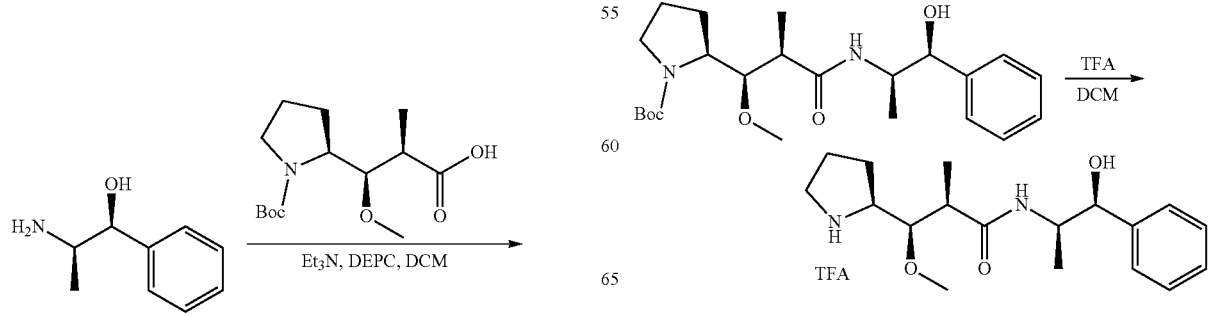

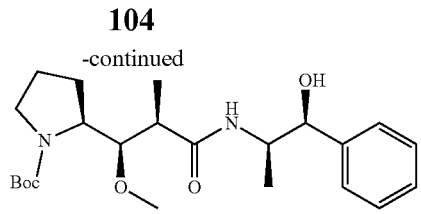

Compound 1D (2.5 g, 8.70 mmol, 1.00 equiv) and (1S,2R)-2-amino-1-phenylpropan-1l-ol (1.315 g, 8.70 mmol, 1.00 equiv) were dissolved in an inert atmosphere in DMF (35 mL). The solution was cooled to 0° C. then DEPC (1.39 mL) and TEA (1.82 mL) were added drop-wise. The reaction mixture was agitated 2 hours at 0° C. then 4 hours at ambient temperature. The reaction mixture was diluted with 200 mL of water and extracted three times with 50 mL of EtOAc. The organic phases were combined, washed once with 50 mL of KHSO$_4$ (1 mol/L), once with 50 mL of NaHCO$_3$ (sat.), once with 50 mL of NaCl (sat.), then dried over sodium sulfate, filtered and concentrated under reduced pressure to yield 3.6 g (98%) of compound 2A in the form of a yellow solid.

Compound 2B: (2R,3R)—N-((1S,2R)-1-hydroxy-1-phenylpropan-2-yl)-3-methoxy-2-methyl-3-((S)-pyrrolidin-2-yl)propanamide 2,2,2-trifluoroacetate Compound 2A (2.7 g, 6.42 mmol, 1.00 equiv) was dissolved in an inert atmosphere in DCM (40 mL) then cooled to 0° C. TFA (25 mL) was added and the solution agitated for 2 hours at 0° C. The reaction mixture was concentrated under reduced pressure to yield 4.4 g of compound 2B in the form of a yellow oil.

Compound 2C: (9H-fluoren-9-yl)methyl ((S)-1-(((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamate

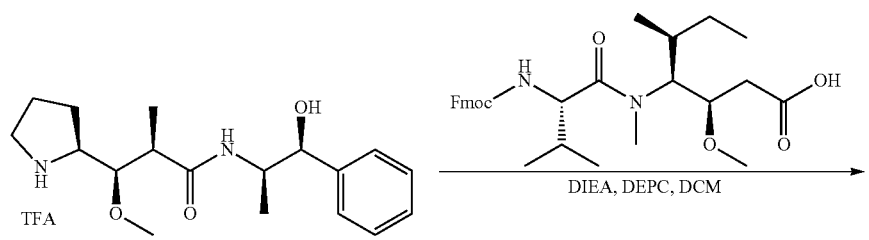

Compounds 2B (4.4 g, 10.13 mmol, 1.00 equiv) and 1W (5.31 g, 10.12 mmol, 1.00 equiv) were dissolved in an inert atmosphere in DCM (45 mL). The solution was cooled to 0° C. then DEPC (1.62 mL) and DIEA (8.4 mL) were added drop-wise. The reaction mixture was agitated for 2 hours at 0° C. then at ambient temperature overnight. The reaction mixture was diluted with 100 mL of water and extracted three times with 50 mL of DCM. The organic phases were combined, washed once with 50 mL of KHSO₄ (1 mol/L), once with 50 mL of NaHCO₃ (sat.), once with 50 mL of NaCl (sat.), then dried over sodium sulfate, filtered and concentrated under pressure to yield 3.3 g (39%) of compound 2C in the form of a yellow solid.

Compound 2D: (S)-2-amino-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethylbutanamide

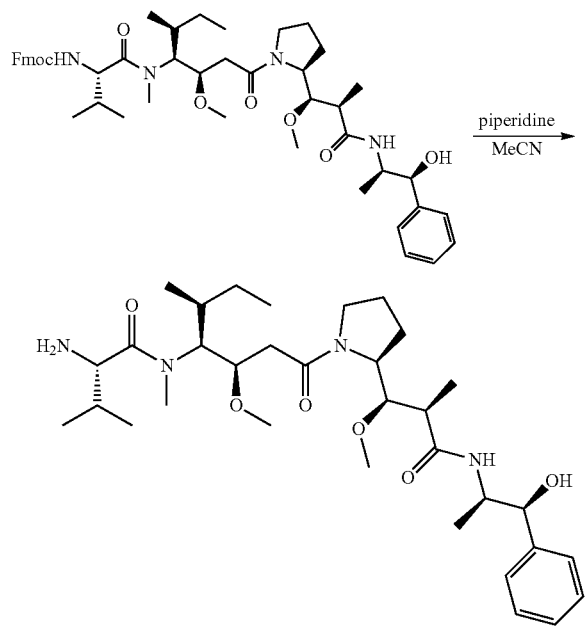

Compound 2C (300 mg, 0.36 mmol, 1.00 eq.) was dissolved in an inert atmosphere in ACN (2 mL) and piperidine (0.5 mL). The solution was left under agitation at ambient temperature overnight then evaporated to dryness under reduced pressure. The residue was purified on a silica column with a mixture of DCM and MeOH (1:100) to yield 150 mg (68%) of compound 2D in the form of a white solid.

Compound 2E: methyl 2-((tert-butoxycarbonyl)amino)isonicotinate

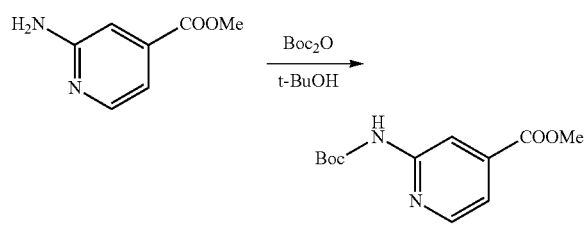

Methyl 2-aminopyridine-4-carboxylate (2 g, 13.14 mmol, 1.00 equiv) was dissolved in tert-butanol (20 mL) after which di-tert-butyl dicarbonate (4.02 g, 18.42 mmol, 1.40 equiv) was added. The reaction mixture was agitated at 60° C. overnight then the reaction was halted through the addition of an aqueous 1M NaHCO₃ solution (50 mL). The solid was recovered by filtration, washed with 50 mL of EtOH then dried in vacuo to yield 2.5 g (75%) of compound 2E in the form of a white solid.

Compound 2F: tert-butyl (4-(hydroxymethyl)pyridin-2-yl)carbamate

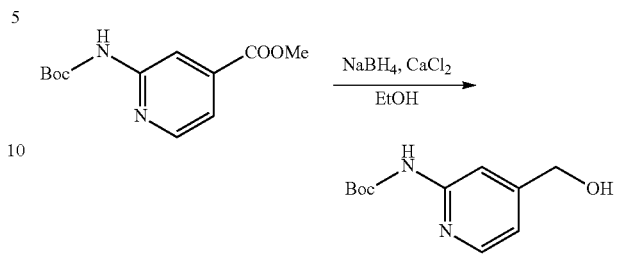

Compound 2E (2.5 g, 9.91 mmol, 1.00 equiv) and CaCl₂ (1.65 g) were dissolved in EtOH (30 mL). The solution was cooled to 0° C. then NaBH₄ (1.13 g, 29.87 mmol, 3.01 equiv) was gradually added. The solution was left under agitation overnight at ambient temperature then the reaction was halted with the addition of water (50 mL). The mixture was extracted three times with 20 mL of EtOAc. The organic phases were combined, washed twice with 20 mL of NaCl (sat.) then dried over sodium sulfate, filtered and concentrated under reduced pressure to yield 2.0 g (90%) of compound 2F in the form of a colourless solid.

Compound 2G: tert-butyl (4-formylpyridin-2-yl)carbamate

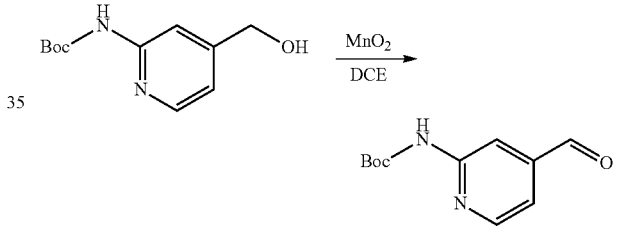

Compound 2F (2.5 g, 11.15 mmol, 1.00 equiv) was dissolved in DCE (25 mL) then 19.4 g (223.14 mmol, 20.02 equiv) of MnO₂ were added. The mixture was left under agitation overnight at 70° C. then the solids were removed by filtering. The filtrate was evaporated to dryness to yield 1.4 g (57%) of compound 2G in the form of a white solid.

Compound 2H: benzyl (S)-2-(((2-((tert-butoxycarbonyl)amino)pyridin-4-yl)methyl)(methyl)amino)-3-methylbutanoate

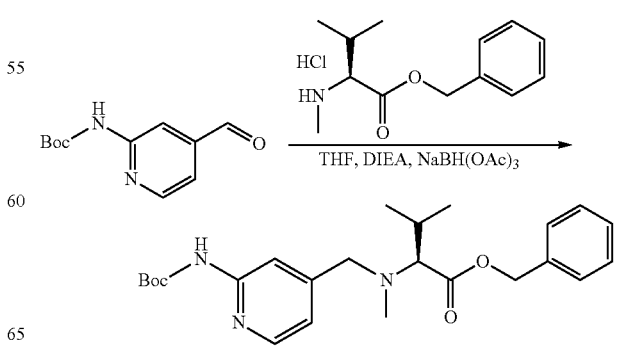

Compound 2G (2.3 g, 10.35 mmol, 1.00 equiv) was dissolved in 25 mL of THF in the presence of compound 1ZC (2.93 g, 11.37 mmol, 1.10 equiv), DIEA (5.39 g, 41.71 mmol, 4.03 equiv) and NaBH(OAc)₃ (4.39 g, 20.71 mmol, 2.00 equiv). The reaction mixture was agitated for 6 hours at ambient temperature then neutralised with 60 mL of NaHCO₃ (sat.) and extracted 3 times with 20 mL of AcOEt. The organic phases were combined, washed twice with 20 mL of NaCl (sat.), dried over sodium sulfate, filtered and concentrated. The residue was purified on a silica column with a mixture of EtOAc and PE (1:15) to yield 2.7 g (61%) of compound 2H in the form of a white solid.

Compound 2I: (S)-2-(((2-((tert-butoxycarbonyl)amino)pyridin-4-yl)methyl)(methyl)amino)-3-methylbutanoic Acid

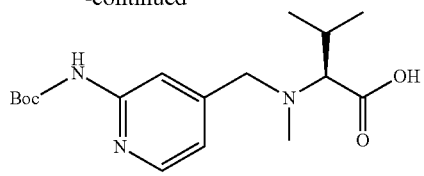

Compound 2H (500 mg, 1.17 mmol, 1.00 equiv) was dissolved in 10 mL of AcOEt and 2 mL of methanol in the presence of Pd/C (250 mg), and hydrogenated for 3 hours at ambient temperature and atmospheric pressure. The reaction medium was filtered and concentrated under reduced pressure to yield 254 mg (64%) of compound 2I in the form of a colourless solid Compound 2J: tert-butyl (4-((3S,6S,9S,10R)-9-((S)-sec-butyl)-10-(2-((S)-2-((1R,2R)-3-(((1 S,2R)-1-hydroxy-1-phenylpropan-2-yl)amino)-1-methoxy-2-methyl-3-oxopropyl)pyrrolidin-1-yl)-2-oxoethyl)-3,6-diisopropyl-2,8-dimethyl-4,7-dioxo-11-oxa-2,5,8-triazadodecyl)pyridin-2-yl) carbamate

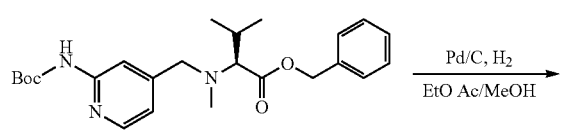

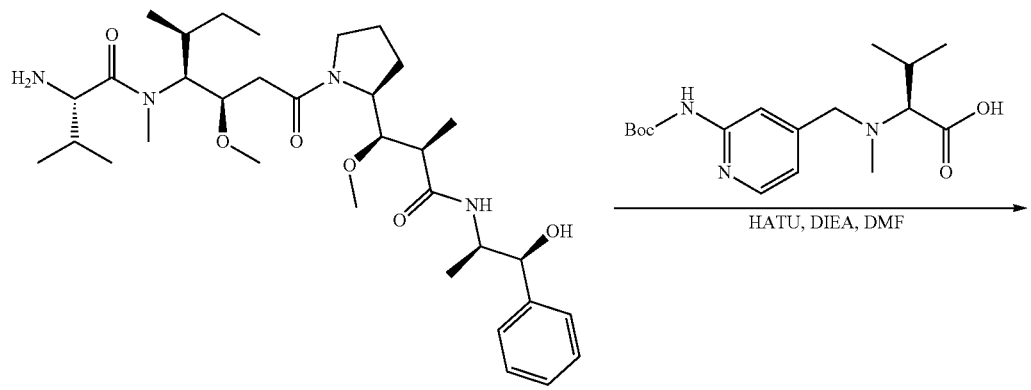

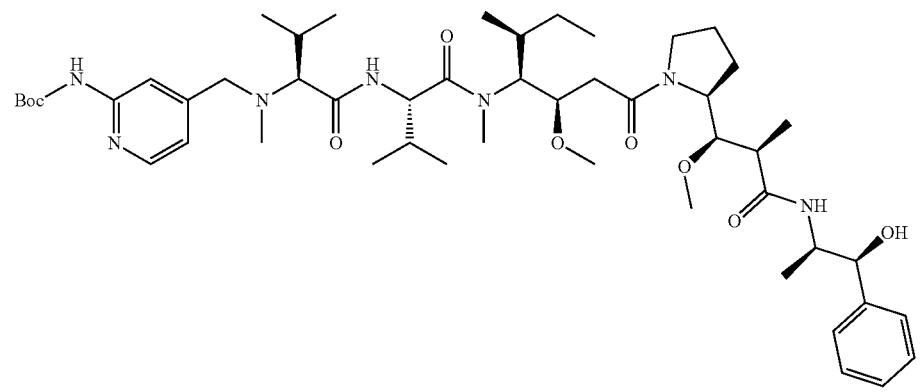

Compound 2J was prepared in similar manner to compound 1ZG from the amine 2D (85.2 mg, 0.14 mmol, 1.50 equiv), the acid 21 (31.7 mg, 0.09 mmol, 1.00 equiv), HATU (42.9 mg, 0.11 mmol, 1.20 equiv) and DIEA (36.7 mg, 0.28 mmol, 3.02 equiv) in DMF (3 mL). After evaporation to dryness, 100 mg of crude product were obtained in the form of a white solid.

Compound 2J (100 mg, 0.11 mmol, 1.00 equiv) was dissolved in 2 mL of DCM and 1 mL of TFA. The reaction was agitated for 1 hour at ambient temperature, then concentrated under reduced pressure. The residue (80 mg) was purified by preparative HPLC (Pre-HPLC-001 SHI-MADZU, SunFire Prep C18 OBD column, 5 μm, 19×150 mm; Eluting phase: water/ACN buffered with 0.05% TFA; Gradient of 20% to 40% ACN in 10 minutes then 40% to 100% ACN in 2 minutes; Waters 2489 UV Detector at 254 nm and 220 nm). Compound 2 was obtained with a yield of 6% (6.3 mg) in the form of a white solid.

LC/MS/UV (Ascentis Express C18 column, 2.7 μm, 4.6× 100 mm; 40° C.; 1.8 mL/min, from 10% to 95% ACN in water (0.05% TFA) in 6 minutes); ESI ($C_{45}H_{73}N_7O_7$, exact mass 823.56) m/z: 824.5 (MH$^+$) and 412.9 (M.2H$^+$/2, 100%), 3.21 min (99.2%, 210 nm)

$^1$H NMR (400 MHz, CD$_3$OD, ppm): δ (Presence of rotamers) 7.81-7.79 (m, 1H); 7.39-7.29 (m, 5H); 6.61-6.59 (m, 2H); 4.84-4.52 (m, 1H); 4.32-4.02 (m, 1H); 3.90-2.98 (m, 10H); 2.90-2.78 (m, 1H); 2.55-0.81 (m, 39H).

Reference Compound 3 methyl ((S)-2-((2R,3R)-3-((S)-1-((3R,4S,5S)-4-((S)—N,3-dimethyl-2-((S)-3-methyl-2-(methyl(pyridin-4-ylmethyl)amino)butanamido)butanamido)-3-methoxy-5-methylheptanoyl)pyrrolidin-2-yl)-3-methoxy-2-methylpropanamido)-3-phenylpropanoate, trifluoroacetic Acid

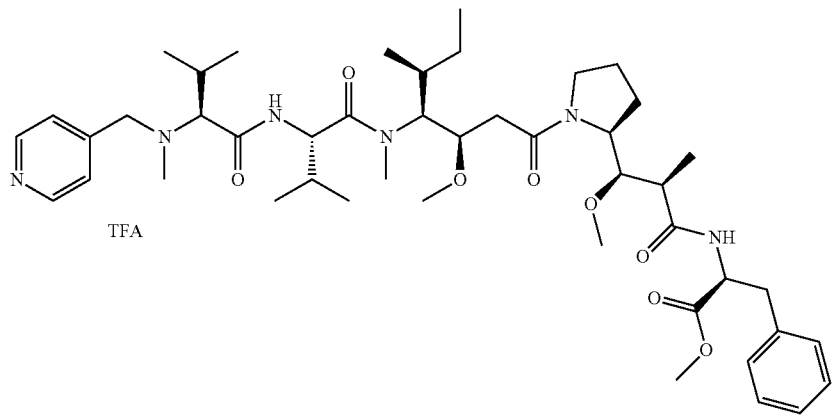 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)Cc1ccncc1)C(C)C]

113

Compound 3A: tert-butyl (S)-2-((1R,2R)-1-methoxy-3-(((S)-1-methoxy-1-oxo-3-phenylpropan-2-yl)amino)-2-methyl-3-oxopropyl)pyrrolidine-1-carboxylate

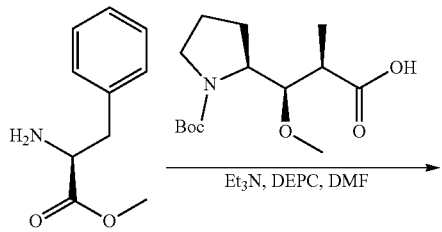

Compound 1D (3 g, 10.44 mmol, 1.00 equiv) and methyl (S)-2-amino-3-phenylpropanoate (2.25 g, 12.55 mmol, 1.20 equiv) were dissolved in an inert atmosphere in DMF (40 mL). The solution was cooled to 0° C. then DEPC (1.67 mL, 1.05 equiv) and TEA (3.64 mL, 2.50 equiv) were added drop-wise. The reaction mixture was agitated 2 hours at 0° C. then at ambient temperature overnight. The reaction mixture was diluted with 100 mL of water and extracted three times with 50 mL EtOAc. The organic phases were combined, washed once with 100 mL of KHSO₄ (1 mol/L), once with 100 mL of NaHCO₃ (sat.), once with 100 mL of NaCl (sat.), then dried over sodium sulfate, filtered and concentrated under pressure to yield 4 g (85%) of compound 3A in the form of a colourless oil.

114

Compound 3B: 2,2,2-trifluoroacetate of methyl (S)-2-((2R,3R)-3-methoxy-2-methyl-3-((S)-pyrrolidin-2-yl)propanamido)-3-phenylpropanoate

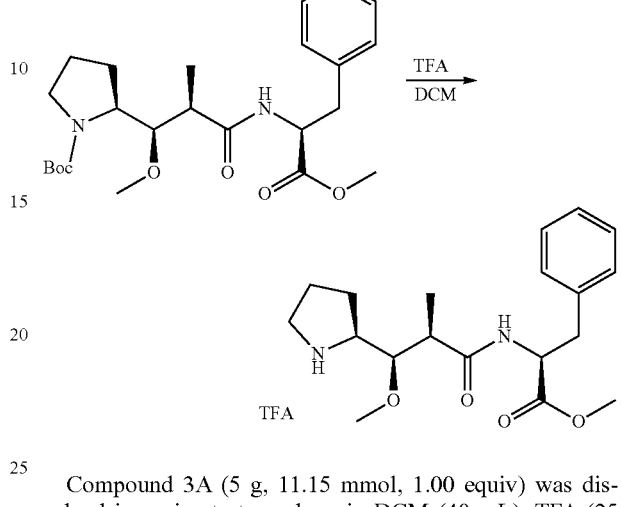

Compound 3A (5 g, 11.15 mmol, 1.00 equiv) was dissolved in an inert atmosphere in DCM (40 mL). TFA (25 mL) was added and the solution agitated for 2 hours. The reaction mixture was concentrated under reduced pressure to yield 8 g of compound 3B in the form of a yellow oil.

Compound 3C: methyl (S)-2-((2R,3R)-3-((S)-1-((3R,4S,5S)-4-((S)-2-((((9H-fluoren-9-yl)methoxy)carbonyl)amino)-N,3-dimethylbutanamido)-3-methoxy-5-methylheptanoyl)pyrrolidin-2-yl)-3-methoxy-2-methylpropanamido)-3-phenylpropanoate

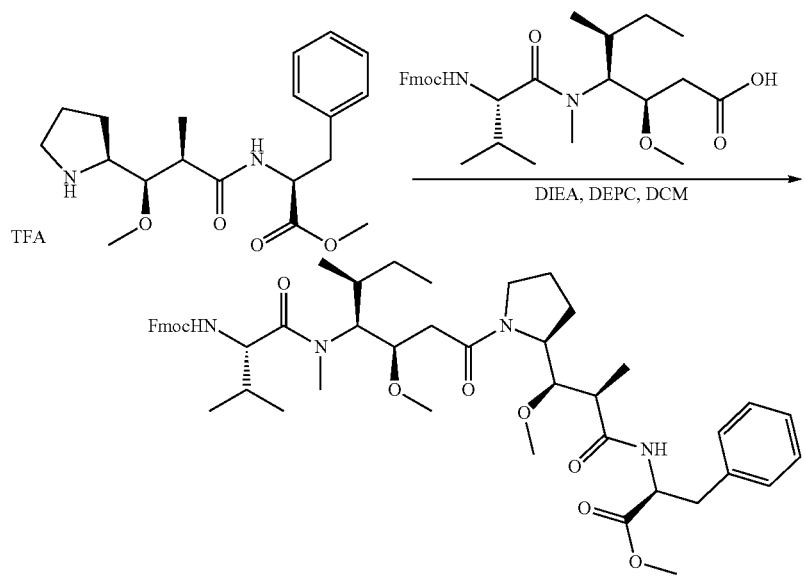

Compounds 3B (8.03 g, 17.36 mmol, 1.00 equiv) and 1W (9.1 g, 17.34 mmol, 1.00 equiv) were dissolved in an inert atmosphere in DCM (80 mL). The solution was cooled to 0° C. then DEPC (2.8 mL) and DIEA (12 mL) were added drop-wise. The reaction mixture was agitated for 2 hours at 0° C. then at ambient temperature overnight. The reaction mixture was diluted with 200 mL of water and extracted three times with 50 mL of DCM. The organic phases were combined, washed once with 50 mL of KHSO₄ (1 mol/L), once with 50 mL of NaHCO₃ (sat.), once with 50 mL of NaCl (sat.), then dried over sodium sulfate, filtered and concentrated under reduced pressure to yield 5 g (34%) of compound 3C in the form of a yellow solid.

Compound 3D: methyl (S)-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanoate

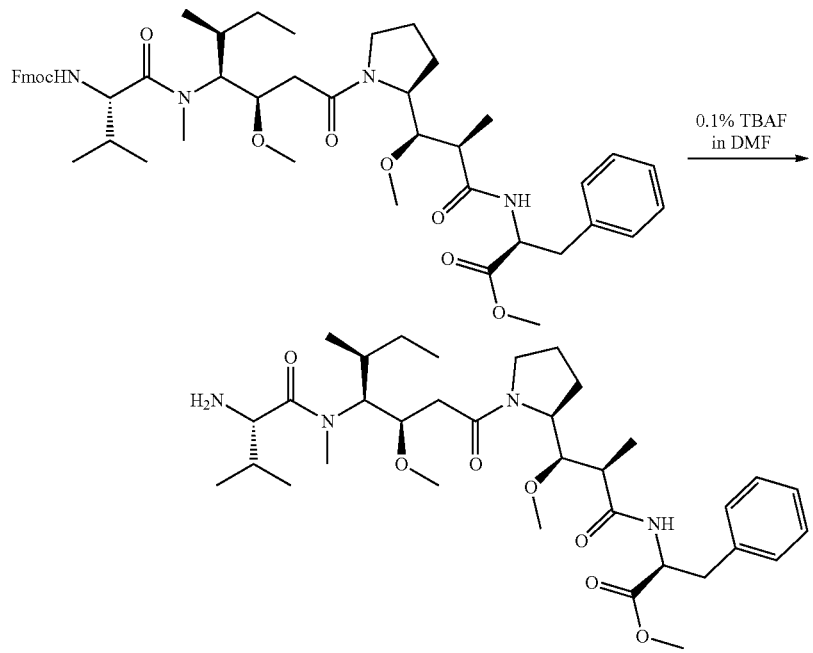

Compound 3C (5.5 g, 6.43 mmol, 1.00 equiv) was dissolved in an inert atmosphere in a solution of tetrabutylammonium fluoride (TBAF, 2.61 g, 9.98 mmol, 1.55 quiv) in DMF (100 mL). The solution was agitated at ambient temperature for 2 hours then diluted with 100 mL of water and extracted three times with 50 mL of EtOAc. The organic phases were combined then dried over sodium sulfate, filtered and concentrated under reduced pressure to yield 3.3 g (81%) of compound 3D in the form of a yellow solid.

Compound 3E: benzyl (S)-3-methyl-2-(methyl(pyridin-4-ylmethyl)amino) butanoate

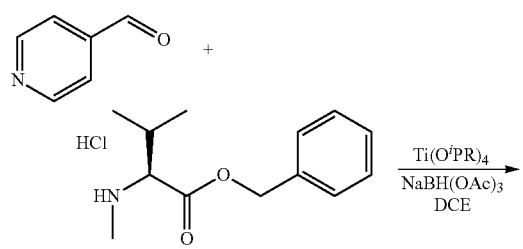

-continued

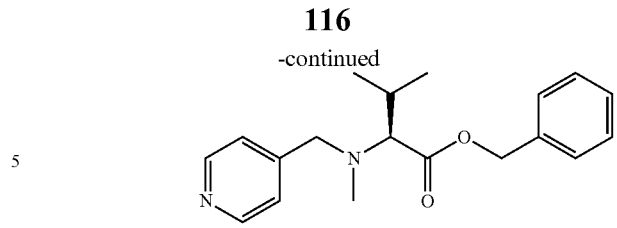

Pyridine-4-carbaldehyde (1 g, 9.34 mmol, 1.00 equiv) was dissolved in 10 mL of 1,2-dichloroethane (DCE) in the presence of compound 1ZC (2.9 g, 11.25 mmol, 1.21 equiv) and titanium isopropoxide (IV) (4.19 mL, 1.40 equiv). The mixture was agitated at ambient temperature for 30 minutes then 2.77 g of NaBH(OAc)₃ (13.07 mmol, 1.40 equiv) were added. The reaction medium was left under agitation overnight then neutralised with 100 mL of water and the mixture extracted 3 times with 50 mL of AcOEt. The organic phases were combined and evaporated to dryness. The residue was purified on a silica column with a mixture of EtOAc and PE (1:20) to yield 1.3 g (45%) of compound 3E in the form of a colourless oil.

Compound 3F: (S)-3-methyl-2-(methyl(pyridin-4-ylmethyl)amino)butanoic Acid

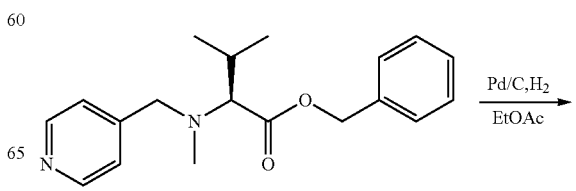

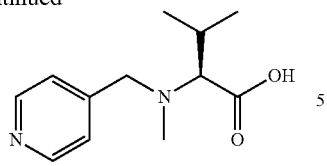

Compound 3E (800 mg, 2.56 mmol, 1.00 equiv) was dissolved in 30 mL of AcOEt in the presence of Pd/C (300 mg) and hydrogenated for 3 hours at ambient temperature and atmospheric pressure. The reaction medium was filtered and concentrated under reduced pressure. The residue was purified on a silica column with a mixture of DCM and MeOH (100:1 to 5:1) to yield 100 mg (18%) of compound 3F in the form of a white solid.

Compounds 3D (50 mg, 0.08 mmol, 1.00 equiv) and 3F (26.34 mg, 0.12 mmol, 1.50 equiv) were dissolved in 3 mL of DCM. The solution was cooled to 0° C. then 0.018 mL of DEPC and 0.0392 mL of DIEA were added. The reaction was agitated at 0° C. for 2 hours then at ambient temperature overnight. The reaction medium was concentrated under reduced pressure and the residue (70 mg) was purified by preparative HPLC (Pre-HPLC-001 SHIMADZU, SunFire Prep C18 OBD column, 5 µm, 19×150 mm; Eluting phase: water/ACN buffered with 0.05% of TFA; Gradient of 20% to 40% ACN in 10 minutes then 40% to 100% ACN in 2 minutes; Waters 2545 UV Detector at 254 nm and 220 nm). Compound 3 was obtained with a yield of 27% (20 mg) in the form of a white solid.

LC/MS/UV (Ascentis Express C18 column, 2.7 µm, 4.6× 100 mm; 40° C.; 1.5 mL/min, 10% to 95% ACN in water (0.05% TFA) in 8 minutes); ESI ($C_{46}H_{72}N_6O_8$, exact mass 836.5) m/z: 837.5 (MH$^+$) and 419.4 (M.2H/2 (100%)), 7.04 min (90.0%, 210 nm)

$^1$H NMR (400 MHz, CD$_3$OD, ppm): δ (Presence of rotamers) 8.76-8.74 (m, 2H); 8.53-8.48 (m, 0.4H, NHCO incomplete exchange); 8.29-8.15 (m, 0.8H, NHCO incomplete exchange); 8.01 (s, 2H), 7.31-7.22 (m, 5H), 4.88-4.68 (m, 3H); 4.31-4.07 (m, 2H); 3.94-2.90 (m, 18H); 2.55-0.86 (m, 38H).

Reference Compound 4

(S)-2-((2R,3R)-3-((S)-1-((3R,4S,5S)-4-((S)—N,3-dimethyl-2-((S)-3-methyl-2-(methyl(pyridin-4-ylmethyl)amino)butanamido)butanamido)-3-methoxy-5-methylheptanoyl)pyrrolidin-2-yl)-3-methoxy-2-methylpropanamido)-3-phenylpropanoic acid, trifluoroacetic Acid

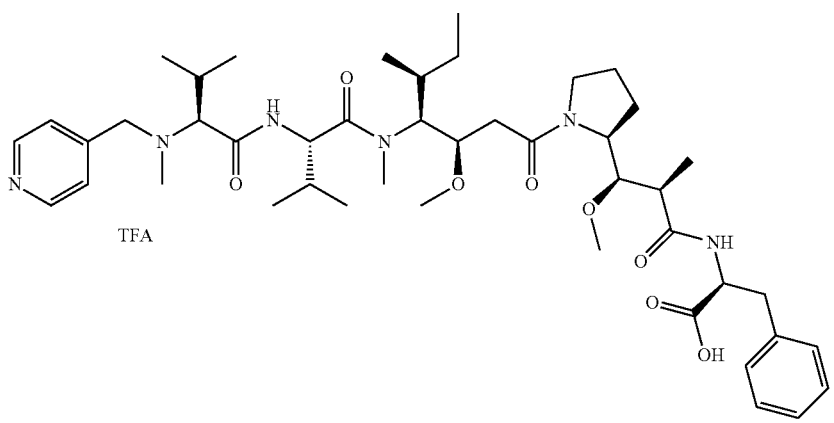 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)Cc1ccncc1)C(C)C]

Compound 3 (100 mg, 0.11 mmol, 1.00 equiv) was dissolved in a mixture of water (5 mL), ACN (5 mL) and piperidine (2.5 mL). The reaction mixture was left under agitation overnight then concentrated under reduced pressure. The residue was purified by preparative HPLC (Pre-HPLC-001 SHIMADZU, SunFire Prep C18 OBD column, 5 μm, 19×150 mm; Eluting phase: water/ACN buffered with 0.05% TFA; Gradient of 20% to 40% ACN in 10 minutes then 40% to 100% ACN in 2 minutes; Waters 2545 UV Detector at 254 nm and 220 nm), to yield 20 mg (20%) of compound 4 in the form of a white solid.

LC/MS/UV (Ascentis Express C18 column, 2.7 μm, 4.6× 100 mm; 40° C.; 1.5 mL/min, 10% to 95% ACN in water (0.05% TFA) in 8 minutes); ESI ($C_{45}H_{70}N_6O_8$, exact mass 822.5) m/z: 823.5 ($MH^+$) and 412.4 ($M.2H^+/2$, 100%), 6.84 min (89.1%, 210 nm).

$^1$H NMR (400 MHz, $CD_3OD$, ppm): δ (Presence of rotamers) 8.79-8.78 (m, 2H); 8.09 (m, 2H); 7.30-7.21 (m, 5H); 4.80-4.80 (m, 1H), 4.36-0.87 (m, 58H).

Reference Compound 6 methyl (S)-2-((2R,3R)-3-((S)-1-((3R,4S,5S)-4-((S)-2-((S)-2-((3-aminopropyl)(methyl)amino)-3-methylbutanamido)-N,3-dimethylbutanamido)-3-methoxy-5-methylheptanoyl)pyrrolidin-2-yl)-3-methoxy-2-methylpropanamido)-3-phenylpropanoate, bis trifluoroacetic Acid

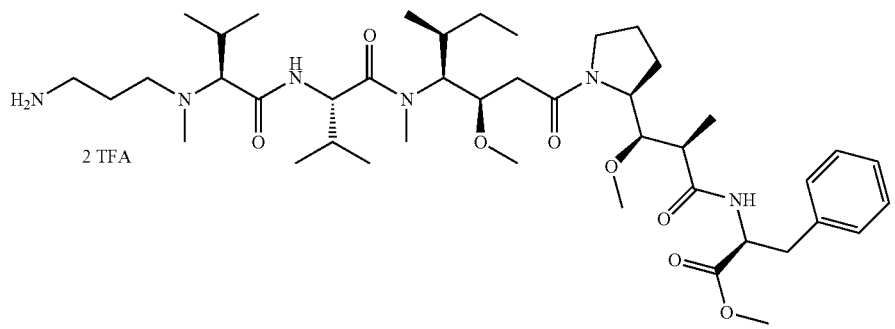 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCCN)C(C)C]

Compound 6A: methyl (2S)-2-[(2R)-2-[(R)-[(2S)-1-[(3R,4S,5S)-4-[(2S)-2-[(2S)-2-[(3-[[(tert-butoxy)carbonyl]amino]propyl)(methyl)amino]-3-methyl butanamido]-N,3-dimethylbutanamido]-3-methoxy-5-methylheptanoyl]pyrrolidin-2-yl](methoxy) methyl]propanamido]-3-phenylpropanoate

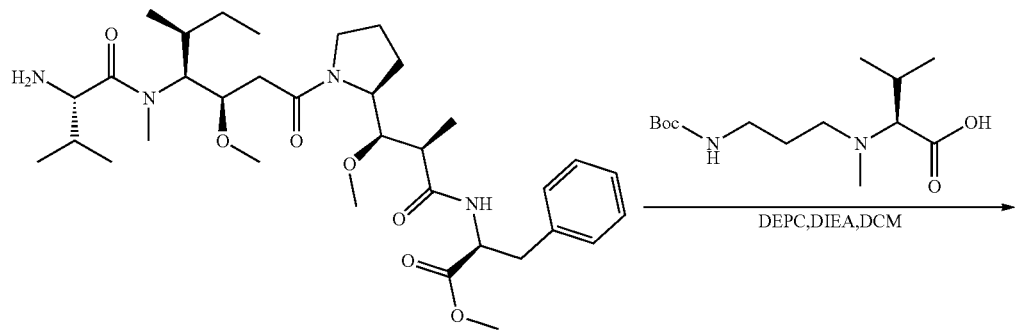

-continued

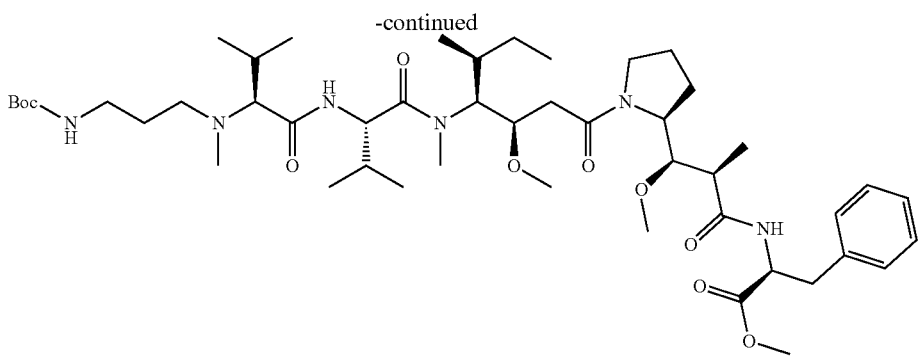

Compound 3D (157.5 mg, 0.25 mmol, 1.00 equiv) was dissolved at 0° C. in an inert atmosphere in 3 mL of DCM in the presence of carboxylic acid 1ZF (78.7 mg, 0.27 mmol, 1.10 equiv), DEPC (46 µl) and DIEA (124 µl). The reaction mixture was agitated 2 hours at low temperature and the cold bath was then removed and agitation continued for 4 hours. It was then concentrated under reduced pressure to yield 200 mg of compound 6A in the form of a crude yellow oil. It was used as such in the following step.

Compound 6A (200 mg, 0.22 mmol, 1.00 equiv) was dissolved in an inert atmosphere at 0° C. in 2 mL of DCM. TFA (1 mL) was added drop-wise and the cold bath removed. The reaction mixture was agitated 1 hour at ambient temperature then concentrated under reduced pressure. The residue was purified by preparative HPLC (Pre-HPLC-001 SHIMADZU, SunFire Prep C18 OBD column, 5 µm, 19×150 mm; Eluting phase: water/ACN buffered with 0.05% TFA; Gradient of 20% to 40% ACN in 10 minutes then 40% to 100% ACN in 2 minutes; Waters 2489 UV Detector at 254 nm and 220 nm), to yield 60 mg (26%, yield in 2 steps) of compound 6 in the form of a white solid.

LC/MS/UV (Zorbax Eclipse Plus C8, 3.5 µm, 4.6×150 mm; 1 mL/min, 40° C., 30 to 80% methanol in water (0.1% $H_3PO_4$) in 18 minutes); ESI ($C_{43}H_{74}N_6O_8$, exact mass 802.56) m/z: 804 (MH$^+$); 11.50 min (91.5%, 210 nm).

$^1$H NMR (300 MHz, CD$_3$OD, ppm): δ (Presence of rotamers) 8.52 (d, 0.3H, NHCO incomplete exchange); 8.25 (d, 0.5H, NHCO incomplete exchange); 7.30-7.22 (m, 5H); 4.9-4.6 (m, 3H); 4.2-4.0 (m, 1H); 4.0-0.86 (m, 61H).

Reference Compound 7

(S)-2-((2R,3R)-3-((S)-1-((3R,4S,5S)-4-((S)-2-((S)-2-((3-aminopropyl)(methyl)amino)-3-methylbutanamido)-N,3-dimethylbutanamido)-3-methoxy-5-methylheptanoyl) pyrrolidin-2-yl)-3-methoxy-2-methylpropanamido)-3-phenylpropanoic acid, bis trifluoroacetic Acid

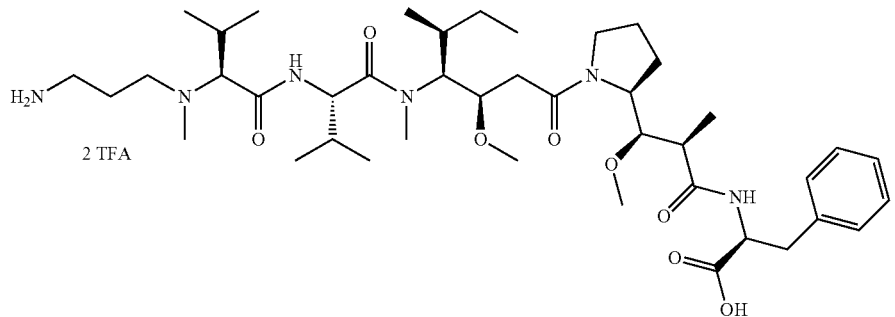 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCCN)C(C)C]

Compound 6 (70 mg, 0.08 mmol, 1.00 equiv) was dissolved in a mixture of water (5 mL), ACN (2.5 mL) and piperidine (5 mL). The reaction mixture was left under agitation overnight at ambient temperature, then concentrated under reduced pressure. The residue was purified by preparative HPLC (Pre-HPLC-001 SHIMADZU, SunFire Prep C18 OBD column, 5 μm, 19×150 mm; Eluting phase: water/ACN buffered with 0.05% TFA; Gradient of 20% to 40% ACN in 10 minutes then 40% to 100% ACN in 2 minutes; UV Waters 2489 UV Detector at 254 nm and 220 nm), to yield 14.6 mg (21%) of compound 7 in the form of a white solid.

LC/MS/UV (Ascentis Express C18, 2.7 μm, 4.6×100 mm; 1.5 mL/min, 40° C., 0 to 80% methanol in water (0.05% TFA) in 8 minutes); ESI ($C_{42}H_{72}N_6O_8$, exact mass 788.54) m/z: 790 (MH$^+$), 5.71 min (96.83%, 210 nm).

$^1$H NMR (300 MHz, CD$_3$OD, ppm): δ (Presence of rotamers) 8.42 (d, 0.3H, NHCO incomplete exchange); 8.15 (d, 0.2H, NHCO incomplete exchange); 7.31-7.21 (m, 5H); 4.9-4.6 (m, 3H); 4.25-4.0 (m, 1H); 4.0-0.86 (m, 59H).

Compound 11

(S)—N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethyl-2-((S)-3-methyl-2-(methyl(4-(methylamino)phenethyl)amino)butanamido)butanamide, trifluoroacetic Acid

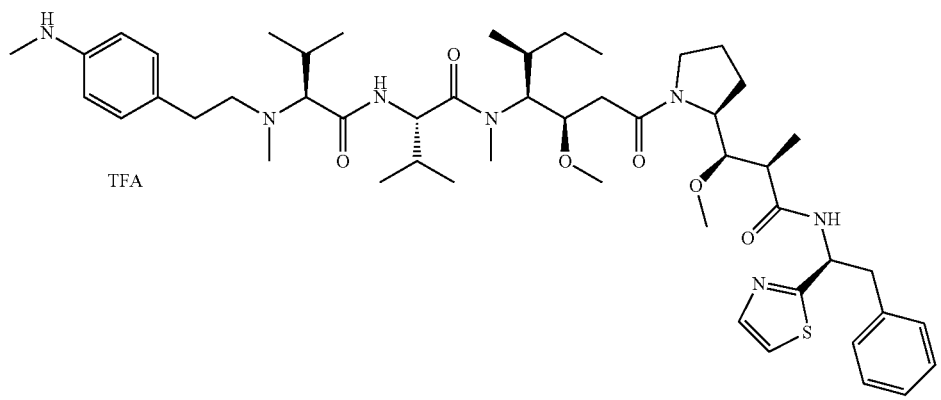 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCc1ccc(NC)cc1)C(C)C]

Compound 11A: tert-butyl N-[4-(2-hydroxyethyl)phenyl]carbamate

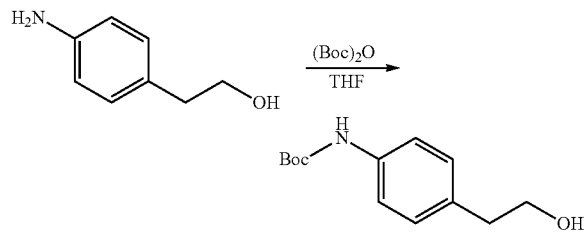

Di-tert-butyl dicarbonate (16.7 g, 77 mmol, 1.05 eq.) was added to a solution of 2-(4-aminophenyl)ethanol (10 g, 72.9 mmol, 1 eq.) in THF (200 mL), and the reaction stirred overnight at ambient temperature. The mixture was diluted with EtOAc (200 mL), washed with water (200 mL), then HCl 1M (100 mL), then saturated aqueous NaHCO$_3$ solution (100 mL) then brine (100 mL). The organic phase was dried over MgSO$_4$ then evaporated to dryness under reduced pressure. The crude product was triturated twice with heptane (150 mL) and dried under vacuum to furnish compound 11A as a white solid (14.7 g, 84%).

Compound 11B: tert-butyl N-[4-(2-oxoethyl)phenyl]carbamate

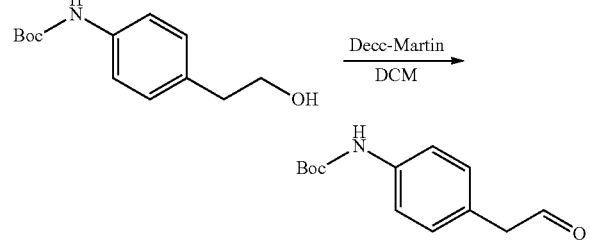

Compound 11A (2.5 g, 10.5 mmol, 1.00 equiv) was dissolved in 25 mL of DCM then cooled to −78° C. A Dess-Martin Periodinane solution (DMP, 6.71 g, 15.8 mmol, 1.5 equiv) in DCM (10 mL) was added drop-wise. The cold bath was removed and agitation continued for 1 hour at ambient temperature. The reaction was neutralised with 60 mL of a 50/50 mixture of sodium bicarbonate-saturated aqueous solution and Na$_2$S$_2$O$_3$-saturated aqueous solution. The resulting solution was extracted 3 times with 30 mL of EtOAc. The organic phases were combined, washed twice with NaCl-saturated aqueous solution, dried over anhydrous sodium sulfate, filtered and concentrated under reduced pressure. The residue was purified on silica gel (EtOAc/PE 1/15) to yield 1.0 g (40%) of compound 11B in the form of a pale yellow solid.

Compound 11C: benzyl (2S)-2-[[2-(4-[[(tert-butoxy)carbonyl]amino]phenyl) ethyl](methyl)amino]-3-methylbutanoate

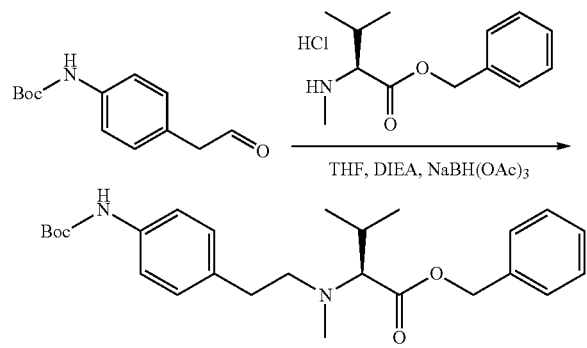

Compound 1ZC (3.5 g, 13.6 mmol, 1.1 equiv) was dissolved in THF (30 mL) in the presence of DIEA (6.4 g, 49.7 mmol, 4.0 equiv), aldehyde 11B (2.9 g, 12.3 mmol, 1.0 equiv) and sodium triacetoxyborohydride (5.23 g, 49.7 mmol, 2.0 equiv). The reaction mixture was left under agitation overnight at ambient temperature, then neutralised with 60 mL of sodium bicarbonate-saturated solution. The resulting solution was extracted 3 times with 30 mL EtOAc. The organic phases were combined, washed twice with NaCl-saturated aqueous solution, dried over anhydrous sodium sulfate, filtered and concentrated under reduced pressure. The residue was purified on silica gel (EtOAc/PE 1:20) to yield 3.7 g (68%) of compound 11C in the form of a yellow oil.

Compound 11D: (2S)-2-[[2-(4-[[(tert-butoxy)carbonyl]amino]phenyl)ethyl](methyl)amino]-3-methylbutanoic Acid

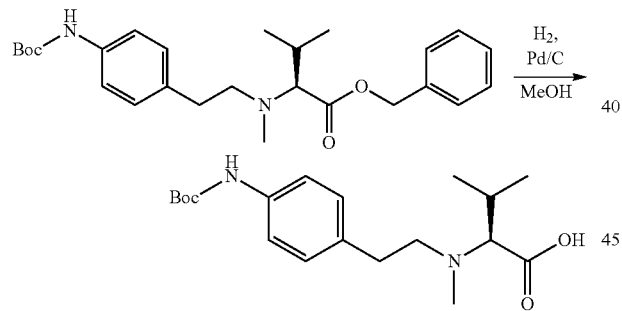

Compound 11C (2 g, 4.5 mmol, 1 equiv) was dissolved in 10 mL of methanol in the presence of Pd/C (2 g) and hydrogenated for 2 hours at normal temperature and pressure. The reaction medium was filtered and concentrated under reduced pressure to yield 1.2 g (75%) of compound 11D in the form of a yellow oil.

Compound 11E: (2S)-2-[[2-(4-[[(tert-butoxy)carbonyl](methyl)amino]phenyl) ethyl](methyl) amino]-3-methylbutanoic Acid

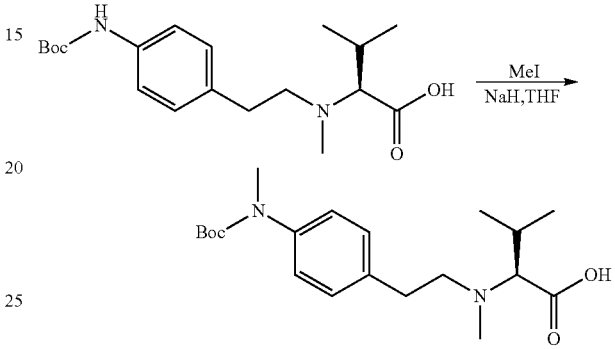

Compound 11D (1.2 g, 3.4 mmol, 1.00 equiv) was dissolved in an inert atmosphere in THF (20 mL). The reaction medium was cooled with an ice bath after which NaH (60% in oil, 549 mg, 13.7 mmol, 4.0 equiv) was added in portions, followed by iodomethane (4.9 g, 34 mmol, 10 equiv). The reaction was left under agitation overnight at ambient temperature, then neutralised with water and washed with 100 mL of EtOAc. The pH of the aqueous solution was adjusted to 6-7 with 1N HCl. This aqueous solution was extracted 3 times with 100 mL of EtOAc. The organic phases were combined, dried over sodium sulfate, filtered and concentrated to yield 800 mg (64%) of compound 11E in the form of a yellow solid.

Compound 11F: tert-butyl N-[4-(2-[[(1S)-1-[[(1S)-1-[[(3R,4S,5S)-3-methoxy-1-[(2S)-2-[(1R,2R)-1-methoxy-2-methyl-2-[[(1 S)-2-phenyl-1-(1,3-thiazol-2-yl)ethyl]carbamoyl]ethyl]pyrrolidin-1-yl]-5-methyl-1-oxoheptan-4yl](methyl)carbamoyl]-2-methylpropyl]carbamoyl]-2-methylpropyl](methyl) amino]ethyl)phenyl]-N-methylcarbamate

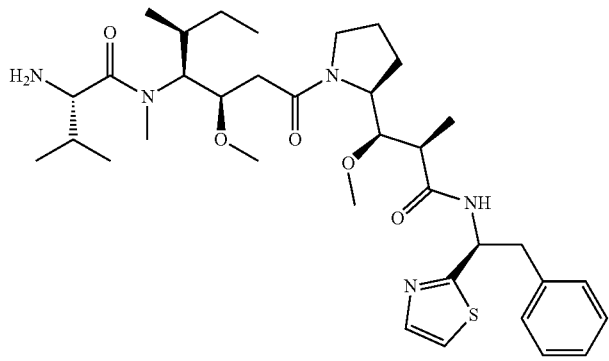

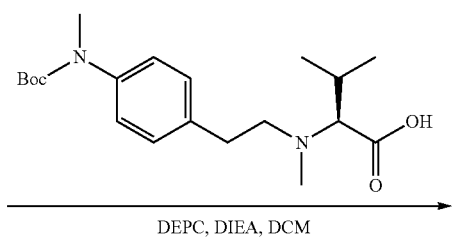

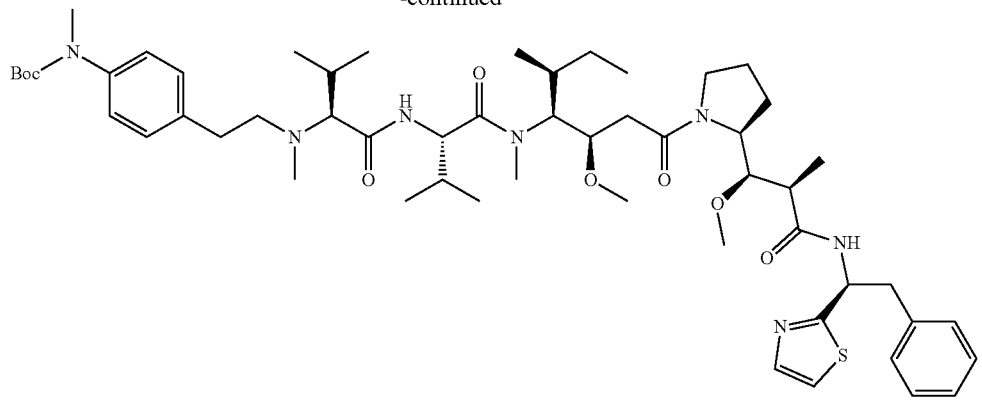

Compound 11F was prepared in similar manner to compound 6A from the amine 1Y (150 mg, 0.22 mmol, 1.2 equiv) and the acid 11E (70 mg, 0.19 mmol, 1.0 equiv). After purification on silica gel (EtOAc/PE 1:1) 100 mg (52%) of desired product were obtained in the form of a pale yellow solid.

Compound 11 was prepared in the same manner as for compound 1 from the intermediate 11F (100 mg, 0.1 mmol). The residue was purified by preparative HPLC (Pre-HPLC-001 SHIMADZU, SunFire Prep C18 OBD column, 5 μm, 19×150 mm; Eluting phase: water/ACN buffered with 0.05% TFA; Gradient of 20% to 40% ACN in 10 minutes then 40% to 100% ACN in 2 minutes; Waters 2489 UV Detector at 254 nm and 220 nm). Compound 11 was obtained with a yield of 39% (39.7 mg) in the form of a white solid.

LC/MS/UV (Eclipse Plus C8, 3.5 μm, 4.6×150 mm; 1 mL/min, 40° C., 50 to 95% methanol in water (0.05% TFA) in 18 minutes); ESI ($C_{50}H_{77}N_7O_6S$, exact mass 903.57) m/z: 904.5 (MH+), 7.53 min (93.68%, 254 nm).

$^1$H NMR (300 MHz, $CD_3OD$, ppm): δ (Presence of rotamers) 8.84 (d, 0.5H, NHCO incomplete exchange); 8.7-8.5 (m, 0.9H, NHCO incomplete exchange); 7.76-7.73 (m, 1H); 7.55-7.4 (m, 1H); 7.28-7.22 (m, 7H); 7.08-7.05 (m, 2H); 5.51-5.72 (m, 1H); 4.9-4.80 (m, 2H); 4.3-0.7 (m, 60H).

Compound 12 methyl (S)-2-((2R,3R)-3-((S)-1-((3R,4S,5S)-4-((S)—N,3-dimethyl-2-((S)-3-methyl-2-(methyl(4-(methylamino)phenethyl)amino)butanamido)butanamido)-3-methoxy-5-methylheptanoyl)pyrrolidin-2-yl)-3-methoxy-2-methylpropanamido)-3-phenylpropanoate, trifluoroacetic Acid

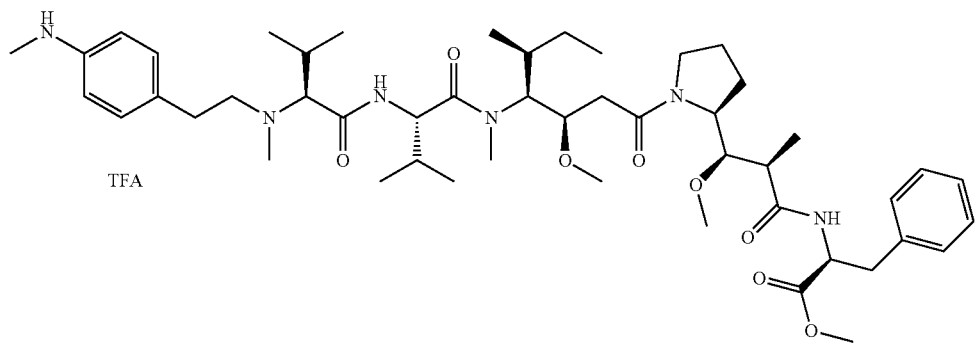 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCc1ccc(NC)cc1)C(C)C]

In the same manner as for the final phases in the synthesis of compound 1, compound 12 was prepared in two steps from the amine 3D (118 mg, 0.19 mmol) and the acid 11E (82 mg, 0.22 mmol). The final residue was purified by preparative HPLC (Pre-HPLC-001 SHIMADZU, SunFire Prep C18 OBD column, 5 μm, 19×150 mm; Eluting phase: water/ACN buffered with 0.05% TFA; Gradient of 20% to 40% ACN in 10 minutes then 40% to 100% ACN in 2 minutes; Waters 2489 UV Detector at 254 nm and 220 nm). Compound 12 was obtained with a yield of 7% (13.7 mg) in the form of a white solid.

LC/MS/UV (Eclipse Plus C8, 3.5 μm, 4.6×150 mm; 1 mL/min, 40° C., 40 to 95% methanol in water (0.05% TFA) in 18 minutes); ESI ($C_{49}H_{78}N_6O_8$, exact mass 878.59) m/z: 879.7 (MH$^+$), 10.07 min (90.6%, 254 nm).

$^1$H:NMR (300 MHz, CD$_3$OD, ppm): δ (Presence of rotamers) 7.40 (se, 2H); 7.38-7.22 (m, 7H); 4.95-4.7 (m, 3H); 4.2-4.0 (m, 1H); 3.9-0.86 (m, 62H).

Compound 13

(S)-2-((2R,3R)-3-((S)-1-((3R,4S,5S)-4-((S)—N,3-dimethyl-2-((S)-3-methyl-2-(methyl(4-(methylamino)phenethyl)amino)butanamido)butanamido)-3-methoxy-5-methyl heptanoyl)pyrrolidin-2-yl)-3-methoxy-2-methylpropanamido)-3-phenylpropanoic acid, trifluoroacetic Acid

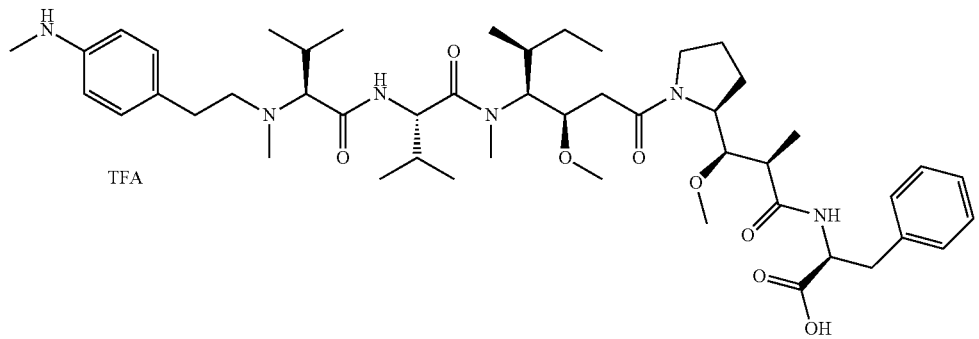 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCc1ccc(NC)cc1)C(C)C]

Compound 13 was prepared in the same manner as for compound 7 from compound 12 (100 mg, 0.10 mmol). The residue was purified by preparative HPLC (Pre-HPLC-001 SHIMADZU, SunFire Prep C18 OBD column, 5 μm, 19×150 mm; Eluting phase: water/ACN buffered with 0.05% TFA; Gradient of 20% to 40% ACN in 10 minutes then 40% to 100% ACN in 2 minutes; Waters 2489 UV Detector at 254 nm and 220 nm). Compound 13 was obtained with a yield of 20% (20 mg) in the form of a white solid.

LC/MS/UV (Ascentis Express C18, 2.7 μm, 4.6×100 mm; 1.5 mL/min, 40° C., 10 to 95% methanol in water (0.05% TFA) in 8 minutes); ESI ($C_{48}H_{76}N_6O_8$, exact mass 864.57) m/z: 865.6 (MH$^+$), 6.05 min (90.9%, 210 nm).

$^1$H NMR: (300 MHz, CD$_3$OD, ppm): δ (Presence of rotamers) 7.32-7.19 (m, 9H); 4.9-4.65 (m, 3H); 4.2-4.0 (m, 1H); 3.9-0.86 (m, 59H).

Compound 14

(S)-2-((S)-2-((3-aminobenzyl)(methyl)amino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethylbutanamide, trifluoroacetic Acid

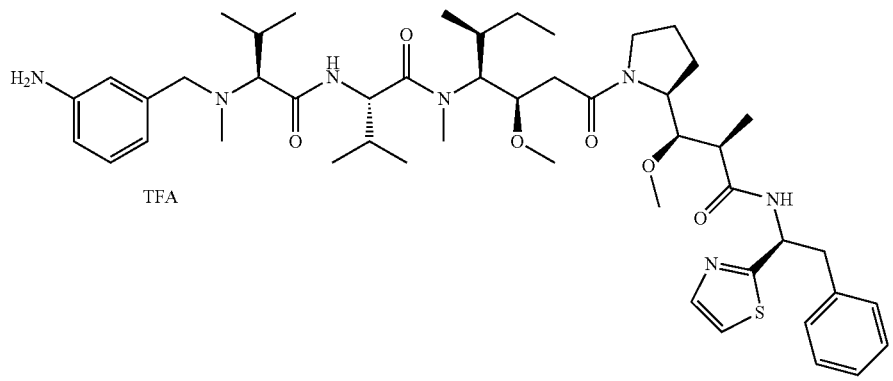 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)Cc1cccc(N)c1)C(C)C]

TFA

Compound 14A: tert-butyl (3-(hydroxymethyl)phenyl) carbamate

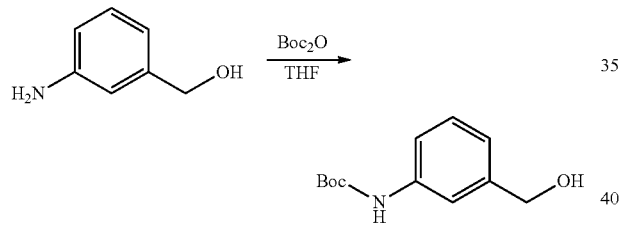

(3-aminophenyl)methanol (3 g, 24.36 mmol, 1.00 equiv) was dissolved in THF (60 mL) after which di-tert-butyl dicarbonate (6.38 g, 29.23 mmol, 1.20 equiv) was then added. The reaction mixture was left under agitation overnight at ambient temperature and the reaction was then diluted by adding 200 mL of water. The product was extracted 3 times with 100 mL of AcOEt and the organic phases were then recombined, dried over sodium sulfate, filtered and concentrated under reduced pressure to yield the crude product (13.85 g of compound 14A) in the form of a yellow oil.

Compound 14B: tert-butyl (3-formylphenyl)carbamate

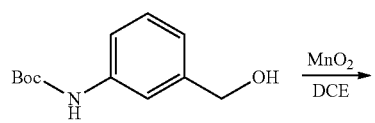

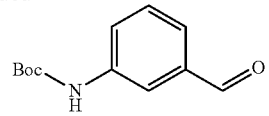

Compound 14A (13.8 g, 61.81 mmol, 1.00 equiv) was dissolved in DCE (400 mL) and MnO₂ (54 g, 621.14 mmol, 10.05 equiv) was then added. The mixture was left under agitation at ambient temperature for 3 days after which the solids were removed by filtering. The filtrate was evaporated to dryness and the residue was purified on a silica column with a mixture of EtOAc and PE (1:30) to yield 3 g (22%) of compound 14B in the form of a white solid.

Compound 14C: benzyl (S)-2-((3-((tert-butoxycarbonyl)amino)benzyl)(methyl)amino)-3-methylbutanoate

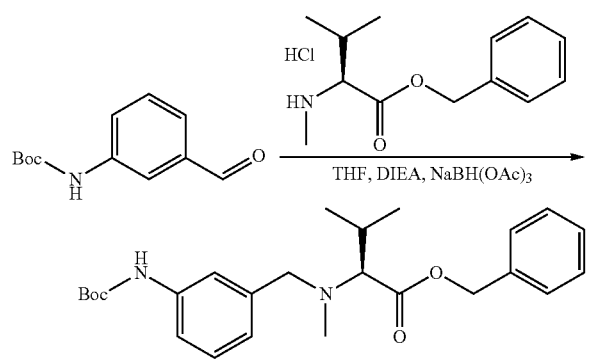

Compound 14B (1 g, 4.52 mmol, 1.00 equiv) was dissolved in 20 mL of THF in the presence of compound 1ZC (1.16 g, 4.50 mmol, 1.00 equiv), DIEA (3 mL) and NaBH(OAc)₃ (1.92 g, 9.06 mmol, 2.01 equiv). The reaction mixture was left under agitation overnight at ambient temperature and then neutralised with 100 mL of water and extracted 3 times with 50 mL of AcOEt. The organic phases were combined, dried over sodium sulfate, filtered and concentrated. The residue was purified on a silica column with a mixture of EtOAc and PE (1:50) to yield 1.9 g (99%) of compound 14C in the form of a white solid.

Compound 14D: (S)-2-((3-((tert-butoxycarbonyl)amino)benzyl)(methyl amino)-3-methylbutanoic Acid

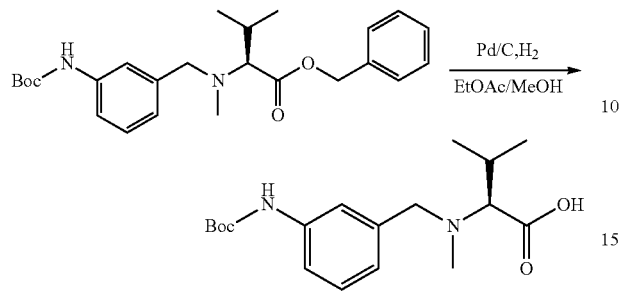

Compound 14C (1 g, 2.34 mmol, 1.00 equiv) was dissolved in 30 mL of AcOEt and 4 mL of methanol in the presence of Pd/C (400 mg) and hydrogenated for 1 hour at ambient temperature and atmospheric pressure. The reaction medium was filtered and concentrated under reduced pressure to yield 680 mg (86%) of compound 14D in the form of a white solid.

Compound 14E: tert-butyl (3-((3 S,6S,9S,10R)-9-((S)-sec-butyl)-3,6-diisopropyl-10-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-2-oxoethyl)-2,8-dimethyl-4,7-dioxo-11-oxa-2,5,8-triazadodecyl)phenyl) carbamate

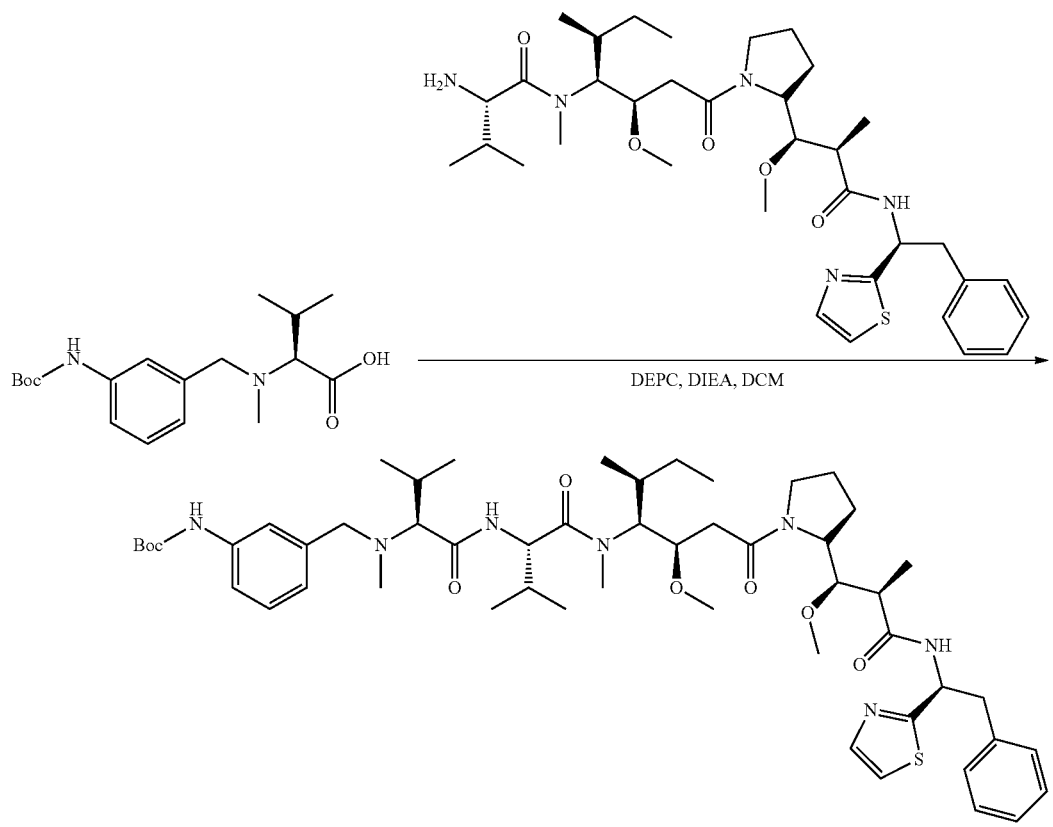

Compound 14E was synthesised in the same manner as for compound 3 from the amine 1Y (100 mg, 0.15 mmol, 1.00 equiv), the acid 14D (102.27 mg, 0.30 mmol, 2.00 equiv), DEPC (0.053 mL) and DIEA (0.046 mL) in DCM (3 mL). The crude product (80 mg) was purified on a silica column with a mixture of EtOAc and PE (1:1) to yield 100 mg (67%) of compound 14E in the form of a pale yellow solid.

Compound 14 was synthesised in the same manner as for compound 2 from the intermediate 14E (100 mg, 0.10 mmol, 1.00 equiv). The crude product (80 mg) was purified by preparative HPLC (Pre-HPLC-001 SHIMADZU, SunFire Prep C18 OBD column, 5 μm, 19×150 mm; Eluting phase: water/ACN buffered with 0.05% TFA; Gradient of 20% to 40% ACN in 10 minutes then 40% to 100% ACN in 2 minutes; Waters 2545 UV Detector at 254 nm and 220 nm). Compound 14 was obtained with a yield of 10% (10 mg) in the form of a white solid.

LC/MS/UV (Eclipse plus C8 column, 3.5 μm, 4.6×150 mm; 40° C.; 1.0 mL/min, 40% to 95% MeOH in water (0.05% TFA) in 18 minutes); ESI ($C_{48}H_{73}N_7O_6S$, exact mass 875.5) m/z: 876.5 ($MH^+$) and 438.9 ($M.2H^+/2$, 100%), 11.35 min (95.6%, 210 nm).

$^1$H NMR (400 MHz, $CD_3OD$, ppm): δ (Presence of rotamers) 8.92-8.86 (m, 0.4H, NH incomplete exchange); 8.70-8.54 (m, 0.6H, NH incomplete exchange); 7.88-7.78 (m, 1H); 7.60-7.50 (m, 1H); 7.45-6.97 (m, 9H); 5.80-5.65 (m, 1H); 4.85-4.70 (m, 1H); 4.40-0.80 (m, 56H).

Compound 15 methyl (S)-2-((2R,3R)-3-((S)-1-((3R,4S,5S)-4-((S)-2-((S)-2-((3-aminobenzyl) (methyl)amino)-3-methylbutanamido)-N,3-dimethylbutanamido)-3-methoxy-5-methylheptanoyl)pyrrolidin-2-yl)-3-methoxy-2-methylpropanamido)-3-phenylpropanoate, trifluoroacetic Acid

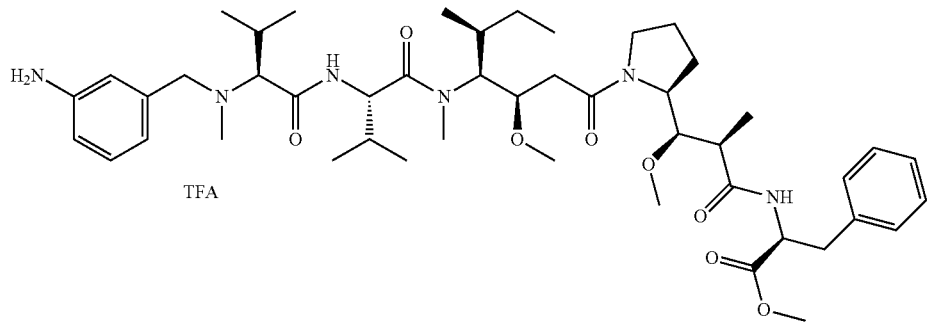 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)Cc1cccc(N)c1)C(C)C]

Compound 15A: methyl (S)-2-((2R,3R)-3-((S)-1-((3R,4S,5S)-4-((S)-2-((S)-2-((3-((tert-butoxycarbonyl)amino)benzyl)(methyl)amino)-3-methylbutanamido)-N,3-dimethylbutanamido)-3-methoxy-5-methylheptanoyl)pyrrolidin-2-yl)-3-methoxy-2-methylpropanamido)-3-phenylpropanoate

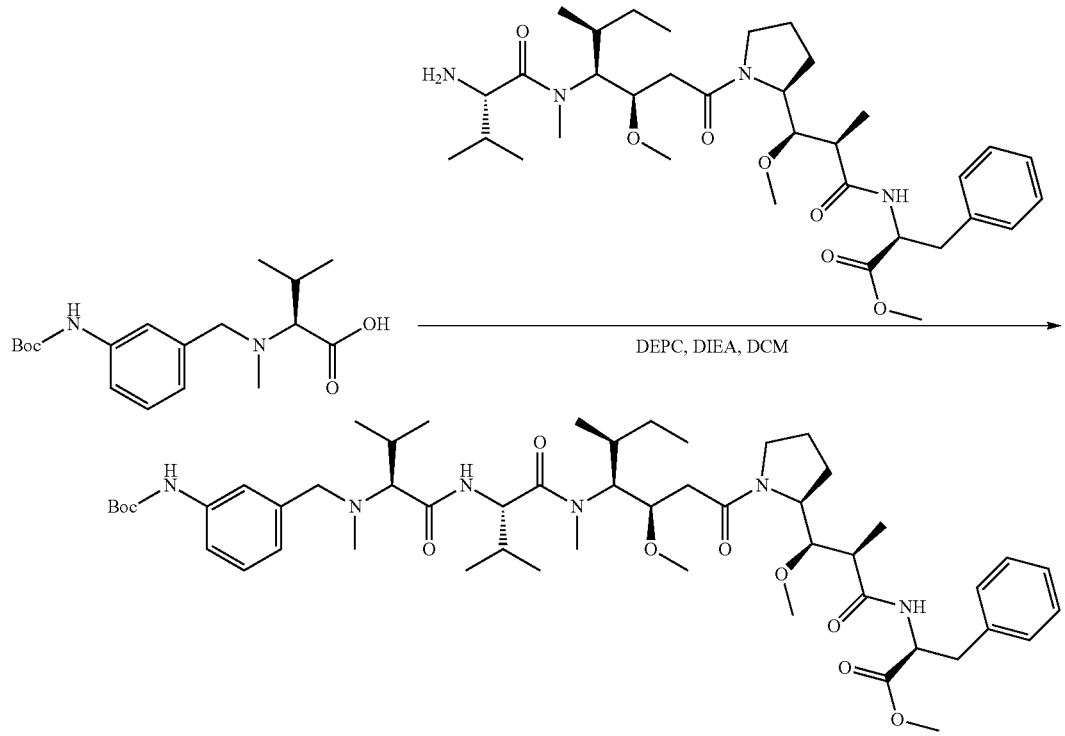

Compound 15A was synthesised in the same manner as for compound 3 from the amine 3D (200 mg, 0.32 mmol, 1.00 equiv), the acid 14D (212.6 mg, 0.63 mmol, 2.00 equiv), DEPC (0.1103 mL) and DIEA (0.157 mL, 3.00 equiv) in DCM (5 mL). The crude product was purified on a silica column with a mixture of EtOAc and PE (1:1) to yield 200 mg (67%) of compound 15A in the form of a yellow solid.

Compound 15: Compound 15 was synthesised in the same manner as for compound 2 from the intermediate 15A (200 mg, 0.21 mmol, 1.00 equiv). The crude product was purified by preparative HPLC (Pre-HPLC-001 SHIMADZU, Sun-Fire Prep C18 OBD column, 5 μm, 19×150 mm; Eluting phase: water/ACN buffered with 0.05% TFA; Gradient of 20% to 40% ACN in 10 minutes then 40% to 100% ACN in 2 minutes; Waters UV Detector 2545 at 254 nm and 220 nm). Compound 15 was obtained with a yield of 19% (38.6 mg) in the form of a white solid.

LC/MS/UV (Ascentis Express C18 column, 2.7 μm, 4.6×100 mm; 40° C.; 1.5 mL/min, 10% to 95% MeOH in water (0.05% TFA) in 8 minutes); ESI ($C_{47}H_{74}N_6O_8$, exact mass 850.5) m/z: 851.5 ($MH^+$) and 426.4 ($M.2H^+/2$, 100%), 6.61 min (91.1%, 210 nm).

$^1H$ NMR (400 MHz, $CD_3OD$, ppm): δ (Presence of rotamers) 7.53-7.42 (m, 1H); 7.35-7.18 (m, 8H); 4.88-4.79 (m, 2H); 4.42-4.00 (m, 3H); 3.93-2.71 (m, 22H); 2.61-0.81 (m, 33H).

Compound 20

(S)-2-((S)-2-((4-aminobenzyl)(methyl)amino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethylbutanamide, trifluoroacetic Acid

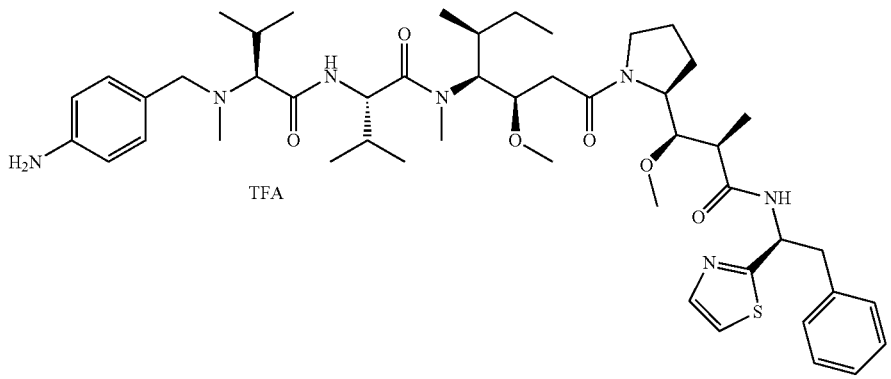 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)Cc1ccc(N)cc1)C(C)C]

Compound 20 was prepared in the same manner as for compound 1, from the amine 1ZC and corresponding aldehyde.

The 4-nitrobenzaldehyde involved in the preparation of compound 20 was commercial.

The synthesis of compound 20 was completed by reducing the nitro group. This was performed as follows: (2S)—N-[(3R,4S,5S)-1-[(2S)-2-[(1R,2R)-2-[[(1S,2R)-1-hydroxy-1-phenylpropan-2-yl]carbamoyl]-1-methoxy-2-methylethyl]pyrrolidin-1-yl]-3-methoxy-5-methyl-1-oxoheptan-4-yl]-N,3-dimethyl-2-[(2S)-3-methyl-2-[methyl[(4-nitrophenyl)methyl]amino]butanamido]butanamide (40 mg, 0.05 mmol, 1.0 equiv) was dissolved in 15 mL of ethanol. Dihydrated tin chloride (II) (317 mg, 1.4 mmol, 30 equiv) was added and the solution left under agitation for 3 days at ambient temperature. The reaction was neutralised with 50 mL of water, then extracted three times with 50 mL of EtOAc. The organic phases were combined, dried over anhydrous sodium sulfate, filtered and concentrated under reduced pressure to yield compound 20 in the crude state (purity: 93.2%; quantity: 21.6 mg).

The compound was purified by preparative HPLC (Pre-HPLC-001 SHIMADZU, SunFire Prep C18 OBD column, 5 µm, 19×150 mm; Eluting phase: water/ACN buffered with 0.05% TFA; Gradient of 20% to 40% ACN in 10 minutes then 40% to 100% ACN in 2 minutes; Waters 2489 UV Detector at 254 nm and 220 nm), to give the corresponding TFA salts in the form of white solids.

$^1$H NMR: (400 MHz, CD$_3$OD, ppm): δ (Presence of rotamers) 7.85-7.80 (m, 1H); 7.6-7.5 (m, 1H); 7.4-7.15 (m, 5H); 7.1-7.05 (m, 2H); 6.73-6.70 (m, 2H); 5.8-5.55 (m, 1H); 5.0-4.7 (m, 2H); 4.25-4.05 (m, 1H); 4.0-0.8 (m, 54H).

LC/MS/UV ESI: (C$_{48}$H$_{73}$N$_7$O$_7$S, exact mass 875.53) m/z 876 (MH$^+$), 439 [75%, (M.2H$^+$)/2]; UV: RT=4.83 min (96.8%, 254 nm). $^1$H NMR (400 MHz, CD$_3$OD, ppm): δ (Presence of rotamers) 7.85-7.80 (m, 1H); 7.6-7.5 (m, 1H); 7.4-7.1 (m, 7H); 6.76-6.72 (m, 2H); 5.8-5.55 (m, 1H); 4.9-4.65 (m, 2H); 4.25-4.05 (m, 1H); 4.0-0.8 (m, 54H).

Compound 29

(S)-2-((2R,3R)-3-((S)-1-((3R,4S,5S)-4-((S)-2-((S)-2-((3-aminobenzyl)(methyl)amino)-3-methylbutanamido)-N,3-dimethylbutanamido)-3-methoxy-5-methylheptanoyl)pyrrolidin-2-yl)-3-methoxy-2-methylpropanamido)-3-phenylpropanoic acid, trifluoroacetic Acid

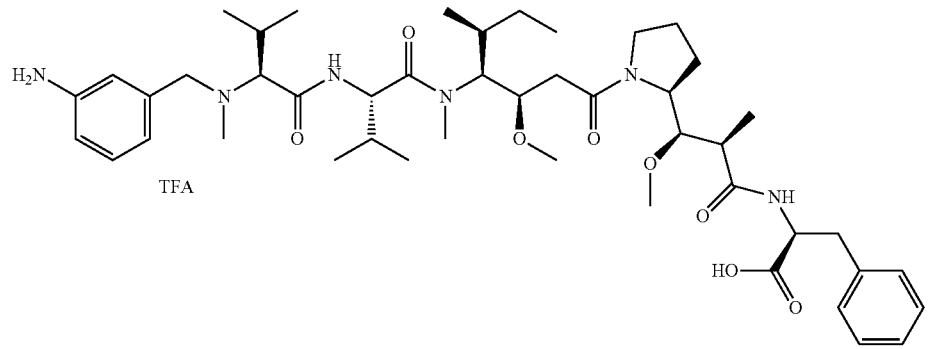 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)Cc1cccc(N)c1)C(C)C]

Compound 15 (100 mg, 0.10 mmol, 1.00 equiv) was dissolved in a mixture of water (5 mL), ACN (5 mL) and piperidine (2.5 mL). The reaction mixture was left under agitation overnight at ambient temperature and then concentrated under reduced pressure. The residue was purified by preparative HPLC (Pre-HPLC-001 SHIMADZU, Sun- Fire Prep C18 OBD column, 5 µm, 19×150 mm; Eluting phase: water/ACN buffered with 0.05% TFA; Gradient of 20% to 40% ACN in 10 minutes then 40% to 100% ACN in 2 minutes; Waters 2545 UV Detector at 254 nm and 220 nm), to yield 20 mg (20%) of compound 29 in the form of a white solid.

LC/MS/UV (Eclipse Plus C8 column, 3.5 µm, 4.6×150 mm; 40° C.; 1.0 mL/min, 40% to 95% MeOH in water (0.05% TFA) in 18 minutes); ESI ($C_{46}H_{72}N_6O_8$, exact mass 836.54) m/z: 837.5 (MH$^+$) and 419.4 (M.2H/2, 100%), 10.61 min (92.5%, 210 nm).

$^1$H NMR: (400 MHz, CD$_3$OD, ppm): δ (Presence of rotamers) 7.38-7.15 (m, 6H); 7.00-6.99 (m, 3H); 4.85-4.68 (m, 2H); 4.37-3.38 (m, 11H); 3.31-2.70 (m, 8H); 2.60-0.82 (m, 35H).

Compound 61

(S)-2-((S)-2-((4-aminophenethyl)(methyl)amino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl) pyrrolidin-1-yl)-5-methyl-1-oxoheptan-4-yl)-N,3-dimethylbutanamide Compound 11D (962 mg, 2.75 mmol) was dissolved in 10 ml of a commercially available solution of HCl in propan-2-ol (5-6 M), and stirred at room temperature for 2 hours. TLC analysis indicated complete consumption of starting material. The solvent was evaporated under reduced pressure, and the resulting yellow solid triturated with Et$_2$O (2×10 ml). The product was dried under vacuum to furnish compound 61A as a yellow solid (322 mg, 47%).

Compound 61

Carboxylic acid 61A (73 mg, 0.23 mmol, 1 eq.) and amine 1Y (150 mg, 0.23 mmol, 1 eq.) were dissolved in dry DMF (2 ml). DIEA (158 µl, 0.90 mmol, 4 eq.) and DECP (also called DEPC) (51 µl, 0.34 mmol, 1.5 eq.) were added and the reaction stirred for 4 hours at room temperature. Analysis by LC-MS showed complete consumption of the starting material. The solvent was evaporated under reduced pressure, and the residue purified by flash chromatography on silica gel (DCM/MeOH) to furnish compound 61 as a light yellow solid (83 mg, 40%).

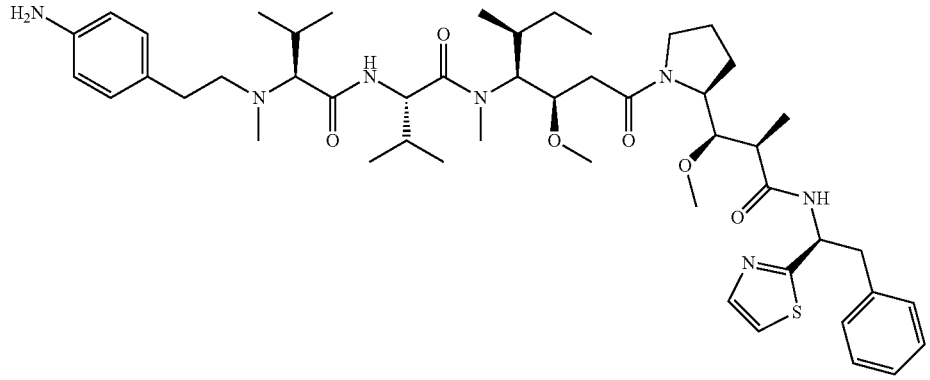 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCc1ccc(N)cc1)C(C)C]

Compound 61A:
N-(4-aminophenethyl)-N-methyl-L-valine dihydrochloride

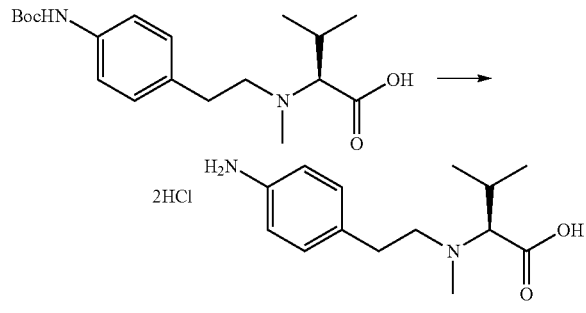

$^1$H NMR: (500 MHz, DMSO-d$_6$, ppm): δ (Presence of rotamers), 8.86 (d, 0.5H, NHCO); 8.65 (d, 0.5H, NHCO), 8.11-8.05 (m, 1H, NHCO), 7.80 (d, 0.5H, thiazole), 7.78 (d, 0.5H, thiazole), 7.65 (d, 0.5H, thiazole), 7.63 (d, 0.5H, thiazole), 7.32-7.12 (m, 5H), 6.83 (d, J=8.3 Hz, 2H), 6.45 (d, J=8.3 Hz, 2H), 5.56-5.49 (m, 0.5H), 5.42-5.35 (m, 0.5H), 4.78 (s, 2H, NH$_2$), 4.74-4.46 (m, 2H), 4.01-0.66 (m, 57H).

HPLC (Xbridge Shield C18, 3.5 µm, 4.6×50 mm; 3.5 ml/min, 40° C., 0 to 95% MeCN in water (0.1% TFA) in 2.25 minutes then 95% MeCN for 0.5 minutes, Tr=1.31 min (96.5%, 220 nm).

m/z (Q-TOF ESI$^+$) 890.5558 (2%, MH$^+$, $C_{49}H_{76}N_7O_6S$ requires 890.5572), 445.7834 (100%, (MH$_2$)$^{2+}$, $C_{49}H_{77}N_7O_6S$ requires 445.7823).

Compound 62

Methyl ((2R,3R)-3-((S)-1-((3R,4S,5S)-4-((S)-2-((S)-2-((4-aminophenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate

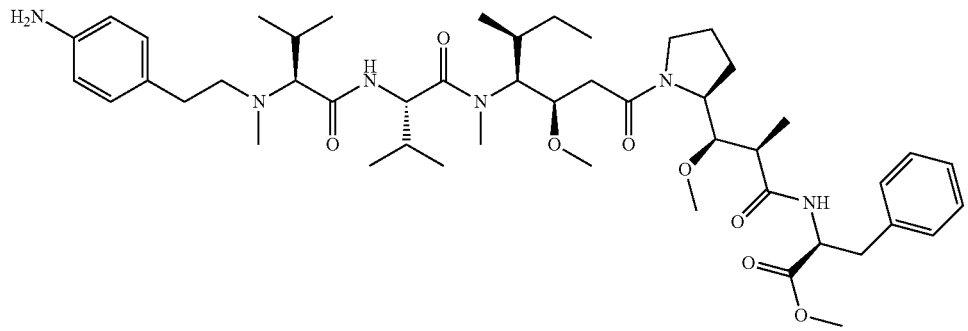 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCc1ccc(N)cc1)C(C)C]

Compound 62 was prepared in the same manner as for compound 61, using carboxylic acid 61A (69 mg, 0.21 mmol, 1 eq.), amine 3D (135 mg, 0.21 mmol, 1 eq.), DIEA (75 µl, 0.43 mmol, 2 eq.) and DECP (49 µl, 0.32 mmol, 1.5 eq.). The crude product was purified by flash chromatography on silica gel (DCM/MeOH) to furnish compound 62 as a yellowish solid (82 mg, 45%).

$^1$H NMR: (500 MHz, DMSO-$d_6$, ppm): δ (Presence of rotamers), 8.50 (d, J=8.3, 0.5H, NHCO); 8.27 (d, J=8.0, 0.5H, NHCO), 8.15-8.04 (m, 1H, NHCO), 7.27-7.13 (m, 5H), 6.86-6.79 (m, 2H), 6.48-6.42 (m, 2H), 4.78 (s, 2H, NH$_2$), 4.74-4.44 (m, 3H), 4.01-3.72 (m, 1.5H), 3.66 (s, 1.5H, CO$_2$Me), 3.63 (s, 1.5H, CO$_2$Me), 3.57-0.65 (m, 55.5H).

HPLC (Xbridge Shield C18, 3.5 µm, 4.6×50 mm; 3.5 ml/min, 40° C., 0 to 95% MeCN in water (0.1% TFA) in 2.25 minutes then 95% MeCN for 0.5 minutes, Tr=1.29 min (95.3%, 220 nm).

m/z (Q-TOF ESI$^+$) 865.5800 (2%, MH$^+$, $C_{48}H_{77}N_6O_8$ requires 865.5797), 433.2937 (100%, (MH$_2$)$^{2+}$, $C_{48}H_{78}N_6O_8$ requires 433.2935).

Compound 63

((2R,3R)-3-((S)-1-((3R,4S,5S)-4-((S)-2-((S)-2-((4-aminophenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine 2,2,2-trifluoroacetate

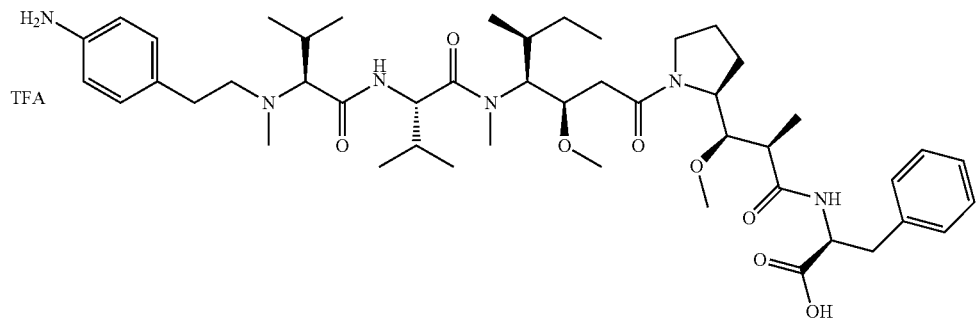 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCc1ccc(N)cc1)C(C)C]

Compound 62 (23 mg, 0.03 mmol) was dissolved in a mixture of water (1 ml) and acetonitrile (1 ml). Piperidine (0.75 ml) was added and the mixture stirred at room temperature for 5 hours. TLC analysis indicated complete consumption of the starting material. The solvent was evaporated under reduced pressure, and the residue purified by preparative HPLC (SunFire Prep column C18 OBD, 5 μm, 19×150 mm; Mobile phase: water/MeCN buffered with 0.1% TFA; Gradient of 20% to 40% MeCN in 10 minutes, then from 40% to 100% MeCN in 2 minutes; Detector UV Waters 2545 at 254 nm et 220 nm). Compound 63 was obtained as a white solid (14 mg, 66%).

$^1$H NMR: (500 MHz, DMSO-$d_6$, ppm): δ (Presence of rotamers), 12.7 (s(br), 1H, $CO_2H$), 9.58 (m(br), 1H); 9.04-8.89 (m, 1H), 8.41 (d, 0.6H, NHCO), 8.15 (d, 0.4H, NHCO), 7.27-7.13 (m, 5H), 7.13-6.99 (m(br), 2H), 6.90-6.64 (s(br), 2H), 4.77-3.40 (m, 10H), 3.34-2.75 (m, 20H), 2.34-1.94 (m, 4H), 1.90-0.7 (m, 25H).

HPLC (Xbridge Shield C18, 3.5 μm, 4.6×50 mm; 3.5 ml/min, 40° C., 0 to 95% MeCN in water (0.1% TFA) in 2.25 minutes then 95% MeCN for 0.5 minutes, Tr=1.24 min (100%, 220 nm).

m/z (Q-TOF ESI$^+$) 851.5641 (6%, MH$^+$, $C_{47}H_{75}N_6O_8$ requires 851.5641), 426.2854 (100%, $(MH_2)^{2+}$, $C_{47}H_{76}N_6O_8$ requires 426.2857).

Example 17: Antiproliferative Activity of the Drugs

Method:
Cell Culture.
A549 (Non Small Cell Lung Cancer—ATCC CCL-185) and MDA-MB-231 (breast adenocarcinoma—ATCC HTB-26) cells were cultured in Minimum Essential Medium Eagle (MEM) with 5% fetal calf serum (FCS) and Dulbecco's modified Eagle Medium (DMEM) with 10% FCS respectively. MCF7 (breast ductal carcinoma—ATCC HTB-22) and SN-12C (kidney carcinoma—ATCC) cells were maintained in RPMI1640 medium (without phenol red for MCF7 cells) containing 10% FCS. All the media were supplemented with fungizone (1.25 μg/mL) and penicillin-streptomycin (100 U/100 μg/mL). Cells were cultured under standard conditions in an incubator at 37° C., 5% $CO_2$ and 95% atmospheric humidity.

Antiproliferative Activity on 4 Tumor Cell Lines.
Selected drugs were investigated for their antiproliferative activity using an ATPlite proliferation assay (Perkin Elmer, Villebon sur Yvette, France) on a comprehensive panel of 4 cell lines. Cells were seeded in 96 well plates ($10^3$ cells/well for A549, $2.10^3$ for MCF7, MDA-MB-231 and SN12C) at day 0 at a concentration to ensure cells remained in logarithmic cell growth phase throughout the 72 h drug treatment period. After a 24 h incubation period, all the cells were treated with serial dilutions of the tested compounds (11 μL of a 10× solution in 1% DMSO—6 wells/condition). To avoid adherence of the compounds onto the tips, tips were changed between two consecutive dilutions. Cells were then placed in 37° C., 5% $CO_2$ incubator. On day 4, cell viability was evaluated by dosing the ATP released by viable cells. The number of viable cells was analyzed in comparison with the number of solvent treated cells. The $EC_{50}$ values were determined with curve fitting analysis (non linear regression model with a sigmoidal dose response, variable hill slope coefficient), performed with the algorithm provided by the GraphPad Software (GraphPad Software Inc., CA, USA).

Results:
Various Drugs:
Various drugs were tested to determine their antiproliferative activity on the MDA-MB-231 cell line following the above-described method. The measured activities gave values of $EC_{50}$<0.1 μM.

The few following examples chosen from among the above exemplified drugs illustrate their fully remarkable antiproliferative properties:
Example 12: $EC_{50}$=5.80×10$^{-10}$ M; Example 13: $EC_{50}$=7.95×10$^{-8}$ M; Example 15: $EC_{50}$=1.70×10$^{-10}$ M; Example 27: $EC_{50}$=1.20×10$^{-10}$ M.

Various Cell Lines:
Compound 15 was tested on different cell lines (A549, MDA-MB-231, MCF-7, SN12C) following the above-described method. The measured activities gave values of $EC_{50}$<0.1 μM on all the tested cell lines.

| $EC_{50}$ (M) | A549 | MDA-MB-231 | MCF-7 | SN12C |
| --- | --- | --- | --- | --- |
| Compound 15 | 1.45 × 10$^{-10}$ | 1.70 × 10$^{-10}$ | 7.15 × 10$^{-10}$ | 2.18 × 10$^{-10}$ |

Comparative Examples

The substitution on the phenyl ring (amino v. carboxyl) was studied in the comparative examples below showing the improved antiproliferative activity of the drugs according to the invention comprising an amino substituent.

| N° | Structure | $EC_{50}$ (M) | |
| --- | --- | --- | --- |
| | | A549 | MDA-MB-231 |
| 12 | [structure] | 1.48 × 10$^{-10}$ | 5.80 × 10$^{-10}$ |

-continued
| N° | Structure | EC$_{50}$ (M) | |
|---|---|---|---|
| | | A549 | MDA-MB-231 |
| 15 | 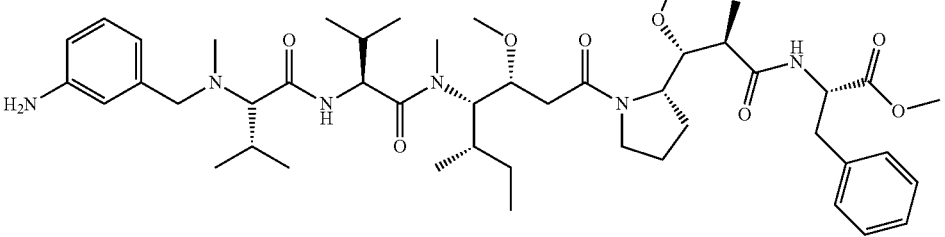 | 1.45 x 10$^{-10}$ | 1.70 x 10$^{-10}$ |
| Comparative example 1 | 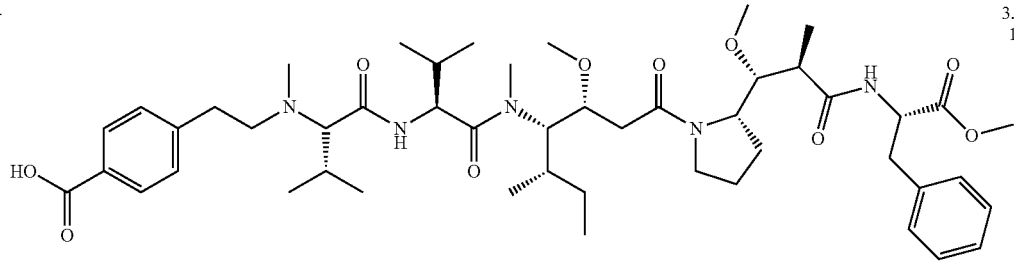 | 3.76 x 10$^{-9}$ | 2.29 x 10$^{-9}$ |
| 13 | 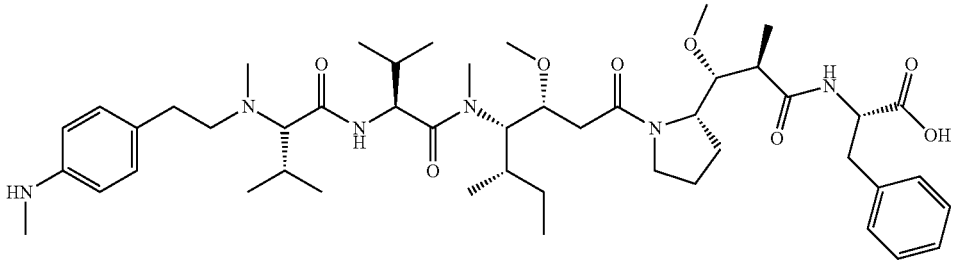 | 2.71 x 10$^{-8}$ | 7.95 x 10$^{-8}$ |
| Comparative example 2 | 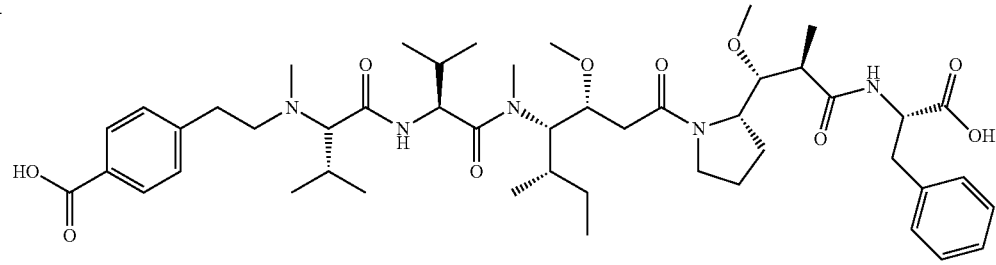 | 4.03 x 10$^{-7}$ | 9.75 x 10$^{-7}$ |

Example 18: Synthesis of the Drug-Linker Moiety

Compound E-11

4-((S)-2-((S)-2-(6-(2,5-dioxo-2,5-dihydro-1H-pyrrol-1-yl)hexanamido)-3-methylbutanamido)-5-ureidopentanamido)benzyl (4-((3R,4S,7S,10S)-4-((S)-sec-butyl)-7,1-diisopropyl-3-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-5,111-dimethyl-6,9-dioxo-2-oxa-5,8,11-triazatridecan-13-yl)phenyl)(methyl)carbamate 2,2,2-trifluoroacetate

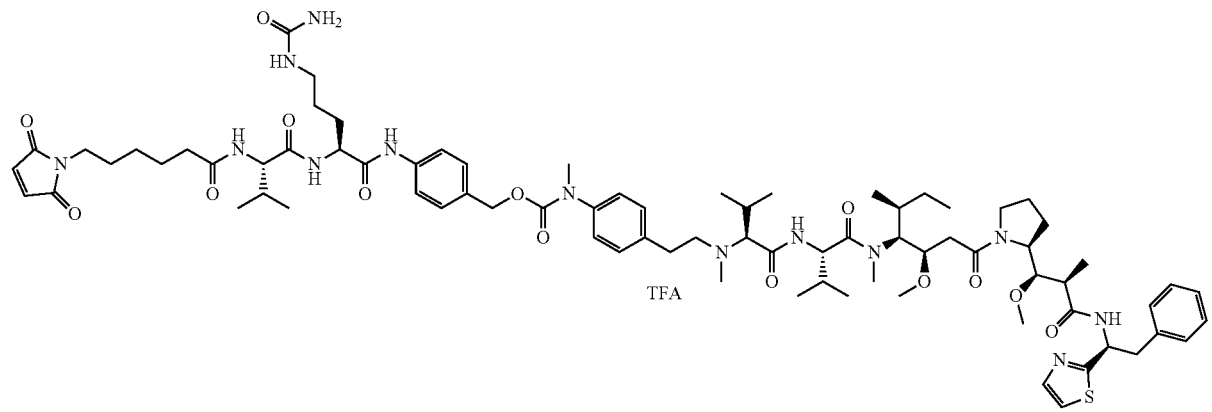 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCc1ccc(N(C)C(=O)OCc2ccc(NC(=O)[C@H](CCCNC(N)=O)NC(=O)[C@@H](NC(=O)CCCCCN3C(=O)C=CC3=O)C(C)C)cc2)cc1)C(C)C]

Compound E-11-1: methyl (S)-2-amino-5-ureidopentanoate hydrochloride

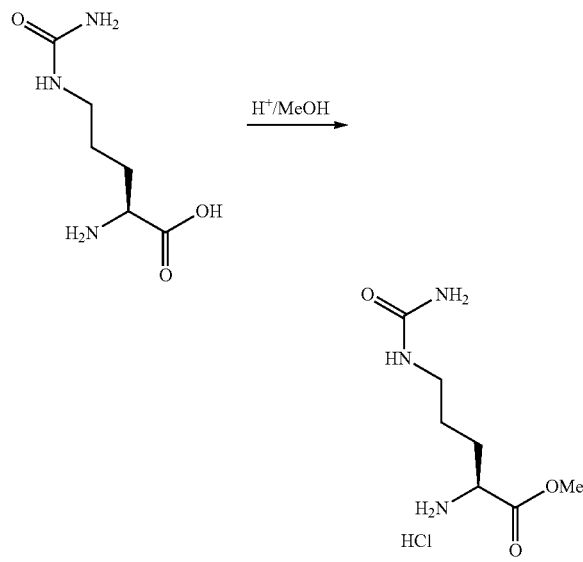

Acetyl chloride (10 mL) was added dropwise to MeOH (120 mL) at 0° C. with stirring. After 20 minutes, L-Citrulline (10 g, 57 mmol, 1.00 eq.) was added and the mixture heated at reflux overnight. The solvent was evaporated under reduced pressure to yield 15 g (116%) of compound E-11-1 as a white solid. The product was used in the next step without further drying.

Compound E-11-2: methyl (S)-2-((S)-2-((tert-butoxycarbonyl)amino)-3-methylbutanamido)-5-ureidopentanoate

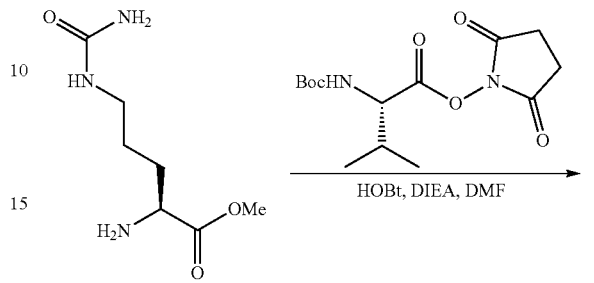

-continued

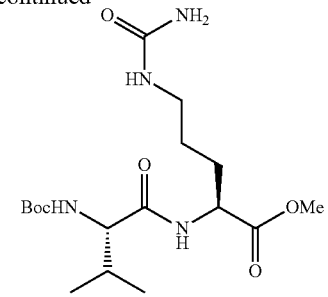

Compound E-11-1 (13 g, 57.6 mmol, 1.1 eq.) was dissolved in DMF (140 mL) at 0° C. under an inert atmosphere. DIEA (30 mL, 173 mmol, 3.0 eq.), hydroxybenzotriazole (HOBt -10.59 g, 69.1 mmol, 1.2 eq.) and Boc-L-valine hydroxysuccinimide ester (Boc-Val-OSu -18.1 g, 57.6 mmol, 1.0 eq.) were added. The reaction mixture was agitated overnight at ambient temperature, then the solvent was evaporated under reduced pressure. The residue was dissolved in water (100 mL) and extracted twice with DCM (150 mL). The organic phases were combined, dried over $Na_2SO_4$ and concentrated under reduced pressure. The residue was purified on silica gel (DCM/MeOH) to yield 18.8 g (84%) of compound E-11-2 as a white solid.

151

Compound E-11-3: (S)-2-((S)-2-((tert-butoxycarbonyl)amino)-3-methyl butanamido)-5-ureidopentanoic Acid

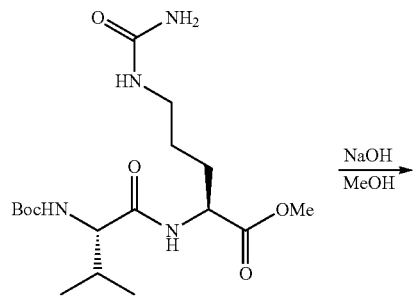

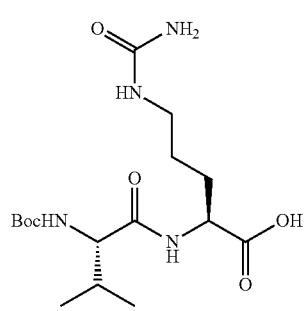

Compound E-11-2 (18.8 g, 48.4 mmol, 1 eq.) was dissolved in MeOH (200 mL) at 0° C. A solution of NaOH 1M (72 mL, 72 mmol, 1.5 eq.) was added and the mixture stirred for 2 hours at room temperature. The MeOH was removed under reduced pressure and the remaining aqueous solution acidified with HCl 1M. The aqueous phase was evaporated to dryness and the residue purified on silica gel (DCM/MeOH) to yield 18 g (99%) of compound E-11-3 as a white solid.

152

Compound E-11-4: tert-butyl ((S)-1-(((S)-1-((4-(hydroxymethyl)phenyl) amino)-1-oxo-5-ureidopentan-2-yl)amino)-3-methyl-1-oxobutan-2-yl)carbamate

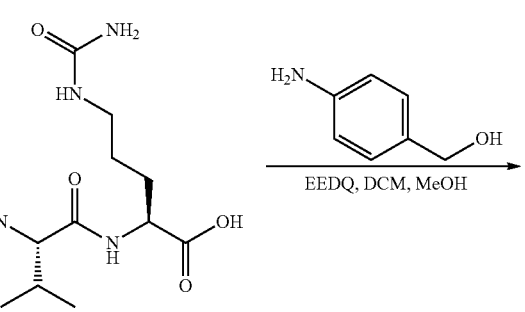

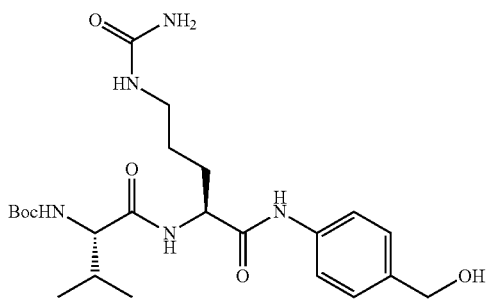

Compound E-11-3 (5 g, 13.4 mmol, 1 eq.) was dissolved in a mixture of dry DCM (65 ml) and dry MeOH (35 ml). (4-aminophenyl)methanol (1.81 g, 14.7 mmol, 1.1 eq.) and N-Ethoxycarbonyl-2-ethoxy-1,2-dihydroquinoline (EEDQ—6.60 g, 26.7 mmol, 2 eq.) were added and the mixture stirred in the dark overnight. The solvents were evaporated under reduced pressure, and the residue purified on silica gel (DCM/MeOH) to yield 5.2 g (73%) of compound E-11-4 as an off-white solid.

Compound E-11-5: tert-butyl ((S)-3-methyl-1-(((S)-1-((4-((((4-nitrophenoxy)carbonyl)oxy)methyl)phenyl)amino)-1-oxo-5-ureidopentan-2-yl) amino)-1-oxobutan-2-yl)carbamate

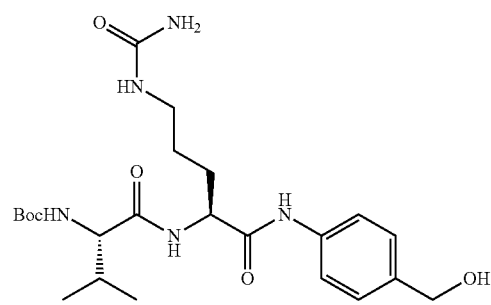

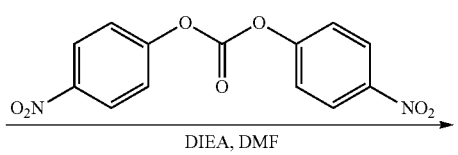

-continued

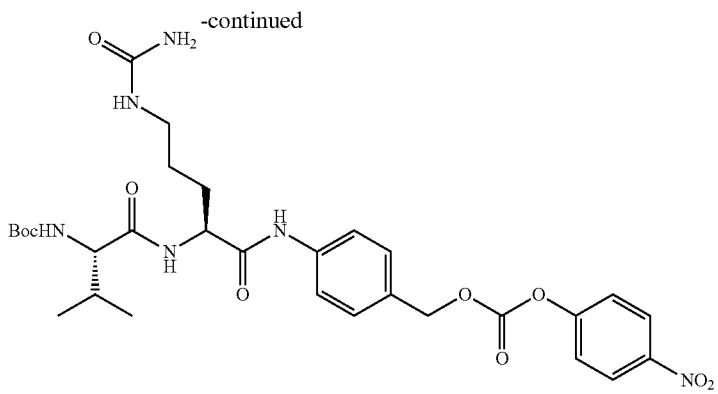

Compound E-11-4 (1.1 g, 2.29 mmol, 1 eq.) was dissolved in dry DMF (5 ml) at ambient temperature under an inert atmosphere. Bis(4-nitrophenyl) carbonate (1.40 g, 4.59 mmol, 2 eq.) was added, followed by DIEA (600 µl, 3.44 mmol, 1.5 eq.), and the resulting yellow solution stirred overnight. The DMF was evaporated under reduced pressure, and the residue purified on silica gel (DCM/MeOH) to yield 1.27 g (84%) of compound E-11-5 as an off-white solid.

Compound E-11-6: 4-((S)-2-((S)-2-((tert-butoxycarbonyl)amino)-3-methylbutanamido)-5-ureidopentanamido)benzyl (4-((3R,4S,7S,10S)-4-((S)-sec-butyl)-7,10-diisopropyl-3-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-5,11-dimethyl-6,9-dioxo-2-oxa-5,8,11-triazatridecan-13-yl)phenyl)(methyl)carbamate 2,2,2-trifluoroacetate

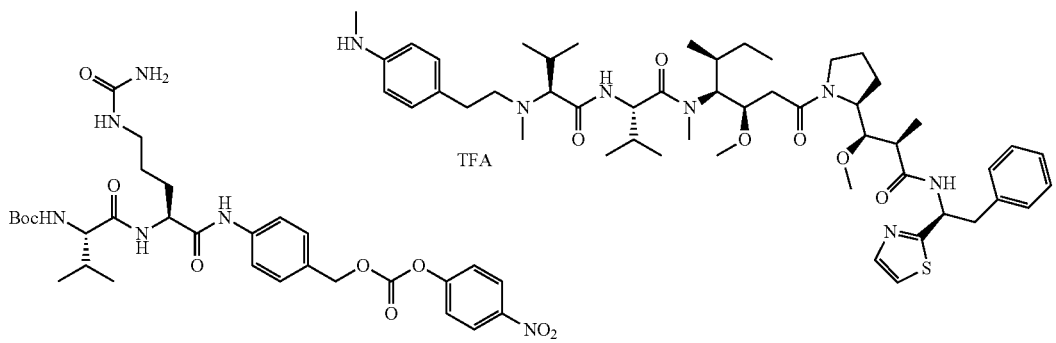

HOBt, DIEA, DMF

-continued

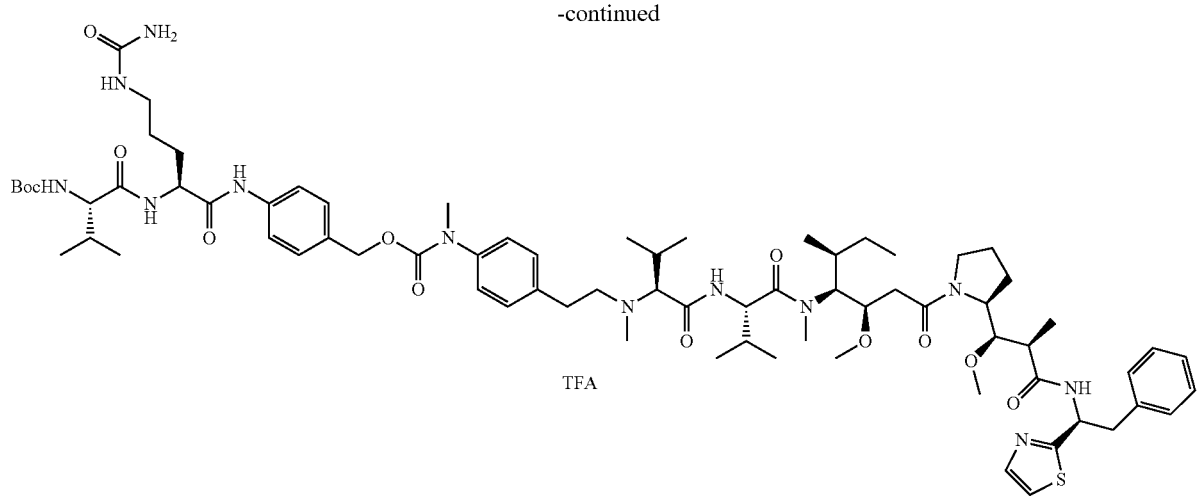

TFA

Carbonate E-11-5 (114 mg, 0.177 mmol, 1.2 eq.) and aniline 11F (150 mg, 0.147 mmol, 1 eq.) were dissolved in dry DMF (4 mL). HOBt (38 mg, 0.295 mmol, 2 eq.) and DIEA (54 μL, 0.295 mmol, 2 eq.) were added and the mixture stirred for the weekend at room temperature. The DMF was evaporated under reduced pressure and the residue purified by flash chromatography on silica, eluting with DCM. The product was repurified by preparative HPLC (Waters 600E, SunFire Prep C18 OBD column, 5 μm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound E-11-6 as a white solid (89 mg, 39%).

Compound E-11

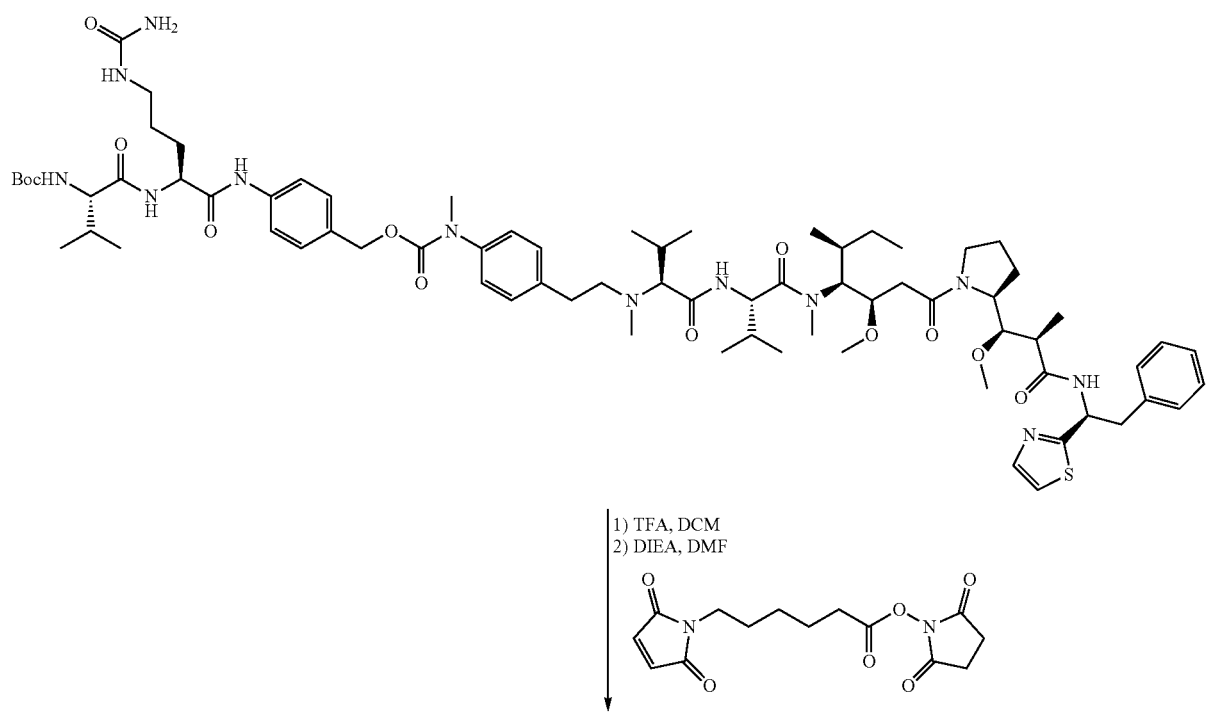

1) TFA, DCM
2) DIEA, DMF

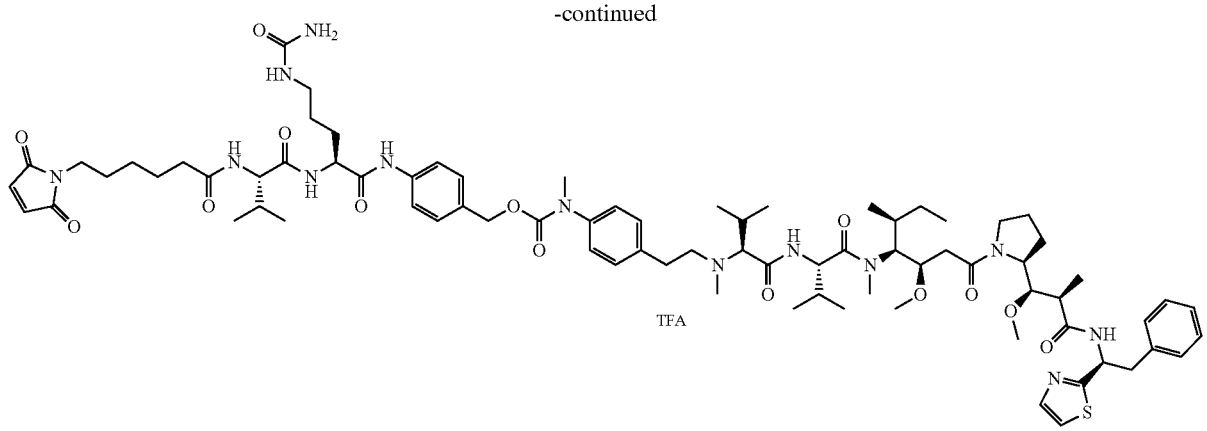

Compound E-11-6 (21 mg, 0.014 mmol, 1.0 eq.) was dissolved in DCM (0.25 mL) and TFA (40 μL) was added. The solution was stirred for 2 hours at room temperature, after which, LC-MS analysis indicated complete consumption of starting material. The mixture was briefly cooled (bath of liquid nitrogen) whilst simultaneously adding DMF (0.5 mL) then DIEA (100 μL) in order to neutralise the TFA. The cooling bath was then removed and 2,5-dioxopyrrolidin-1-yl 6-(2,5-dioxo-2,5-dihydro-1H-pyrrol-1-yl)hexanoate (4 mg, 0.012 mmol, 1 eq.) was added. The mixture was stirred at room temperature for 48 hours and the product purified by preparative HPLC (Waters 600E, SunFire Prep C18 OBD column, 5 μm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound E-11 as a white solid (11 mg, 54%).

m/z (Q-TOF MS ESI+) 1524.8282 (2%, MNa+, $C_{79}H_{115}N_{13}NaO_{14}S$ requires 1524.8299), 751.9283 (100%, $(MH_2)^{2+}$, $C_{79}H_{117}N_{13}O_{14}S$ requires 751.9276).

Compound E-12 methyl ((2R,3R)-3-((S)-1-((3R,4S,5S)-4-((S)-2-((S)-2-((4-((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)(methyl)amino)phenethyl)(methyl) amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate 2,2,2-trifluoroacetate

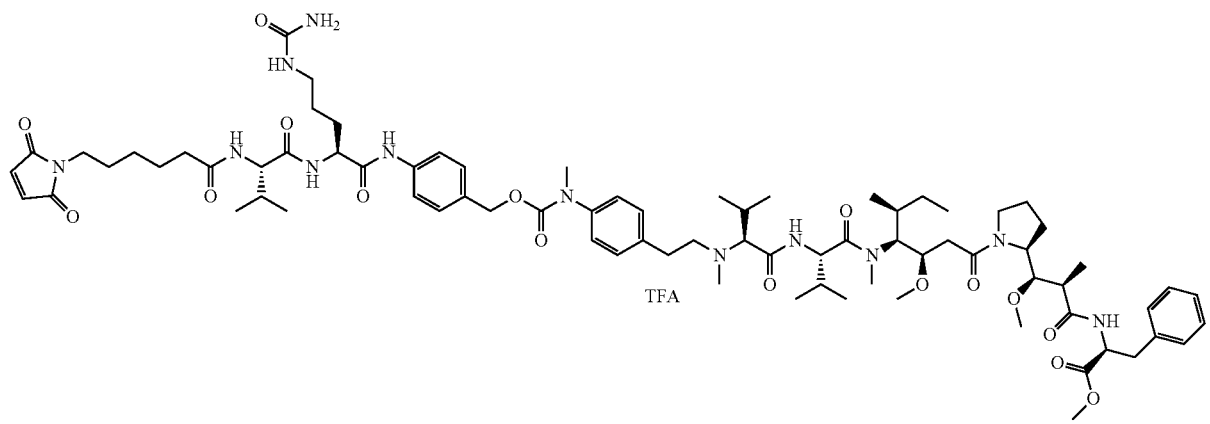 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCc1ccc(N(C)C(=O)OCc2ccc(NC(=O)[C@H](CCCNC(N)=O)NC(=O)[C@@H](NC(=O)CCCCCN3C(=O)C=CC3=O)C(C)C)cc2)cc1)C(C)C]

Compound E-12-1: tert-butyl ((S)-3-methyl-1-oxo-1-(((S)-1-oxo-1-((4-((((perfluorophenoxy)carbonyl)oxy)methyl)phenyl)amino)-5-ureidopentan-2-yl)amino)butan-2-yl)carbamate

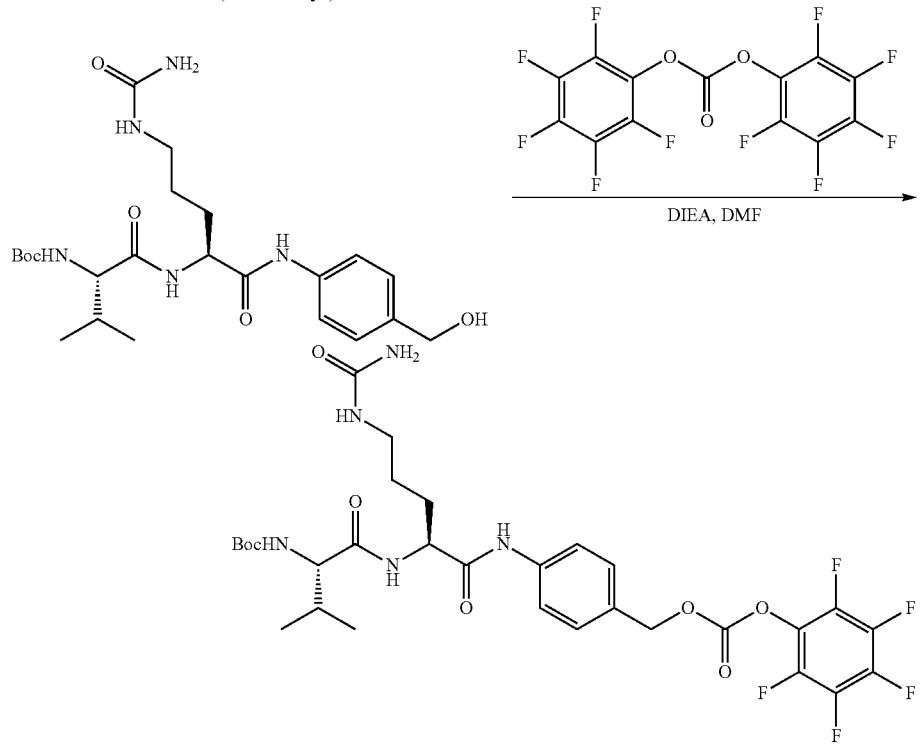

Compound E-11-4 (670 mg, 1.26 mmol, 1 eq.) was dissolved in dry DMF (6 ml) at 0° C. under an inert atmosphere. Bis(perfluorophenyl) carbonate (991 mg, 2.51 mmol, 2 eq.) was added, followed by DIEA (329 µl, 1.89 mmol, 1.5 eq.), and the resulting colourless solution stirred for 30 minutes at room temperature. The DMF was evaporated under reduced pressure, and the residue purified on silica gel (DCM/MeOH) to yield 836 mg (96%) of compound E-12-1 as an off-white solid.

Compound E-12-2: methyl ((2R,3R)-3-((S)-1-((3R,4S,5S)-4-((S)-2-((S)-2-((4-((((4-((S)-2-((S)-2-((tert-butoxycarbonyl)amino)-3-methylbutanamido)-5-ureidopentanamido)benzyl)oxy)carbonyl)(methyl)amino)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate 2,2,2-trifluoroacetate

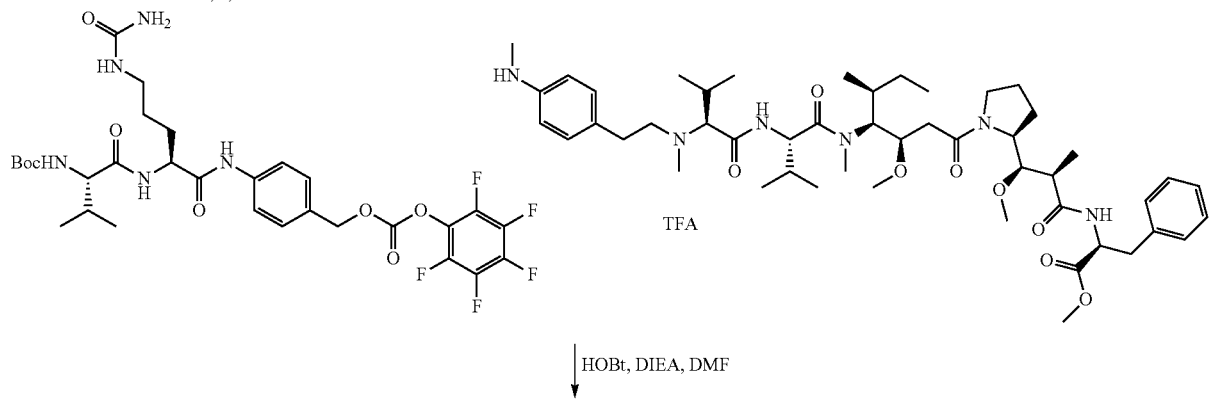

HOBt, DIEA, DMF

-continued

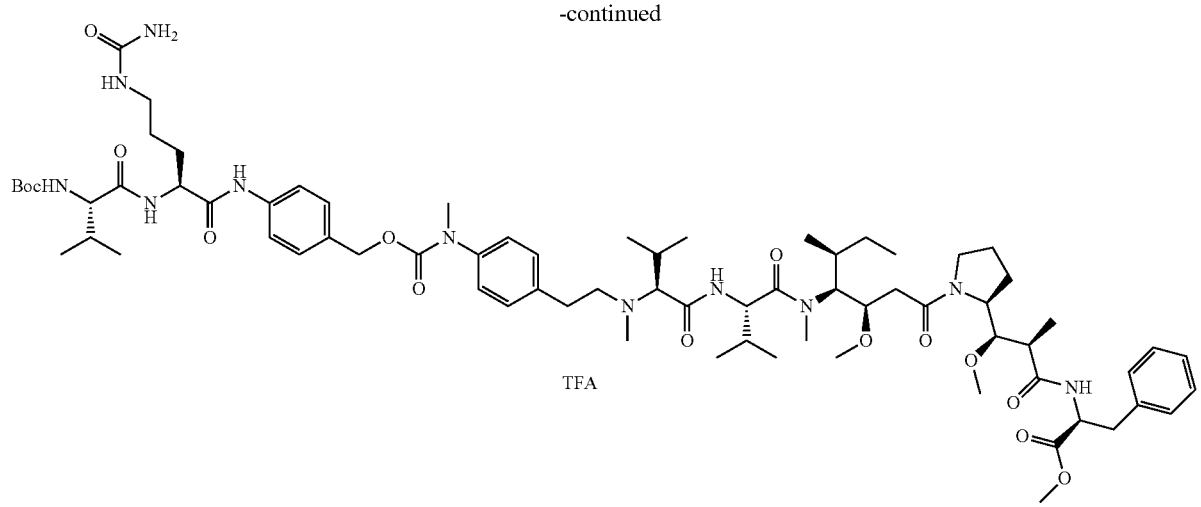

Aniline 12 (165 mg, 0.189 mmol, 1.0 eq.) was dissolved in DMF (5 mL) at 0° C. under an inert atmosphere. Carbonate E-12-1 (194 mg, 0.282 mmol, 1.5 eq.), HOBt (51 mg, 0.375 mmol, 2 eq.) and DIEA (66 HL, 0.375 mmol, 2 eq.) were added and the mixture stirred at room temperature for 8 hours. The solvent was evaporated under reduced pressure and the residue purified by preparative HPLC (Waters 600E, SunFire Prep C18 OBD column, 5 μm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound E12-7 as a white solid (247 mg, 77%).

Compound E-12-3: methyl ((2R,3R)-3-((S)-0.282 mmol-((3R,4S,5S)-4-((S)-2-((S)-2-((4-((((4-((S)-2-((S)-2-amino-3-methylbutanamido)-5-ureidopentanamido)benzyl)oxy) carbonyl)(methyl) amino) phenethyl)(methyl) amino)-3-methylbutanamido)-N, 3-dimethylbutanamido)-3-methoxy-5-methylheptanoyl)pyrrolidin-2-yl)-3-methoxy-2-methylpropanoyl)-L-phenylalaninate bis(2,2,2-trifluoroacetate)

-continued
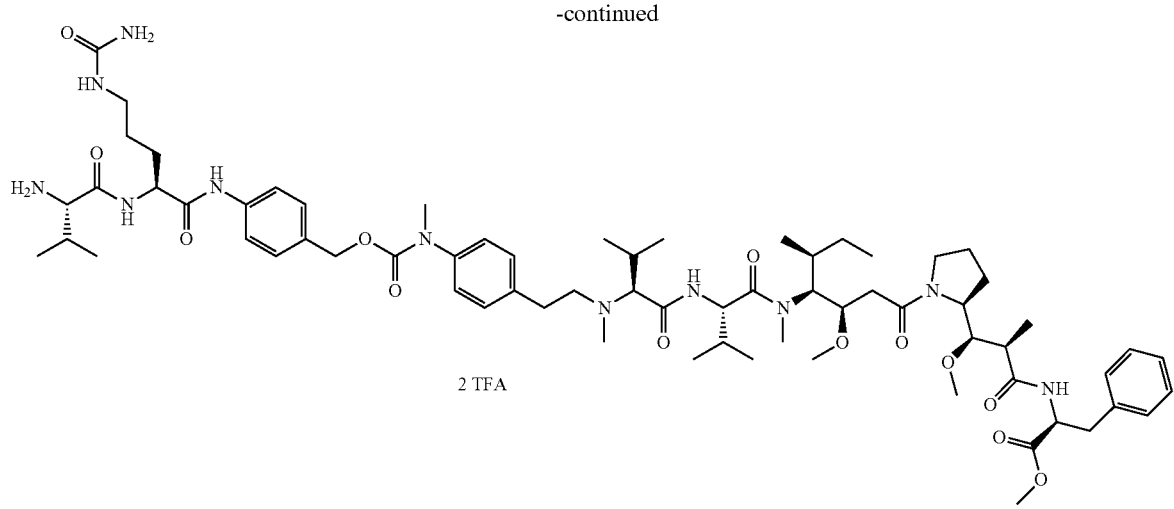
2 TFA
Compound E-12-2 (5.6 mg, 4.04 μmol, 1.0 eq.) was dissolved TFA (100 μL). After 5 minutes, 2 ml of water was added and the mixture lyophilised overnight to yield compound E-12-3 as an off-white solid (5.6 mg, 98%).
Compound E-12
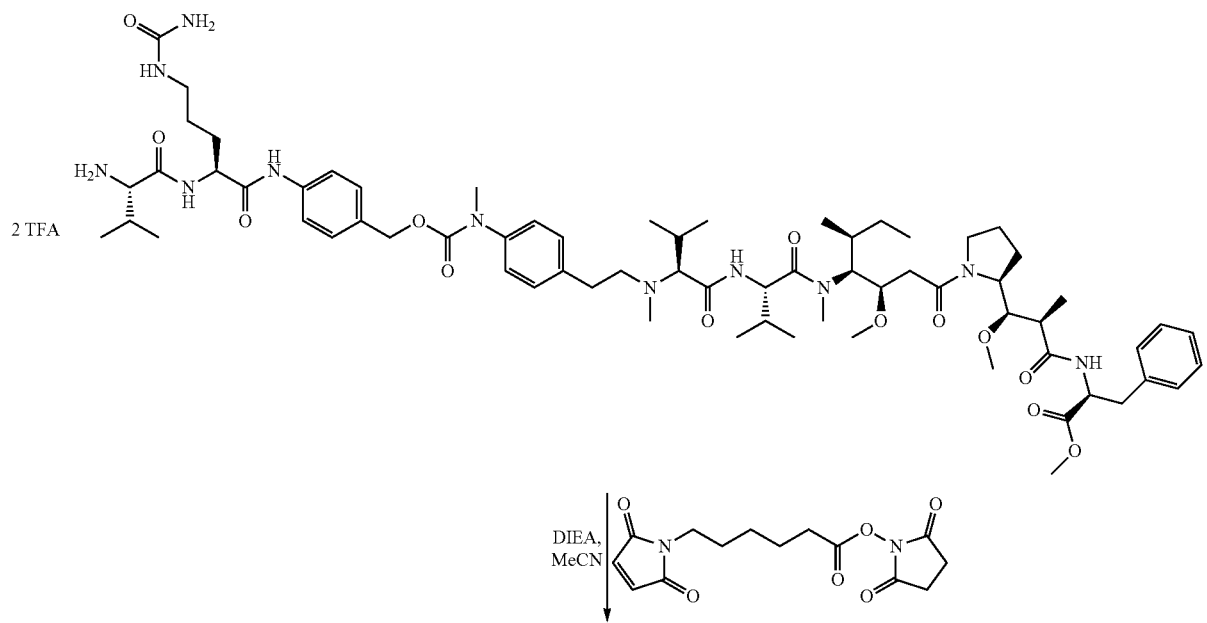
2 TFA
DIEA, MeCN -continued

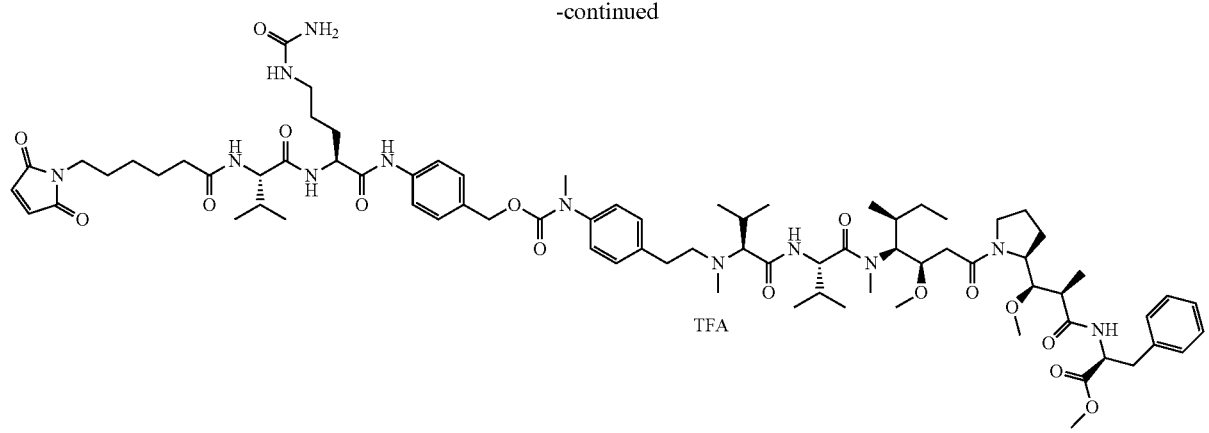

Compound E-12-3 (5.6 mg, 4 μmol, 1.0 eq.) was dissolved in acetonitrile (0.5 mL), and DIEA (5 μL, 7 eq.) was added, followed by 2,5-dioxopyrrolidin-1-yl 6-(2,5-dioxo-2,5-dihydro-1H-pyrrol-1-yl)hexanoate (2.5 mg, 8 μmol, 2 eq.). The mixture was stirred for 6 hours at room temperature. After controlling the reaction by LC-MS, 200 μL of water was added, and the resulting solution purified by preparative HPLC (Waters 600E, SunFire Prep C18 OBD column, 5 μm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound E-12 as a white solid (4.6 mg, 70%).

m/z (Q-TOF MS ESI+) 739.4389 (100%, $(MH_2)^2$, $C_{78}H_{118}N_{12}O_{16}$ requires 739.4389).

Compound E-13

((2R,3R)-3-((S)-1-((3R,4S,5S)-4-((S)-2-((S)-2-((4-(((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)(methyl)amino)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine 2,2,2-trifluoroacetate

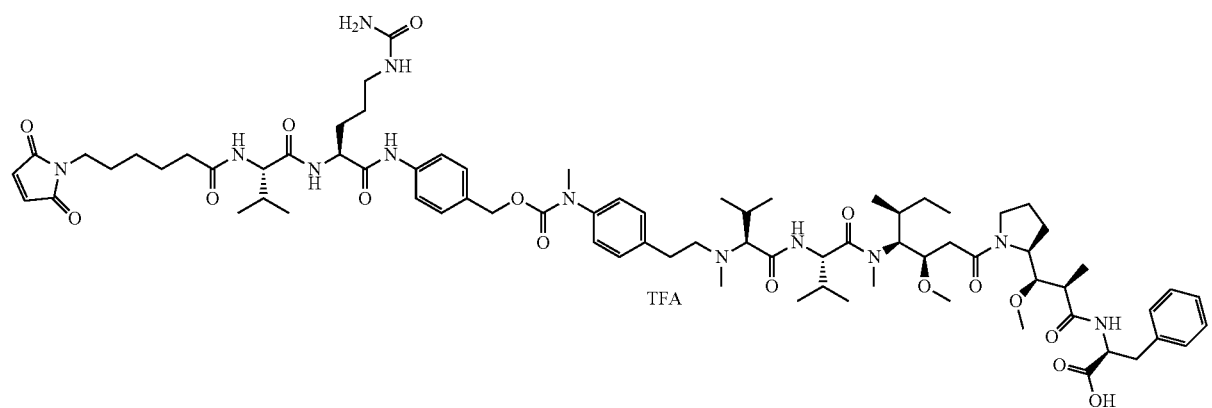 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCc1ccc(N(C)C(=O)OCc2ccc(NC(=O)[C@H](CCCNC(N)=O)NC(=O)[C@@H](NC(=O)CCCCCN3C(=O)C=CC3=O)C(C)C)cc2)cc1)C(C)C]

Compound E-13-1: ((2R,3R)-3-((S)-1-((3R,4S,5S)-4-((S)-2-((S)-2-((4-(((((4-((S)-2-((S)-2-((tert-butoxycarbonyl)amino)-3-methylbutanamido)-5-ureidopentanamido)benzyl)oxy)carbonyl)(methyl)amino)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine

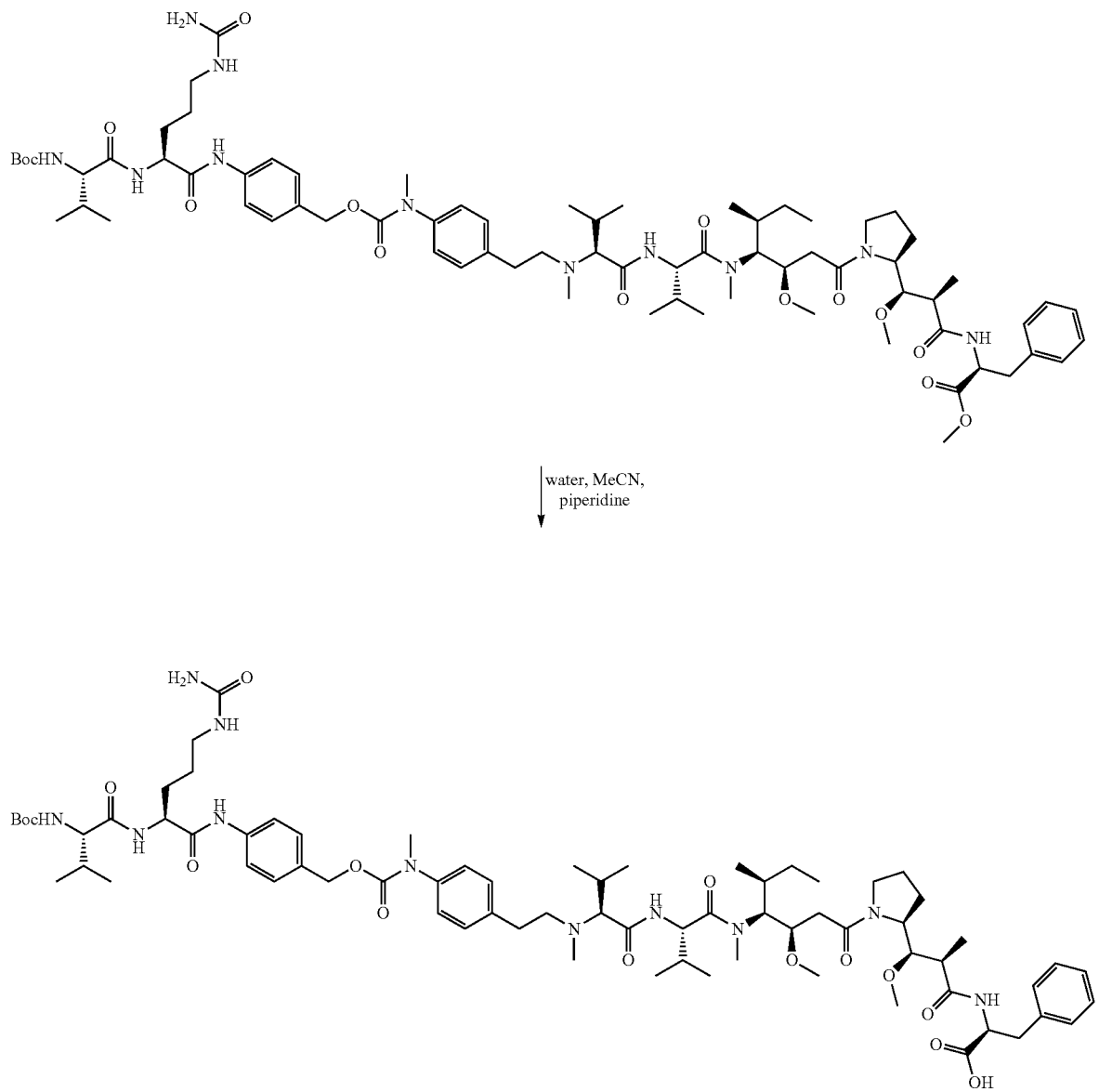

Compound E-12-2 (185 mg, 0.123 mmol, 1.0 eq.) was dissolved in a mixture of water (5 mL) and acetonitrile (5 mL) at room temperature. Piperidine (3.67 mL, 300 eq.) was added and the mixture stirred for 6 hours at room temperature. The solvents were evaporated to dryness under reduced pressure, and the residue triturated with $Et_2O$ (60 mL). The solid was rinsed with twice $Et_2O$ (20 ml) and dried under vacuum to yield compound E-13-1 as an off-white solid (175 mg, 95%).

Compound E-13-2: ((2R,3R)-3-((S)-1-((3R,4S,5S)-4-((S)-2-((S)-2-((4-(((((4-((S)-2-((S)-2-amino-3-methylbutanamido)-5-ureidopentanamido)benzyl)oxy)carbonyl)(methyl)amino)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine bis (2,2,2-trifluoroacetate)

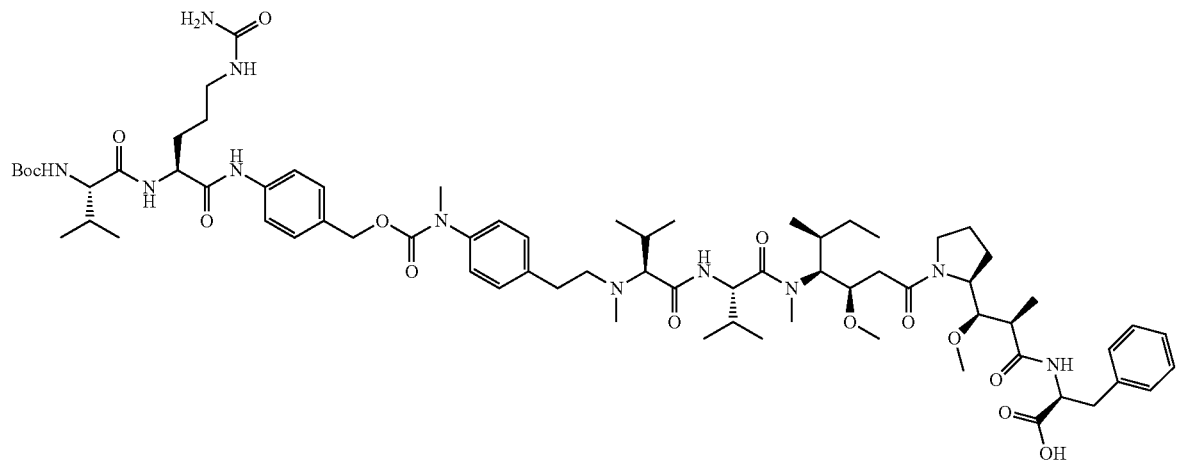

↓ TFA

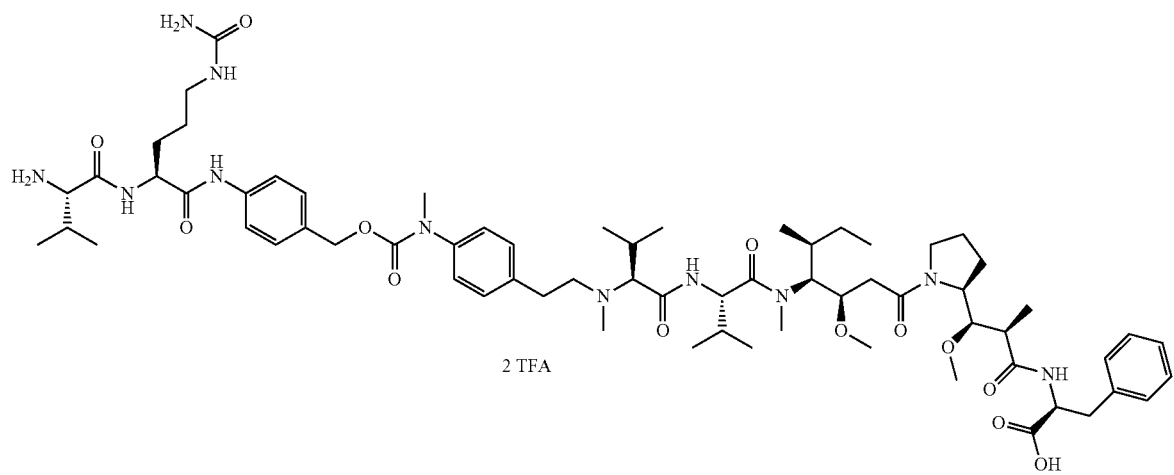

Compound E-13-1 (175 mg, 0.128 mmol, 1.0 eq.) was dissolved TFA (200 µL). After 5 minutes, water (1 mL) and acetonitrile (1 mL) were added and the solution lyophilised overnight to yield compound E-13-2 as an off-white solid (180 mg, 87%).

Compound E-13: ((2R,3R)-3-((S)-1-((3R,4S,5S)-4-((S)-2-((S)-2-((4-((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)(methyl)amino)phenethyl)(methyl)amino)-3-methylbutanamido)-N,3-dimethylbutanamido)-3-methoxy-5-methylheptanoyl) pyrrolidin-2-yl)-3-methoxy-2-methylpropanoyl)-L-phenylalanine, 2,2,2-trifluoroacetate

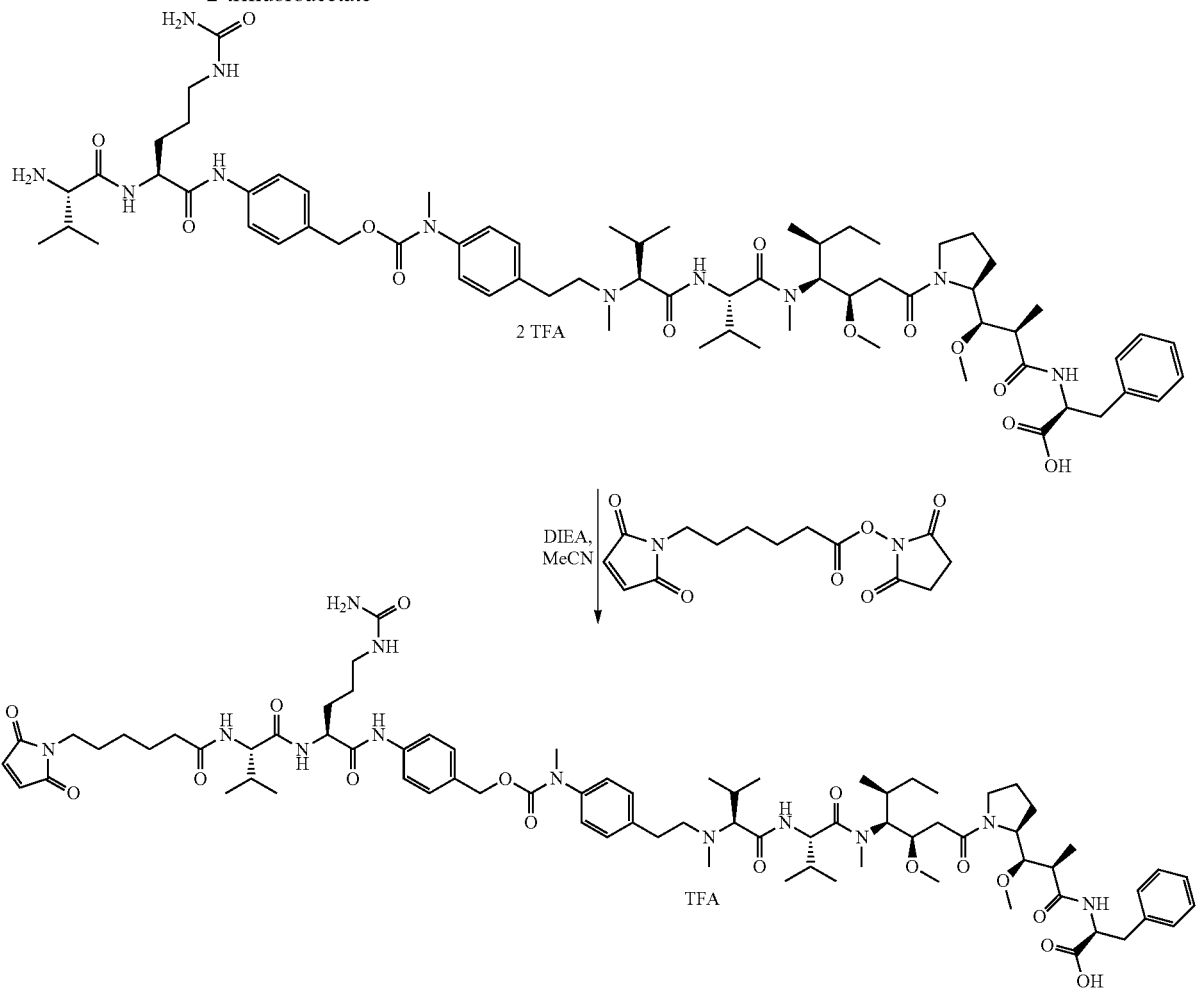

Compound E-13-2 (80 mg, 0.058 mmol, 1.0 eq.) was dissolved in a mixture of acetonitrile (1.5 mL) and DMF (0.4 mL). DIEA (50 μL, 0.289 mmol, 5 eq.) was added, followed by 2,5-dioxopyrrolidin-1-yl 6-(2,5-dioxo-2,5-dihydro-1H-pyrrol-1-yl)hexanoate (36 mg, 0.116 mmol, 2 eq.). The mixture was stirred for 3 hours at room temperature. After controlling the reaction by LC-MS, the solvent was evaporated under reduced pressure and the residue purified by preparative HPLC (Waters 600E, SunFire Prep C18 OBD column, 5 μm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound E-13 as a white solid (32 mg, 35%).

m/z (Q-TOF MS ESI−) 1461.8336 (100%, (M-H)−, $C_{77}H_{113}N_{12}O_{16}$ requires 1461.8403). m/z (Q-TOF MS ESI+) 1463.8565 (2%, MH+, $C_{77}H_{115}N_{12}O_{16}$ requires 1463.8549), 732.4317 (100%, $(MH_2)^{2+}$, $C_{77}H_{116}N_{12}O_{16}$ requires 732.4311).

Compound E-15 methyl ((2R,3R)-3-((S)-1-((3R,4S,5S)-4-((S)-2-((S)-2-((3-((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)amino)benzyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate 2,2,2-trifluoroacetate

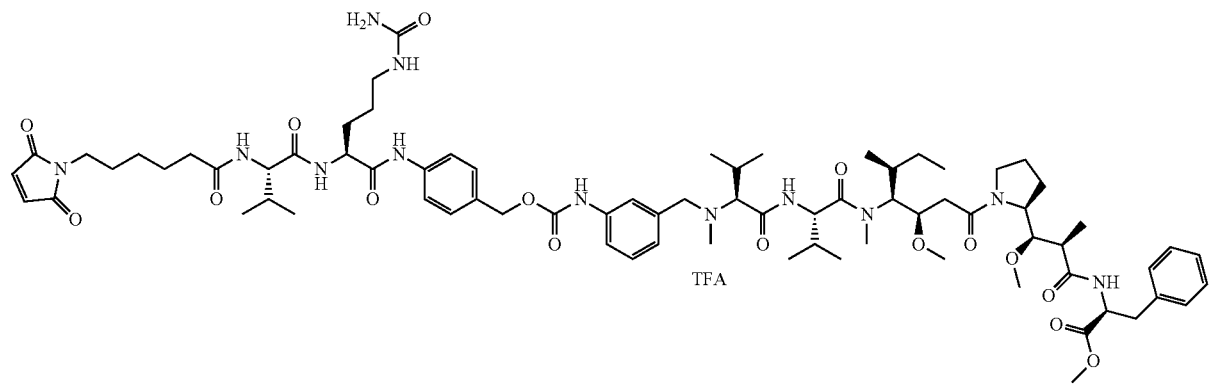 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)Cc1cccc(NC(=O)OCc2ccc(NC(=O)[C@H](CCCNC(N)=O)NC(=O)[C@@H](NC(=O)CCCCCN3C(=O)C=CC3=O)C(C)C)cc2)c1)C(C)C]

Compound E-15-1: methyl ((2R,3R)-3-((S)-1-((3R,4S,5S)-4-((S)-2-((S)-2-((3-((((4-((S)-2-((S)-2-((tert-butoxycarbonyl)amino)-3-methylbutanamido)-5-ureidopentanamido)benzyl)oxy)carbonyl)amino)benzyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate 2,2,2-trifluoroacetate

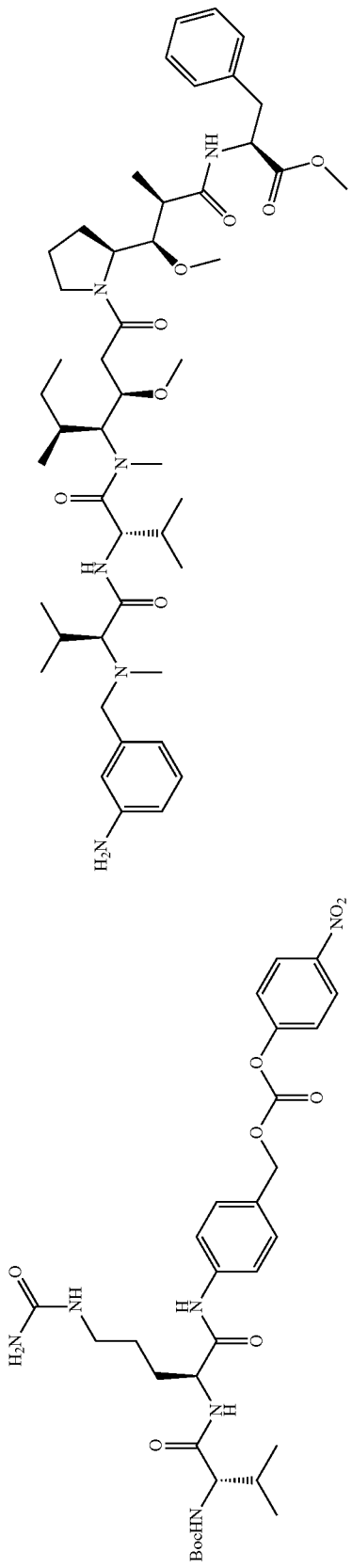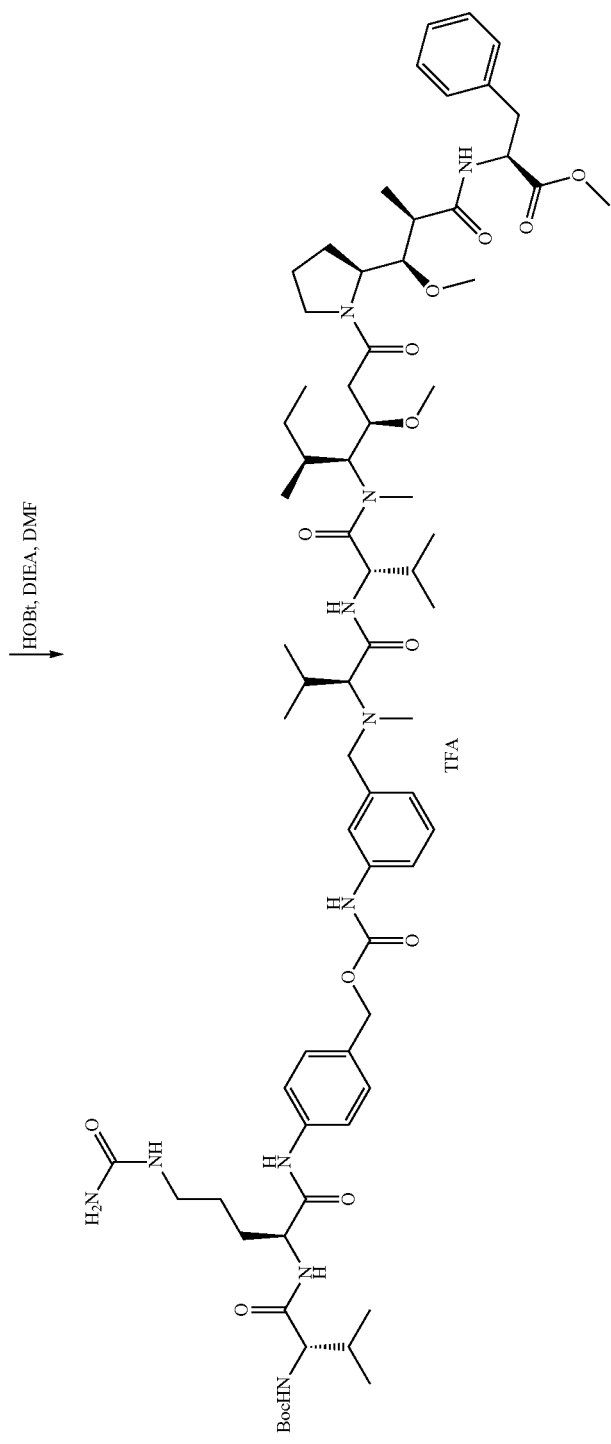

Compound E-15-1 was prepared according to the same method as for compound E-11-6, using carbonate E-11-5 (28 mg, 0.044 mmol, 1 eq.), aniline 15 (42 mg, 0.044 mmol, 1 eq.), HOBt (3 mg, 0.022 mmol, 0.5 eq.), and DIEA (15 μL, 0.087 mmol, 2 eq.) in DMF (2 mL). Compound E-15-1 was isolated as a white solid (8.2 mg, 13%).

Compound E-15-2: methyl ((2R,3R)-3-((S)-1-((3R,4S,5S)-4-((S)-2-((S)-2-((3-((((4-((S)-2-((S)-2-amino-3-methylbutanamido)-5-ureidopentanamido)benzyl) oxy) carbonyl)amino)benzyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate bis(2,2,2-trifluoroacetate)

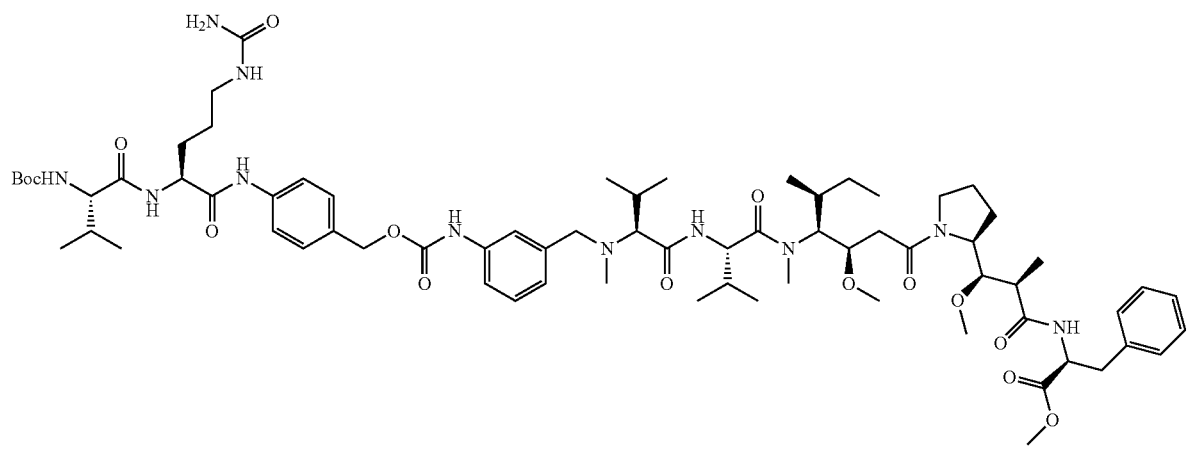

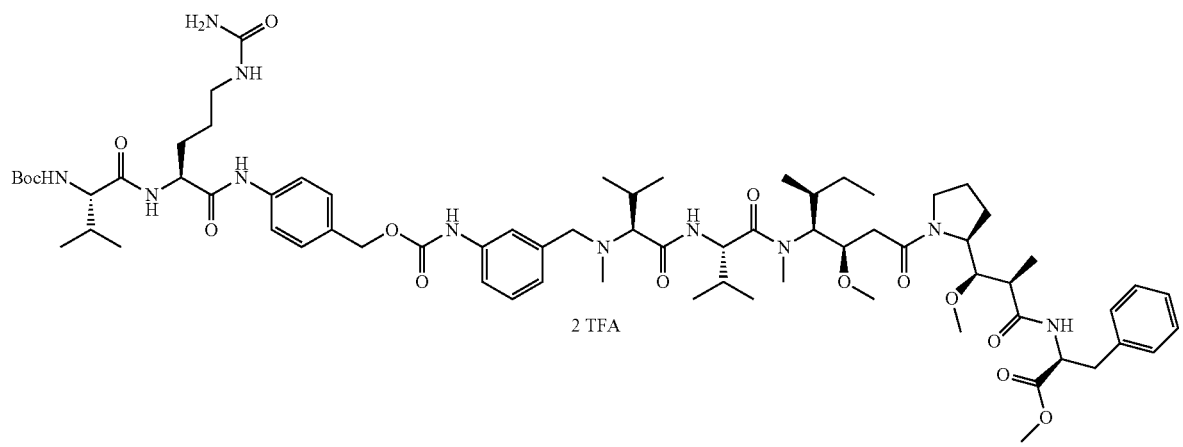

Compound E-15-1 (8.2 mg, 5.58 μmol, 1.0 eq.) was dissolved in TFA (200 μL). After 5 minutes, water (1 mL) was added and the solution lyophilised overnight to yield compound E-15-8 as a white solid (7.6 mg, 99%).

Compound E-15
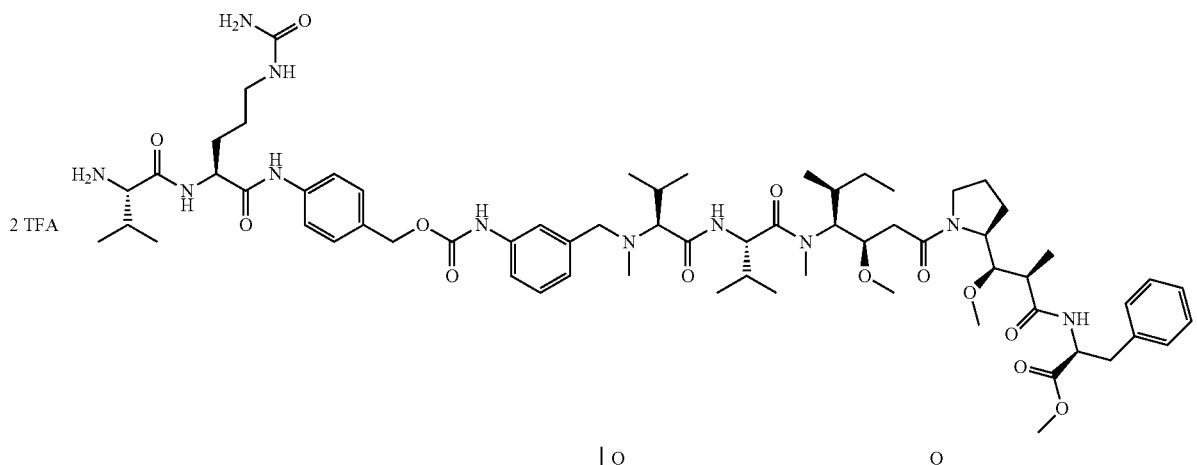
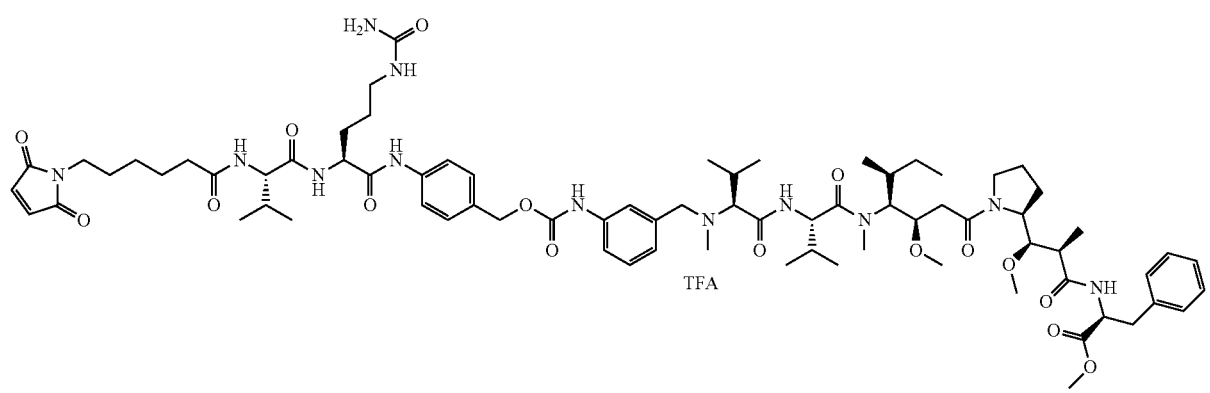
Compound E-15 was prepared according to the same method as for compound E-12, using amine E-15-2 (7.6 mg, 5.55 μmol, 1 eq.), 2,5-dioxopyrrolidin-1l-yl 6-(2,5-dioxo-2,5-dihydro-1H-pyrrol-1-yl)hexanoate (2 mg, 6.65 μmol, 1.2 eq.) and DIEA (5 μL, 0.028 mmol, 5 eq.) in acetonitrile (0.5 mL). Compound E-15 was isolated as a white solid (4.2 mg, 48%).
m/z (Q-TOF MS ESI+) 1471.8169 (2%, MNa$^+$, $C_{76}H_{112}N_{12}NaO_{16}$ requires 1471.8211), 725.4223 (100%, $(MH_2)^{2+}$, $C_{76}H_{114}N_{12}O_{16}$ requires 725.4232), 483.9482 (10%, $(MH_3)^{3+}$, C76H15N12O16 requires 483.9513).

Compound F-13

((2R,3R)-3-((S)-1-((3R,4S,5S)-4-((S)-2-((S)-2-((4-((S)-2-((S)-2-(6-(2,5-dioxo-2,5-dihydro-1H-pyrrol-1-yl)hexanamido)-3-methylbutanamido)-N-methyl-5-ureidopentanamido)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine 2,2,2-trifluoroacetate

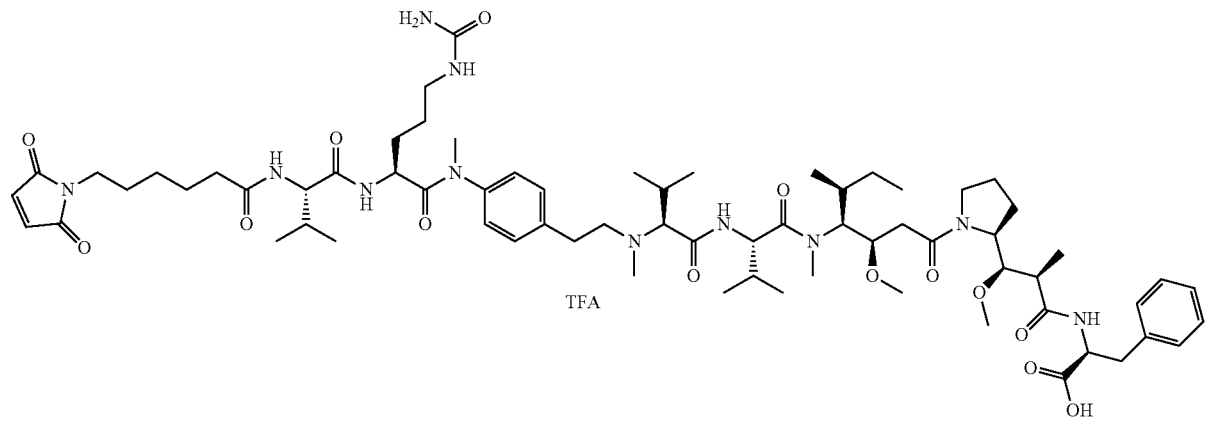 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCc1ccc(N(C)C(=O)[C@H](CCCNC(N)=O)NC(=O)[C@@H](NC(=O)CCCCCN2C(=O)C=CC2=O)C(C)C)cc1)C(C)C]

Compound F-13-1: benzyl N-(4-((tert-butoxycarbonyl)(methyl)amino) phenethyl)-N-methyl-L-valinate

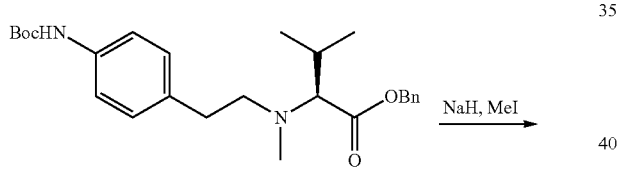

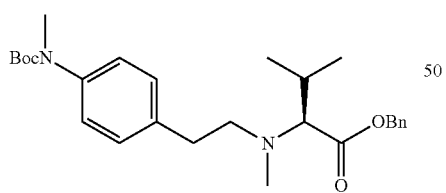

Compound 11C (250 mg, 0.567 mmol, 1 eq.) was dissolved in THF (10 ml) followed by the addition of NaH (60% suspension in mineral oil, 68 mg, 1.702 mmol, 3 eq.). The mixture was stirred for 5 minutes before adding iodomethane (106 µL, 1.702 mmol, 3 eq.). The reaction was stirred for 2 hours at room temperature before quenching with water and separating between EtOAc (100 mL) and water (50 mL). The organic phase was dried over MgSO₄ and evaporated to dryness to yield compound F-13-1 as a yellow oil (250 mg, 97%), which was used without further purification.

Compound F-13-2: benzyl N-methyl-N-(4-(methyl-amino)phenethyl)-L-valinate

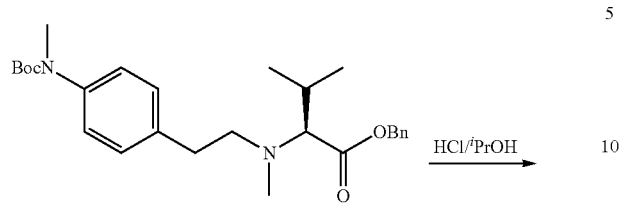

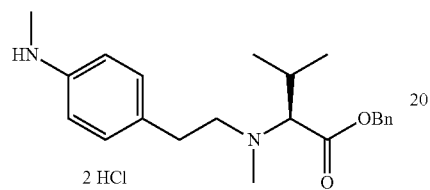

Boc-protected aniline F-13-1 (250 mg, 0.550 mmol, 1 eq) was dissolved in MeOH (5 mL) followed by the addition of 1 mL of a commercially-available solution of HCl in $^i$PrOH (5-6 M). The solution was stirred at room temperature for 2 hours before evaporating to dryness under reduced pressure. The resulting yellow oil was triturated with Et$_2$O to yield compound F-13-2 as a yellow solid (202 mg, 94%).

Compound F-13-3: benzyl N-(4-((S)-2-((S)-2-((tert-butoxycarbonyl)amino)-3-methylbutanamido)-N-methyl-5-ureidopentanamido)phenethyl)-N-methyl-L-valinate

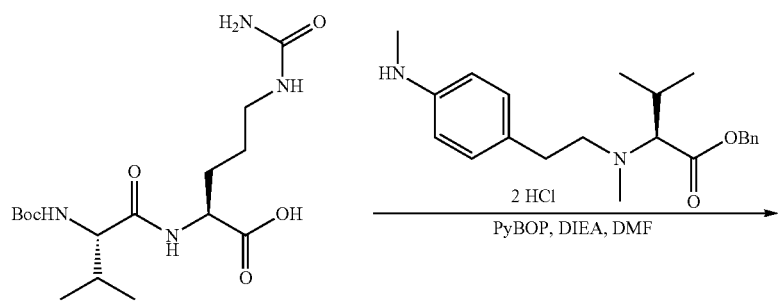

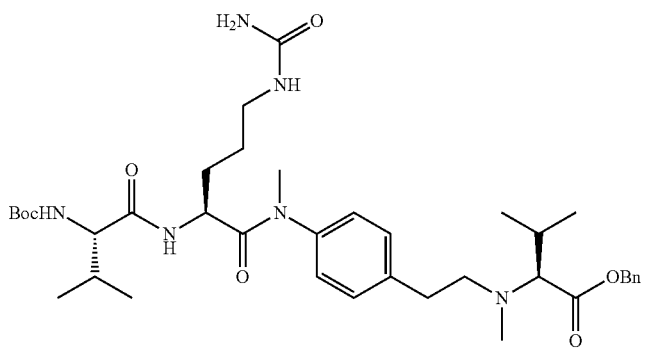

Acid E-11-3 (190 mg, 0.508 mmol, 1.5 eq.) was dissolved in dry DMF (1 ml), followed by the addition of DIEA (118 μL, 0.677 mmol, 2 eq.), benzotriazol-1-yl-oxytripyrrolidinophosphonium hexafluorophosphate (PyBOP—264 mg, 0.508 mmol, 1.5 eq.) and aniline F-13-2 (120 mg, 0.339 mmol, 1 eq.). The mixture was stirred at room temperature overnight and the solvents evaporated under reduced pressure. The residue was purified by preparative HPLC (Waters 600E, SunFire Prep C18 OBD column, 5 μm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound F-13-3 as a white solid (140 mg, 45%).

Compound F-13-4: N-(4-((S)-2-((S)-2-((tert-butoxycarbonyl)amino)-3-methylbutanamido)-N-methyl-5-ureidopentanamido)phenethyl)-N-methyl-L-valine

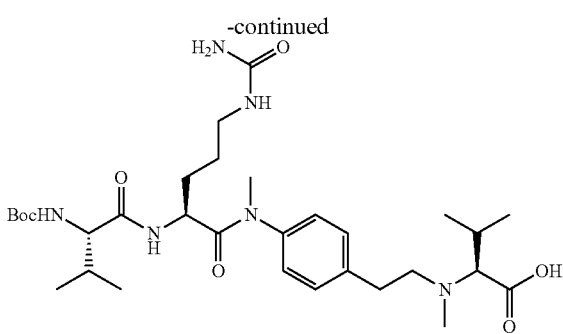

Compound F-13-3 (116 mg, 0.163 mmol, 1 eq.) was dissolved in MeOH (5 ml) in the presence of Pd/C 10% (30 mg) and hydrogenated for 2 hours at ambient temperature and atmospheric pressure. The reaction medium was filtered and concentrated under reduced pressure to yield 110 mg (99%) of compound F-13-4 as a beige solid.

Compound F-13-5: methyl ((2R,3R)-3-((S)-1-((3R,4S,5S)-4-((S)-2-((S)-2-((4-((S)-2-((S)-2-((tert-butoxycarbonyl)amino)-3-methylbutanamido)-N-methyl-5-ureidopentanamido)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate 2,2,2-trifluoroacetate

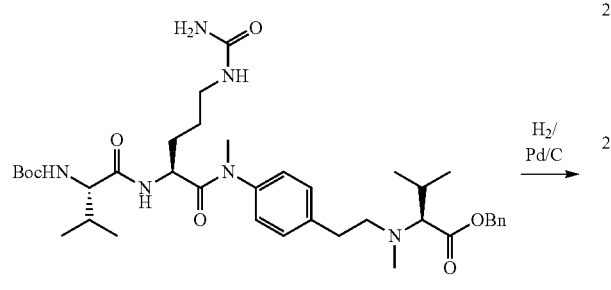

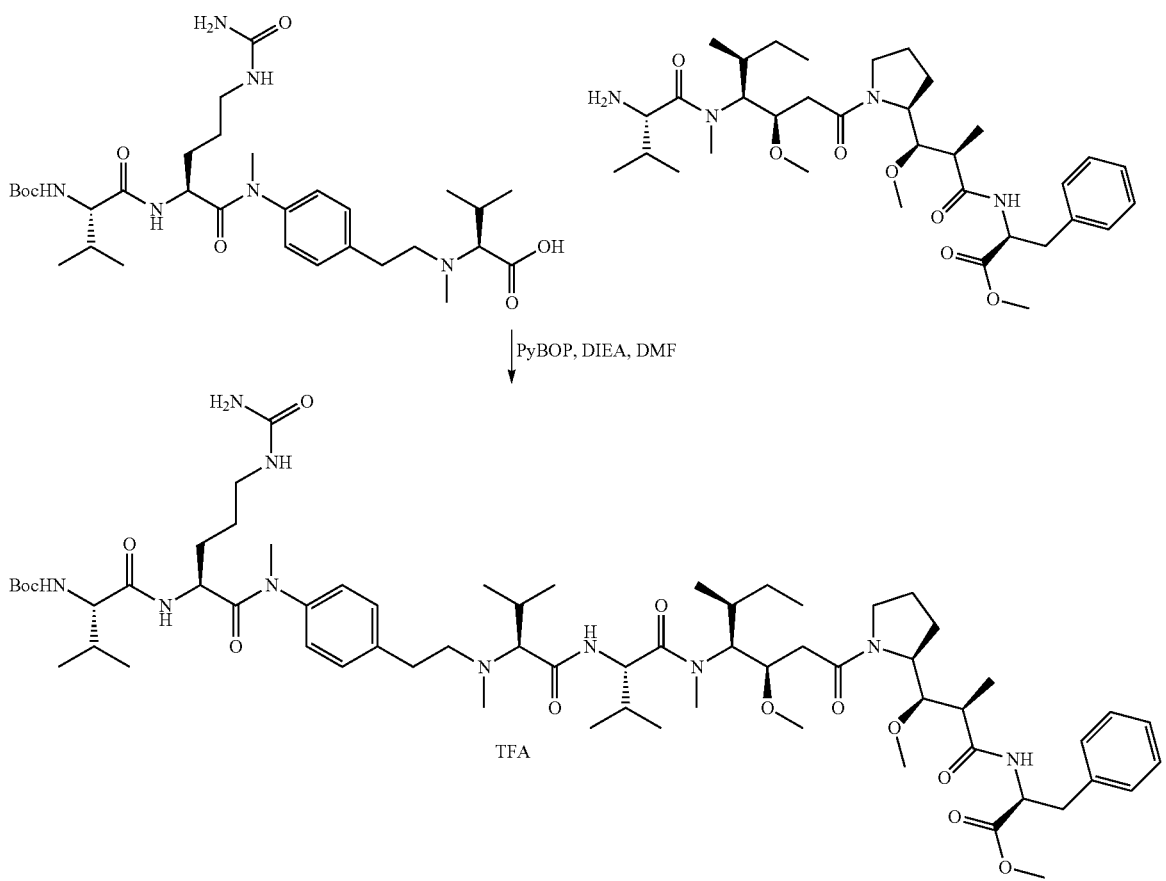

Amine 3D (89 mg, 0.140 mmol, 1 eq.) and acid F-13-4 (145 mg, 0.210 mmol, 1.5 eq.) were dissolved in dry DMF (4 mL), and PyBOP (109 mg, 0.210 mmol, 1.5 eq.) and DIEA (73 µL, 0.420 mmol, 3 eq.) were added. The mixture was stirred for 1 hour at room temperature and the solvent evaporated. The residue was separated between EtOAc and water, and the organic phase dried over MgSO$_4$, filtered and evaporated under reduced pressure. The crude product was purified by preparative HPLC (Waters 600E, SunFire Prep C18 OBD column, 5 µm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound F-13-5 as a white solid (140 mg, 73%).

Compound F-13-6: ((2R,3R)-3-((S)-1-((3R,4S,5S)-4-((S)-2-((S)-2-((4-((S)-2-((S)-2-((tert-butoxycarbonyl)amino)-3-methylbutanamido)-N-methyl-5-ureidopentanamido) phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine 2,2,2-trifluoroacetate

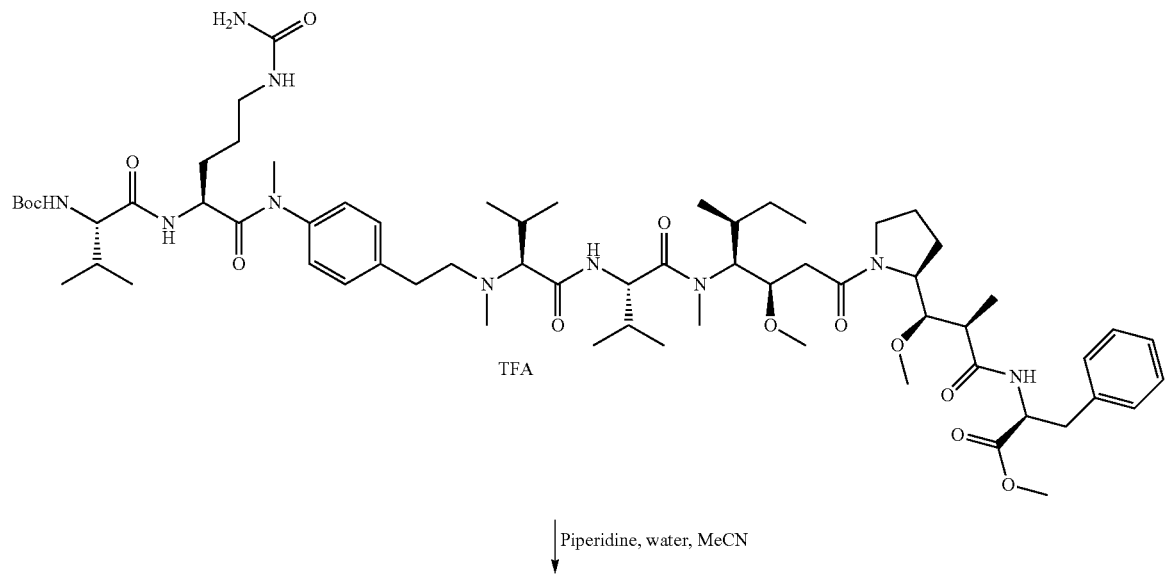

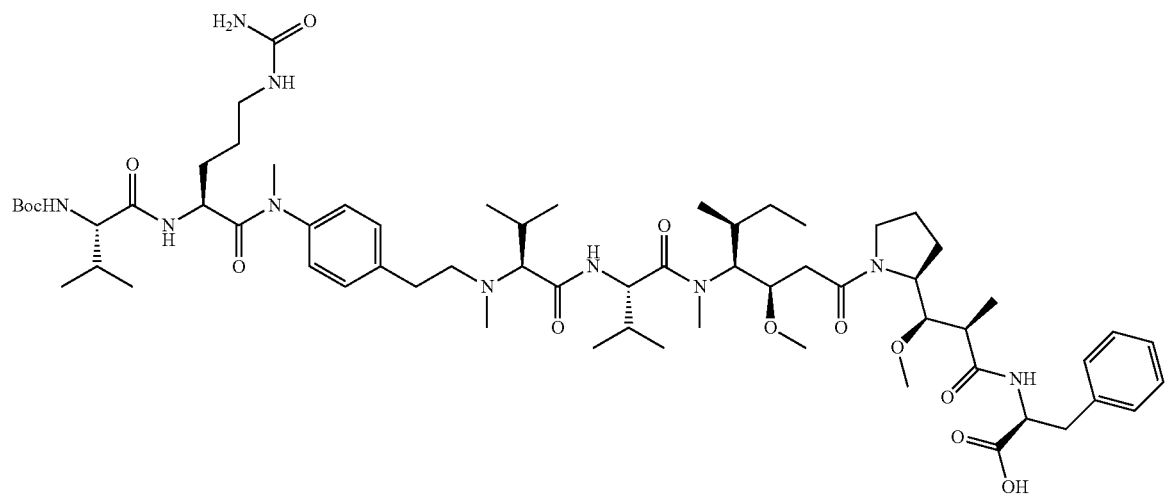

Compound F-13-5 (140 mg, 0.104 mmol, 1 eq.) was dissolved in a mixture of water (4 mL), acetonitrile (4 mL) and piperidine (2 mL) and stirred at room temperature for 4 hours. The solvent was evaporated under reduced pressure and the residue purified by preparative HPLC (Waters 600E, SunFire Prep C18 OBD column, 5 μm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound F-13-6 as a white solid (115 mg, 83%).

Compound F-13

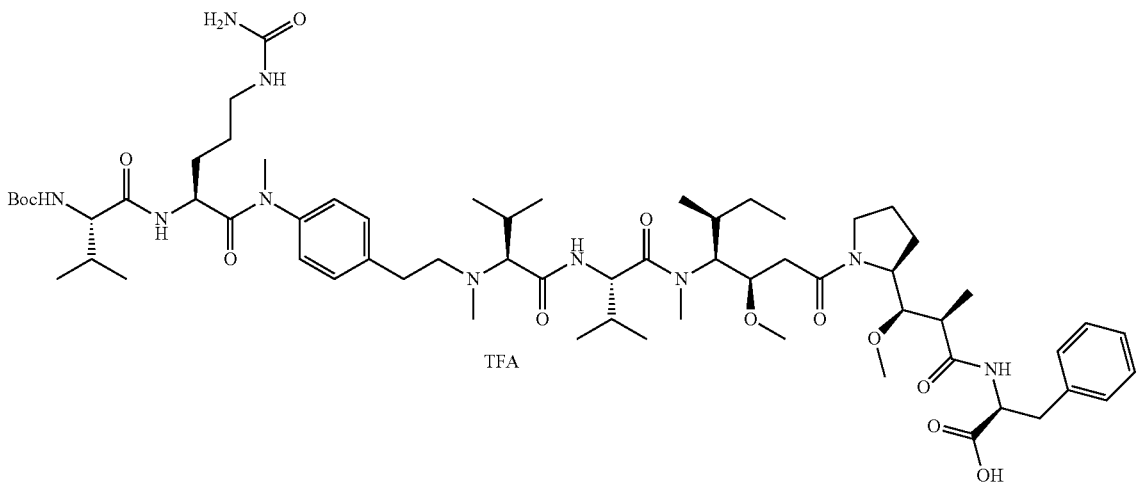

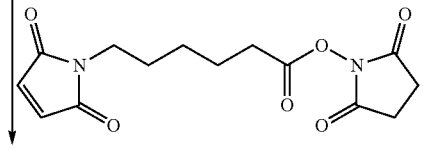

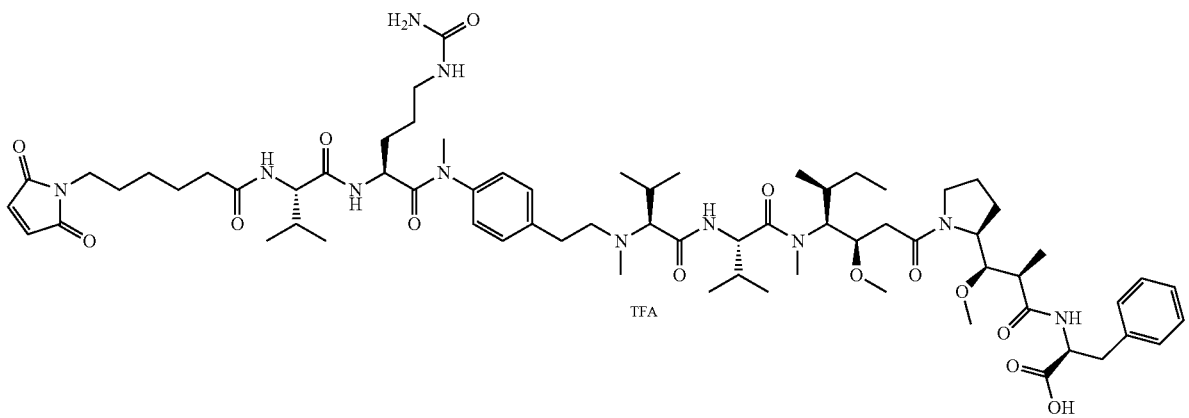

Compound F-13 was prepared according to the same method as for compound E-11, using Boc-protected amine F-13-6 (55 mg, 0.041 mmol, 1.0 eq.) in DCM (0.5 mL) and TFA (100 μL, 30 eq.), followed by dilution with DMF (1 mL), quenching with (DIEA (320 μL, 45 eq) then reaction with 2,5-dioxopyrrolidin-1-yl 6-(2,5-dioxo-2,5-dihydro-1H-pyrrol-1-yl)hexanoate (15 mg, 0.049 mmol, 1.2 eq.). After purification by preparative HPLC and lyophilisation, compound F-13 was obtained as a white solid (14 mg, 24%).

m/z (Q-TOF MS ESI+) 1314.8067 (2%, MH+, $C_{69}H_{108}N_{11}O_{14}$ requires 1314.8072), 657.9067 (100%, $(MH_2)^{2+}$, $C_{69}H_{109}N_{11}O_{14}$ requires 657.9072).

Compound F-61

N—((S)-1-(((S)-1-((4-((3R,4S,7S,10S)-4-((S)-sec-butyl)-7,10-diisopropyl-3-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-5,11-dimethyl-6,9-dioxo-2-oxa-5,8,11-triazatridecan-13-yl)phenyl)amino)-1-oxo-5-ureidopentan-2-yl)amino)-3-methyl-1-oxobutan-2-yl)-6-(2,5-dioxo-2,5-dihydro-1H-pyrrol-1-yl) hexanamide 2,2,2-trifluoroacetate

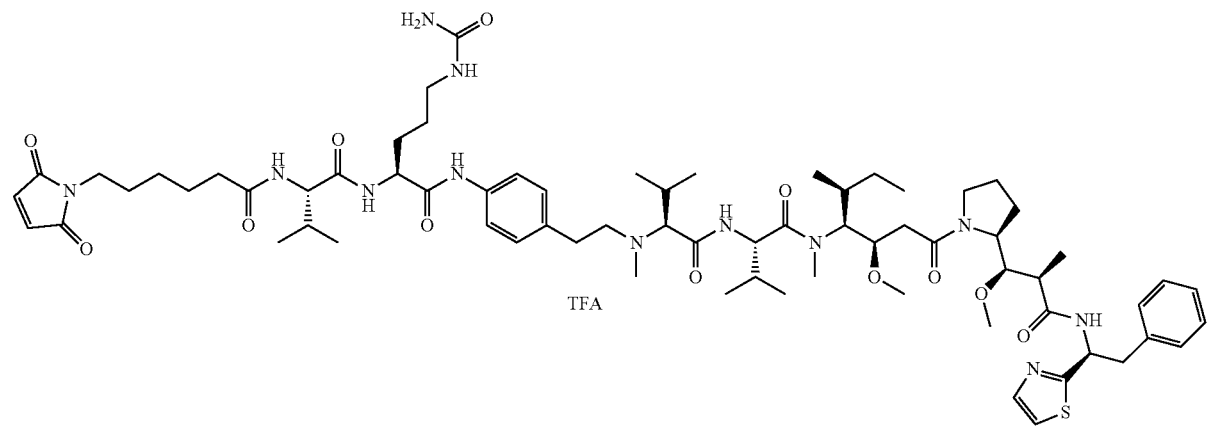 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCc1ccc(NC(=O)[C@H](CCCNC(N)=O)NC(=O)[C@@H](NC(=O)CCCCCN2C(=O)C=CC2=O)C(C)C)cc1)C(C)C]

Compound F-61-1: benzyl N-(4-aminophenethyl)-N-methyl-L-valinate dihydrochloride

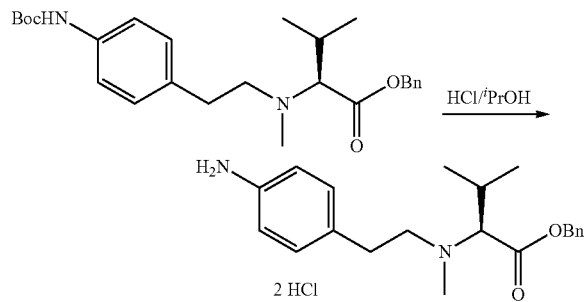

Compound 11C (1.0 g, 2.27 mmol, 1 eq.) was dissolved in 8 mL of a commercially-available solution of HCl in $^i$PrOH (5-6 M). The mixture was stirred for 2 hours at room temperature before evaporating to dryness under reduced pressure. The residue was triturated twice with Et₂O (30 mL) and dried under vacuum to yield compound F-61-1 as a white solid (916 mg, 98%).

Compound F-61-2: benzyl N-(4-((S)-2-((S)-2-((tert-butoxycarbonyl)amino)-3-methylbutanamido)-5-ureidopentanamido)phenethyl)-N-methyl-L-valinate

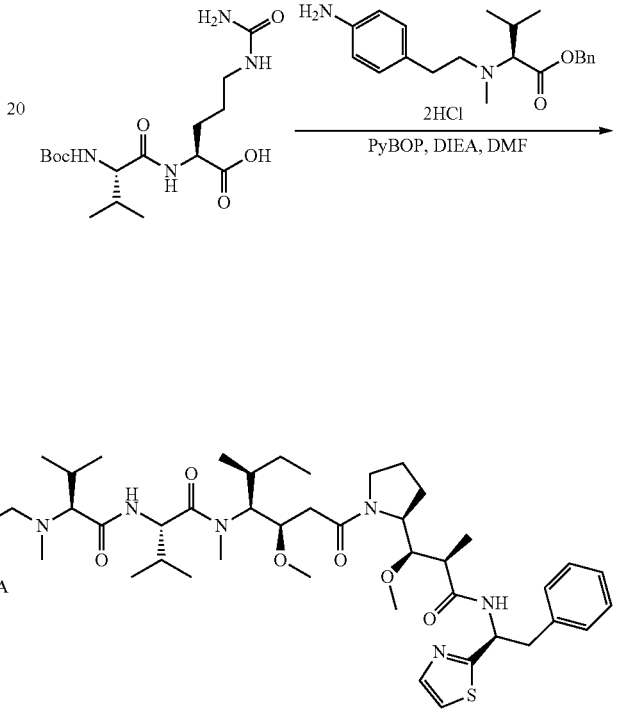

-continued

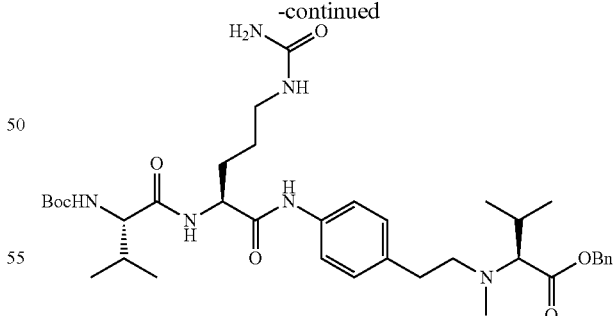

Acid E-11-3 (769 mg, 2.05 mmol, 1.5 eq.) was dissolved in dry DMF (2.5 ml) followed by the addition of DIEA (957 μL, 5.48 mmol, 4 eq.) and PyBOP (1.07 g, 2.05 mmol, 1.5 eq.). Aniline F-61-1 (566 mg, 1.369 mmol, 1 eq.) was added and the mixture stirred at room temperature overnight. The solvents were evaporated under reduced pressure, and the residue purified on silica gel (DCM/MeOH) to yield 969 mg (102%) of compound F-61-2 as a white solid.

Compound F-61-3: N-(4-((S)-2-((S)-2-((tert-butoxycarbonyl)amino)-3-methylbutanamido)-5-ureidopentanamido)phenethyl)-N-methyl-L-valine Compound F-61-2 (969 mg, 1.28 mmol, 1 eq.) was dissolved in MeOH (20 ml) in the presence of Pd/C 10% (270 mg) and hydrogenated for 3 hours at ambient temperature and atmospheric pressure. The reaction medium was filtered and concentrated under reduced pressure, and the residue purified on silica gel (DCM/MeOH/AcOH) to yield 520 mg (67%) of compound F-61-3 as a white solid.

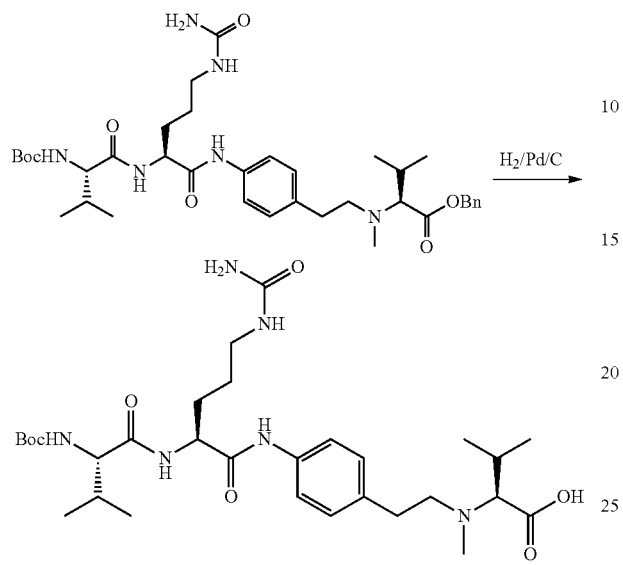

Compound F-61-4: tert-butyl ((S)-1-(((S)-1-((4-((3R,4S,7S,10S)-4-((S)-sec-butyl)-7,10-diisopropyl-3-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-5,11-dimethyl-6,9-dioxo-2-oxa-5,8,11-triazatridecan-13-yl)phenyl)amino)-1-oxo-5-ureidopentan-2-yl)amino)-3-methyl-1-oxobutan-2-yl)carbamate 2,2,2-trifluoroacetate

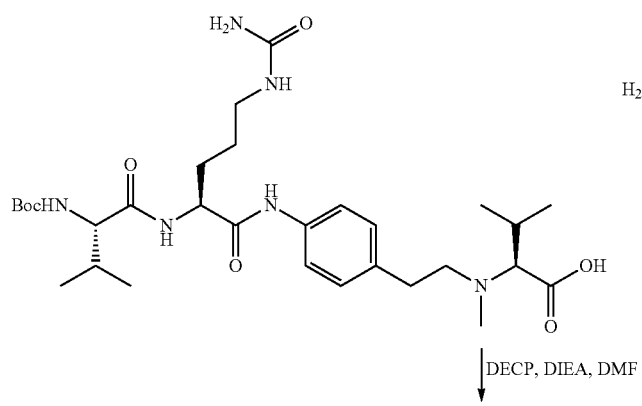

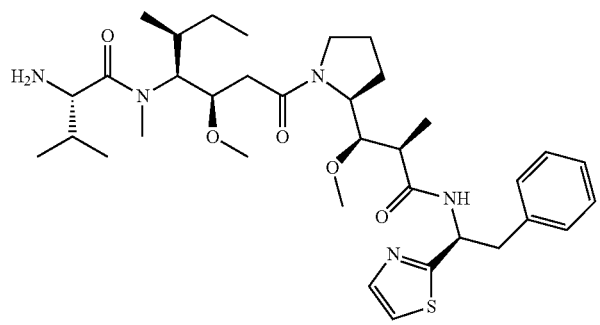

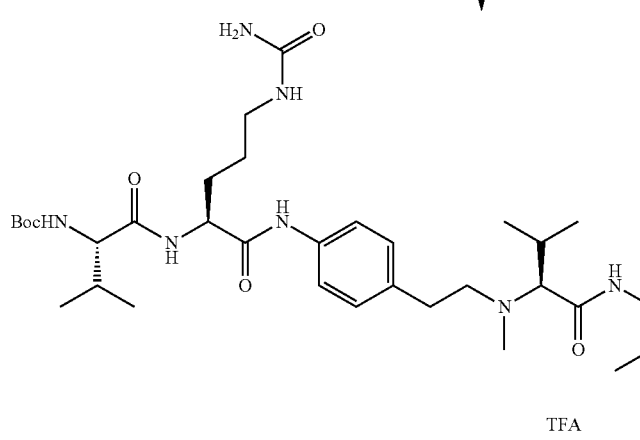

Acid F-61-3 (67.5 mg, 0.111 mmol, 1.5 eq.) was dissolved in dry DMF (2 mL) and DECP (17 μL, 0.111 mmol, 1.5 eq.) and DIEA (39 μL, 0.223 mmol, 3 eq.) were added. After stirring for 15 minutes at room temperature, amine 1Y (50 mg, 0.074 mmol, 1 eq.) was added and the solution stirred overnight. The solvent was evaporated under reduced pressure, and the residue purified by preparative HPLC (Waters 600E, SunFire Prep C18 OBD column, 5 μm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound F61-4 as a white solid (28 mg, 28%).

Compound F-61-5: (S)-2-((S)-2-amino-3-methylbutanamido)-N-(4-((3R,4S,7S,10S)-4-((S)-sec-butyl)-7,10-diisopropyl-3-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-5,11-dimethyl-6,9-dioxo-2-oxa-5,8,11-triazatridecan-13-yl)phenyl)-5-ureidopentanamide bis(2,2,2-trifluoroacetate)

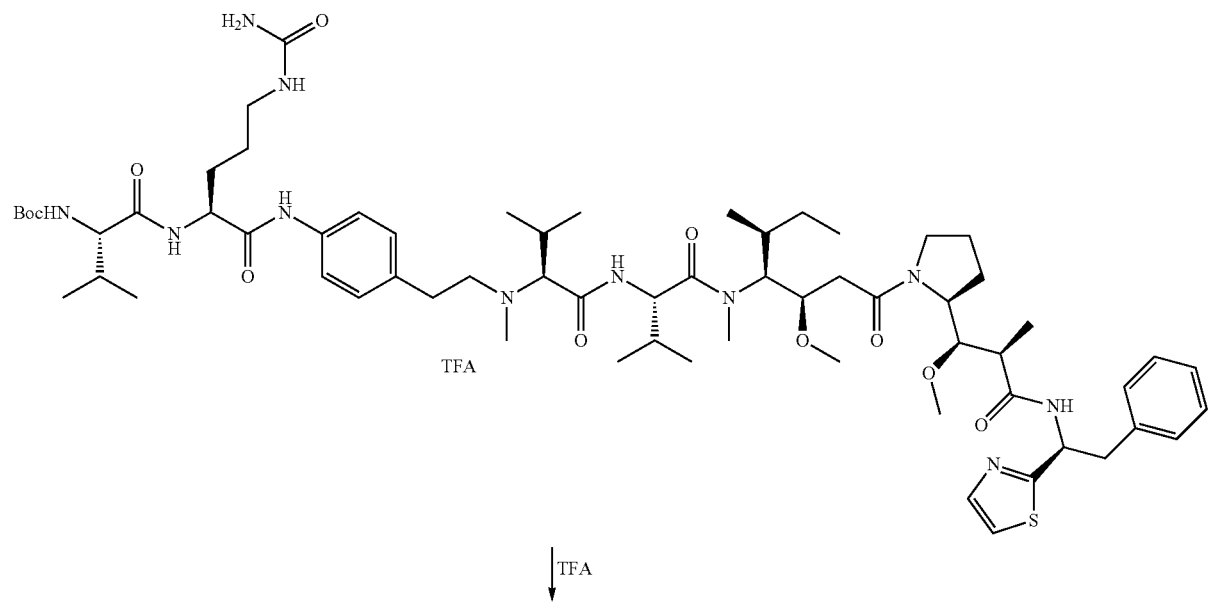

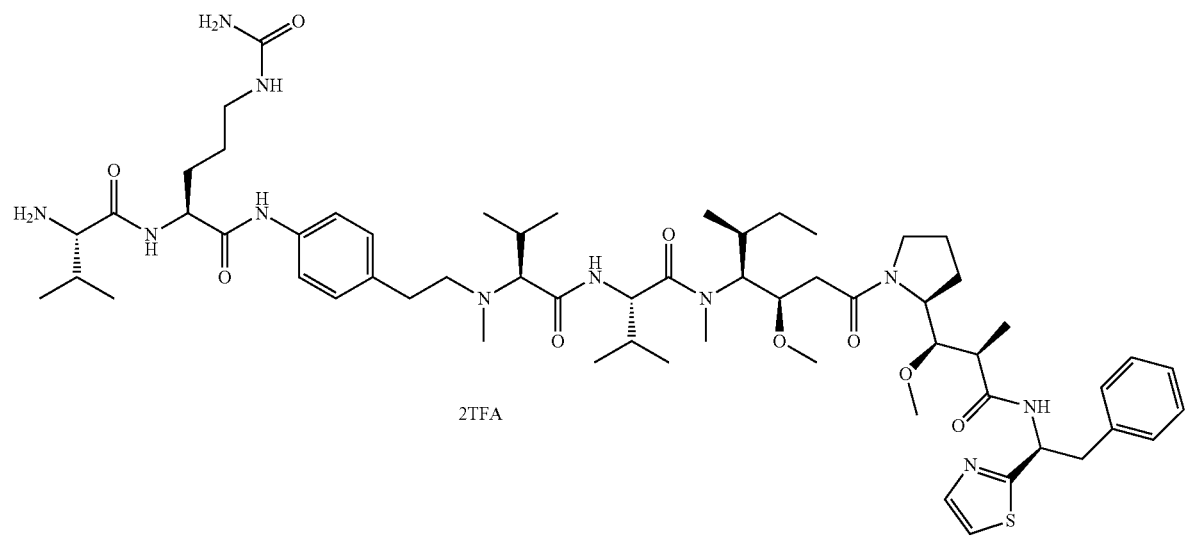

Compound F-61-4 (28 mg, 0.021 mmol, 1.0 eq.) was dissolved in TFA (200 µL). After 5 minutes, water (2 mL) and acetonitrile (0.5 mL) were added and the solution lyophilised overnight to yield compound F-61-5 as a colourless oil (38 mg, 134%).

Compound F-61

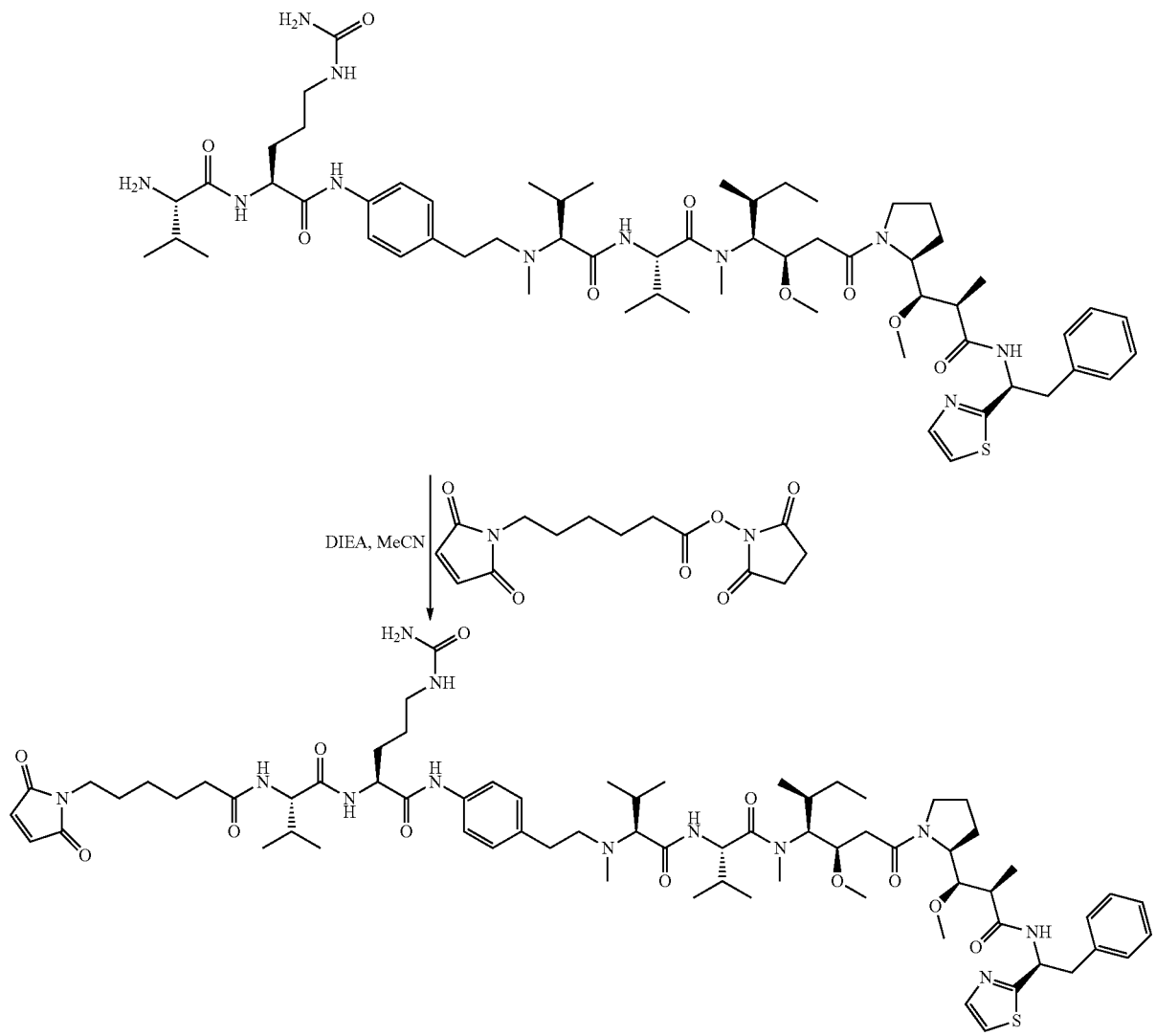

Compound F-61-5 (28.3 mg, 0.020 mmol, 1 eq.) was dissolved in acetonitrile (0.5 mL), followed by 2,5-dioxopyrrolidin-1-yl 6-(2,5-dioxo-2,5-dihydro-1H-pyrrol-1-yl)hexanoate (9 mg, 0.029 µmol, 1.4 eq.) and DIEA (25 µL, 0.143 mmol, 7 eq.). The mixture was stirred for 4.5 hours, after which time HPLC analysis showed the presence of starting material but complete consumption of the succinimide. Supplementary 2,5-dioxopyrrolidin-1-yl 6-(2,5-dioxo-2,5-dihydro-1H-pyrrol-1-yl)hexanoate was therefore added (3 mg, 0.01 µmol, 0.5 eq.) and the reaction stirred for 1.5 hours. HPLC analysis showed complete consumption of the starting material. The solvent was evaporated to dryness and the residue triturated twice with a mixture of EtOAc/Et₂O (80/20) to yield compound F-61 as an off-white solid (19.4 mg, 70%).

m/z (Q-TOF MS ESI+) 1361.7725 (2%, MNa+, $C_{70}H_{106}N_{12}NaO_{12}S$ requires 1361.7666), 670.3961 (100%, $(MH_2)^{2+}$, $C_{70}H_{108}N_{12}O_{12}S$ requires 670.3960).

Compound F-62 methyl ((2R,3R)-3-((S)-1-((3R,4S,5S)-4-((S)-2-((S)-2-((4-((S)-2-((S)-2-(6-(2,5-dioxo-2,5-dihydro-1H-pyrrol-1-yl)hexanamido)-3-methylbutanamido)-5-ureidopentanamido)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate 2,2,2-trifluoroacetate

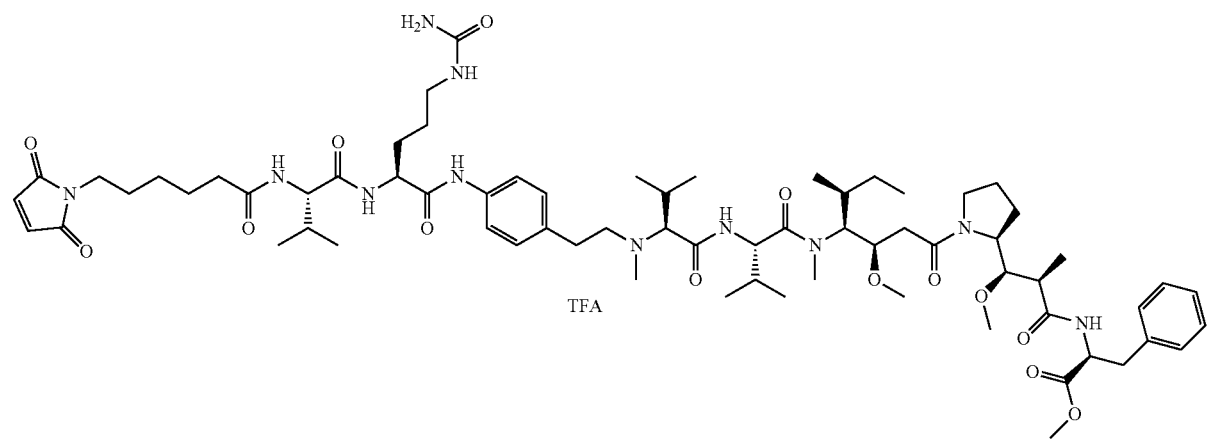 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCc1ccc(NC(=O)[C@H](CCCNC(N)=O)NC(=O)[C@@H](NC(=O)CCCCCN2C(=O)C=CC2=O)C(C)C)cc1)C(C)C]

Compound F-62-1: methyl ((2R,3R)-3-((S)-1-((3R,4S,5S)-4-((S')-2-((S)-2-((4-((S)-2-((S)-2-((tert-butoxycarbonyl)amino)-3-methylbutanamido)-5-ureidopentanamido)phenethyl)(methyl)amino)-3-methylbutanamido)-N, 3-dimethylbutanamido)-3-methoxy-5-methylheptanoyl)pyrrolidin-2-yl)-3-methoxy-2-methylpropanoyl)-L-phenylalaninate 2,2,2-trifluoroacetate

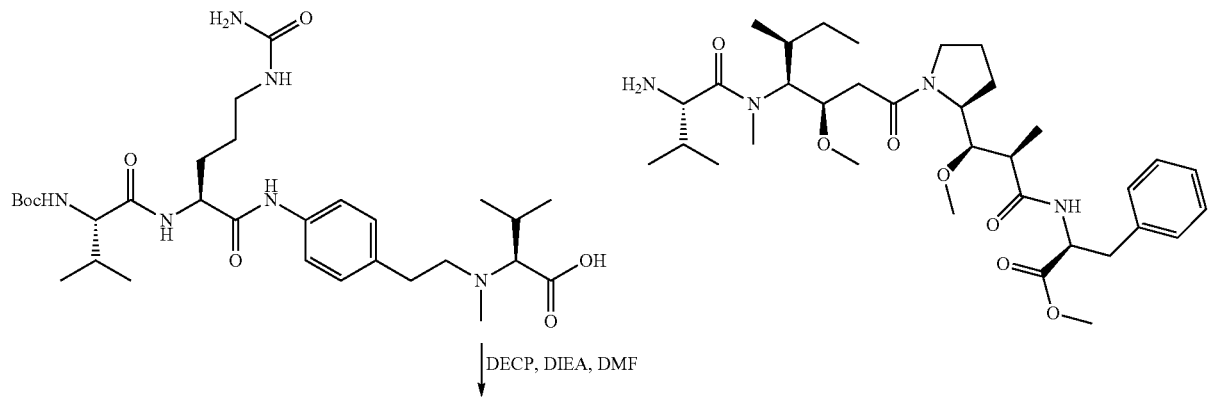

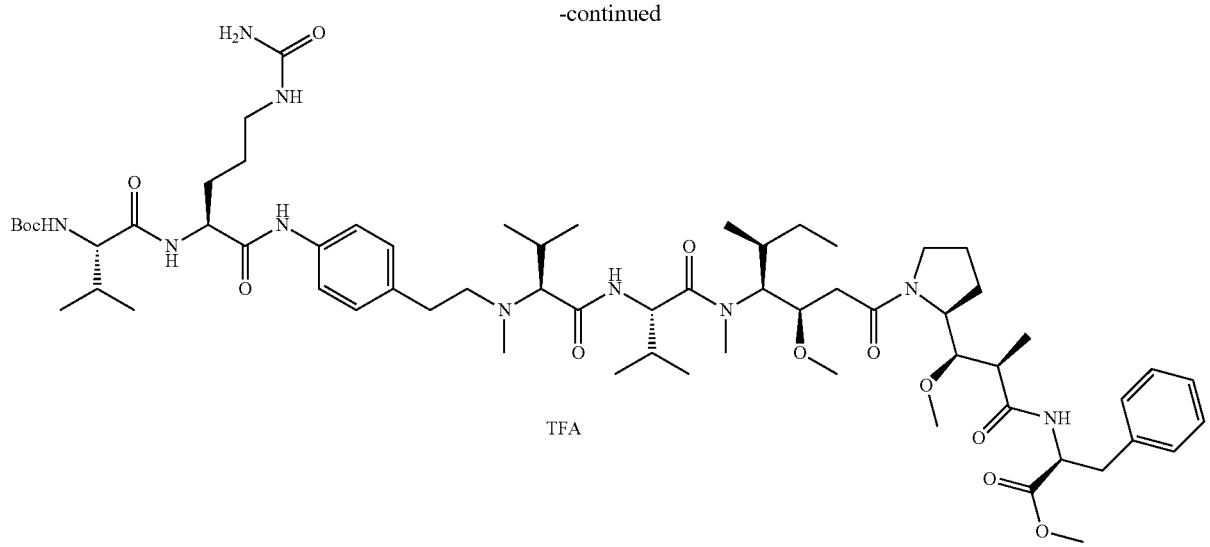

Compound F-62-1 was prepared in similar manner to compound F-61-4 from amine 3D (100 mg, 0.158 mmol, 0.9 eq.), acid F-61-3 (108 mg, 0.178 mmol, 1 eq.), DECP (41 µL, 0.267 mmol, 1.5 eq.) and DIEA (93 µL, 0.534 mmol, 3 eq.) in DMF (2 mL). After purification by preparative HPLC, compound F-62-1 was obtained as a white solid (93 mg, 39%).

Compound F-62-2: methyl ((2R,3R)-3-((S)-1-((3R,4S,5S)-4-((S)-2-((S)-2-((4-((S)-2-((S)-2-amino-3-methylbutanamido)-5-ureidopentanamido)phenethyl)(methyl) amino)-3-methylbutanamido)-N,3-dimethylbutanamido)-3-methoxy-5-methylheptanoyl) pyrrolidin-2-yl)-3-methoxy-2-methylpropanoyl)-L-phenylalaninate bis(2,2,2-trifluoroacetate)

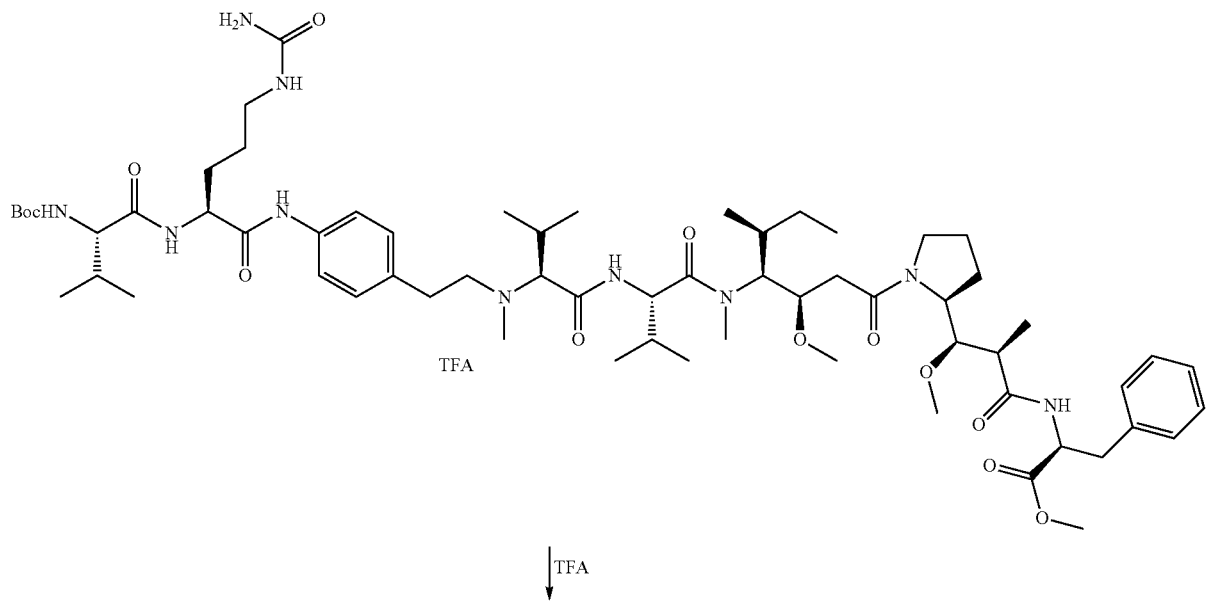

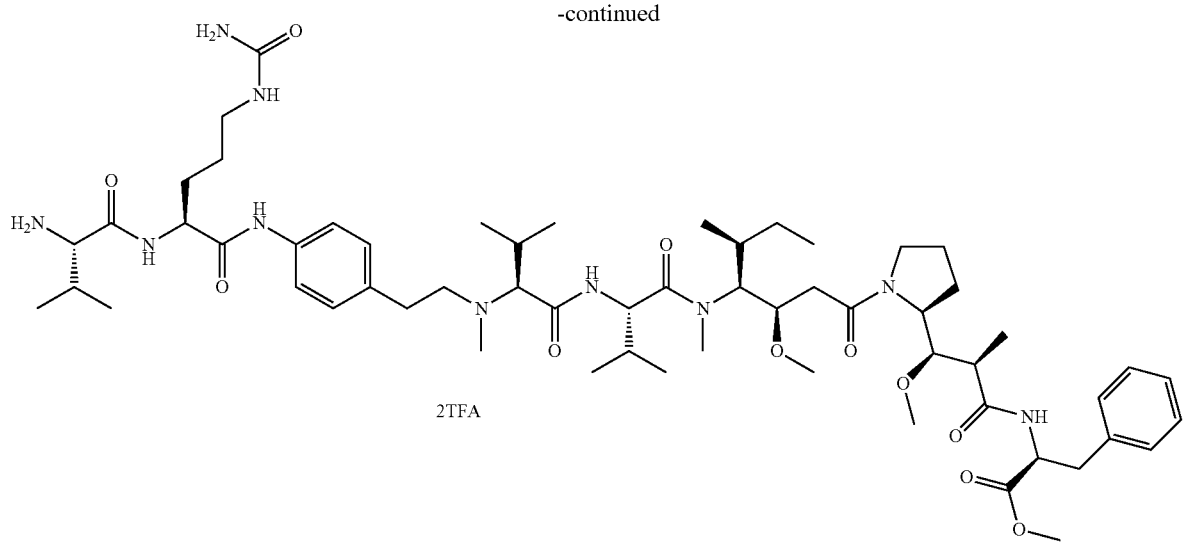
2TFA
Compound F-62-1 (35 mg, 0.026 mmol, 1.0 eq.) was dissolved in TFA (200 μL). After 10 minutes, water (2 mL) and acetonitrile (0.5 mL) were added and the solution lyophilised overnight to yield compound F-62-2 as a white solid (34 mg, 105%).
Compound F-62: 174
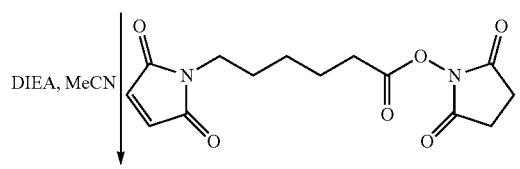

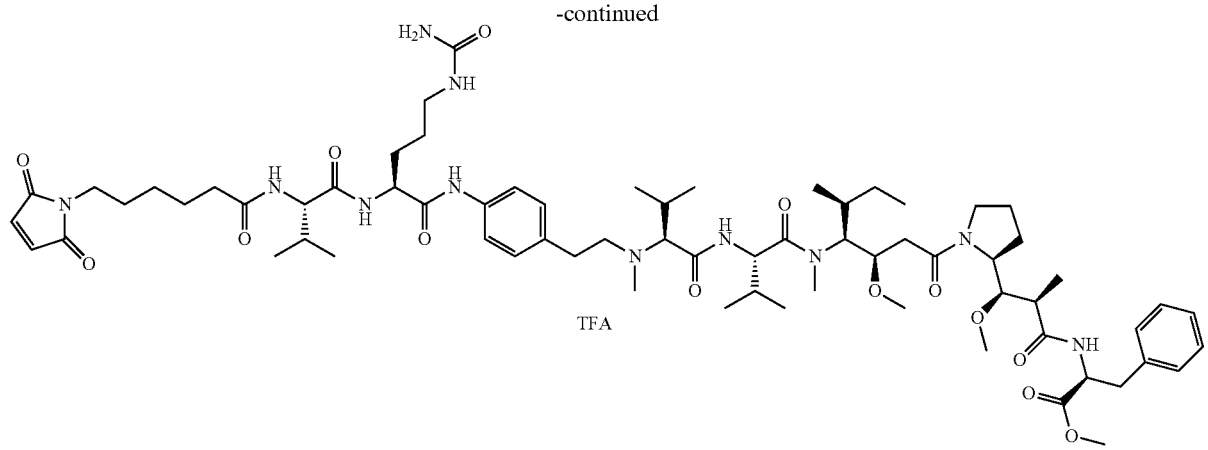

Amine F-62-2 (34 mg, 5.55 μmol, 1 eq.) was dissolved in acetonitrile (3 mL). DIEA (5 μL, 0.028 mmol, 5 eq.) and 2,5-dioxopyrrolidin-1-yl 6-(2,5-dioxo-2,5-dihydro-1H-pyrrol-1-yl)hexanoate (2 mg, 6.65 μmol, 1.2 eq.) were added. HPLC analysis showed complete consumption of the starting material. The solvent was evaporated to dryness and the residue triturated with a mixture of EtOAc/Et$_2$O (80/20). The crude product was purified by preparative HPLC (Waters 600E, SunFire Prep C18 OBD column, 5 μm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound F-62 as a white solid (5.5 mg, 13%).

m/z (Q-TOF MS ESI+) 1336.7859 (2%, MNa$^+$, C$_{69}$H$_{107}$N$_{11}$NaO$_{14}$ added. HPLCNaO$_{14}$ analysis showed 1336.7891), 657.9073 (100%, (MH$_2$)$^{2+}$, C$_{69}$H$_{109}$N$_{11}$O$_{14}$ requires 657.9072).

Compound F-63

((2R,3R)-3-((S)-1-((3R,4S,5S)-4-((S)-2-((S)-2-((4-((S)-2-((S)-2-(6-(2,5-dioxo-2,5-dihydro-1H-pyrrol-1-yl)hexanamido)-3-methylbutanamido)-5-ureidopentanamido)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine 2,2,2-trifluoroacetate

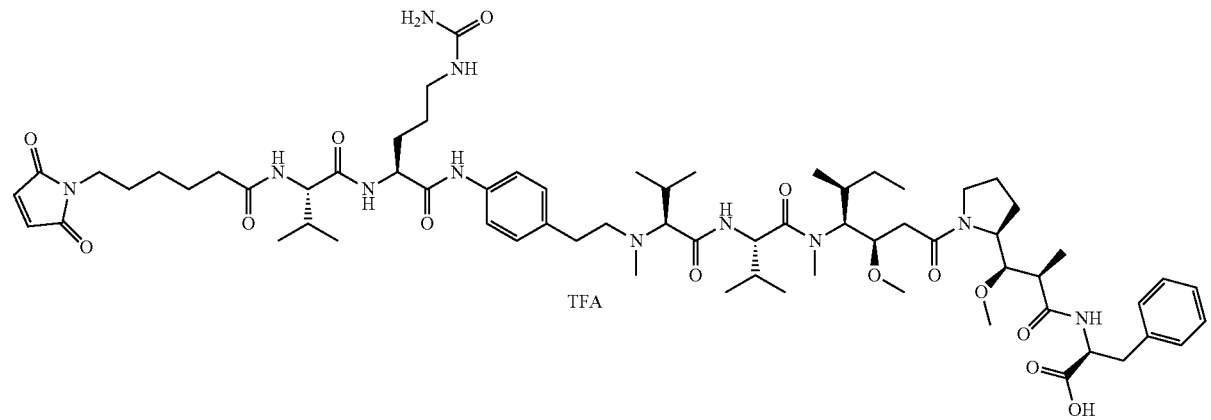 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCc1ccc(NC(=O)[C@H](CCCNC(N)=O)NC(=O)[C@@H](NC(=O)CCCCCN2C(=O)C=CC2=O)C(C)C)cc1)C(C)C]

Compound F-63-1: ((2R,3R)-3-((S)-1-((3R,4S,5S)-4-((S)-2-((S)-2-((4-((S)-2-((S)-2-((tert-butoxycarbonyl)amino)-3-methylbutanamido)-5-ureidopentanamido)phenethyl) (methyl)amino)-3-methylbutanamido)-N, 3-dimethylbutanamido)-3-methoxy-5-methylheptanoyl)pyrrolidin-2-yl)-3-methoxy-2-methylpropanoyl)-L-phenylalanine

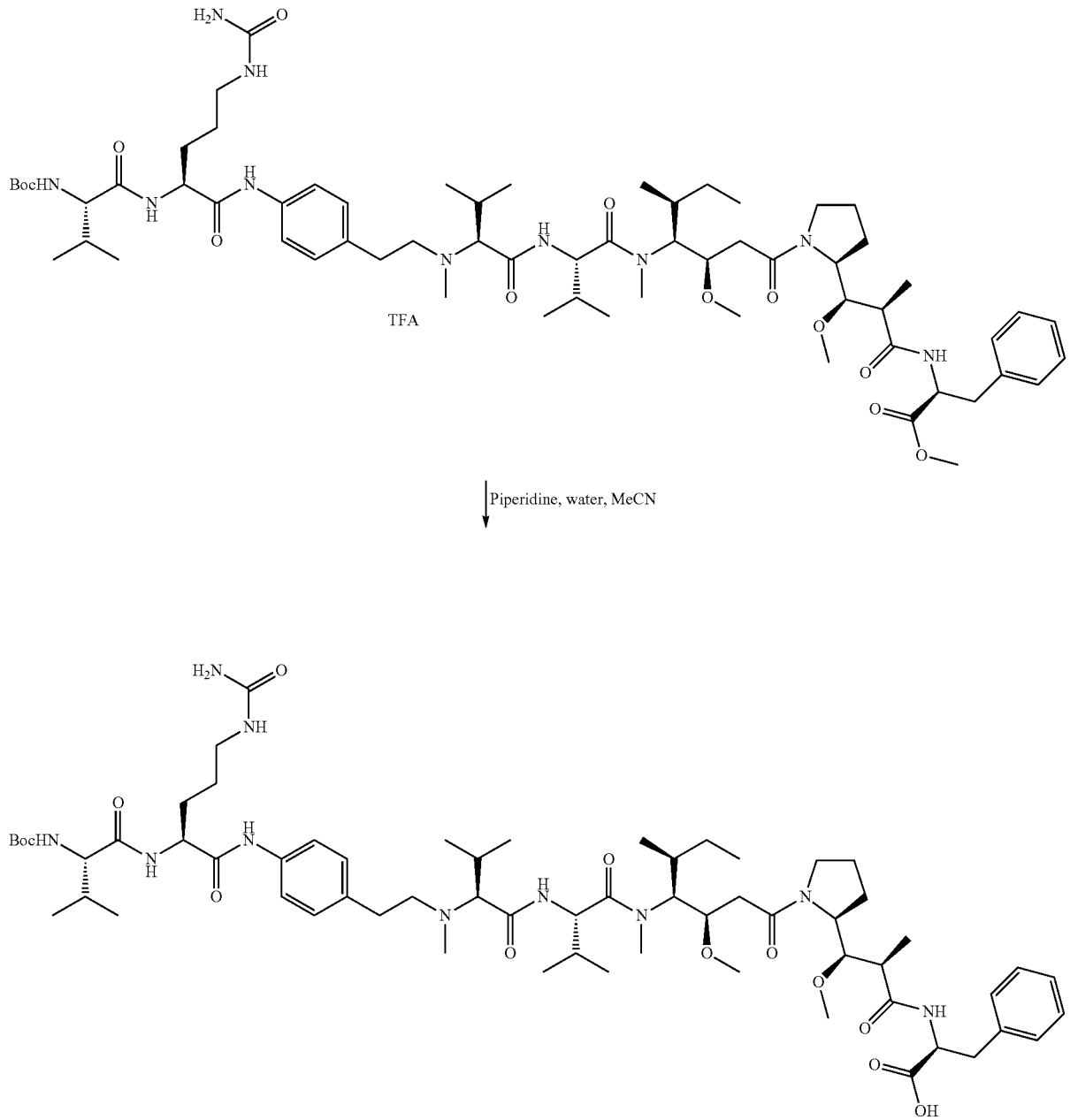

Compound F-62-1 (157 mg, 0.118 mmol, 1 eq.) was dissolved in a mixture of water (4.5 mL), acetonitrile (4.5 mL) and piperidine (3.5 mL) and stirred at room temperature for 5 hours. The solvent was evaporated under reduced pressure and the residue triturated Et$_2$O (60 mL). The solid was collected by filtration and rinsed twice with Et$_2$O (10 mL) to yield compound F-63-1 as an off-white solid (153 mg, 100%).

Compound F-63-2: ((2R,3R)-3-((S)-1-((3R,4S,5S)-4-((S)-2-((S)-2-((4-((S)-2-((S)-2-amino-3-methylbutanamido)-5-ureidopentanamido)phenethyl)(methyl)amino)-3-methylbutanamido)-N,3-dimethylbutanamido)-3-methoxy-5-methylheptanoyl) pyrrolidin-2-yl)-3-methoxy-2-methylpropanoyl)-L-phenylalanine bis 2,2,2-trifluoroacetate

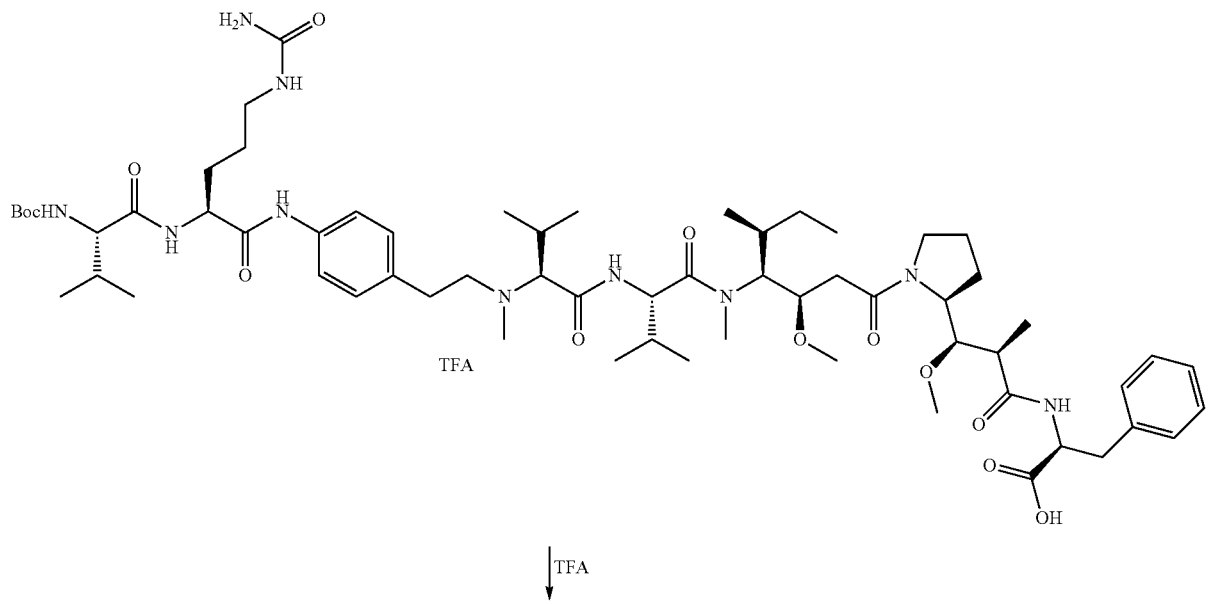

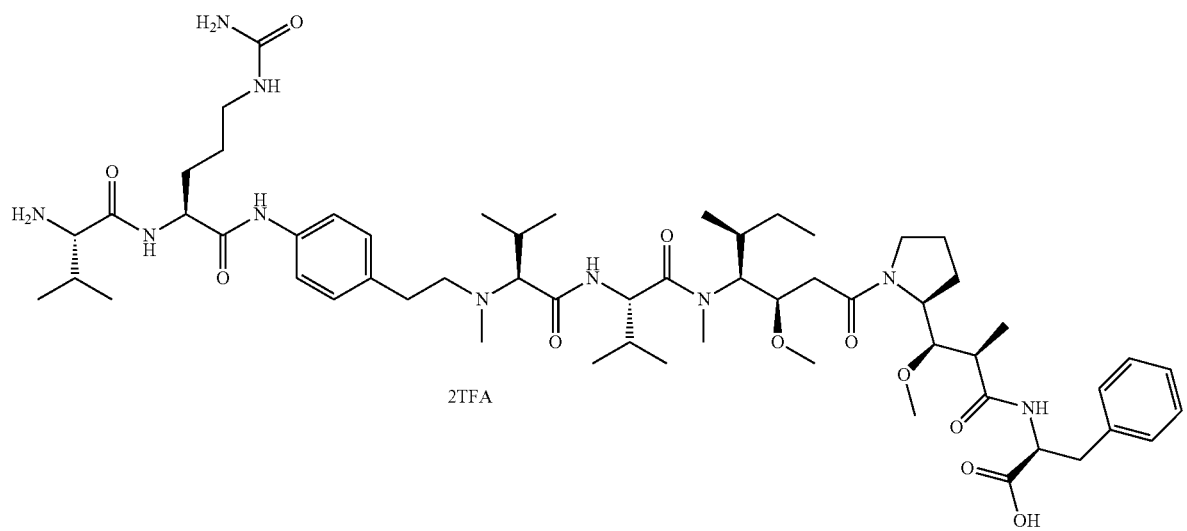

Compound F-63-1 (153 mg, 0.127 mmol, 1.0 eq.) was dissolved in TFA (200 μL). After 10 minutes, water (2 mL) and acetonitrile (0.5 mL) were added and the solution lyophilised overnight to yield compound F-63-2 as a white solid (34 mg, 105%).

Compound F-63

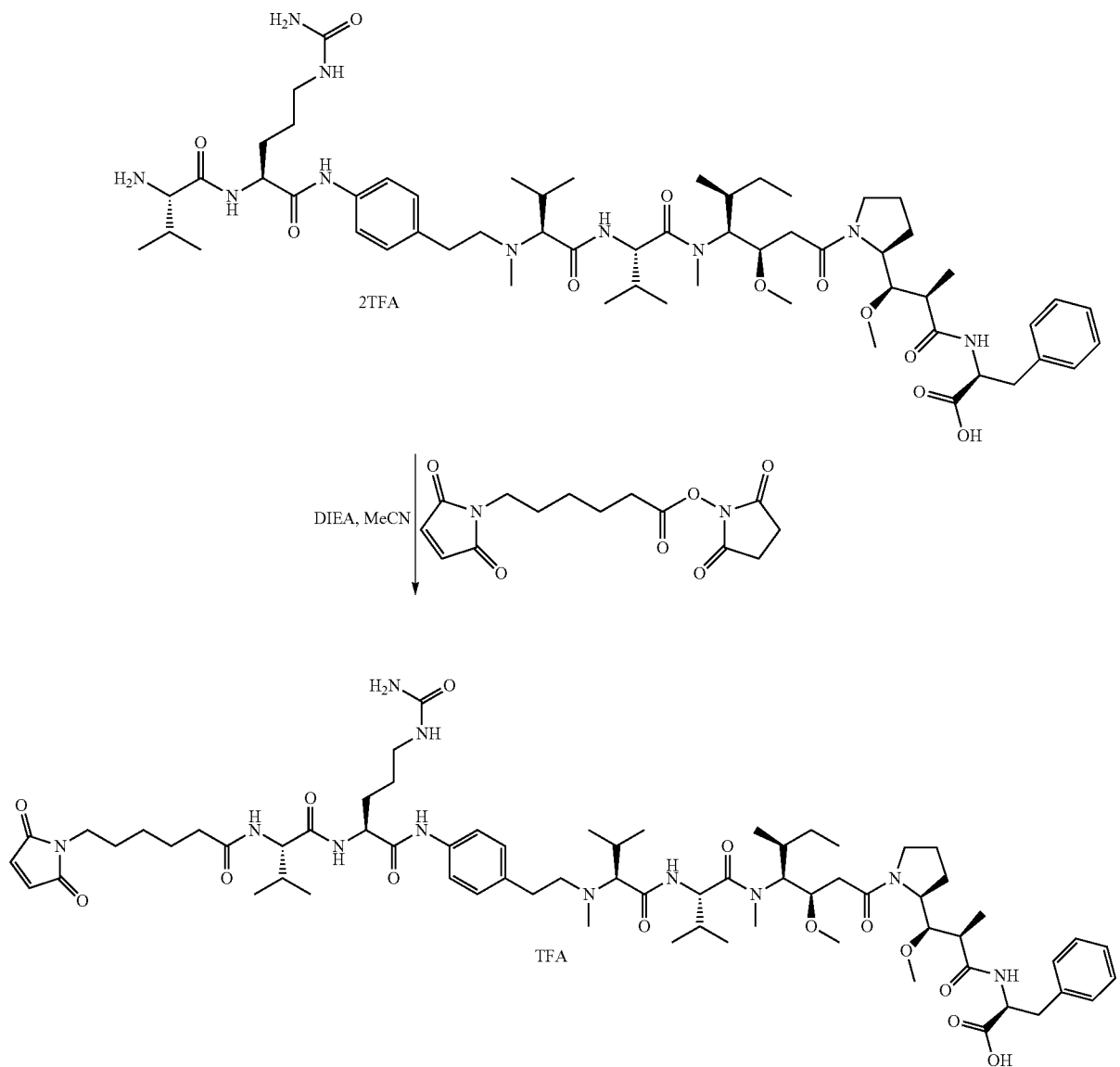 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCc1ccc(NC(=O)[C@H](CCCNC(N)=O)NC(=O)[C@@H](N)C(C)C)cc1)C(C)C ; O=C(CCCCCN1C(=O)C=CC1=O)ON1C(=O)CCC1=O ; CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCc1ccc(NC(=O)[C@H](CCCNC(N)=O)NC(=O)[C@@H](NC(=O)CCCCCN2C(=O)C=CC2=O)C(C)C)cc1)C(C)C]

Amine F-63-2 (100 mg, 0.082 mmol, 1 eq.) was dissolved in a mixture of acetonitrile (2 mL) and DMF (0.5 mL), and 2,5-dioxopyrrolidin-1-yl 6-(2,5-dioxo-2,5-dihydro-1H-pyrrol-1-yl)hexanoate (45 mg, 0.147 mmol, 1.8 eq.) and DIEA (71 μL, 0.409 mmol, 5 eq.) were added. After stirring at room temperature for 4.5 hours, the solvent was evaporated under reduced pressure. The crude product was purified by preparative HPLC (Waters 600E, SunFire Prep C18 OBD column, 5 μm, 19×100 mm; Eluting phase: water/MeCN buffered with 0.10 TFA; Gradient of 5% to 100% MeCN in 15 minutes; Waters 2487 UV Detector at 220 nm). The selected fractions were combined and lyophilised to furnish compound F-63 as a white solid after (42 mg, 36%).

m/z (Q-TOF MS ESI+) 1300.7901 (2%, MH$^+$, $C_{68}H_{106}N_{11}O_{14}$ requires 1300.7915), 650.8990 (100%, $(MH_2)^{2+}$, $C_{68}H_{107}N_{11}O_{14}$ requires 650.8994).

Compound G-12 methyl ((2R,3R)-3-((S)-1-((3R,4S,5S)-4-((S)-2-((S)-2-((4-(6-(2,5-dioxo-2,5-dihydro-1H-pyrrol-1-yl)-N-methylhexanamido)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate 2,2,2-trifluoroacetate

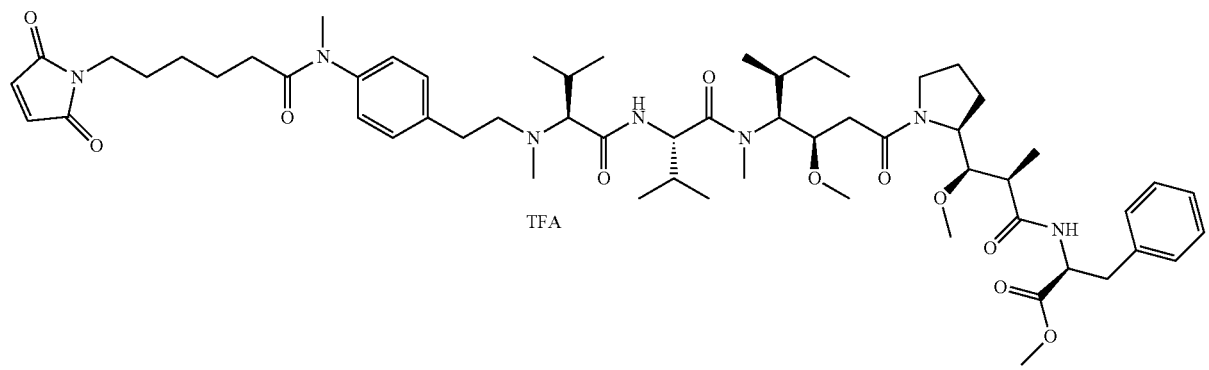 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCc1ccc(N(C)C(=O)CCCCCN2C(=O)C=CC2=O)cc1)C(C)C]

Compound G-12-1: benzyl N-(4-aminophenethyl)-N-methyl-L-valinate dihydrochloride

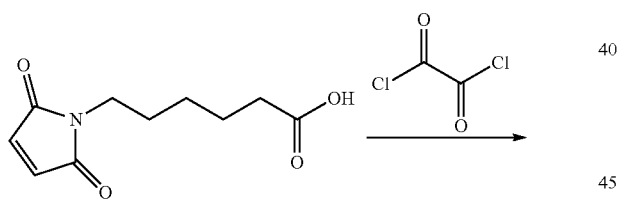

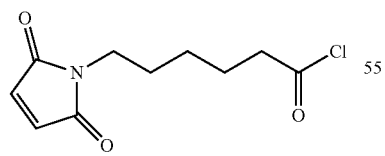

Into oxalyl chloride (3 mL) was dissolved 6-(2,5-dioxo-2,5-dihydro-1H-pyrrol-1-yl)hexanoic acid (200 mg, 0.947 mmol, 1 eq.). The solution was stirred at room temperature for 5 hours before evaporating to dryness under reduced pressure. Compound G-12-1 was obtained as a beige solid (217 mg, 100%) and used in the next step without purification.

Compound G-12

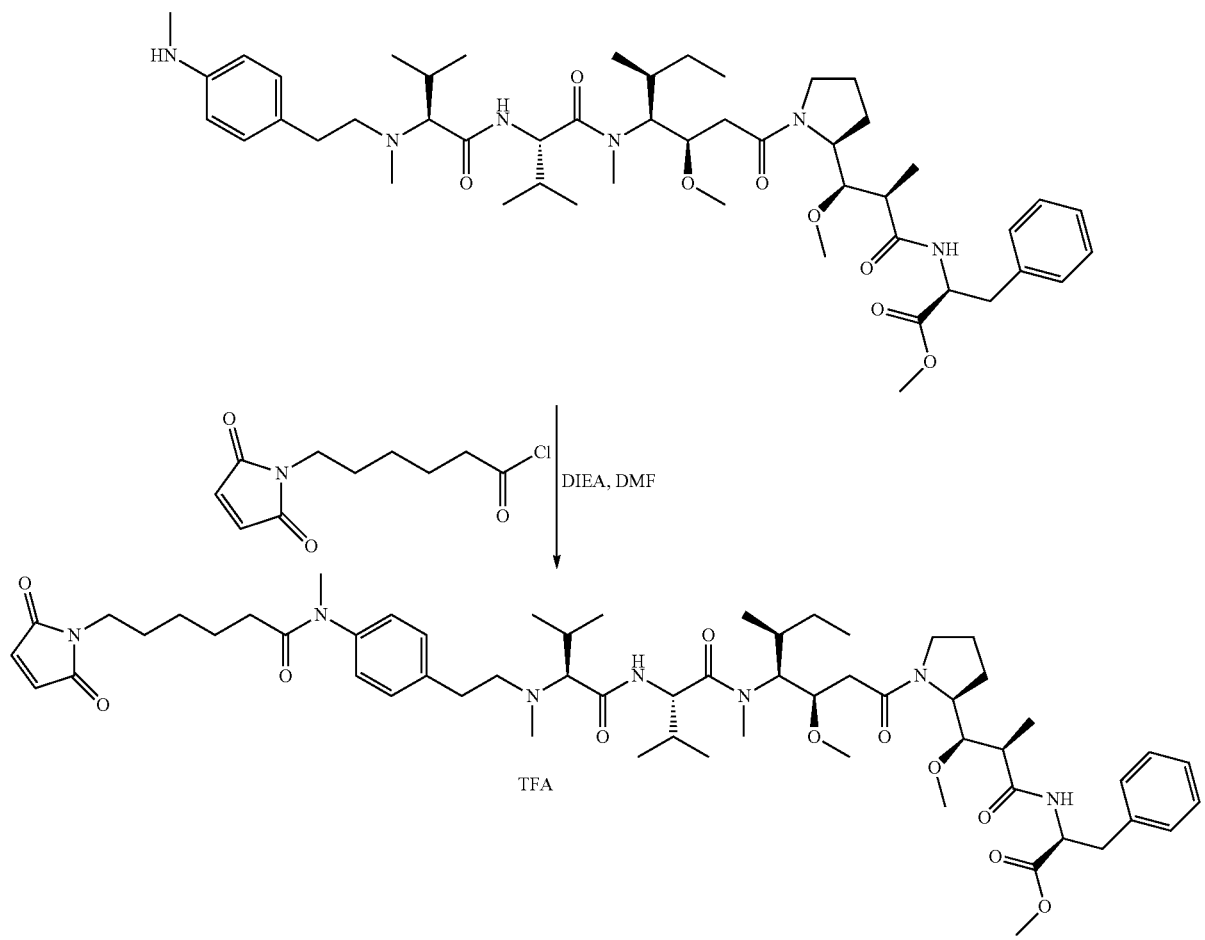

Aniline 12 (40 mg, 0.045 mmol, 1 eq.) was dissolved in dry DCM (1 mL) at 0° C. and DIEA (8 µL, 0.045 mmol, 1 eq.) was added. After stirring for 30 minutes, a solution of compound G-12-1 (10 mg, 0.45 mmol, 1 eq.) in dry DCM (1 mL) was introduced and the reaction stirred for 1 hour at 0° C. The mixture was diluted with DCM (25 ml) and washed twice with water (20 mL), once with brine (10 mL). The organic phase was dried over $Na_2SO_4$, filtered and evaporated under reduced pressure to yield the crude product as a light brown solid (54 mg). This was purified by flash chromatography on silica gel (DCM/MeOH) followed by preparative HPLC (Waters 600E, SunFire Prep C18 OBD column, 5 µm, 19×100 mm; Eluting phase: water/MeCN buffered with 0.1% TFA; Gradient of 5% to 100% MeCN in 15 minutes; Waters 2487 UV Detector at 220 nm). The isolated product was lyophilised to yield a white solid (23 mg), which was repurified by preparative HPLC and the selected fractions combined and lyophilised to furnish compound G-12 as a white solid (9 mg, 16%).

m/z (Q-TOF MS ESI+) 1094.6543 (20%, $MNa^+$, $C_{59}H_{89}N_7NaO_{11}$ requires 1094.6512), 1072.6722 (16%, $MH^+$, $C_{59}H_{90}N_7O_{11}$ requires 1072.6693), 536.8358 (100%, $(MH_2)^{2+}$, $C_{59}H_{91}N_7O_{11}$ requires 536.8383).

Compound G-13
((2R,3R)-3-((S)-1-((3R,4S,5S)-4-((S)-2-((S)-2-((4-(6-(2,5-dioxo-2,5-dihydro-1H-pyrrol-1-yl)-N-methylhexanamido)phenethyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalanine 2,2,2-trifluoroacetate
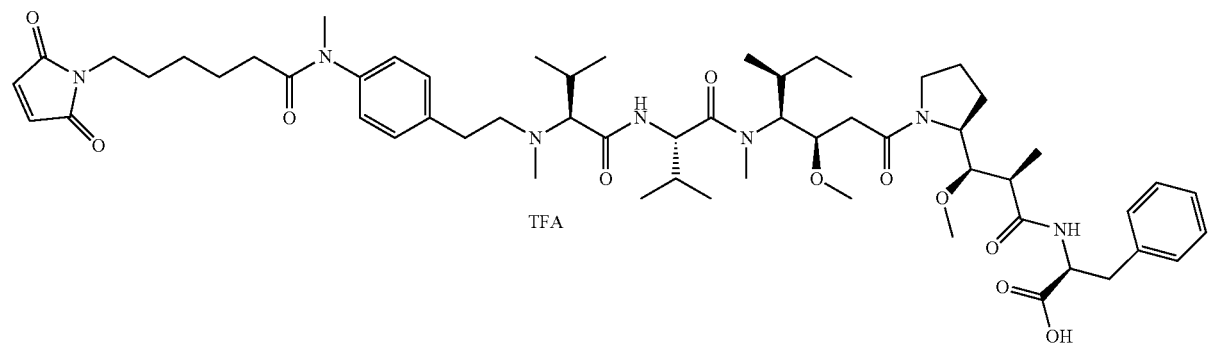 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCc1ccc(N(C)C(=O)CCCCCN2C(=O)C=CC2=O)cc1)C(C)C]
Compound G-13
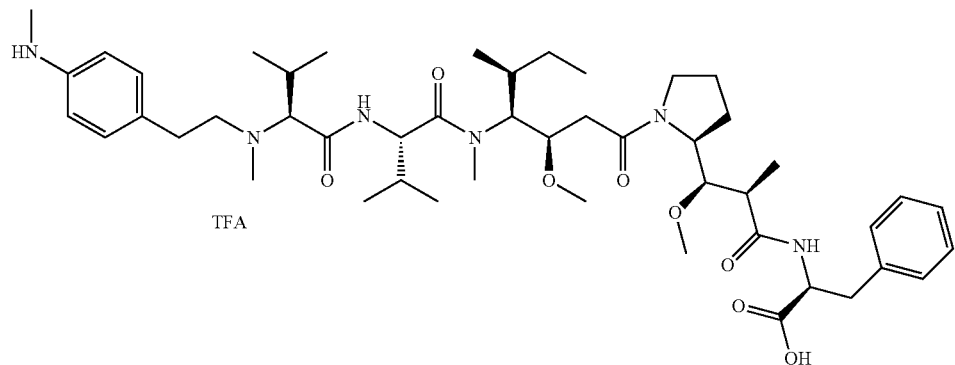
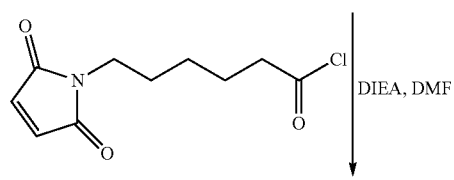
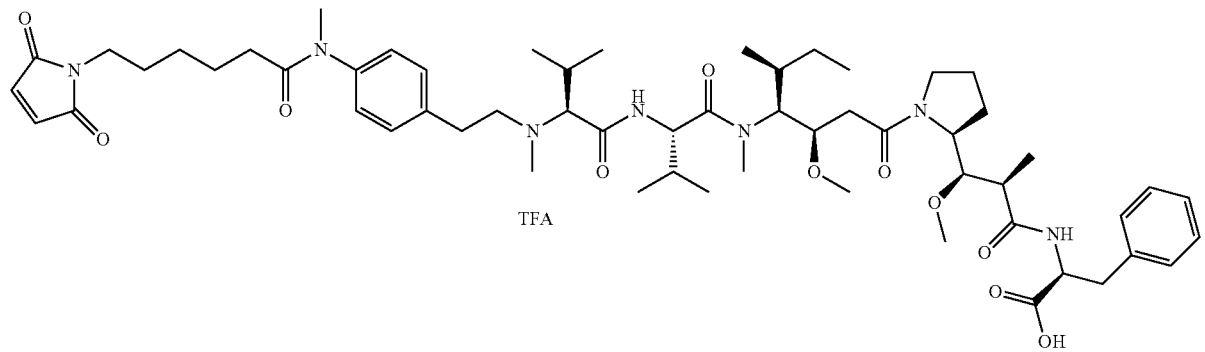

Aniline 13 (15 mg, 0.015 mmol, 1 eq.) was dissolved in dry DCM (1.5 mL) at 0° C. and DIEA (8 µL, 0.046 mmol, 3 eq.) was added. A solution of compound G-12-1 (3.5 mg, 0.046 mmol, 1 eq.) in dry DCM (0.5 mL) was introduced and the reaction stirred for 1.5 hours at 0° C. The solvent was evaporated under reduced pressure and the crude product purified by preparative HPLC (Waters 600E, SunFire Prep C18 OBD column, 5 µm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound G-13 as a white solid (11.4 mg, 62%).

m/z (Q-TOF MS ESI+) 1058.6510 (30%, MH$^+$, $C_{58}H_{88}N_7O_{11}$ requires 1058.6536), 529.8285 (100%, $(MH_2)^{2+}$, $C_{58}H_{89}N_7O_{11}$ requires 529.8305).

Compound G-15 methyl ((2R,3R)-3-((S)-1-((3R,4S,5S)-4-((S)-2-((S)-2-((3-(6-(2,5-dioxo-2,5-dihydro-1H-pyrrol-1-yl)hexanamido)benzyl)(methyl)amino)-3-methylbutanamido)-N,3-dimethylbutanamido)-3-methoxy-5-methylheptanoyl)pyrrolidin-2-yl)-3-methoxy-2-methylpropanoyl)-L-phenylalaninate 2,2,2-trifluoroacetate

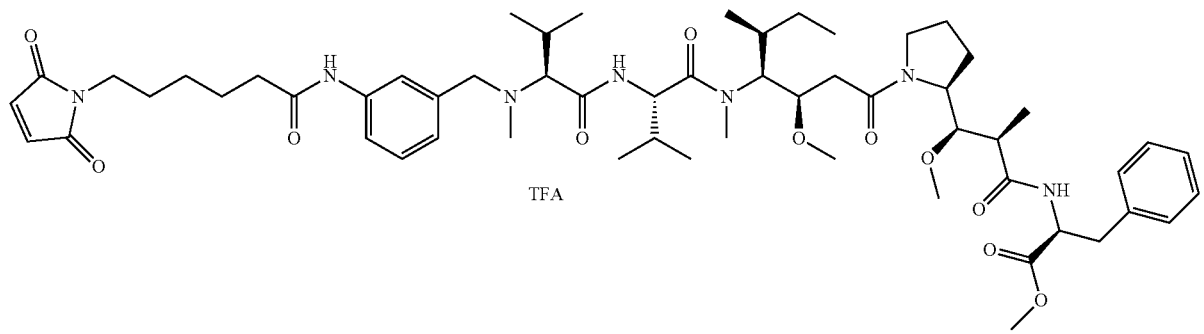 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)Cc1cccc(NC(=O)CCCCCN2C(=O)C=CC2=O)c1)C(C)C]

Compound G-15

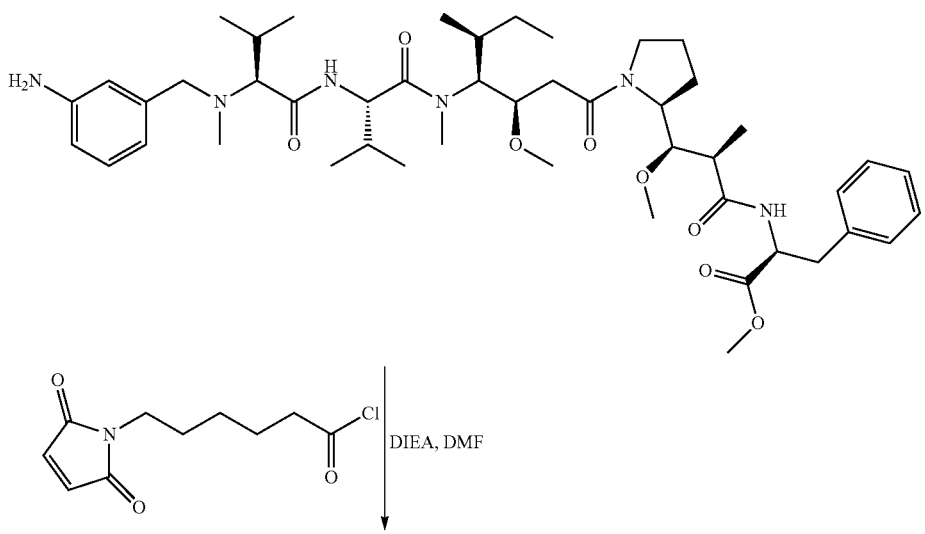

-continued

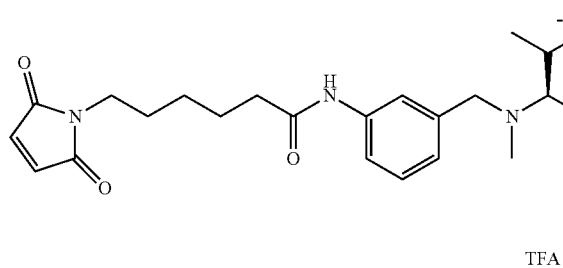

TFA

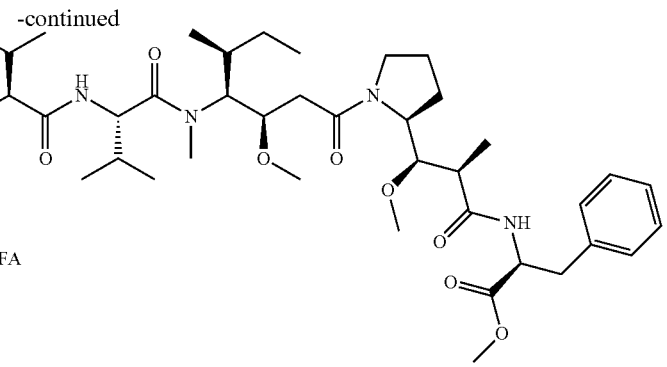

Aniline 15 (40 mg, 0.047 mmol, 1 eq.) was dissolved in dry DCM (2 mL) at 0° C. and DIEA (10 μL, 0.056 mmol, 1.2 eq.) was added. A solution of compound G-12-1 (108 mg, 0.47 mmol, 10 eq.) in dry DCM (1 mL) was introduced and the reaction stirred for 1.5 hours at 0° C. The mixture was diluted with DCM (10 ml) and washed twice with water (5 mL). The organic phase was dried over MgSO$_4$, filtered and evaporated under reduced pressure to yield the crude product as a beige solid. This was purified by preparative HPLC (Waters 600E, SunFire Prep C18 OBD column, 5 μm, 19×100 mm; Eluting phase: water/MeCN buffered with 0.1% TFA; Gradient of 5% to 100% MeCN in 15 minutes; Waters 2487 UV Detector at 220 nm). The selected fractions were combined and lyophilised to furnish compound G15 as a white solid (27 mg, 50%).

m/z (Q-TOF MS ESI+) 1066.6517 (2%, MNa$^+$, C$_{57}$H$_{85}$N$_7$NaO$_{11}$ requires 1066.6199), 522.8224 (100%, (MH$_2$)$^{2+}$, C$_{57}$H$_{87}$N$_7$O$_{11}$ requires 522.8226).

Example 19: ADC Synthesis, Purification and Characterization

The procedure described below applies to chimeric and humanized IgG1 forms. It must be undertood that for any other forms, such as IgG2, IgG4, etc., the person skilled n the art would be capable of adapatting this procedure using the general knowledge.

Second IGF-1R Antibodies (1-5 mg/ml) were partially reduced with Tris(2-carboxyethyl)phosphine hydrochloride (TCEP) in 10 mM borate buffer pH 8.4 containing 150 mM NaCl and 2 mM EDTA for 2 h at 37° C. Typically, 2.5-3 molar equivalents of TCEP were used to target a Drug-to-Antibody Ratios (DAR) of around 4, respectively. The partial antibody reduction was confirmed by SDS-PAGE analysis under non reducing conditions. Before Linker-Drug coupling to the released interchain cysteine residues, the reduction mixture was allowed to cool to room temperature. The antibody concentration was then adjusted to 1 mg/ml with 10 mM borate buffer pH 8.4 containing 150 mM NaCl and 2 mM EDTA, and a 5 molar excess of drug to antibody was added from a 10 mM solution in dimethyl sulfoxide (DMSO). The final DMSO concentration was adjusted to 10% to maintain the solubility of the drug in the aqueous medium during coupling. The reaction was carried out for 1 h at room temperature. The drug excess was quenched by addition of 1.5 moles of N-acetylcysteine per mole of drug and incubation for 1 h at room temperature. After dialysis against 25 mM His buffer pH 6.5 containing 150 mM NaCl overnight at 4° C., the antibody-drug-conjugates were purified by using methods known to persons skilled in the art based with commercial chromatography columns and ultrafiltration units. First, the non coupled drug and the ADC aggregates were eliminated by size exclusion chromatography (SEC) on S200 (GE Life Sciences) or TSK G3000 SW (Tosoh) column. The purified ADC monomers were then concentrated to 2-3 mg/ml by ultrafiltration on 30 or 50 kDa MWCO filtration units or by affinity chromatography on Protein A. The purified ADCs were stored at 4° C. after sterile filtration on 0.2 μm filter. They were further analyzed by SDS-PAGE under reducing and non reducing conditions to confirm drug conjugation and by SEC on analytical S200 or TSK G3000 SWXL columns to determine the content of monomers and aggregated forms. Protein concentrations were determined by using the bicinchoninic acid (BCA) assay with IgG as standard. The DAR was estimated for each purified ADC by HIC and LC-MS. Typically, the content of aggregated forms was lower than 5% and the DAR was comprised between 3.5 and 5.

Example 20: Cytotoxicity Evaluation of IGF-1R Antibodies Coupled with Different Drugs 20.1 Evaluation of the Chimeric Second IGF-1R Antibodies on MCF-7 Cells The five second IGF-1R antibodies were shown to be rapidly internalized into lysosomes and to have a lower binding capacity into acidic environments. In that respect, those secondf IGF-1R Abs had all properties to be used as ADCs. Thus, the five chimeric anti-IGF-1R antibodies were coupled with three different compounds (G-13; E-13 and F-63). The drug antibody ratio of those ADCs was about 4. In order to evaluate the non specific cytotoxicity, an irrelevant chimeric antibody c9G4 was also coupled with those compounds at the same DAR. MCF-7 cells were incubated with increasing concentrations of each ADCs at 37° C. for 6 days in complete culture medium. Cell viability was assessed using a luminescent cell viability assay (CellTiter-Glo, Promega). Luminescent signal was read using a the Mithras plate reader (Berthold Technologies). The irrelevant chimeric antibody c9G4 coupled with either E-13, G-13 or F-63 showed no or modest cytotoxic activity on MCF-7 cells (FIG. 26). On the contrary, addition of all other ADCs obtained after coupling second IGF-1R antibodies with either E-13, G-13 or F-63 decreased dramatically MCF-7 cell viability.

20.2 Evaluation of the Chimeric Second IGF-1R Antibodies on Normal Cells

The expression levels of IGF-1R were evaluated on primary normal cells (PromoCell GmbH) using c208F2 mAb. For that purpose, cells (0.5×10$^6$ cells/ml) were incubated with 10 μg/ml of c208F2 antibody for 20 min. at 4° C. in FACS buffer (PBS, 0.1% BSA, 0.01% NaN3). They were then washed 3 times and incubated with the appropriate secondary antibody coupled with Alexa 488 for 20 additional minutes at 4° C. in the dark before being washed 3 times in FACS buffer. The binding of second IGF-1R antibody was immediately performed on viable cells which were identified using propidium iodide (that stains dead cells). The expression level (Bmax) was low on normal cells (Table 15) compared to IGF-1R expression on MCF-7 cells (see example 5, table 9).

TABLE 15

| Normal Cells | Bmax |
|---|---|
| Human Aortic Endothelial Cells (HAoEC) | 21 |
| Human Pulmonary Microvascular Endothelial Cells (HPMEC) | 33 |
| Human Bronchial Smooth Muscle Cells (HBSMC) | 26 |
| Human Renal Epithelial Cells (HREpC) | 110 |
| Human Urethelial Cells (HUC) | 181 |

The cytotoxicity of the ADC c208F2-G-13 was evaluated on normal cells. The cells were incubated with increasing concentrations of c208F2-G-13 at 37° C. for 6 days in complete culture medium. Cell viability was assessed using a luminescent cell viability assay (CellTiter-Glo, Promega). Luminescent signal was read using a the Mithras plate reader (Berthold Technologies). No major cytotoxicity was observed on HBSMC, HPMEC, HAoEC and HREpC (FIG. 30). Minor cell toxicity was measured on HUC only at high concentrations of c208F2-G-13.

20.3 Evaluation of the Humanized Variants of the hz208F2

The sixteen humanized variants of the 208F2 were coupled with the compound G-13. The drug antibody ratio of those ADCs was about 4. In order to evaluate the non specific cytotoxicity, an irrelevant chimeric antibody c9G4 was also coupled with those compounds at the same DAR. The chimeric antibody c208F2 was also coupled with G-13. MCF-7 cells were incubated with increasing concentrations of each ADCs at 37° C. for 6 days in complete culture medium. Cell viability was assessed using a luminescent cell viability assay (CellTiter-Glo, Promega). Luminescent signal was read using a Mithras plate reader (Berthold Technologies). The irrelevant chimeric antibody c9G4 coupled with either G-13 showed no or modest cytotoxic activity on MCF-7 cells (FIG. 31). On the contrary, addition of all other ADCs obtained after coupling anti-IGF-1R antibodies with G-13 decreased dramatically MCF-7 cell viability. The ability of the sixteen humanized variants to induce cell cytotoxicity was at least equivalent even better to the one measured with the chimeric form c208F2-G-13 as shown in Table 16 and illustrated with one humanized variant in FIG. 31.

TABLE 16

| | | EC50 |
|---|---|---|
| Chimeric mAb | c208F2-G-13 | 9.0E−11 |
| Humanized variants | Hz208F2 (H026/L024)-G-13 | 1.1E−10 |
| | hz208F2 (H037/L018)-G-13 | 3.7E−11 |

TABLE 16-continued

| | EC50 |
|---|---|
| hz208F2 (H047/L018)-G-13 | 4.4E−11 |
| hz208F2 (H049/L018)-G-13 | 6.6E−11 |
| hz208F2 (H051/L018)-G-13 | 3.6E−11 |
| hz208F2 (H052/L018)-G-13 | 3.4E−11 |
| hz208F2 (H057/L018)-G-13 | 5.2E−11 |
| hz208F2 (H068/L018)-G-13 | 6.2E−11 |
| hz208F2 (H070/L018)-G-13 | 5.7E−11 |
| hz208F2 (H071/L018)-G-13 | 8.5E−11 |
| hz208F2 (H076/L018)-G-13 | 5.3E−11 |
| hz208F2 (H077/L018)-G-13 | 3.0E−11 |
| hz208F2 (H037/L021)-G-13 | 3.9E−11 |
| hz208F2 (H049/L021)-G-13 | 5.2E−11 |
| hz208F2 (H052/L021)-G-13 | 3.7E−11 |
| hz208F2 (H076/L021)-G-13 | 4.5E−11 |

Example 21: In Vivo Activity of the c208F2 Antibody Conjugated to Either E-13, G-13 or F-63 Compounds in the MCF-7 Xenograft Model In order to confirm that the in vitro efficacy of the c208F2 coupled to G-13, E-13 or F-63 compounds could be translated in vivo, they have been tested in the MCF-7 xenograft model.

All animal procedures were performed according to the guidelines of the 2010/63/UE Directive on the protection of animals used for scientific purposes. The protocol was approved by the Animal Ethical Committee of the Pierre Fabre Institute. Five millions MCF-7 cells were injected subcutaneous into 7 weeks old Swiss/Nude mice. Prior to cell injection, oestrogen pellets (Innovative Research of America) were implanted to the left flank to mice in order to release estrogens necessary to the in vivo growth of MCF-7 tumors.

Twenty days after MCF-7 cell implantation, when tumors reached an average size of 120-150 mm$^3$, the animals were divided into groups of 5 mice according to tumor size and aspect. The different treatments were inoculated by intraperitoneal injections. The health status of animals was monitored daily. Tumor volume was measured twice a week with an electronic calliper until study end. Tumor volume is calculated with the following formula: i/6×length×width× height. Toxicity was evaluated following the weight of animals three times per week. Statistical analyses were performed at each measure using a Mann-Whitney test. All compounds were injected intraperitoneally (i.p.). In this example, the anti-tumor activity of c208F2 mAb coupled with either E-13, F-13 or F-63 at about DAR 4 was evaluated after 2 injections of a 7 mg/kg dose at D20 and D27 (FIGS. 27A, 27B and 27C). In parallel the capped-drug moieties E-13, F-13 and F-63 were injected at the equivalent dose of the one corresponding to 7 mg/kg of c208F2-E-13, c208F2-F-13 and c208F2-F-63 DAR about 4.

Injection of either c208-E-13 (FIG. 22A), c208F2-G-13 (FIG. 27B) or c208F2-F-63 (FIG. 27C) significantly inhibited and even induced a complete tumor growth regression (p<0.05 vs corresponding capped-drug). No statistical activity difference between c208-E-13, c208F2-G-13 and c208F2-F-63 could be noted. Capped drugs had no effect on MCF-7 tumor growth (p>0.05 vs control group)

A second set of experiments was performed with c208F2 coupled with either E-13 or G-13 and with the irrelevant antibody c9G4 coupled with either E-13 or G-13 in MCF-7 xenograft models as described previously. Mice were injected i.p. with 7 mg/kg of each ADCs at D20 and D27 (FIGS. 28A and 28B).

Injection of both c9G4-E-13 and c9G4-F-13 affected moderately and transiently the growth of MCF-7 xenograft tumors. However, this second experiment confirmed that injections of either c208-E-13 or c208F2-G-13 induced complete tumor regression since D43 showing the high anti-tumor activity of those ADCs.

Example 22: In Vivo Activity of the hz208F2 Antibody Conjugated to G-13 Compound in the 3+ MCF-7 Xenograft Model Humanized forms of 208F2 coupled to G-13 compound have been evaluated in vivo, in the MCF-7 xenograft model.

All animal procedures were performed according to the guidelines of the 2010/63/UE Directive on the protection of animals used for scientific purposes. The protocol was approved by the Animal Ethical Committee of the Pierre Fabre Institute. Five millions MCF-7 cells were injected subcutaneous into 7 weeks old Swiss/Nude mice. Prior to cell injection, oestrogen pellets (Innovative Research of America) were implanted to the left flank to mice in order to release estrogens necessary to the in vivo growth of MCF-7 tumors.

Twenty days after MCF-7 cell implantation, when tumors reached an average size of 120-150 $mm^3$, the animals were divided into groups of 6 mice according to tumor size and aspect. The different treatments were inoculated by intraperitoneal injections as a 4 injection protocol; one injection every four days (Q4d4). The health status of animals was monitored daily. Tumor volume was measured twice a week with an electronic calliper until study end. Tumor volume is calculated with the following formula: n/6×length×width×height. Toxicity was evaluated following the weight of animals three times per week. Statistical analyses were performed at each measure using a Mann-Whitney test. All compounds were injected intraperitoneally (i.p.). In this example, the anti-tumor activity of c208F2 mAb coupled to G-13 compound was compared to different humanized forms also coupled to G-13 (FIG. 32). Tested humanized forms were described in the Table 17 bellow:

TABLE 17

| Humanized forms | Corresponding VH/VL | Other name of hz form | Corresponding ADC |
|---|---|---|---|
| 208F2_085hz0107 (G1) | H057/L018 | n/a | hz208F2 (H057/L018)-G-13 |
| 208F2_085hz0119 (G1) | H070/L018 | n/a | hz208F2 (H070/L018)-G-13 |
| 208F2_085hz0126 (G1) | H077/L018 | hz208F2-4 | hz208F2 (H077/L018)-G-13 |
| hz208F2 (VH3VL3) | H26/L024 | n/a | hz208F2 (H026/L024)-G-13 |

Injection of either c208-G-13 or 208F2 humanized forms significantly inhibited and even induced a complete tumor growth regression (p<0.05 vs corresponding control). No statistical activity difference between c208F2-G-13 and the tested humanized forms was observed.

A second set of experiments was performed with either c208F2 or hz208F2-4 coupled to G-13 in MCF-7 xenograft models as described previously (FIGS. 33A and 33B respectively). Mice were injected i.p. with 3 mg/kg of each ADCs, every four days for 4 injections (Q4d4) or only once.

The same strong anti-tumor activity was observed when the ADC was injected four times or only once in the MCF-xenograft model.

Example 23: In Vivo Activity of the 208F2 Antibody Conjugated to G-13 or E-13 Compounds in the 2+ CaOV-3 Xenograft Model Anti-tumoral activity was also studied in a 2+ expressive tumor, the CaOV-3 xenograft model which is an ovarian carcinoma cell line. For that proposal, mice were injected subcutaneously at D0 with $7\times10^6$ cells. When tumours reached approximately 120 $mm^3$ (19 days post tumour cell injection), animals were divided into 5 groups of 5 mice with comparable tumour size and treated intraperitoneally with c208F2 coupled with either E-13 or G-13 and with the irrelevant antibody c9G4 coupled with either E-13 or G-13. Mice were injected i.p. with 3 mg/kg of each ADCs for a 6 injections cycle; one injection every four days. The mice were followed for the observation of xenograft growth rate. Tumour volume was calculated by the formula: r/6×length×width×height.

Compared to the c9G4-E-13 which moderately and transiently induced a growth slowdown, injection of c9G4-G-13 did not affect the growth of CaOV-3 xenograft tumors. In the meantime, injections of either c208F2-E-13 or c208F2-G-13 induced 95% and 77% respectively of tumor growth inhibition at day 50 (FIGS. 34A and 34B).

Example 24: Evaluation of the Binding Competition Between First (810D12 or 816C12) and Second (208F2) IGF-1R Antibodies The aim of the experiment is to define if both mouse monoclonal antibodies m810D12 and m816C12 bind to a region of a soluble form of h-IGF1R out and away of the binding site of the humanized antibody 208F2 (variant Hz208F2-4).

The experiment was run on a Biacore X100 device based on the Surface Plasmon Resonance technology. A CM5 sensor chip was activated with a mouse anti-polyHistidine IgG1 monoclonal antibody chemically linked to the carboxymethyldextran matrix using the amine coupling chemistry. Typically, 12451 RU and 12257 RU of antibodies were grafted on the flowcell 1 (FC1) and flowcell 2 (FC2) respectively. The classical HBS-EP+ buffer was used as the running buffer. This buffer was also used for the preparation of the solutions of the proteins. The experiment was carried at 25° C. and at a flow rate of 10l/min.

Figure 35:
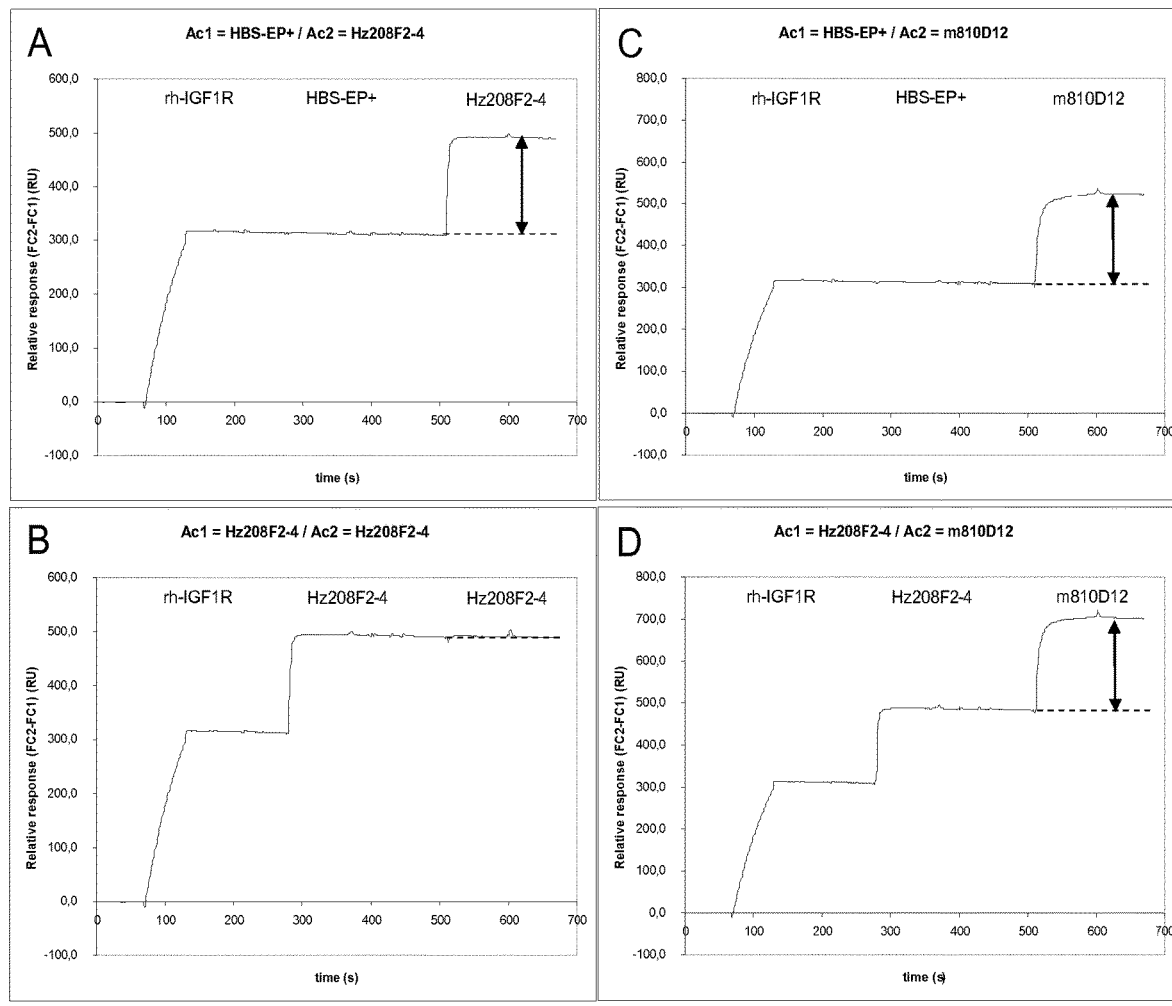

The soluble form of IGF1R produced in house is a heterotetramer composed by two alpha chains and two extracellular domains of the beta chains completed by a 6 Histidine sequence at their C-terminal end. The protein is injected during one minute on the FC2 at the concentration of 30 μg/ml (about 80 nM). The antibodies are injected at the concentration of 50 μg/ml (about 330 nM). Either a first antibody solution (FIGS. 35B and 35D) or the running buffer (FIGS. 35A and 35C) is injected during 90 s on both flowcells. A second antibody solution is then injected on both flow cells. The absence of binding of the second antibody after the binding of the first antibody is the proof that both antibodies bind to a nearby site on the antigen (FIG. 35B) At the opposite the binding of the second antibody after the binding of the first antibody is the proof that the binding site of the second antibody is out and away of the binding site of the first antibody (FIG. 35D). At the end of each cycle, the sensor chip surface is regenerated by an injection of a Glycine, HCl 10 mM pH 1.5 buffer during 30 s.

The levels of binding of the Ac2 (arrows) without (FIGS. 35A and 35B) or with an Ac1 (FIGS. 35C and 35D) were recorded 20 s after the end of the injection. The data are represented on the histogram graph in FIG. 36.

Used as the Ac1, Hz208F2-4 completely blocks the binding of itself but has practically no effect on the binding of both mouse monoclonal antibodies (m810D12 and m816C12) when the three antibodies are used as Ac2.

Conclusion: the binding sites of each mouse monoclonal m810D12 and m816C12 is out and sufficiently far from the binding site of Hz208F2-4 antibody to allow the binding of each mouse monoclonal antibody on a h-IGF1R linked to the Hz208F2-4 antibody.

Example 25: In Vivo Activity of the 208F2 Antibody Conjugated to G-13 Compounds in the $2^+$ NCI-H2122 Xenograft Model Anti-tumoral activity was also studied in a second $2^+$ expressive tumor, the NCI-H2122 xenograft model which is non-small cell lung cancer cell line. For that proposal, mice were injected subcutaneously at D0 with $7 \times 10^6$ cells. When tumours reached approximately 170 mm$^3$ (13 days post tumour cell injection), animals were divided into 3 groups of 6 mice with comparable tumour size and treated intraperitoneally with 208F2 coupled with G-13. Mice were injected i.p. with 5 or 10 mg/kg of ADC for a 4 injections cycle; one injection every seven days. The mice were followed for the observation of xenograft growth rate. Tumour volume was calculated by the formula: $\pi/6 \times$length$\times$width$\times$height.

Injections of 208F2-G-13 induced stagnant tumor growth during more than 30 days (FIG. 37).

Example 26: In Vivo Activity and Ex Vivo Analysis of the hz208F2 Antibody Conjugated to G-13 Compound in the $3^+$ MCF-7 Xenograft Model (Proliferation and Target Commitment Using Either m810D12 or m816C12)

Humanized forms of 208F2 coupled to G-13 compound have been evaluated in vivo, in the MCF-7 xenograft model to validate its activity and target commitment.

All animal procedures were performed according to the guidelines of the 2010/63/UE Directive on the protection of animals used for scientific purposes. The protocol was approved by the Animal Ethical Committee of the Pierre Fabre Institute. Five millions MCF-7 cells were injected subcutaneous into 7 weeks old Swiss/Nude mice. Prior to cell injection, oestrogen pellets (Innovative Research of America) were implanted to the left flank to mice in order to release estrogens necessary to the in vivo growth of MCF-7 tumors.

Twenty days after MCF-7 cell implantation, when tumors reached an average size of 120-150 mm$^3$, the animals were divided into i) 2 groups of 6 mice according to tumor size and aspect to follow anti-tumor activity and ii) 15 groups of 3 mice for IHC studies (1 group for T0, and 2×7 groups for Control and 208F2-G-13). The different treatments were inoculated by intraperitoneal injections as a single injection protocol, at 3 mg/kg for 208F2-G-13. The health status of animals was monitored daily. Tumor volume was measured twice a week with an electronic calliper until study end. Tumor volume is calculated with the following formula: $\pi/6 \times$length$\times$width$\times$height. Toxicity was evaluated following the weight of animals three times per week. Statistical analyses were performed at each measure using a Mann-Whitney test. Tumor removal for IHC analysis were performed at T0 (corresponding to the day of randomization, before compound injections), then, 3 tumor of each lot, 208F2-G-13 and Control, were removed 6 h, 4 days, 7 days, 14 days, and 26 days, after injection. Tumors were formol fixed and paraffin embebded, then stained using Ki67 antibody to follow proliferation and m810D12 or m816C12 to follow IGF-1R expression.

IGF-1R and Ki67 expression in control group was verified from T0 to 14 days post randomization to verify tumor growth impact on either IGF-1R expression and proliferation. Whatever the tested time, IGF-1R and Ki67 staining levels stayed stable in tumor (FIG. 38). IGF-1R was scored 3+ from T0 to 14 days post randomization and proliferative index (Ki67) >80%.

Then tumors were analyzed after a single injection of 208F2-G-13 (FIG. 39). Tumor growth inhibition observed in mice was traduced by a strong decrease of Ki67 expression in tumor, from 83% at T0 to 13% 26 days after a single injection (FIG. 39 panel A). IGF-1R expression was followed 26 days after 208F2-G-13 single injection using either m816C12 or m810D12 (FIG. 39B). After 4 days and to day 26, IGF-1R level in the tumor dramatically decrease which i) traduced target commitment after 208F2-G-13. and ii) the capability of m816C12 and m810D12 to follow 208F2-G-13 activity.

Example 27: Prevalence Study of IGF-1R with m810D12 or m816C12

IGF-1R prevalence in human cancer using either m810D12 or m816C12 was studied on Tumor Micro Array (TMA) from Superbiochips. Slides were stained as described previously and cores were analyzed for the membranous IGF-1R expression using Roche Ventana algorithm (Table 18). IGF-1R was not detected on normal tissues (breast and lung) whereas high level (3+) of IGF-1R was found in 60% of breast cancer, in more than 50% of lung squamous cell carcinoma and in 30% of head and neck carcinoma (larynx, squamous carcinoma).

TABLE 18

| Organ | Statue | % of negative cases 0+ | % of positive cases total (1 + 2 + 3) | 1+ | 2+ | 3+ |
|---|---|---|---|---|---|---|
| Breast: 10 cases | normal | 90 | 10 | 10 | 0 | 0 |
| | tumoral | 0 | 100 | 10 | 30 | 60 |
| Lung: 56 cases | normal | 100 | 0 | 0 | 0 | 0 |
| Squamous, well differentiated: 13 cases | tumoral | 0 | 100 | 0 | 55 | 45 |
| Squamous, moderalty differentiated: 15 cases | tumoral | 13 | 87 | 0 | 27 | 60 |
| Squamous, poorly differentiated: 8 cases | tumoral | 24 | 76 | 0 | 38 | 38 |
| Adenocarcinoma, well differentiated: 4 cases | tumoral | 33 | 66 | 33 | 33 | 0 |
| Adenocarcinoma, moderatly differentiated: 3 cases | tumoral | 0 | 100 | 75 | 25 | 0 |
| Bronchioalveolar carcinoma: 6 cases | tumoral | 33 | 66 | 0 | 33 | 33 |
| Large cell: 7 cases | tumoral | 0 | 100 | 20 | 60 | 20 |
| Larynx squamous (SC): 33 cases | tumoral | 5 | 95 | 20 | 45 | 30 |

The invention claimed is:

1. A method of treating a cancer expressing IGF-1R in a subject in need thereof, said method comprising the steps of
a) determining whether the subject is IGF-1R(+),
wherein said determining comprises contacting a biological sample of the subject with a first anti-IGF-1R antibody,
and wherein binding of said first anti-IGF-1R antibody to the biological sample indicates that the subject is IGF-1R(+);
said first anti-IGF-1R antibody being selected from the group consisting of:
i) an antibody, or an antigen-binding fragment thereof, said antibody comprising:
a heavy chain with CDR-H1 of SEQ ID No. 1, CDR-H2 of SEQ ID No. 2, and CDR-H3 of SEQ ID No. 3; and
a light chain with CDR-L1 of SEQ ID No. 4, CDR-L2 of SEQ ID No. 5, and CDR-L3 of SEQ ID No. 6; and
ii) an antibody, or an antigen-binding fragment thereof, said antibody comprising:
a heavy chain with CDR-H1 of SEQ ID No. 11, CDR-H2 of sequence SEQ ID No. 12 and CDR-H3 of sequence SEQ ID No. 13; and
a light chain with CDR-L1 of sequence SEQ ID No. 14, CDR-L2 of sequence SEQ ID No. 15, and CDR-L3 of sequence SEQ ID No. 16; and
b) if said subject is IGF-1R(+), administering a composition to said subject, said composition comprising an antibody-drug-conjugate of formula (I):

Ab-(L-D)$_n$     (I)

or a pharmaceutically acceptable salt thereof, wherein
Ab is a second anti-IGF-1R antibody, or an antigen binding fragment thereof, comprising:
three heavy chain CDRs of sequence SEQ ID Nos. 21, 22 and 23 and
three light chain CDRs of sequence SEQ ID Nos. 24, 25 and 26;
L is a linker;
D is a drug moiety; and
n is an integer from 1 to 12.

2. The method of claim 1, wherein said first and second anti-IGF-1R antibodies do not bind to the same IGF-1R epitope.

3. The method of claim 1, wherein said first anti-IGF-1R antibody is:
i) an antibody comprising:
a heavy chain variable domain of sequence SEQ ID No. 7, or any sequence with at least 90% of homology with the sequence SEQ ID No. 7; and/or
a light chain variable domain of sequence SEQ ID No. 8, or any sequence with at least 90% of homology with the sequence SEQ ID No. 8; or
ii) an antibody comprising:
a heavy chain variable domain of sequence SEQ ID No. 17, or any sequence with at least 90% of homology with the sequence SEQ ID No. 17; and/or
a light chain variable domain of sequence SEQ ID No. 18, or any sequence with at least 90% of homology with the sequence SEQ ID No. 18.

4. The method of claim 1, wherein said first anti-IGF-1R antibody is:
i) antibody 810D12 produced by the hybridoma deposited at the CNCM, Institut Pasteur, Paris, on Sep. 17, 2014, under number 1-4893; or
ii) antibody 816C12 produced by the hybridoma deposited at the CNCM, Institut Pasteur, Paris, on Sep. 17, 2014, under number 1-4894.

5. The method of claim 1, wherein Ab is selected from the group consisting of:
a) an antibody comprising:
three heavy chain CDRs of sequence SEQ ID Nos. 27, 22 and 23 and
three light chain CDRs of sequence SEQ ID Nos. 29, 25 and 31;
b) an antibody comprising:
three heavy chain CDRs of sequence SEQ ID Nos. 27, 22 and 23 and
three light chain CDRs of sequence SEQ ID Nos. 30, 25 and 31;
c) an antibody comprising:
three heavy chain CDRs of sequence SEQ ID Nos. 27, 22 and 23 and
three light chain CDRs of sequence SEQ ID Nos. 29, 25 and 32; and d) an antibody comprising
three heavy chain CDRs of sequence SEQ ID Nos. 28, 22 and 23 and
three light chain CDRs of sequence SEQ ID Nos. 29, 25 and 31.

6. The method of claim 1, wherein Ab is selected from the group consisting of:
a) an antibody comprising:
a heavy chain comprising a variable domain of sequence selected from SEQ ID Nos. 33, 39, 41, 43, 45, 47, 49, 51, 53, 55, 57 and 59, and any sequence with at least 80% identity with SEQ ID No. 33, 39, 41, 43, 45, 47, 49, 51, 53, 55, 57 or 59; and
a light chain comprising three light chain CDRs of sequences SEQ ID Nos. 29, 25 and 31;
b) an antibody comprising:
a light chain comprising a variable domain of sequence selected from SEQ ID Nos. 34, 37 and 60, and any sequence with at least 80% identity with SEQ ID Nos. 34, 37 or 60; and
a heavy chain comprising three heavy chain CDRs of sequences SEQ ID Nos. 27, 22 and 23; or
c) an antibody comprising:
a heavy chain comprising a variable domain of sequence selected from SEQ ID Nos. 33, 39, 41, 43, 45, 47, 49, 51, 53, 55, 57 and 59, and any sequence with at least 80% identity with SEQ ID Nos. 33, 39, 41, 43, 45, 47, 49, 51, 53, 55, 57 and 59; and
a light chain comprising a variable domain of sequence selected from SEQ ID Nos. 34, 37 and 60, and any sequence with at least 80% identity with SEQ ID Nos. 34, 37 or 60.

7. The method of claim 1, wherein Ab comprises:
a) a heavy chain of sequence selected from SEQ ID Nos. 35, 40, 42, 44, 46, 48, 50, 52, 54, 56, 58 and 61, and any sequence with at least 80% identity with SEQ ID Nos. 35, 40, 42, 44, 46, 48, 50, 52, 54, 56, 58 or 61; and
b) a light chain of sequence selected from SEQ ID Nos. 36, 38 and 62, and any sequence with at least 80% identity with SEQ ID Nos. 36, 38 or 62.

8. The method of claim 1, wherein Ab is selected from the group consisting of:
antibodies 208F2, 212A11, 214F8, 219D6 and 213B10.

9. The method of claim 1, wherein the drug moiety D is selected from the group consisting of alkylating agents, anti-metabolites, anti-tumor antibiotics, mitotic inhibitors, chromatin function inhibitors, anti-angiogenesis agents, anti-estrogens, anti-androgens, chelating agents, Iron absorption stimulant, Cyclooxygenase inhibitors, Phosphodiesterase inhibitors, DNA inhibitors, DNA synthesis inhibitors, Apoptosis stimulants, Thymidylate inhibitors, T cell inhibitors, Interferon agonists, Ribonucleoside triphosphate reductase inhibitors, Aromatase inhibitors, Estrogen receptor antagonists, Tyrosine kinase inhibitors, Cell cycle inhibitors, Taxanes, Tubulin inhibitors, angiogenesis inhibitors, macrophage stimulants, Neurokinin receptor antagonists, Cannabinoid receptor agonists, Dopamine receptor agonists, granulocytes stimulating factor agonists, Erythropoietin receptor agonists, somatostatin receptor agonists, LHRH agonists, Calcium sensitizers, VEGF receptor antagonists, interleukin receptor antagonists, osteoclast inhibitors, radical formation stimulants, endothelin receptor antagonists, *Vinca* alkaloid, anti-hormone, and immunomodulators.

10. The method of claim 1, wherein the drug moiety D is an auristatin, a dolostatin 10, or a derivative thereof.

11. The method of claim 10, wherein the drug moiety D is a compound of formula (II):

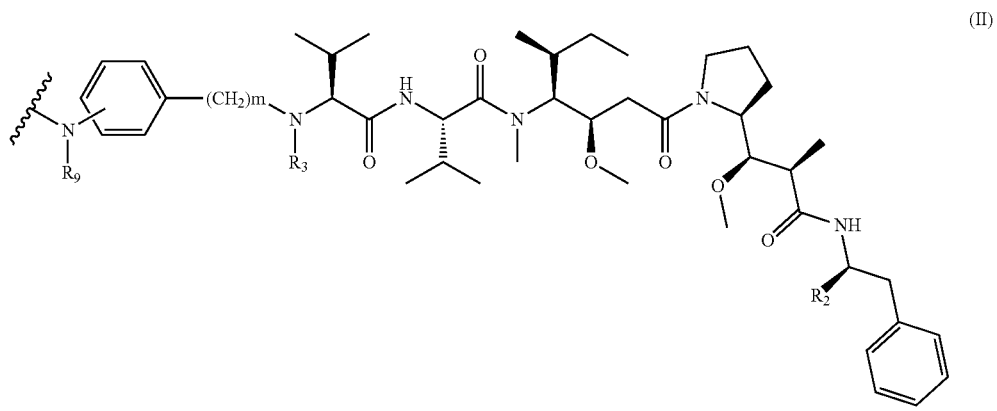

(II)

wherein:
$R_2$ is COOH, COOCH$_3$ or thiazolyl;
$R_3$ is H or $(C_1$-$C_6)$alkyl;
$R_9$ is H or $(C_1$-$C_6)$alkyl;
m is an integer from 1 to 8;
the wavy line indicates the point of attachment to L.

12. The method of claim 1, wherein L is a linker of formula (III):

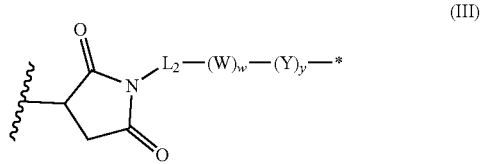

(III)

wherein
$L_2$ is $(C_4$-$C_{10})$cycloalkyl-carbonyl, $(C_2$-$C_6)$alkyl, or $(C_2$-$C_6)$alkyl-carbonyl, W is an amino acid unit; w is an integer from 0 to 5;
Y is PAB-carbonyl with PAB being
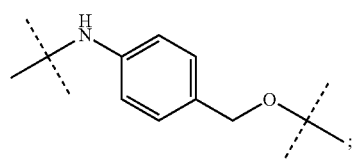
y is 0 or 1;
the asterisk indicates the point of attachment to D; and
the wavy line indicates the point of attachment to Ab.
13. The method of claim 1, wherein the antibody-drug-conjugate has the formula:
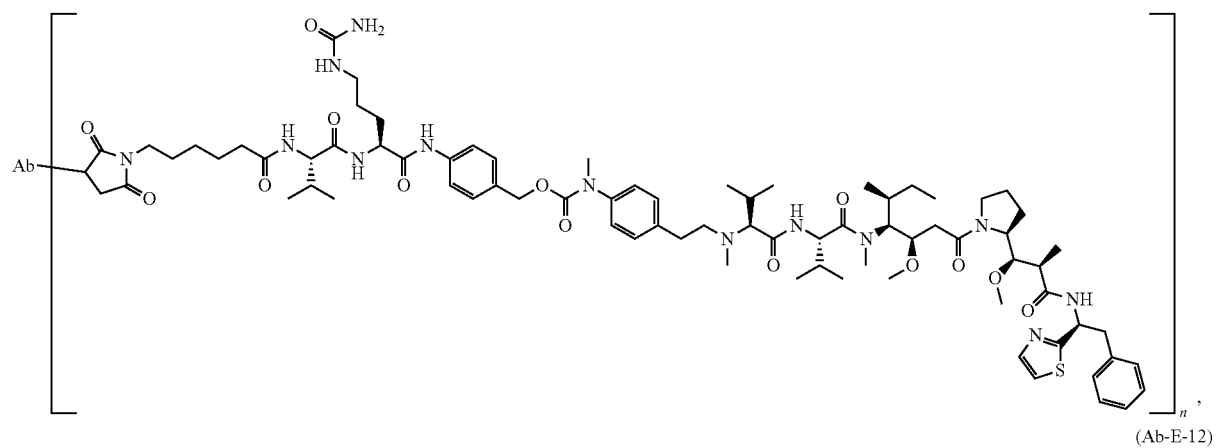
(Ab-E-11)
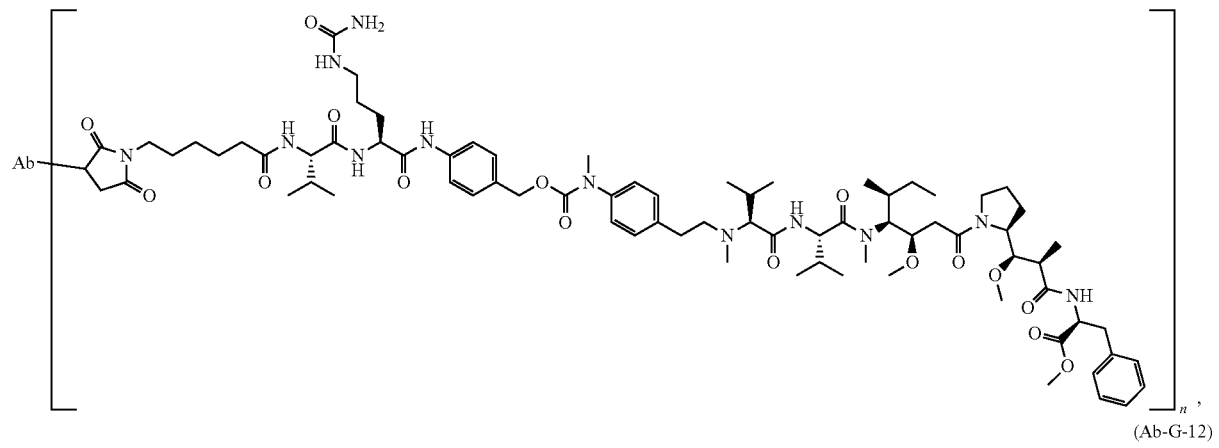
(Ab-E-12)
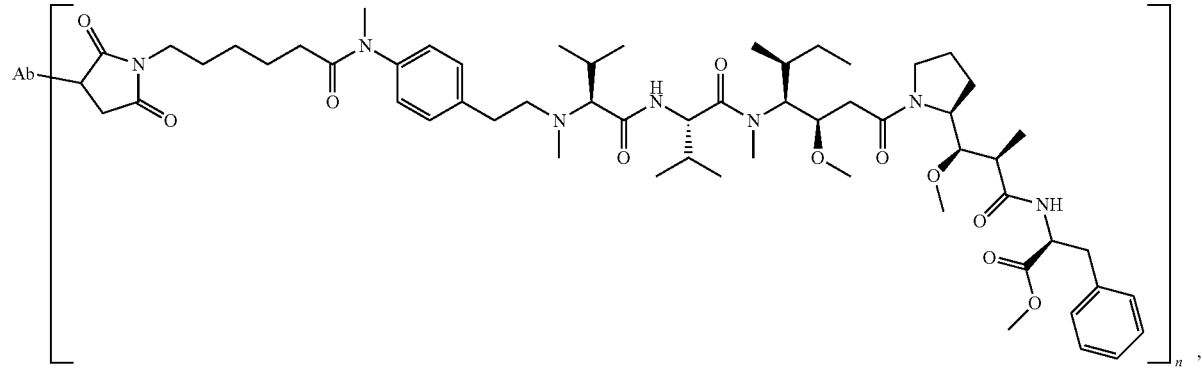
(Ab-G-12)

-continued
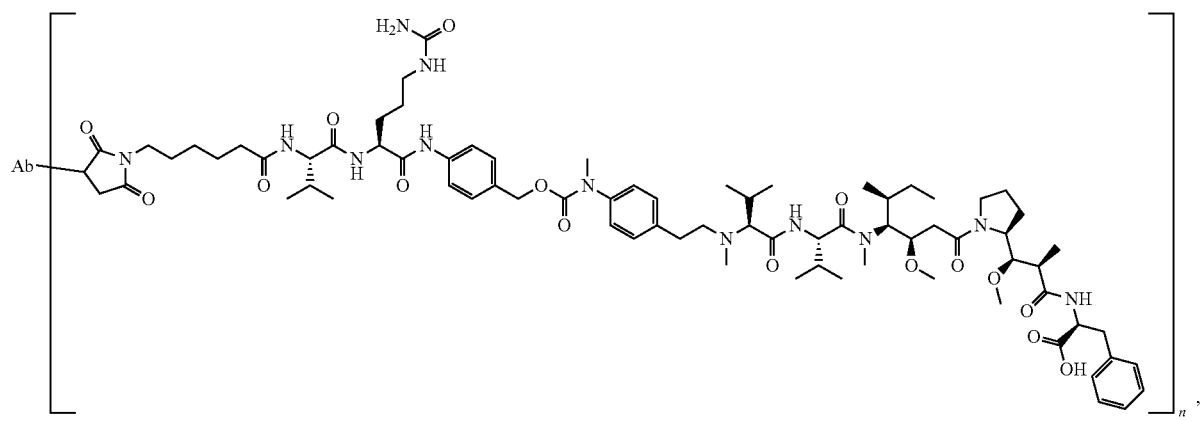
(Ab-E-13)
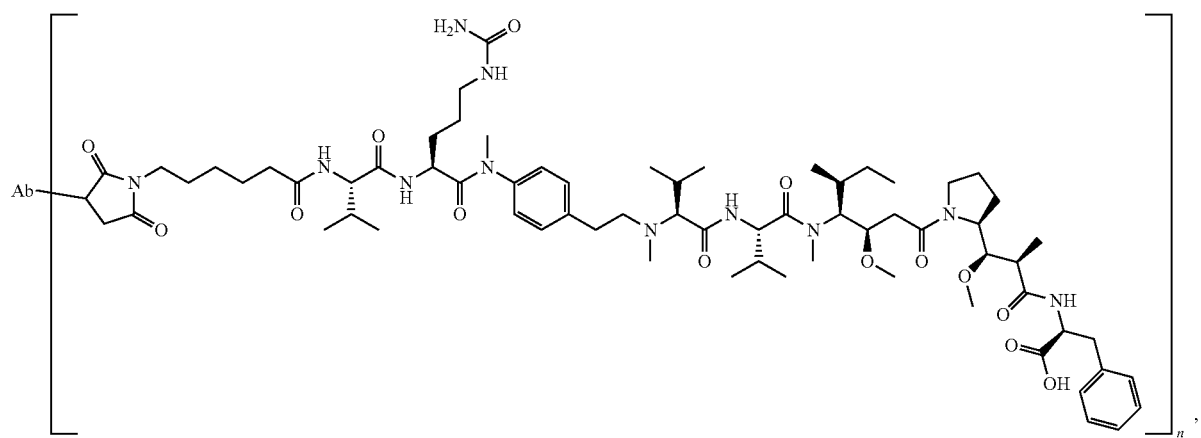
(Ab-F-13)
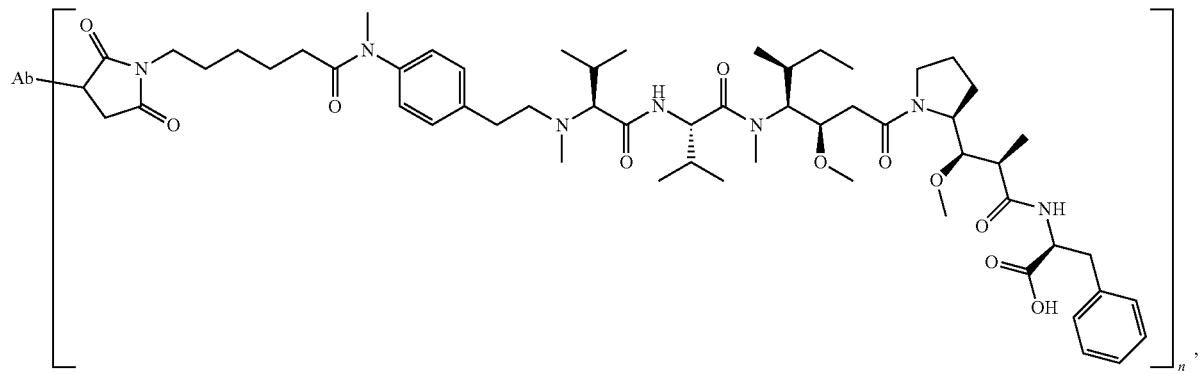
(Ab-G-13)

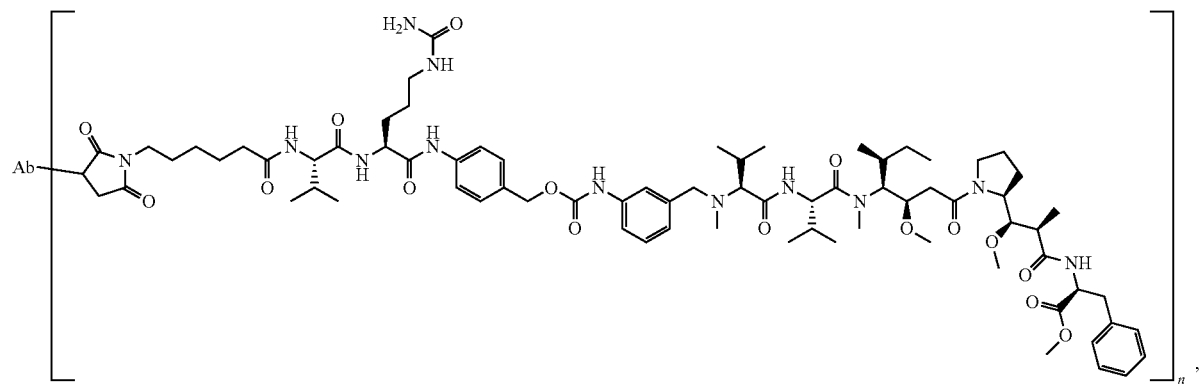
(Ab-E-15)
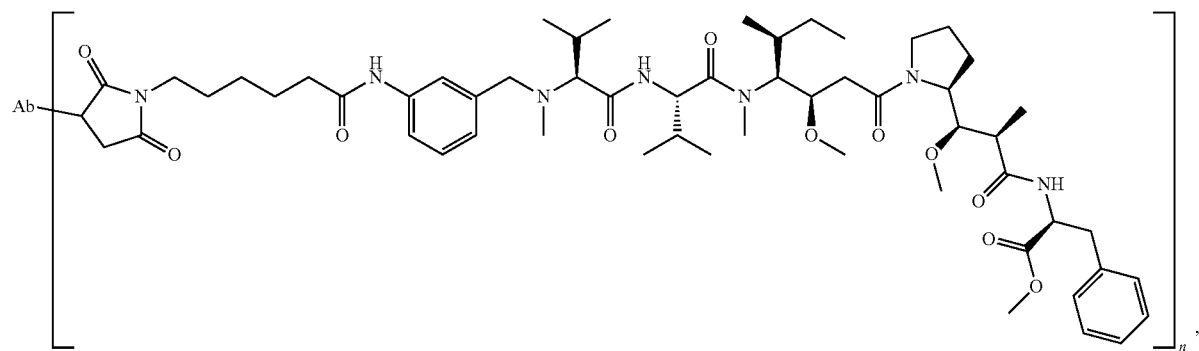
(Ab-G-15)
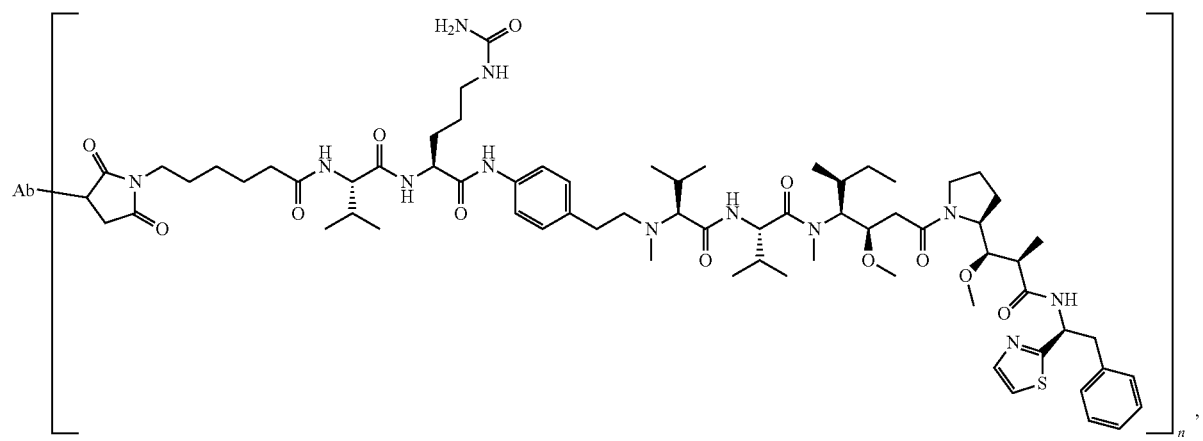
(Ab-F-61)

-continued

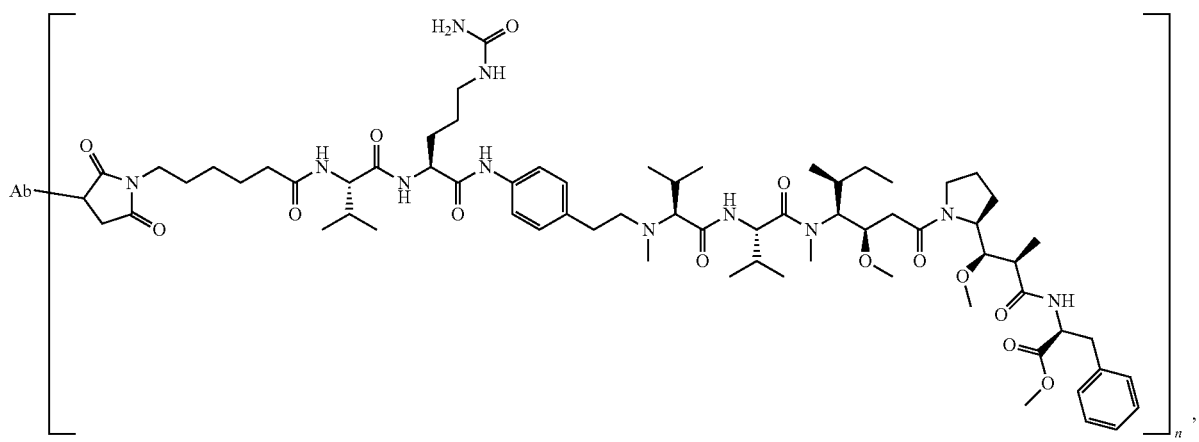

(Ab-F-62)

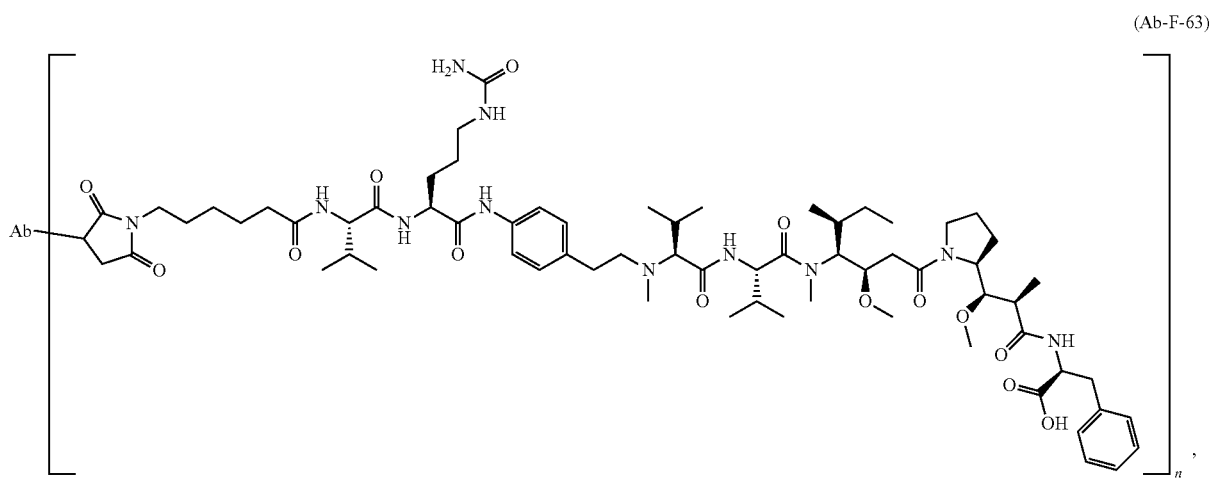

(Ab-F-63)

or a pharmaceutically acceptable salt thereof,
wherein Ab is selected from the group consisting of:
antibodies 208F2, 212A11, 214F8, 219D6 and 213B10.

14. A kit comprising:
    a) a first anti-IGF-1R antibody selected from the group consisting of:
        i) an antibody, or an antigen-binding fragment thereof, said antibody comprising:
        a heavy chain with CDR-H1 of SEQ ID No. 1, CDR-H2 of SEQ ID No. 2, and CDR-H3 of SEQ ID No. 3; and
        a light chain with CDR-L1 of SEQ ID No. 4, CDR-L2 of SEQ ID No. 5, and CDR-L3 of SEQ ID No. 6; and
        ii) an antibody, or an antigen-binding fragment thereof, said antibody comprising:
        a heavy chain with CDR-H1 of SEQ ID No. 11, CDR-H2 of sequence SEQ ID No. 12 and CDR-H3 of sequence SEQ ID No. 13; and
        a light chain with CDR-L1 of sequence SEQ ID No. 14, CDR-L2 of sequence SEQ ID No. 15, and CDR-L3 of sequence SEQ ID No. 16; and
    b) an antibody-drug-conjugate of formula (I):

$$Ab\text{-}(L\text{-}D)_n \quad (I)$$

or a pharmaceutically acceptable salt thereof,
wherein
Ab is a second anti-IGF-1R antibody, or an antigen binding fragment thereof, capable of binding to the human IGF-1R, said antibody comprising
    three heavy chain CDRs of sequence SEQ ID Nos. 21, 22 and 23 and
    three light chain CDRs of sequence SEQ ID Nos. 24, 25 and 26;
L is a linker; and
D is a drug moiety of formula (II):

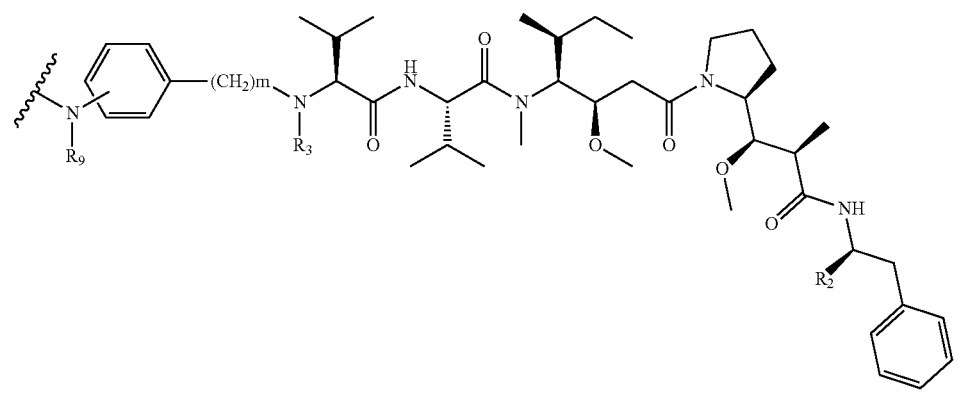
(II)
wherein:
  R₂ is COOH, COOCH₃ or thiazolyl;
  R₃ is H or (C₁-C₆)alkyl;
  R₉ is H or (C₁-C₆)alkyl;
  m is an integer from 1 to 8;
  the wavy line indicates the point of attachment to L; and
  n is an integer from 1 to 12.
* * * * *